(12) United States Patent
Hsieh et al.

(10) Patent No.: US 7,972,785 B2
(45) Date of Patent: Jul. 5, 2011

(54) BIOMARKERS FOR LIVER FIBROTIC INJURY

(75) Inventors: Hui-Chu Hsieh, Changhua (TW); Tzu-Ling Tseng, Chiayi (TW); Li-Jen Su, Chiayi (TW); Chi-Ying Huang, Taipei (TW); Shih-Lan Hsu, Taipei (TW)

(73) Assignees: Industrial Technology Research Institute (ITRI), Hsinchu (TW); National Health Research Institutes (NHRI), Miaoli County (TW)

( * ) Notice: Subject to any disclaimer, the term of this patent is extended or adjusted under 35 U.S.C. 154(b) by 326 days.

(21) Appl. No.: 11/656,389

(22) Filed: Jan. 23, 2007

(65) Prior Publication Data

US 2007/0184476 A1 Aug. 9, 2007

Related U.S. Application Data

(60) Provisional application No. 60/761,959, filed on Jan. 24, 2006.

(51) Int. Cl.
*C12Q 1/68* (2006.01)
*G01N 33/53* (2006.01)

(52) U.S. Cl. .......................................... 435/6; 435/7.92

(58) Field of Classification Search .................. None
See application file for complete search history.

(56) References Cited

U.S. PATENT DOCUMENTS

| | | | |
|---|---|---|---|
| 6,156,501 A | 12/2000 | McGall et al. | |
| 2006/0246489 A1* | 11/2006 | Svetlov et al. | ............ 435/6 |

FOREIGN PATENT DOCUMENTS

EP  1 150 123 A1  10/2001

OTHER PUBLICATIONS

The Merck Manuals Online Medical Library, [online]. Whitehouse Station, NJ: Merck Research Laboratories, 2007. [retrieved on Apr. 7, 2009]. Retrieved from the Internet: < URL: http://www.merck.com/mmpe/print/sec03/ch026/ch026b.html>. Fibrosis, pp. 1-3.*
Afdhal Clinical Chemistry 2004, 50:1299-1300.*
Bast, Jr. et al. Clinical Cancer Research, 2005, vol. 11, pp. 6103-6108.*
LaBaer et al. Journal of Proteome Research, 2005, vol. 4, pp. 1053-1059.*
Baker Nature Biotechnology, 2005, vol. 23, pp. 297-304.*
Honda et al. Journal of Autoimmunity 2005, 25:133-140.*
Ala-Kokko, Leena, et al., "Gene expression of type I, III and IV collagens in hepatic fibrosis induced by dimethylnitrosamine in the rat," Biochem. J., 244:75-79 (1987).
Rosenberg, William M. C., et al., "Serum markers detect the presence of liver fibrosis: A cohort study," Gastroenterology, 127:1704-1713 (2004).

Yi-Chao, Hsu, et al., "Increases in fibrosis-related gene transcripts in livers of dimethylnitrosamine-intoxicated rats," J. Biomed Sci, 11:408-417 (2004).
Shackel, Nicholas A, et al., "Gene array analysis and the liver," Hepatology, 36(6):1313-1325 (2002).
Utsunomiya, Tohru, et al., "A gene-expression signature can quantify the degree of hepatic fibrosis in the rat," Journal of Hepatology, 41:399-406 (2004).
Imaoka, Susumu, et al., "Localization of rat cytochrome P450 in various tissues and comparison of arachidonic acid metabolism by rat P450 with that by human P450 orthologs," Drug Metab. Pharmacokinet, 20(6)478-484 (2005).
Wong, V. S., et al., "Serum hyaluronic acid is a useful marker of liver fibrosis in chronic hepatitis C virus infection," Journal of viral Hepatitis, 5:187-192 (1998).
Ala-Kokko, L., et al., "Gene expression of type I, III and IV collagens in hepatic fibrosis induced by dimethylnitrosamine in the rat," Biochem. J. 244:75-79 (1987).
Arthur, M.J.P., et al., "Tissue inhibitors of metalloproteinases, hepatic stellate cells and liver fibrosis," J. Gastroenterol. Hepatol. 13 (Suppl.):S33-38 (1998).
Bataller, R. and Brenner, D.A., "Liver fibrosis," J. Clin. Invest. 115(2):209-218 (2005).
Bauer, M. and Schuppan, D., "TGFβ1 in liver fibrosis: time to change paradigms?," FEBS Letts. 502:1-3 (2001).
Benyon, R.C. and Arthur, M.J., "Extracellular matrix degradation and the role of hepatic stellate cells," Semin. Liver Dis. 21(3):373-84 (2001).
Day, C.P., "Non-alcoholic steatohepatitis (NASH): where are we now and where are we going?," Gut 50:585-588 (2002).
Desouza, L., et al., "Search for cancer markers from endometrial tissues using differentially labeled tags iTRAQ and cICAT with multidimensional liquid chromatography and tandem mass spectrometry," J. Proteome Res. 4(2):377-386 (2005).
Dooley, S., et al., "Transforming growth factor β signal transduction in hepatic stellate cells via Smad2/3 phosphorylation, a pathway that is abrogated during in vitro progression to myofibroblasts. TGFβ signal transduction during transdifferentiation of hepatic stellate cells," FEBS Letts. 502:4-10 (2001).
Friedman, S.L., "Liver fibrosis—from bench to bedside," J. Hepatol. 38 (Suppl. 1):S38-53 (2003).
Friedman, S.L., "Molecular regulation of hepatic fibrosis, an integrated cellular response to tissue injury," J. Biol. Chem. 275(4):2247-2250 (2000).
Friedman, S.L., "Seminars in medicine of the Beth Israel Hospital, Boston: The cellular basis of hepatic fibrosis—Mechanisms and treatment strategies," N. Engl. J. Med. 328(25):1828-1835 (1993).
George, J., et al., "Dimethylnitrosamine-induced liver injury in rats: the early deposition of collagen," Toxicol. 156:129-138 (2001).
Gressner, A.M., et al., "Roles of TGF-β in hepatic fibrosis," Front. Biosci. 7:d793-807 (2002).

(Continued)

*Primary Examiner* — Sharon Wen
(74) *Attorney, Agent, or Firm* — Finnegan, Henderson, Farabow, Garrett & Dunner LLP

(57) ABSTRACT

The present invention provides a method for detecting liver fibrotic injury, including fibrosis and/or cirrhosis, by assaying biological samples for differential expression of at least one gene encoding a protein chosen from SEQ ID NO: 1-SEQ ID NO: 63 and human orthologs thereof, wherein differential expression of at least one gene suggests the presence of liver fibrosis or cirrhosis. The invention also provides a kit containing nucleic acid probes or antibodies for detecting liver fibrosis and/or cirrhosis by assaying the differential expression of proteins encoded by SEQ ID NO: 1-SEQ ID NO: 63 and human orthologs thereof.

3 Claims, 8 Drawing Sheets

OTHER PUBLICATIONS

Haggerty, H.G. and Holsapple, M.P., "Role of metabolism in dimethylnitrosamine-induced immunosuppression: a review," *Toxicol.* 63:1-23 (1990).

Hayaska, A. and Saisho, H., "Serum markers as tools to monitor liver fibrosis," *Digestion* 59:381-384 (1998).

Hernández-Muñoz, R., et al., "Adenosine reverses a preestablished $CCl_4$-induced micronodular cirrhosis through enhancing collagenolytic activity and stimulating hepatocyte cell proliferation in rats," *Hepatol.* 34:677-687 (2001).

Hippo, Y., et al., "Global gene expression analysis of gastric cancer by oligonucleotide microarrays," *Cancer Res.* 62:233-240 (2002).

Iizuka, N., et al., "Differential gene expression in distinct virologic types of hepatocellular carcinoma: association with liver cirrhosis," *Oncogene* 22:3007-3014 (2003).

Iredale, J.P., "Cirrhosis: new research provides a basis for rational and targeted treatments," *BMJ* 327:143-147 (2003).

Iredale, J.P., "Tissue inhibitors of metalloproteinases in liver fibrosis," *Int. J. Biochem. Cell Biol.* 29(1):43-54 (1997).

Ishak, K., et al., "Histological grading and staging of chronic hepatitis," *J. Hepatol.* 22:696-699 (1995).

Jézéquel, A.M., et al., "A morphological study of the early stages of hepatic fibrosis induced by low doses of dimethylnitrosamine in the rat," *J. Hepatol.* 5:174-181 (1987).

Ji, J., et al., "Comprehensive analysis of the gene expression profiles in human gastric cancer cell lines," *Oncogene* 21:6549-6556 (2002).

Knodell, R.G., et al., "Formulation and application of a numerical scoring system for assessing histological activity in asymptomatic chronic active hepatitis," *Hepatol.* 1(5):431-435 (1981).

López-De León, A. and Rojkind, M., "A simple micromethod for collagen and total protein determination in formalin-fixed paraffin-embedded sections," *J. Histochem. Cytochem.* 33(8):737-743 (1985).

Marvanová, M., et al., "Microarray analysis of nonhuman primates: validation of experimental models in neurological disorders," *FASEB J.* 17:929-931 (2003).

Mazzocca, A., et al., "Expression of transmembrane 4 superfamily (TM4SF) proteins and their role in hepatic stellate cell motility and wound healing migration," *J. Hepatol.* 37:322-330 (2002).

Mirsalis, J.C., and Butterworth, B.E., "Detection of unscheduled DNA synthesis in hepatocytes isolated from rats treated with genotoxic agents: an in vivo—in vitro assay for potential carcinogens and mutagens," *Carcinogenesis* 1:621-624 (1980).

Morgan, C.L., Newman, D.J., Burrin, J.M., and Price, C.P., "The matrix effects on kinetic rate constants of antibody-antigen interactions reflect solvent viscosity," *J. Immunol. Meth.* 217:51-60 (1998).

Neubauer, K., et al., "Accumulation and cellular localization of fibrinogen/fibrin during short-term and long-term rat liver injury," *Gastroenterol.* 108:1124-1135 (1995).

Nielsen, P.E., et al., "Sequence-selective recognition of DNA by strand displacement with a thymine-substituted polyamide," *Science.* 254(5037):1497-1500 (1991).

Okita, K., et al., "Current strategies for chemoprevention of hepatocellular carcinoma," *Oncology* 62 (Suppl. 1):24-28 (2002).

Sambrook et al., *Molecular Cloning: A Laboratory Manual*, vol. 3, pp. A8.40-A8.45 and A8.52-A8.55 (3d ed., Cold Spring Harbor Laboratory Press, Cold Spring Harbor, New York 2001).

Schuppan, D., et al., "Hepatitis C and liver fibrosis," *Cell Death Differ.* 10:S59-67 (2003).

Seth, D., et al., "Gene expression profiling of alcoholic liver disease in the baboon (*Papio hamadryas*) and human liver," *Am. J. Pathol.* 163(6):2303-2317 (2003).

Strauss, W.M., "Hybridization With Radioactive Probes," in *Current Protocols in Molecular Biology* 6.3.1-6.3.6, (John Wiley & Sons, N.Y. 2000).

Waring, J.F., et al., "Microarray analysis of hepatotoxins in vitro reveals a correlation between gene expression profiles and mechanisms of toxicity," *Toxicol. Letts.* 120:359-368 (2001).

Waring, J.F., et al., "Clustering of hepatotoxins based on mechanism of toxicity using gene expression profiles," *Toxicol. Appl. Pharmacol.* 175:28-42 (2001).

Wright, M.E., et al., "Mass spectrometry-based expression profiling of clinical prostate cancer," *Mol. Cell. Proteomics* 4.4:545-554 (2005).

Zhuang, G., et al., "Measurement of Association Rate Constant of Antibody-Antigen Interactions in Solution Based on Enzyme-Linked Immunosorbent Assay," *J. Biosci. Bioeng.* 92(4):330-336 (2001).

\* cited by examiner

A

B

| Factor (scores) | | DMN-treatment | | | Control |
|---|---|---|---|---|---|
| | | 1-2 wk n (%) | 3-4 wk n (%) | 5-6 wk n (%) | 1-6 wk n (%) |
| Necroinflammatory | A0 | 0 (0) | 1 (9) | 4 (44) | 100 (24) |
| | A(1-3) | 5 (62.5) | 3 (27) | 4 (44) | 0 (0) |
| | A(4-6) | 3 (36.5) | 7 (64) | 1 (12) | 0 (0) |
| Fibrosis | F(0-1) | 6 (75) | 1 (9) | 2 (22) | 100 (24) |
| | F(2-3) | 2 (25) | 10 (91) | 7 (78) | 0 (0) |
| Fatty change | - | 7 (87.5) | 11 (100) | 9 (100) | 100 (24) |
| | + | 1 (12.5) | 0 (0) | 0 (0) | 0 (0) | n: number of rats

| Vimentin ratio of DMN-treated and control rats at $2^{nd}$, $4^{th}$ and $6^{th}$ weeks |||
|---|---|---|
| Week 2 | Week 4 | Week 6 |
| 2.43 | 3.41 | 3.44 |

B

M: Marker
1: Control $2^{nd}$ week
2: DMN $2^{nd}$ week-1
3: DMN $2^{nd}$ week-2
4: Control $4^{th}$ week
5: DMN $4^{th}$ week-1
6: DMN $4^{th}$ week-2
7: Control $6^{th}$ week
8: DMN $6^{th}$ week-1
9: DMN $6^{th}$ week-2

SEQUENCE LISTING

```
<160> NUMBER OF SEQ ID NOS: 120

<210> SEQ ID NO 1
<211> LENGTH: 494
<212> TYPE: PRT
<213> ORGANISM: Rattus sp.

<400> SEQUENCE: 1
```

Met Glu Leu Leu Gly Phe Thr Thr Leu Ala Leu Val Val Ser Val Thr
1               5                   10                  15

Cys Leu Ser Leu Leu Ser Val Trp Thr Lys Leu Arg Thr Arg Gly Arg
            20                  25                  30

Leu Pro Pro Gly Pro His Pro Ser His Tyr Trp Glu Ser Thr Ala
        35                  40                  45

Thr Glu Pro Gln Gly His Pro Ala Ser Leu Ser Lys Leu Ala Lys Glu
    50                  55                  60

Tyr Gly Pro Val Tyr Thr Leu Tyr Phe Gly Thr Ser Pro Thr Val Val
65                  70                  75                  80

Leu His Gly Tyr Asp Val Val Lys Glu Ala Leu Leu Gln Gln Gly Asp
                85                  90                  95

Glu Phe Leu Gly Arg Gly Pro Leu Pro Ile Ile Glu Asp Thr His Lys
            100                 105                 110

Gly Tyr Gly Leu Ile Phe Ser Asn Gly Glu Arg Trp Lys Val Met Arg
        115                 120                 125

Arg Phe Ser Leu Met Thr Leu Arg Asn Phe Gly Met Gly Lys Arg Ser
    130                 135                 140

Leu Glu Glu Arg Val Gln Glu Glu Ala Trp Cys Leu Val Glu Glu Leu
145                 150                 155                 160

Gln Lys Thr Lys Ala Gln Pro Phe Asp Pro Thr Phe Ile Leu Ala Cys
                165                 170                 175

Ala Pro Cys Asn Val Ile Cys Ser Ile Leu Phe Asn Asp Arg Phe Gln
            180                 185                 190

Tyr Asn Asp Lys Thr Phe Leu Asn Leu Met Asp Leu Leu Asn Lys Asn
        195                 200                 205

Phe Gln Gln Val Asn Ser Val Trp Cys Gln Met Tyr Asn Leu Trp Pro
    210                 215                 220

Thr Ile Ile Lys Tyr Leu Pro Gly Lys His Ile Glu Phe Ala Lys Arg
225                 230                 235                 240

Ile Asp Asp Val Lys Asn Phe Ile Leu Glu Lys Val Lys Glu His Gln
                245                 250                 255

Lys Ser Leu Asp Pro Ala Asn Pro Arg Asp Tyr Ile Asp Cys Phe Leu
            260                 265                 270

Ser Lys Ile Glu Glu Glu Lys Asp Asn Leu Lys Ser Glu Phe His Leu
        275                 280                 285

-continued

Glu Asn Leu Ala Val Cys Gly Ser Asn Leu Phe Thr Ala Gly Thr Glu
    290                 295                 300

Thr Thr Ser Thr Thr Leu Arg Phe Gly Leu Leu Leu Met Lys Tyr
305                 310                 315                 320

Pro Glu Val Gln Ala Lys Val His Glu Leu Asp Arg Val Ile Gly
                325                 330                 335

Arg His Gln Pro Pro Ser Met Lys Asp Lys Met Lys Leu Pro Tyr Thr
                340                 345                 350

Asp Ala Val Leu His Glu Ile Gln Arg Tyr Ile Thr Leu Val Gly Ser
                355                 360                 365

Ser Leu Pro His Ala Val Val Gln Asp Thr Lys Phe Arg Asp Tyr Val
    370                 375                 380

Ile Pro Lys Gly Thr Thr Val Leu Pro Met Leu Ser Ser Val Met Leu
385                 390                 395                 400

Asp Gln Lys Glu Phe Ala Asn Pro Glu Lys Phe Asp Pro Gly His Phe
                405                 410                 415

Leu Asp Lys Asn Gly Cys Phe Lys Lys Thr Asp Tyr Phe Val Pro Phe
                420                 425                 430

Ser Leu Gly Lys Arg Ala Cys Val Gly Glu Ser Leu Ala Arg Met Glu
                435                 440                 445

Leu Phe Leu Phe Phe Thr Thr Leu Leu Gln Lys Phe Ser Leu Lys Thr
    450                 455                 460

Leu Val Glu Pro Lys Asp Leu Asp Ile Lys Pro Ile Thr Thr Gly Ile
465                 470                 475                 480

Ile Asn Leu Pro Pro Pro Tyr Lys Leu Cys Leu Val Pro Arg
                485                 490

<210> SEQ ID NO 2
<211> LENGTH: 500
<212> TYPE: PRT
<213> ORGANISM: Rattus sp.

<400> SEQUENCE: 2

Met Glu Leu Leu Ala Gly Thr Gly Leu Trp Pro Met Ala Ile Phe Thr
1               5                   10                  15

Val Ile Phe Ile Leu Leu Val Asp Leu Met His Arg Arg Gln Arg Trp
                20                  25                  30

Thr Ser Arg Tyr Pro Pro Gly Pro Val Pro Trp Pro Val Leu Gly Asn
            35                  40                  45

Leu Leu Gln Val Asp Leu Cys Asn Met Pro Tyr Ser Met Tyr Lys Leu
    50                  55                  60

Gln Asn Arg Tyr Gly Asp Val Phe Ser Leu Gln Met Gly Trp Lys Pro
65                  70                  75                  80

Val Val Val Ile Asn Gly Leu Lys Ala Val Gln Glu Leu Leu Val Thr
                85                  90                  95

Cys Gly Glu Asp Thr Ala Asp Arg Pro Glu Met Pro Ile Phe Gln His
                100                 105                 110

Ile Gly Tyr Gly His Lys Ala Lys Gly Val Val Leu Ala Pro Tyr Gly
            115                 120                 125

Pro Glu Trp Arg Glu Gln Arg Arg Phe Ser Val Ser Thr Leu Arg Asn
    130                 135                 140

Phe Gly Val Gly Lys Lys Ser Leu Glu Gln Trp Val Thr Asp Glu Ala
145                 150                 155                 160

Ser His Leu Cys Asp Ala Leu Thr Ala Glu Ala Gly Arg Pro Leu Asp
                165                 170                 175

```
Pro Tyr Thr Leu Leu Asn Lys Ala Val Cys Asn Val Ile Ala Ser Leu
            180                 185                 190

Ile Tyr Ala Arg Arg Phe Asp Tyr Gly Asp Pro Asp Phe Ile Lys Val
            195                 200                 205

Leu Lys Ile Leu Lys Glu Ser Met Gly Glu Gln Thr Gly Leu Phe Pro
    210                 215                 220

Glu Val Leu Asn Met Phe Pro Val Leu Arg Ile Pro Gly Leu Ala
225                 230                 235                 240

Asp Lys Val Phe Pro Gly Gln Lys Thr Phe Leu Thr Met Val Asp Asn
            245                 250                 255

Leu Val Thr Glu His Lys Lys Thr Trp Asp Pro Asp Gln Pro Pro Arg
            260                 265                 270

Asp Leu Thr Asp Ala Phe Leu Ala Glu Ile Glu Lys Ala Lys Gly Asn
            275                 280                 285

Pro Glu Ser Ser Phe Asn Asp Ala Asn Leu Arg Leu Val Val Asn Asp
    290                 295                 300

Leu Phe Gly Ala Gly Met Val Thr Thr Ser Ile Thr Leu Thr Trp Ala
305                 310                 315                 320

Leu Leu Leu Met Ile Leu His Pro Asp Val Gln Cys Arg Val Gln Gln
            325                 330                 335

Glu Ile Asp Glu Val Ile Gly Gln Val Arg His Pro Glu Met Ala Asp
            340                 345                 350

Gln Ala His Met Pro Phe Thr Asn Ala Val Ile His Glu Val Gln Arg
            355                 360                 365

Phe Ala Asp Ile Val Pro Met Asn Leu Pro His Lys Thr Ser Arg Asp
    370                 375                 380

Ile Glu Val Gln Gly Phe Leu Ile Pro Lys Gly Thr Thr Leu Ile Pro
385                 390                 395                 400

Asn Leu Ser Ser Val Leu Lys Asp Glu Thr Val Trp Glu Lys Pro Leu
            405                 410                 415

Arg Phe His Pro Glu His Phe Leu Asp Ala Gln Gly Asn Phe Val Lys
            420                 425                 430

His Glu Ala Phe Met Pro Phe Ser Ala Gly Arg Arg Ala Cys Leu Gly
            435                 440                 445

Glu Pro Leu Ala Arg Met Glu Leu Phe Leu Phe Phe Thr Cys Leu Leu
    450                 455                 460

Gln Arg Phe Ser Phe Ser Val Pro Thr Gly Gln Pro Arg Pro Ser Asp
465                 470                 475                 480

Tyr Gly Val Phe Ala Phe Leu Leu Ser Pro Ser Pro Tyr Gln Leu Cys
            485                 490                 495

Ala Phe Lys Arg
        500

<210> SEQ ID NO 3
<211> LENGTH: 2505
<212> TYPE: PRT
<213> ORGANISM: Rattus sp.

<400> SEQUENCE: 3

Met Glu Glu Val Val Ile Ala Gly Met Ser Gly Lys Leu Pro Glu Ser
1               5                   10                  15

Glu Asn Leu Gln Glu Phe Trp Ala Asn Leu Ile Gly Gly Val Asp Met
            20                  25                  30

Val Thr Asp Asp Asp Arg Arg Trp Lys Ala Gly Leu Tyr Gly Leu Pro
        35                  40                  45
```

```
Lys Arg Ser Gly Lys Leu Lys Asp Leu Ser Lys Phe Asp Ala Ser Phe
        50                  55                  60

Phe Gly Val His Pro Lys Gln Ala His Thr Met Asp Pro Gln Leu Arg
65                  70                  75                  80

Leu Leu Leu Glu Val Ser Tyr Glu Ala Ile Val Asp Gly Gly Ile Asn
                    85                  90                  95

Pro Ala Ser Leu Arg Gly Thr Asn Thr Gly Val Trp Val Gly Val Ser
                100                 105                 110

Gly Ser Glu Ala Ser Glu Ala Leu Ser Arg Asp Pro Glu Thr Leu Leu
            115                 120                 125

Gly Tyr Ser Met Val Gly Cys Gln Arg Ala Met Met Ala Asn Arg Leu
    130                 135                 140

Ser Phe Phe Phe Asp Phe Lys Gly Pro Ser Ile Ala Leu Asp Thr Ala
145                 150                 155                 160

Cys Ser Ser Ser Leu Leu Ala Leu Gln Asn Ala Tyr Gln Ala Ile Arg
                165                 170                 175

Ser Gly Glu Cys Pro Ala Ala Ile Val Gly Gly Ile Asn Leu Leu Leu
            180                 185                 190

Lys Pro Asn Thr Ser Val Gln Phe Met Lys Leu Gly Met Leu Ser Pro
    195                 200                 205

Asp Gly Thr Cys Arg Ser Phe Asp Asp Ser Gly Asn Gly Tyr Cys Arg
210                 215                 220

Ala Glu Ala Val Val Ala Val Leu Leu Thr Lys Lys Ser Leu Ala Arg
225                 230                 235                 240

Arg Val Tyr Ala Thr Ile Leu Asn Ala Gly Thr Asn Thr Asp Gly Cys
                245                 250                 255

Lys Glu Gln Gly Val Thr Phe Pro Ser Gly Glu Ala Gln Glu Gln Leu
            260                 265                 270

Ile Arg Ser Leu Tyr Gln Pro Gly Gly Val Ala Pro Glu Ser Leu Glu
    275                 280                 285

Tyr Ile Glu Ala His Gly Thr Gly Thr Lys Val Gly Asp Pro Gln Glu
290                 295                 300

Leu Asn Gly Ile Thr Arg Ser Leu Cys Ala Phe Arg Gln Ser Pro Leu
305                 310                 315                 320

Leu Ile Gly Ser Thr Lys Ser Asn Met Gly His Pro Glu Pro Ala Ser
                325                 330                 335

Gly Leu Ala Ala Leu Thr Lys Val Leu Leu Ser Leu Glu Asn Gly Val
            340                 345                 350

Trp Ala Pro Asn Leu His Phe His Asn Pro Asn Pro Glu Ile Pro Ala
    355                 360                 365

Leu Leu Asp Gly Arg Leu Gln Val Val Asp Arg Pro Leu Pro Val Arg
370                 375                 380

Gly Gly Ile Val Gly Ile Asn Ser Phe Gly Phe Gly Gly Ala Asn Val
385                 390                 395                 400

His Val Ile Leu Gln Pro Asn Thr Gln Gln Ala Pro Ala Pro Ala Pro
                405                 410                 415

His Ala Ala Leu Pro His Leu Leu His Ala Ser Gly Arg Thr Met Glu
            420                 425                 430

Ala Val Gln Gly Leu Leu Glu Gln Gly Arg Gln His Ser Gln Asp Leu
    435                 440                 445

Ala Phe Val Ser Met Leu Asn Asp Ile Ala Ala Thr Pro Thr Ala Ala
450                 455                 460

Met Pro Phe Arg Gly Tyr Thr Val Leu Gly Val Glu Gly His Val Gln
```

```
                465                 470                 475                 480
            Glu Val Gln Gln Val Pro Ala Ser Gln Arg Pro Leu Trp Phe Ile Cys
                            485                 490                 495
            Ser Gly Met Gly Thr Gln Trp Arg Gly Met Gly Leu Ser Leu Met Arg
                            500                 505                 510
            Leu Asp Ser Phe Arg Glu Ser Ile Leu Arg Ser Asp Glu Ala Leu Lys
                            515                 520                 525
            Pro Leu Gly Val Lys Val Ser Asp Leu Leu Ser Thr Asp Glu His
                            530                 535                 540
            Thr Phe Asp Asp Ile Val His Ser Phe Val Ser Leu Thr Ala Ile Gln
            545                 550                 555                 560
            Ile Ala Leu Ile Asp Leu Leu Thr Ser Met Gly Leu Lys Pro Asp Gly
                            565                 570                 575
            Ile Ile Gly His Ser Leu Gly Glu Val Ala Cys Gly Tyr Ala Asp Gly
                            580                 585                 590
            Cys Leu Ser Gln Arg Glu Ala Val Leu Ala Ala Tyr Trp Arg Gly Gln
                            595                 600                 605
            Cys Ile Lys Asp Ala Asn Leu Pro Ala Gly Ser Met Ala Ala Val Gly
                            610                 615                 620
            Leu Ser Trp Glu Glu Cys Lys Gln Arg Cys Pro Pro Gly Val Val Pro
            625                 630                 635                 640
            Ala Cys His Asn Ser Glu Asp Thr Val Thr Ile Ser Gly Pro Gln Ala
                            645                 650                 655
            Ala Val Asn Glu Phe Val Glu Gln Leu Lys Gln Glu Gly Val Phe Ala
                            660                 665                 670
            Lys Glu Val Arg Thr Gly Gly Leu Ala Phe His Ser Tyr Phe Met Glu
                            675                 680                 685
            Gly Ile Ala Pro Thr Leu Leu Gln Ala Leu Lys Lys Val Ile Arg Glu
                            690                 695                 700
            Pro Arg Pro Arg Ser Ala Arg Trp Leu Ser Thr Ser Ile Pro Glu Ala
            705                 710                 715                 720
            Gln Trp Gln Ser Ser Leu Ala Arg Thr Ser Ala Glu Tyr Asn Val
                            725                 730                 735
            Asn Asn Leu Val Ser Pro Val Leu Phe Gln Glu Ala Leu Trp His Val
                            740                 745                 750
            Pro Glu His Ala Val Val Leu Glu Ile Ala Pro His Ala Leu Leu Gln
                            755                 760                 765
            Ala Val Leu Lys Arg Gly Val Lys Pro Ser Cys Thr Ile Ile Pro Leu
                            770                 775                 780
            Met Lys Arg Asp His Lys Asp Asn Leu Glu Phe Phe Leu Thr Asn Leu
            785                 790                 795                 800
            Gly Lys Val His Leu Thr Gly Ile Asp Ile Asn Pro Asn Ala Leu Phe
                            805                 810                 815
            Pro Pro Val Glu Phe Pro Val Pro Arg Gly Thr Pro Leu Ile Ser Pro
                            820                 825                 830
            His Ile Lys Trp Asp His Ser Gln Thr Trp Asp Ile Pro Val Ala Glu
                            835                 840                 845
            Asp Phe Pro Asn Gly Ser Ser Ser Ser Ala Thr Val Tyr Asn Ile
                            850                 855                 860
            Asp Ala Ser Ser Glu Ser Ser Asp His Tyr Leu Val Asp His Cys Ile
            865                 870                 875                 880
            Asp Gly Arg Val Leu Phe Pro Gly Thr Gly Tyr Leu Tyr Leu Val Trp
                            885                 890                 895
```

```
Lys Thr Leu Ala Arg Ser Leu Ser Leu Ser Leu Glu Glu Thr Pro Val
            900                 905                 910

Val Phe Glu Asn Val Thr Phe His Gln Ala Thr Ile Leu Pro Arg Thr
        915                 920                 925

Gly Thr Val Pro Leu Glu Val Arg Leu Leu Glu Ala Ser His Ala Phe
    930                 935                 940

Glu Val Ser Asp Ser Gly Asn Leu Ile Val Ser Gly Lys Val Tyr Gln
945                 950                 955                 960

Trp Glu Asp Pro Asp Ser Lys Leu Phe Asp His Pro Glu Val Pro Ile
                965                 970                 975

Pro Ala Glu Ser Glu Ser Val Ser Arg Leu Thr Gln Gly Glu Val Tyr
            980                 985                 990

Lys Glu Leu Arg Leu Arg Gly Tyr Asp Tyr Gly Pro His Phe Gln Gly
        995                 1000                1005

Val Tyr Glu Ala Thr Leu Glu Gly Glu Gln Gly Lys Leu Leu Trp
    1010                1015                1020

Lys Asp Asn Trp Val Thr Phe Met Asp Thr Met Leu Gln Ile Ser
    1025                1030                1035

Ile Leu Gly Phe Ser Lys Gln Ser Leu Gln Leu Pro Thr Arg Val
    1040                1045                1050

Thr Ala Ile Tyr Ile Asp Pro Ala Thr His Leu Gln Lys Val Tyr
    1055                1060                1065

Met Leu Glu Gly Asp Thr Gln Val Ala Asp Val Thr Thr Ser Arg
    1070                1075                1080

Cys Leu Gly Val Thr Val Ser Gly Gly Val Tyr Ile Ser Arg Leu
    1085                1090                1095

Gln Thr Thr Ala Thr Ser Arg Arg Gln Gln Glu Gln Leu Val Pro
    1100                1105                1110

Thr Leu Glu Lys Phe Val Phe Thr Pro His Val Glu Pro Glu Cys
    1115                1120                1125

Leu Ser Glu Ser Ala Ile Leu Gln Lys Glu Leu Gln Leu Cys Lys
    1130                1135                1140

Gly Leu Ala Lys Ala Leu Gln Thr Lys Ala Thr Gln Gln Gly Leu
    1145                1150                1155

Lys Met Thr Val Pro Gly Leu Glu Asp Leu Pro Gln His Gly Leu
    1160                1165                1170

Pro Arg Leu Leu Ala Ala Ala Cys Gln Leu Gln Leu Asn Gly Asn
    1175                1180                1185

Leu Gln Leu Glu Leu Gly Glu Val Leu Ala Arg Glu Arg Leu Leu
    1190                1195                1200

Leu Pro Glu Asp Pro Leu Ile Ser Gly Leu Leu Asn Ser Gln Ala
    1205                1210                1215

Leu Lys Ala Cys Ile Asp Thr Ala Leu Glu Asn Leu Ser Thr Leu
    1220                1225                1230

Lys Met Lys Val Val Glu Val Leu Ala Gly Glu Gly His Leu Tyr
    1235                1240                1245

Ser His Ile Ser Ala Leu Leu Asn Thr Gln Pro Met Leu Gln Leu
    1250                1255                1260

Glu Tyr Thr Ala Thr Asp Arg His Pro Gln Ala Leu Lys Asp Val
    1265                1270                1275

Gln Thr Lys Leu Gln Gln His Asp Val Ala Gln Gly Gln Trp Asp
    1280                1285                1290

Pro Ser Gly Pro Ala Pro Thr Asn Leu Gly Ala Leu Asp Leu Val
    1295                1300                1305
```

```
Val Cys Asn Cys Ala Leu Ala Thr Leu Gly Asp Pro Ala Leu Ala
    1310                1315                1320

Leu Asp Asn Met Val Ala Ala Leu Lys Asp Gly Gly Phe Leu Leu
    1325                1330                1335

Met His Thr Val Leu Lys Gly His Ala Leu Gly Glu Thr Leu Ala
    1340                1345                1350

Cys Leu Pro Ser Glu Val Gln Pro Gly Pro Ser Phe Leu Ser Gln
    1355                1360                1365

Glu Glu Trp Glu Ser Leu Phe Ser Arg Lys Ala Leu His Leu Val
    1370                1375                1380

Gly Leu Lys Lys Ser Phe Tyr Gly Thr Ala Leu Phe Leu Cys Arg
    1385                1390                1395

Arg Leu Ser Pro Gln Asp Lys Pro Ile Phe Leu Pro Val Glu Asp
    1400                1405                1410

Thr Ser Phe Gln Trp Val Asp Ser Leu Lys Ser Ile Leu Ala Thr
    1415                1420                1425

Ser Ser Ser Gln Pro Val Trp Leu Thr Ala Met Asn Cys Pro Thr
    1430                1435                1440

Ser Gly Val Val Gly Leu Val Asn Cys Leu Arg Lys Glu Pro Gly
    1445                1450                1455

Gly His Arg Ile Arg Cys Ile Leu Leu Ser Asn Leu Ser Ser Thr
    1460                1465                1470

Ser His Val Pro Lys Leu Asp Pro Gly Ser Ser Glu Leu Gln Lys
    1475                1480                1485

Val Leu Glu Ser Asp Leu Val Met Asn Val Tyr Arg Asp Gly Ala
    1490                1495                1500

Trp Gly Ala Phe Arg His Phe Gln Leu Glu Gln Asp Lys Pro Glu
    1505                1510                1515

Glu Gln Thr Ala His Ala Phe Val Asn Val Leu Thr Arg Gly Asp
    1520                1525                1530

Leu Ala Ser Ile Arg Trp Val Ser Ser Pro Leu Lys His Met Gln
    1535                1540                1545

Pro Pro Ser Ser Ser Gly Ala Gln Leu Cys Thr Val Tyr Tyr Ala
    1550                1555                1560

Ser Leu Asn Phe Arg Asp Ile Met Leu Ala Thr Gly Lys Leu Ser
    1565                1570                1575

Pro Asp Ala Ile Pro Gly Lys Trp Ala Ser Arg Asp Cys Met Leu
    1580                1585                1590

Gly Met Glu Phe Ser Gly Arg Asp Lys Cys Gly Arg Arg Val Met
    1595                1600                1605

Gly Leu Val Pro Ala Glu Gly Leu Ala Thr Ser Val Leu Leu Ser
    1610                1615                1620

Pro Asp Phe Leu Trp Asp Val Pro Ser Ser Trp Thr Leu Glu Glu
    1625                1630                1635

Ala Ala Ser Val Pro Val Val Tyr Thr Thr Ala Tyr Tyr Ser Leu
    1640                1645                1650

Val Val Arg Gly Arg Ile Gln His Gly Glu Thr Val Leu Ile His
    1655                1660                1665

Ser Gly Ser Gly Gly Val Gly Gln Ala Ala Ile Ser Ile Ala Leu
    1670                1675                1680

Ser Leu Gly Cys Arg Val Phe Thr Thr Val Gly Ser Ala Glu Lys
    1685                1690                1695

Arg Ala Tyr Leu Gln Ala Arg Phe Pro Gln Leu Asp Asp Thr Ser
```

-continued

```
              1700                1705                1710

Phe Ala Asn Ser Arg Asp Thr Ser Phe Glu Gln His Val Leu Leu
    1715                1720                1725

His Thr Gly Gly Lys Gly Val Asp Leu Val Leu Asn Ser Leu Ala
    1730                1735                1740

Glu Glu Lys Leu Gln Ala Ser Val Arg Cys Leu Ala Gln His Gly
    1745                1750                1755

Arg Phe Leu Glu Ile Gly Lys Phe Asp Leu Ser Asn Asn His Pro
    1760                1765                1770

Leu Gly Met Ala Ile Phe Leu Lys Asn Val Thr Phe His Gly Ile
    1775                1780                1785

Leu Leu Asp Ala Leu Phe Glu Gly Ala Asn Asp Ser Trp Arg Glu
    1790                1795                1800

Val Ala Glu Leu Leu Lys Ala Gly Ile Arg Asp Gly Val Val Lys
    1805                1810                1815

Pro Leu Lys Cys Thr Val Phe Pro Lys Ala Gln Val Glu Asp Ala
    1820                1825                1830

Phe Arg Tyr Met Ala Gln Gly Lys His Ile Gly Lys Val Leu Val
    1835                1840                1845

Gln Val Arg Glu Glu Glu Pro Glu Ala Met Leu Pro Gly Ala Gln
    1850                1855                1860

Pro Thr Leu Ile Ser Ala Ile Ser Lys Thr Phe Cys Pro Glu His
    1865                1870                1875

Lys Ser Tyr Ile Ile Thr Gly Gly Leu Gly Gly Phe Gly Leu Glu
    1880                1885                1890

Leu Ala Arg Trp Leu Val Leu Arg Gly Ala Gln Arg Leu Val Leu
    1895                1900                1905

Thr Ser Arg Ser Gly Ile Arg Thr Gly Tyr Gln Ala Lys His Val
    1910                1915                1920

Arg Glu Trp Arg Arg Gln Gly Ile His Val Leu Val Ser Thr Ser
    1925                1930                1935

Asn Val Ser Ser Leu Glu Gly Ala Arg Ala Leu Ile Ala Glu Ala
    1940                1945                1950

Thr Lys Leu Gly Pro Val Gly Gly Val Phe Asn Leu Ala Met Val
    1955                1960                1965

Leu Arg Asp Ala Met Leu Glu Asn Gln Thr Pro Glu Leu Phe Gln
    1970                1975                1980

Asp Val Asn Lys Pro Lys Tyr Asn Gly Thr Leu Asn Leu Asp Arg
    1985                1990                1995

Ala Thr Arg Glu Ala Cys Pro Glu Leu Asp Tyr Phe Val Ala Phe
    2000                2005                2010

Ser Ser Val Ser Cys Gly Arg Gly Asn Ala Gly Gln Ser Asn Tyr
    2015                2020                2025

Gly Phe Ala Asn Ser Thr Met Glu Arg Ile Cys Glu Gln Arg Arg
    2030                2035                2040

His Asp Gly Leu Pro Gly Leu Ala Val Gln Trp Gly Ala Ile Gly
    2045                2050                2055

Asp Val Gly Ile Ile Leu Glu Ala Met Gly Thr Asn Asp Thr Val
    2060                2065                2070

Val Gly Gly Thr Leu Pro Gln Arg Ile Ser Ser Cys Met Glu Val
    2075                2080                2085

Leu Asp Leu Phe Leu Asn Gln Pro His Ala Val Leu Ser Ser Phe
    2090                2095                2100

Val Leu Val Glu Lys Lys Ala Val Ala His Gly Asp Gly Glu Ala
    2105                2110                2115
```

-continued

```
Gln Arg Asp Leu Val Lys Ala Val Ala His Ile Leu Gly Ile Arg
2120                2125                2130

Asp Leu Ala Gly Ile Asn Leu Asp Ser Ser Leu Ala Asp Leu Gly
    2135                2140                2145

Leu Asp Ser Leu Met Gly Val Glu Val Arg Gln Ile Leu Glu Arg
    2150                2155                2160

Glu His Asp Leu Val Leu Pro Ile Arg Glu Val Arg Gln Leu Thr
    2165                2170                2175

Leu Arg Lys Leu Gln Glu Met Ser Ser Lys Ala Gly Ser Asp Thr
    2180                2185                2190

Glu Leu Ala Ala Pro Lys Ser Lys Asn Asp Thr Ser Leu Lys Gln
    2195                2200                2205

Ala Gln Leu Asn Leu Ser Ile Leu Leu Val Asn Pro Glu Gly Pro
    2210                2215                2220

Thr Leu Thr Arg Leu Asn Ser Val Gln Ser Ser Glu Arg Pro Leu
    2225                2230                2235

Phe Leu Val His Pro Ile Glu Gly Ser Ile Thr Val Phe His Ser
    2240                2245                2250

Leu Ala Ala Lys Leu Ser Val Pro Thr Tyr Gly Leu Gln Cys Thr
    2255                2260                2265

Gln Ala Ala Pro Leu Asp Ser Ile Pro Asn Leu Ala Ala Tyr Tyr
    2270                2275                2280

Ile Asp Cys Ile Lys Gln Val Gln Pro Glu Gly Pro His Arg Val
    2285                2290                2295

Ala Gly Tyr Ser Phe Gly Ala Cys Val Ala Phe Glu Met Cys Ser
    2300                2305                2310

Gln Leu Gln Ala Gln Gln Gly Pro Ala Pro Ala His Asn Asn Leu
    2315                2320                2325

Phe Leu Phe Asp Gly Ser His Thr Tyr Val Leu Ala Tyr Thr Gln
    2330                2335                2340

Ser Tyr Arg Ala Lys Leu Thr Pro Gly Cys Glu Ala Glu Ala Glu
    2345                2350                2355

Ala Glu Ala Ile Cys Phe Phe Ile Lys Gln Phe Val Asp Ala Glu
    2360                2365                2370

His Ser Lys Val Leu Glu Ala Leu Leu Pro Leu Lys Ser Leu Glu
    2375                2380                2385

Asp Arg Val Ala Ala Ala Val Asp Leu Ile Thr Arg Ser His Gln
    2390                2395                2400

Ser Leu Asp Arg Arg Asp Leu Ser Phe Ala Ala Val Ser Phe Tyr
    2405                2410                2415

Tyr Lys Leu Arg Ala Ala Asp Gln Tyr Lys Pro Lys Ala Lys Tyr
    2420                2425                2430

His Gly Asn Val Ile Leu Leu Arg Ala Lys Thr Gly Gly Thr Tyr
    2435                2440                2445

Gly Glu Asp Leu Gly Ala Asp Tyr Asn Leu Ser Gln Val Cys Asp
    2450                2455                2460

Gly Lys Val Ser Val His Ile Ile Glu Gly Asp His Arg Thr Leu
    2465                2470                2475

Leu Glu Gly Arg Gly Leu Glu Ser Ile Ile Asn Ile Ile His Ser
    2480                2485                2490

Ser Leu Ala Glu Pro Arg Val Ser Val Arg Glu Gly
    2495                2500                2505
```

```
<210> SEQ ID NO 4
<211> LENGTH: 381
<212> TYPE: PRT
<213> ORGANISM: Rattus sp.

<400> SEQUENCE: 4

Met Asn Pro Phe Ser Ser Glu Ser Ala Trp Leu Cys Leu Thr Ala Thr
1               5                   10                  15

Ala Val Leu Gly Gly Met Leu Leu Cys Lys Ala Trp Ser Ser Gly Gln
            20                  25                  30

Leu Arg Ser Gln Val Val Cys Leu Ala Gly Leu Trp Gly Gly Ala Cys
        35                  40                  45

Leu Leu Ser Leu Ser Leu Leu Cys Ser Leu Phe Leu Leu Ser Val Ser
    50                  55                  60

Cys Phe Phe Leu Leu Tyr Val Ser Ser Ser Asp Gln Asp Leu Leu Pro
65                  70                  75                  80

Val Asp Gln Lys Ala Val Leu Val Thr Gly Ala Asp Ser Gly Phe Gly
                85                  90                  95

His Ala Leu Ala Lys His Leu Asp Lys Leu Gly Phe Thr Val Phe Ala
            100                 105                 110

Gly Val Leu Asp Lys Glu Gly Pro Gly Ala Glu Glu Leu Arg Lys Asn
        115                 120                 125

Cys Ser Glu Arg Leu Ser Val Leu Gln Met Asp Val Thr Lys Pro Glu
    130                 135                 140

Gln Ile Lys Asp Val His Ser Glu Val Ala Glu Lys Ile Gln Asp Lys
145                 150                 155                 160

Gly Leu Trp Ala Val Val Asn Asn Ala Gly Val Leu His Phe Pro Ile
                165                 170                 175

Asp Gly Glu Leu Ile Pro Met Thr Val Tyr Arg Lys Cys Met Ala Val
            180                 185                 190

Asn Phe Phe Gly Ala Val Glu Val Thr Lys Val Phe Leu Pro Leu Leu
        195                 200                 205

Arg Lys Ser Lys Gly Arg Leu Val Asn Val Ser Ser Met Gly Ala Met
    210                 215                 220

Ile Pro Phe Gln Met Val Ala Ala Tyr Ala Ser Thr Lys Ala Ala Ile
225                 230                 235                 240

Ser Met Phe Ser Ala Val Ile Arg Gln Glu Leu Ala Lys Trp Gly Val
                245                 250                 255

Lys Val Val Thr Ile His Pro Gly Gly Phe Gln Thr Asn Ile Val Gly
            260                 265                 270

Ser Gln Asp Ser Trp Asp Lys Met Glu Lys Glu Ile Leu Asp His Phe
        275                 280                 285

Ser Lys Glu Ile Gln Glu Asn Tyr Gly Gln Glu Tyr Val His Thr Gln
    290                 295                 300

Lys Leu Ala Leu Pro Val Met Arg Glu Met Ser Asn Pro Asp Ile Thr
305                 310                 315                 320

Pro Val Leu Arg Asp Ile Gln His Ala Ile Cys Ala Lys Asn Pro Ser
                325                 330                 335

Ser Phe Tyr Cys Ser Gly Arg Met Thr Tyr Leu Trp Ile Cys Phe Ala
            340                 345                 350

Ala Tyr Ser Pro Ile Ser Leu Leu Asp Tyr Ile Leu Lys Asn Tyr Phe
        355                 360                 365

Thr Pro Lys Leu Met Pro Arg Ala Leu Arg Thr Ala Ser
    370                 375                 380
```

```
<210> SEQ ID NO 5
<211> LENGTH: 295
<212> TYPE: PRT
<213> ORGANISM: Rattus sp.

<400> SEQUENCE: 5

Met Glu Thr Ser Met Pro Glu Tyr Tyr Glu Val Phe Gly Asp Phe His
1               5                   10                  15

Gly Phe Leu Met Asp Lys Leu Phe Thr Lys Tyr Trp Glu Asp Val Glu
            20                  25                  30

Thr Phe Ser Ala Arg Pro Asp Asp Leu Leu Val Val Thr Tyr Pro Lys
        35                  40                  45

Ser Gly Ser Thr Trp Ile Gly Glu Ile Val Asp Met Ile Tyr Lys Glu
    50                  55                  60

Gly Asp Val Glu Lys Cys Lys Glu Asp Ala Ile Phe Asn Arg Ile Pro
65                  70                  75                  80

Tyr Leu Glu Cys Arg Asn Glu Asp Leu Ile Asn Gly Ile Lys Gln Leu
                85                  90                  95

Lys Glu Lys Glu Ser Pro Arg Ile Val Lys Thr His Leu Pro Ala Lys
            100                 105                 110

Leu Leu Pro Ala Ser Phe Trp Glu Lys Asn Cys Lys Ile Ile Tyr Leu
        115                 120                 125

Cys Arg Asn Ala Lys Asp Val Val Val Ser Tyr Tyr Tyr Phe Phe Leu
    130                 135                 140

Ile Met Lys Ser Tyr Pro Asn Pro Lys Ser Phe Ser Glu Phe Val Glu
145                 150                 155                 160

Lys Phe Met Glu Gly Gln Val Pro Tyr Gly Ser Trp Tyr Asp His Val
                165                 170                 175

Lys Ser Trp Trp Glu Lys Ser Lys Asn Ser Arg Val Leu Phe Met Phe
            180                 185                 190

Tyr Glu Asp Met Lys Glu Asp Ile Arg Arg Glu Val Val Lys Leu Ile
        195                 200                 205

Glu Phe Leu Glu Arg Asp Pro Ser Ala Glu Leu Val Asp Arg Ile Ile
    210                 215                 220

Gln His Thr Ser Phe Gln Glu Met Lys Asn Asn Pro Cys Thr Asn Tyr
225                 230                 235                 240

Ser Met Leu Pro Glu Thr Met Ile Asp Leu Lys Val Ser Pro Phe Met
                245                 250                 255

Arg Lys Gly Ile Val Gly Asp Trp Lys Asn His Phe Pro Glu Ala Leu
            260                 265                 270

Arg Glu Arg Phe Glu Glu His Tyr Gln Gln Gln Met Lys Asp Cys Pro
        275                 280                 285

Val Lys Phe Arg Ala Glu Leu
    290                 295

<210> SEQ ID NO 6
<211> LENGTH: 1585
<212> TYPE: PRT
<213> ORGANISM: Rattus sp.

<400> SEQUENCE: 6

Met Ser Ser Leu Gln Glu Leu Cys Ser Gly Leu Pro Leu Arg Pro Leu
1               5                   10                  15

Pro Glu Asn Arg Gly Arg Trp Ala Gly Val Pro His Ala Pro Val Arg
            20                  25                  30

Thr Pro Asp Leu Ser Pro Glu Glu Gln Leu Ala Leu Arg Asn Ala
        35                  40                  45
```

-continued

```
Leu Arg Tyr Phe Pro Pro Asp Val Gln Lys Leu Leu Ala Leu Glu Phe
     50                  55                  60

Ala Gln Glu Leu Arg Gln Phe Gly His Ile Tyr Met Tyr Arg Phe Cys
 65                  70                  75                  80

Pro Ser Ile Glu Met Arg Ala Tyr Pro Ile Glu Gln Tyr Pro Cys Arg
                 85                  90                  95

Thr Arg Ala Ala Ala Ala Ile Met His Met Ile Met Asn Asn Leu Asp
                100                 105                 110

Pro Ala Val Ala Gln Phe Pro Gln Glu Leu Val Thr Tyr Gly Gly Asn
                115                 120                 125

Gly Gln Val Phe Ser Asn Trp Ala Gln Val Trp Val Gln Gly Ala Ser
    130                 135                 140

Ser His Leu Gln Ser Pro Pro Cys Ala Leu Ser Ile Gln Phe Trp Leu
145                 150                 155                 160

Thr Met Ser Tyr Leu Ser Lys Met Thr Glu Glu Gln Thr Leu Val Met
                165                 170                 175

Tyr Ser Gly His Pro Leu Gly Leu Phe Pro Ser Ser His Ala Pro
                180                 185                 190

Arg Leu Val Ile Thr Asn Gly Met Val Pro Asn Tyr Ser Ser Arg
                195                 200                 205

Thr Glu Tyr Glu Lys Leu Phe Ala Leu Gly Val Thr Met Tyr Gly Gln
210                 215                 220

Met Thr Ala Gly Ser Tyr Cys Tyr Ile Gly Pro Gln Gly Ile Val His
225                 230                 235                 240

Gly Thr Val Leu Thr Val Leu Asn Ala Gly Arg Arg Tyr Leu Gly Ile
                245                 250                 255

Glu Asp Leu Ala Gly Lys Val Phe Val Thr Ser Gly Leu Gly Gly Met
                260                 265                 270

Ser Gly Ala Gln Ala Lys Ala Ala Val Ile Val Gly Cys Ile Gly Val
    275                 280                 285

Ile Ala Glu Val Asp Lys Ala Ala Leu Val Lys Arg His Gln Gln Gly
    290                 295                 300

Trp Leu Met Glu Val Thr Asp Ser Leu Asp His Cys Ile Ala Arg Leu
305                 310                 315                 320

Arg Glu Ala Arg Lys Lys Lys Glu Val Leu Ser Leu Gly Tyr His Gly
                325                 330                 335

Asn Val Val Asp Leu Trp Glu Arg Leu Val His Glu Leu Asp Thr Thr
                340                 345                 350

Gly Glu Leu Leu Val Asp Leu Gly Ser Asp Gln Thr Ser Cys His Asn
    355                 360                 365

Pro Phe Asn Gly Gly Tyr Tyr Pro Val Gln Leu Ser Phe Ser Glu Ala
    370                 375                 380

Gln Ser Leu Met Ser Ser Asn Pro Ala Ala Phe Lys Asn Leu Val Gln
385                 390                 395                 400

Glu Ser Leu Arg Arg His Ile Ser Ala Ile Asn Arg Leu Ala Gln Glu
                405                 410                 415

Lys Phe Phe Phe Trp Asp Tyr Gly Asn Ala Phe Leu Leu Glu Ala Gln
                420                 425                 430

Arg Ala Gly Ala Asp Val Glu Lys Lys Gly Ala Asn Lys Thr Glu Phe
                435                 440                 445

Arg Tyr Pro Ser Tyr Val Gln His Ile Met Gly Asp Ile Phe Ser Gln
    450                 455                 460

Gly Phe Gly Pro Phe Arg Trp Val Cys Thr Ser Gly Asn Pro Gln Asp
```

-continued

```
            465                 470                 475                 480
        Leu Thr Val Thr Asp His Leu Ala Thr Ser Val Leu Glu Lys Ala Ile
                            485                 490                 495

Ala Asp Gly Gly Asp Thr Ser Gly Trp Val Val Leu Arg Ser Asp Ser
                            500                 505                 510

Cys Phe Cys Gly Ala Leu Gly Gly Leu Cys Gln Ile Leu Gln Glu Ser
                            515                 520                 525

Lys Asp His Arg Leu Leu His Lys Gly Thr Ser Thr Phe Arg Ser
                            530                 535                 540

His Ser Leu Lys Ala Val Leu Met Lys Ala Ser Val Lys Leu Gln Tyr
        545                 550                 555                 560

Met Asp Asn Ile Arg Trp Ile Arg Glu Ala Ala Lys His Gln Leu Val
                            565                 570                 575

Val Gly Ser Gln Ala Arg Ile Leu Tyr Ser Asp Gln Lys Gly Arg Val
                            580                 585                 590

Ala Ile Ala Val Ala Ile Asn Gln Ala Ile Ala Ser Gly Lys Ile Lys
                            595                 600                 605

Ala Pro Val Val Leu Ser Arg Asp His His Asp Val Ser Gly Thr Asp
                            610                 615                 620

Ser Pro Phe Arg Glu Thr Ser Asn Ile Tyr Asp Gly Ser Ala Phe Cys
        625                 630                 635                 640

Ala Asp Met Ala Val Gln Asn Phe Val Gly Asp Ala Cys Arg Gly Ala
                            645                 650                 655

Thr Trp Val Ala Leu His Asn Gly Gly Val Gly Trp Gly Glu Val
                            660                 665                 670

Ile Asn Gly Gly Phe Gly Leu Val Leu Asp Gly Thr Pro Glu Ala Glu
                            675                 680                 685

Gln Lys Ala Arg Met Met Leu Ser Trp Asp Val Ser Asn Gly Val Ala
                            690                 695                 700

Arg Arg Cys Trp Ser Gly Asn Pro Lys Ala Tyr Glu Ile Ile Cys Gln
        705                 710                 715                 720

Thr Met His Asp Asn Ser Gly Leu Val Val Thr Leu Pro His Glu Val
                            725                 730                 735

Ala Asp Glu Gln Val Leu Arg Gln Asp Leu Leu Gln Gly Lys Pro Gly
                            740                 745                 750

Leu Arg Ala Leu Gln Arg Gly His Arg Glu Asp Glu Lys Gln Ser Arg
                            755                 760                 765

Glu Val Gln Ser Leu Ser Ala Ser Ser Gly Pro Cys Asp Arg Arg Leu
                            770                 775                 780

Gly Leu Lys Ala Lys His Ser Gln Leu Gly Gly Pro Ala Pro Ala Pro
        785                 790                 795                 800

Pro Pro Gly Ser Leu Val Thr Thr Val Pro Thr Ala Leu Ala Arg His
                            805                 810                 815

Ala His Ala His Gly Pro Arg Ala Arg Ala Ala Arg Asp Ala Thr Leu
                            820                 825                 830

Gly Cys Thr Leu Arg Leu Ala Leu Thr Glu Thr Pro Gly Gly Arg Thr
                            835                 840                 845

Leu Gly Val Ala Arg Met Pro Gly Arg Ala Gly Pro Leu Phe Ser Gly
                            850                 855                 860

Gly Cys Gly Ser Asp Ala Ser Ala Gly Pro Lys Met Asp Leu Pro Ala
        865                 870                 875                 880

Val Leu Ala Ala Pro Ala Thr Arg Gly Asp Gln His Gly Gly Gly Pro
                            885                 890                 895
```

-continued

Ser Arg Leu Arg Arg Gly Thr Gly Pro Ser Leu Gly Ala Gly Pro Gly
            900                 905                 910

Arg Arg Arg Leu Leu Leu Arg Ser Pro Glu Asp Gly Gly Pro Gly
            915                 920                 925

Pro Arg Gln Glu Glu Ala Pro Gly Pro Ser Pro Pro Pro Glu Asp
            930                 935                 940

Gly Gly Asp Ser Phe Val Val Leu Glu Val Pro Arg Ala Ala Asp
945                 950                 955                 960

Thr His Glu Gln Glu Glu Thr Glu Pro Asp Ser Gly Ala Ser Pro Thr
                965                 970                 975

Glu Gln Val Pro Ala Ala Ala Pro Gly Ala Ala Leu Ala Gly Thr Val
            980                 985                 990

Thr Ile His Asn Gln Asp Leu Leu Val Arg Phe Asp Arg Gly Val Phe
            995                 1000                1005

Thr Leu Ala Ala Ala Pro Ala Pro Ala Thr Gln Gly Leu His Pro
    1010                1015                1020

Ala Thr Thr Pro Gly Leu Glu Pro Ser Ser Ala Ala Ala Ser Arg
    1025                1030                1035

Arg Gly Pro Val Ala Ala Ser Ala Gly Ser Pro Ala Tyr Arg Cys
    1040                1045                1050

Pro Glu Pro Gln Cys Ala Leu Ser Phe Ala Lys Lys His Gln Leu
    1055                1060                1065

Lys Val His Leu Leu Thr His Gly Ser Leu Gln Gly Arg Arg Pro
    1070                1075                1080

Phe Lys Cys Pro Leu Asp Gly Cys Gly Trp Ala Phe Thr Thr Ser
    1085                1090                1095

Tyr Lys Leu Lys Arg His Leu Gln Ser His Asp Lys Leu Arg Pro
    1100                1105                1110

Phe Ser Cys Pro Val Gly Gly Cys Gly Lys Lys Phe Thr Thr Val
    1115                1120                1125

Tyr Asn Leu Lys Ala His Met Lys Gly His Glu Gln Glu Ser Leu
    1130                1135                1140

Phe Lys Cys Glu Val Cys Ala Glu Arg Phe Pro Thr His Ala Lys
    1145                1150                1155

Leu Asn Ser His Gln Arg Ser His Phe Glu Pro Glu Arg Pro Tyr
    1160                1165                1170

Lys Cys Asp Phe Pro Gly Cys Glu Lys Thr Phe Ile Thr Val Ser
    1175                1180                1185

Ala Leu Phe Ser His Asn Arg Ala His Phe Arg Glu Gln Glu Leu
    1190                1195                1200

Phe Ser Cys Ser Phe Pro Gly Cys Asn Lys Gln Tyr Asp Lys Ala
    1205                1210                1215

Cys Arg Leu Lys Ile His Leu Arg Ser His Thr Gly Glu Arg Pro
    1220                1225                1230

Phe Ile Cys Asp Ser Asp Ser Cys Gly Trp Thr Phe Thr Ser Met
    1235                1240                1245

Ser Lys Leu Leu Arg His Lys Arg Lys His Asp Asp Asp Arg Arg
    1250                1255                1260

Phe Thr Cys Pro Val Glu Gly Cys Gly Lys Ser Phe Thr Arg Ala
    1265                1270                1275

Glu His Leu Lys Gly His Ser Ile Thr His Leu Gly Thr Lys Pro
    1280                1285                1290

Phe Glu Cys Pro Val Glu Gly Cys Cys Ala Arg Phe Ser Ala Arg
    1295                1300                1305

```
Ser Ser Leu Tyr Ile His Ser Lys Lys His Leu Gln Asp Val Gly
    1310                1315                1320

Thr Pro Lys Ser Arg Cys Pro Val Ser Ser Cys Asn Arg Leu Phe
    1325                1330                1335

Thr Ser Lys His Ser Met Lys Ala His Met Val Arg Gln His Ser
    1340                1345                1350

Arg Arg Gln Asp Leu Val Pro Gln Leu Glu Ala Pro Ser Ser Leu
    1355                1360                1365

Thr Pro Ser Ser Glu Leu Ser Pro Gly Gln Ser Glu Leu Thr
    1370                1375                1380

Asn Ile Asp Leu Ala Ala Leu Phe Ser Asp Thr Pro Ala Asn Ser
    1385                1390                1395

Ser Ser Ser Thr Ala Gly Ser Asp Glu Ala Leu Asn Ser Gly Ile
    1400                1405                1410

Leu Thr Ile Asp Val Thr Ser Val Ser Ser Ser Leu Gly Gly Asn
    1415                1420                1425

Leu Pro Thr Asn Asn Ser Leu Gly Pro Met Asp Pro Leu Val
    1430                1435                1440

Leu Val Ala His Ser Asp Met Pro Pro Ser Leu Asp Ser Pro Leu
    1445                1450                1455

Val Leu Gly Thr Pro Ala Thr Val Leu Gln Pro Gly Ser Phe Ser
    1460                1465                1470

Ala Asp Asp Ser Gln Ala Met Ser Thr Gly Ala Val Gly Cys Leu
    1475                1480                1485

Val Ala Leu Pro Met Arg Asn Leu Ser Gln Asp Ser Pro Ala Leu
    1490                1495                1500

Thr Pro Ser Asn Asn Leu Thr Ala Leu Gly Thr Thr Pro Thr Ser
    1505                1510                1515

Ser Asp Thr Thr Gln Glu Thr Ala Ser Val Pro Asp Leu Leu Val
    1520                1525                1530

Pro Ile Lys Val Glu Gln Asp Leu Ser Pro Val Pro Asp Val Val
    1535                1540                1545

Gln Gly Gln Lys Glu Ser His Gly Pro Ser Val Leu Ser Ser Ser
    1550                1555                1560

Ala Glu Arg Leu Gly Ala Gln Lys Asp Ser Glu Leu Ser Ala Gly
    1565                1570                1575

Thr Gly Ser Leu Tyr Leu Val
    1580                1585

<210> SEQ ID NO 7
<211> LENGTH: 113
<212> TYPE: PRT
<213> ORGANISM: Rattus sp.

<400> SEQUENCE: 7

Met Ala Ala Lys Thr Gly Ser Gln Leu Glu Arg Ser Ile Ser Thr Ile
1               5                   10                  15

Ile Asn Val Phe His Gln Tyr Ser Arg Lys Tyr Gly His Pro Asp Thr
            20                  25                  30

Leu Asn Lys Ala Glu Phe Lys Glu Met Val Asn Lys Asp Leu Pro Asn
        35                  40                  45

Phe Leu Lys Arg Glu Lys Arg Asn Glu Asn Leu Leu Arg Asp Ile Met
    50                  55                  60

Glu Asp Leu Asp Thr Asn Gln Asp Asn Gln Leu Ser Phe Glu Glu Cys
65                  70                  75                  80
```

Met Met Leu Met Gly Lys Leu Ile Phe Ala Cys His Glu Lys Leu His
            85                  90                  95

Glu Asn Asn Pro Arg Gly His Asp Arg His Gly Lys Gly Cys Gly
            100                 105                 110

Lys

<210> SEQ ID NO 8
<211> LENGTH: 375
<212> TYPE: PRT
<213> ORGANISM: Rattus sp.

<400> SEQUENCE: 8

Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
            85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
            165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
            245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
            325                 330                 335

```
Tyr Ser Val Trp Ile Gly Gly Ser Ile Leu Ala Ser Leu Ser Thr Phe
                340                 345                 350

Gln Gln Met Trp Ile Ser Lys Gln Glu Tyr Asp Glu Ser Gly Pro Ser
            355                 360                 365

Ile Val His Arg Lys Cys Phe
        370             375

<210> SEQ ID NO 9
<211> LENGTH: 501
<212> TYPE: PRT
<213> ORGANISM: Rattus sp.

<400> SEQUENCE: 9

Met Ser Ser Pro Ala Gln Pro Ala Val Pro Ala Pro Leu Ala Asn Leu
1               5                   10                  15

Lys Ile Gln His Thr Lys Ile Phe Ile Asn Asn Glu Trp His Asp Ser
                20                  25                  30

Val Ser Gly Lys Lys Phe Pro Val Leu Asn Pro Ala Thr Glu Glu Val
            35                  40                  45

Ile Cys His Val Glu Glu Gly Asp Lys Ala Asp Val Asp Lys Ala Val
        50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Asn Lys Leu Ala Asp Leu Met
                85                  90                  95

Glu Arg Asp Arg Leu Leu Leu Ala Thr Ile Glu Ala Ile Asn Gly Gly
            100                 105                 110

Lys Val Phe Ala Asn Ala Tyr Leu Ser Asp Leu Gly Gly Ser Ile Lys
        115                 120                 125

Ala Leu Lys Tyr Cys Ala Gly Trp Ala Asp Lys Ile His Gly Gln Thr
    130                 135                 140

Ile Pro Ser Asp Gly Asp Ile Phe Thr Phe Thr Arg Arg Glu Pro Ile
145                 150                 155                 160

Gly Val Cys Gly Gln Ile Ile Pro Trp Asn Phe Pro Leu Leu Met Phe
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Met Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Val Asp
225                 230                 235                 240

Lys Val Ala Phe Thr Gly Ser Thr Gln Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Phe Ala Asp Ala Asp Leu Asp Ile Ala Val
        275                 280                 285

Glu Phe Ala His His Gly Val Phe Tyr His Gln Gly Gln Cys Cys Val
    290                 295                 300

Ala Ala Ser Arg Ile Phe Val Glu Glu Ser Val Tyr Asp Glu Phe Val
305                 310                 315                 320

Arg Lys Ser Val Glu Arg Ala Lys Lys Tyr Val Leu Gly Asn Pro Leu
                325                 330                 335
```

```
Thr Gln Gly Ile Asn Gln Gly Pro Gln Ile Asp Lys Glu Gln His Asp
                340                 345                 350

Lys Ile Leu Asp Leu Ile Glu Ser Gly Lys Lys Glu Gly Ala Lys Leu
            355                 360                 365

Glu Cys Gly Gly Gly Arg Trp Gly Asn Lys Gly Phe Phe Val Gln Pro
        370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Ile Asp Asp
                405                 410                 415

Val Ile Lys Arg Ala Asn Asn Thr Thr Tyr Gly Leu Ala Ala Gly Val
            420                 425                 430

Phe Thr Lys Asp Leu Asp Arg Ala Ile Thr Val Ser Ser Ala Leu Gln
        435                 440                 445

Ala Gly Val Val Trp Val Asn Cys Tyr Met Ile Leu Ser Ala Gln Cys
    450                 455                 460

Pro Phe Gly Gly Phe Lys Met Ser Gly Asn Gly Arg Glu Leu Gly Glu
465                 470                 475                 480

His Gly Leu Tyr Glu Tyr Thr Glu Leu Lys Thr Val Ala Met Lys Ile
                485                 490                 495

Ser Gln Lys Asn Ser
            500

<210> SEQ ID NO 10
<211> LENGTH: 204
<212> TYPE: PRT
<213> ORGANISM: Rattus sp.

<400> SEQUENCE: 10

Met Ala Glu Gln Glu Pro Thr Ala Glu Gln Leu Ala Gln Ile Ala Ala
1               5                   10                  15

Glu Asn Glu Glu Asp Glu His Ser Val Asn Tyr Lys Pro Pro Ala Gln
            20                  25                  30

Lys Ser Ile Gln Glu Ile Gln Glu Leu Asp Lys Asp Asp Glu Ser Leu
        35                  40                  45

Arg Lys Tyr Lys Glu Ala Leu Leu Gly Arg Val Ala Val Ser Ala Asp
    50                  55                  60

Pro Asn Val Pro Asn Val Ile Val Thr Arg Leu Thr Leu Val Cys Ser
65                  70                  75                  80

Thr Ala Pro Gly Pro Leu Glu Leu Asp Leu Thr Gly Asp Leu Glu Ser
                85                  90                  95

Phe Lys Lys Gln Ser Phe Val Leu Lys Glu Gly Val Glu Tyr Arg Ile
            100                 105                 110

Lys Ile Ser Phe Arg Val Asn Arg Glu Ile Val Ser Gly Met Lys Tyr
        115                 120                 125

Ile Gln His Thr Tyr Arg Lys Gly Val Lys Ile Asp Lys Thr Asp Tyr
    130                 135                 140

Met Val Gly Ser Tyr Gly Pro Arg Ala Glu Glu Tyr Glu Phe Leu Thr
145                 150                 155                 160

Pro Met Glu Glu Ala Pro Lys Gly Met Leu Ala Arg Gly Ser Tyr Asn
                165                 170                 175

Ile Lys Ser Arg Phe Thr Asp Asp Lys Thr Asp His Leu Ser Trp
            180                 185                 190

Glu Trp Asn Leu Thr Ile Lys Lys Glu Trp Lys Asp
        195                 200
```

```
<210> SEQ ID NO 11
<211> LENGTH: 261
<212> TYPE: PRT
<213> ORGANISM: Rattus sp.

<400> SEQUENCE: 11

Met Ala Ser Ala Asp Trp Gly Tyr Asp Ser Lys Asn Gly Pro Asp Gln
1               5                   10                  15

Trp Ser Lys Leu Tyr Pro Ile Ala Asn Gly Asn Gln Ser Pro Ile
            20                  25                  30

Asp Ile Lys Thr Ser Glu Ala Lys His Asp Ser Ser Leu Lys Pro Val
            35                  40                  45

Ser Val Ser Tyr Asn Pro Ala Thr Ala Lys Glu Ile Val Asn Val Gly
50                  55                  60

His Ser Phe His Val Val Phe Asp Asp Ser Ser Asn Gln Ser Val Leu
65                  70                  75                  80

Lys Gly Gly Pro Leu Ala Asp Ser Tyr Arg Leu Thr Gln Phe His Phe
                85                  90                  95

His Trp Gly Asn Ser Asn Asp His Gly Ser Glu His Thr Val Asp Gly
            100                 105                 110

Ala Lys Tyr Ser Gly Glu Leu His Leu Val His Trp Asn Ser Ala Lys
            115                 120                 125

Tyr Ser Ser Ala Ala Glu Ala Ile Ser Lys Ala Asp Gly Leu Ala Ile
130                 135                 140

Ile Gly Val Leu Met Lys Val Gly Pro Ala Asn Pro Asn Leu Gln Lys
145                 150                 155                 160

Val Leu Asp Ala Leu Ser Ser Val Lys Thr Lys Gly Lys Arg Ala Pro
                165                 170                 175

Phe Thr Asn Phe Asp Pro Ser Ser Leu Leu Pro Ser Ser Leu Asp Tyr
            180                 185                 190

Trp Thr Tyr Phe Gly Ser Leu Thr His Pro Pro Leu His Glu Ser Val
            195                 200                 205

Thr Trp Val Ile Cys Lys Glu Ser Ile Ser Leu Ser Pro Glu Gln Leu
210                 215                 220

Ala Gln Leu Arg Gly Leu Leu Ser Ser Ala Glu Gly Glu Pro Ala Val
225                 230                 235                 240

Pro Val Leu Ser Asn His Arg Pro Pro Gln Pro Leu Lys Gly Arg Thr
                245                 250                 255

Val Arg Ala Ser Phe
            260

<210> SEQ ID NO 12
<211> LENGTH: 260
<212> TYPE: PRT
<213> ORGANISM: Rattus sp.

<400> SEQUENCE: 12

Met Ser His His Trp Gly Tyr Ser Lys Ser Asn Gly Pro Glu Asn Trp
1               5                   10                  15

His Lys Glu Phe Pro Ile Ala Asn Gly Asp Arg Gln Ser Pro Val Asp
            20                  25                  30

Ile Asp Thr Gly Thr Ala Gln His Asp Pro Ser Leu Gln Pro Leu Leu
            35                  40                  45

Ile Cys Tyr Asp Lys Val Ala Ser Lys Ser Ile Val Asn Asn Gly His
50                  55                  60

Ser Phe Asn Val Glu Phe Asp Asp Ser Gln Asp Phe Ala Val Leu Lys
```

```
                65                  70                  75                  80
Glu Gly Pro Leu Ser Gly Ser Tyr Arg Leu Ile Gln Phe His Phe His
                    85                  90                  95
Trp Gly Ser Ser Asp Gly Gln Gly Ser Glu His Thr Val Asn Lys Lys
                100                 105                 110
Lys Tyr Ala Ala Glu Leu His Leu Val His Trp Asn Thr Lys Tyr Gly
                115                 120                 125
Asp Phe Gly Lys Ala Val Gln His Pro Asp Gly Leu Ala Val Leu Gly
            130                 135                 140
Ile Phe Leu Lys Ile Gly Pro Ala Ser Gln Gly Leu Gln Lys Ile Thr
145                 150                 155                 160
Glu Ala Leu His Ser Ile Lys Thr Lys Gly Lys Arg Ala Ala Phe Ala
                165                 170                 175
Asn Phe Asp Pro Cys Ser Leu Leu Pro Gly Asn Leu Asp Tyr Trp Thr
                180                 185                 190
Tyr Pro Gly Ser Leu Thr Thr Pro Pro Leu Leu Glu Cys Val Thr Trp
                195                 200                 205
Ile Val Leu Lys Glu Pro Ile Thr Val Ser Ser Glu Gln Met Ser His
            210                 215                 220
Phe Arg Lys Leu Asn Phe Asn Ser Glu Gly Glu Ala Glu Glu Leu Met
225                 230                 235                 240
Val Asp Asn Trp Arg Pro Ala Gln Pro Leu Lys Asn Arg Lys Ile Lys
                245                 250                 255
Ala Ser Phe Lys
            260

<210> SEQ ID NO 13
<211> LENGTH: 490
<212> TYPE: PRT
<213> ORGANISM: Rattus sp.

<400> SEQUENCE: 13

Met Asp Pro Val Val Leu Leu Ser Leu Phe Phe Leu Leu Phe
1               5                   10                  15
Leu Ser Leu Trp Arg Leu Ser Ser Arg Gly Lys Leu Pro Pro Gly
                20                  25                  30
Pro Thr Pro Leu Pro Ile Ile Gly Asn Phe Phe Gln Val Asp Met Lys
                35                  40                  45
Asp Ile Arg Gln Ser Leu Thr Asn Phe Ser Lys Thr Tyr Gly Pro Val
            50                  55                  60
Tyr Thr Leu Tyr Val Gly Ser Gln Pro Thr Val Val Leu His Gly Tyr
65                  70                  75                  80
Glu Ala Leu Lys Glu Ala Leu Val Asp His Gly Glu Glu Phe Ser Gly
                85                  90                  95
Arg Gly Arg Leu Pro Ile Cys Glu Lys Val Ala Lys Gly Gln Gly Ile
                100                 105                 110
Ala Phe Ser His Gly Asn Val Trp Lys Ala Thr Arg His Phe Thr Val
                115                 120                 125
Lys Thr Leu Arg Asn Leu Gly Met Gly Lys Gly Thr Ile Glu Asp Lys
                130                 135                 140
Val Gln Glu Glu Ala Lys Trp Leu Val Lys Glu Leu Lys Thr Asn
145                 150                 155                 160
Gly Ser Pro Cys Asp Pro Gln Phe Ile Met Gly Cys Ala Pro Gly Asn
                165                 170                 175
Val Ile Cys Cys Ile Ile Leu Gln Asn Arg Phe Asp Tyr Glu Asp Lys
```

```
                    180                 185                 190
Asp Phe Leu Asn Leu Ile Glu Lys Val Asn Glu Ala Val Lys Ile Ile
            195                 200                 205

Ser Ser Pro Gly Ile Gln Val Phe Asn Ile Phe Pro Ile Leu Leu Asp
        210                 215                 220

Tyr Cys Pro Gly Asn His Asn Ile Tyr Leu Lys Asn Tyr Thr Trp Val
225                 230                 235                 240

Lys Ser Tyr Leu Leu Glu Lys Ile Lys Glu His Glu Glu Ser Leu Asp
            245                 250                 255

Val Ser Asn Pro Arg Asp Phe Ile Asp Tyr Phe Leu Ile Glu Arg Asn
        260                 265                 270

Gln Glu Asn Ala Asn Gln Trp Met Asn Tyr Thr Leu Glu His Leu Ala
            275                 280                 285

Ile Met Val Thr Asp Leu Phe Phe Ala Gly Ile Glu Thr Val Ser Ser
        290                 295                 300

Thr Met Arg Phe Ala Leu Leu Leu Met Lys Tyr Pro His Val Thr
305                 310                 315                 320

Ala Lys Val Gln Glu Glu Ile Asp His Val Ile Gly Arg His Arg Ser
            325                 330                 335

Pro Ser Met Gln Asp Arg Ser His Met Pro Tyr Thr Asn Ala Met Val
        340                 345                 350

His Glu Val Gln Arg Tyr Ile Asp Ile Gly Pro Asn Gly Leu Leu His
            355                 360                 365

Asp Val Thr Cys Asp Thr Lys Phe Arg Asn Tyr Phe Ile Pro Lys Gly
        370                 375                 380

Thr Ala Val Leu Thr Ser Leu Thr Ser Val Leu His Asp Ser Lys Glu
385                 390                 395                 400

Phe Pro Asn Pro Glu Met Phe Asp Pro Gly His Phe Leu Asp Glu Asn
            405                 410                 415

Gly Asn Phe Lys Lys Ser Asp Tyr Phe Ile Pro Phe Ser Ala Gly Lys
        420                 425                 430

Arg Met Cys Leu Gly Glu Ser Leu Ala Arg Met Glu Leu Phe Leu Phe
            435                 440                 445

Leu Thr Thr Ile Leu Gln Asn Phe Lys Leu Lys Ser Leu Val Asp Pro
450                 455                 460

Lys Asp Ile Asn Thr Thr Pro Ile Cys Ser Ser Leu Ser Ser Val Pro
465                 470                 475                 480

Pro Thr Phe Gln Met Arg Phe Ile Pro Leu
            485                 490

<210> SEQ ID NO 14
<211> LENGTH: 609
<212> TYPE: PRT
<213> ORGANISM: Rattus sp.

<400> SEQUENCE: 14

Met Ser Glu Trp Glu Ser Tyr Tyr Lys Thr Glu Gly Glu Glu Glu Glu
1               5                   10                  15

Glu Glu Glu Gln Ser Pro Asp Thr Asn Gly Glu Tyr Lys Tyr Ser Gly
            20                  25                  30

Arg Asp Ser Leu Ile Phe Leu Val Asp Ala Ser Arg Ala Met Phe Glu
        35                  40                  45

Ser Gln Gly Glu Asp Glu Leu Thr Pro Phe Asp Met Ser Ile Gln Cys
    50                  55                  60

Ile Gln Ser Val Tyr Thr Ser Lys Ile Ile Ser Ser Asp Arg Asp Leu
```

```
             65                  70                  75                  80
Leu Ala Val Val Phe Tyr Gly Thr Glu Lys Asp Lys Asn Ser Val Asn
                 85                  90                  95
Phe Lys Ser Ile Tyr Val Leu Gln Asp Leu Asp Asn Pro Gly Ala Lys
                100                 105                 110
Arg Val Leu Glu Leu Asp Arg Phe Lys Gly Gln Gln Gly Lys Lys His
                115                 120                 125
Phe Arg Asp Thr Ile Gly His Gly Ser Asp Tyr Ser Leu Ser Glu Val
            130                 135                 140
Leu Trp Val Cys Ala Asn Leu Phe Ser Asp Val Gln Phe Lys Met Ser
145                 150                 155                 160
His Lys Arg Ile Met Leu Phe Thr Asn Glu Asp Asp Pro His Gly Asn
                    165                 170                 175
Asp Ser Ala Lys Ala Ser Arg Ala Arg Thr Lys Ala Ser Asp Leu Arg
                180                 185                 190
Asp Thr Gly Ile Phe Leu Asp Leu Met His Leu Lys Lys Arg Gly Gly
                195                 200                 205
Phe Asp Val Ser Leu Phe Tyr Arg Asp Ile Ile Ser Ile Ala Glu Asp
        210                 215                 220
Glu Asp Leu Gly Val His Phe Glu Glu Ser Ser Lys Leu Glu Asp Leu
225                 230                 235                 240
Leu Arg Lys Val Arg Ala Lys Glu Thr Lys Arg Val Leu Ser Arg
                    245                 250                 255
Leu Lys Phe Lys Leu Gly Lys Asp Val Ala Leu Met Val Gly Val Tyr
                260                 265                 270
Asn Leu Val Gln Lys Ala Asn Lys Pro Phe Pro Val Arg Leu Tyr Arg
                275                 280                 285
Glu Thr Asn Glu Pro Val Lys Thr Lys Thr Arg Thr Phe Asn Val Asn
        290                 295                 300
Thr Gly Ser Leu Leu Pro Ser Asp Thr Lys Arg Ser Leu Thr Phe
305                 310                 315                 320
Gly Thr Arg Gln Ile Val Leu Glu Lys Glu Thr Glu Glu Leu Lys
                325                 330                 335
Arg Phe Asp Glu Pro Gly Leu Ile Leu Met Gly Phe Lys Pro Met Val
                340                 345                 350
Met Leu Lys Asn His His Tyr Leu Arg Pro Ser Leu Phe Leu Tyr Pro
            355                 360                 365
Glu Glu Ser Leu Val Asn Gly Ser Ser Thr Leu Phe Ser Ala Leu Leu
        370                 375                 380
Thr Lys Cys Val Glu Lys Glu Val Ile Ala Val Cys Arg Tyr Thr Ala
385                 390                 395                 400
Arg Lys Asn Val Ser Pro Tyr Phe Val Ala Leu Val Pro Gln Glu Glu
                405                 410                 415
Glu Leu Asp Asp Gln Asn Ile Gln Val Thr Pro Ala Gly Phe Gln Leu
            420                 425                 430
Val Phe Leu Pro Tyr Ala Asp Asp Lys Arg Lys Val Pro Phe Thr Glu
                435                 440                 445
Lys Val Met Ala Asn Pro Glu Gln Ile Asp Lys Met Lys Ala His Val
            450                 455                 460
Gln Lys Leu Arg Phe Thr Tyr Arg Ser Asp Ser Phe Glu Asn Pro Val
465                 470                 475                 480
Leu Gln Gln His Phe Arg Asn Leu Glu Ala Leu Ala Leu Asp Met Met
            485                 490                 495
```

-continued

```
Glu Ser Glu Gln Val Val Asp Leu Thr Leu Pro Lys Val Glu Ala Ile
            500                 505                 510
Lys Lys Arg Leu Gly Ser Leu Ala Asp Glu Phe Lys Glu Leu Val Tyr
        515                 520                 525
Pro Pro Gly Tyr Asn Pro Glu Gly Lys Ile Ala Lys Arg Lys Ala Asp
    530                 535                 540
Asn Glu Gly Ser Ala Ser Lys Lys Pro Lys Val Glu Leu Ser Glu Glu
545                 550                 555                 560
Glu Leu Lys Asp Leu Phe Ala Lys Gly Thr Leu Gly Lys Leu Thr Val
                565                 570                 575
Pro Ala Leu Arg Asp Ile Cys Lys Ala Tyr Gly Leu Lys Ser Gly Pro
            580                 585                 590
Lys Lys Gln Glu Leu Leu Glu Ala Leu Ser Arg His Leu Glu Lys Thr
        595                 600                 605
Asp

<210> SEQ ID NO 15
<211> LENGTH: 1961
<212> TYPE: PRT
<213> ORGANISM: Rattus sp.

<400> SEQUENCE: 15

Met Ala Gln Gln Ala Ala Asp Lys Tyr Leu Tyr Val Asp Lys Asn Phe
1               5                   10                  15
Ile Asn Asn Pro Leu Ala Gln Ala Asp Cys Gly Ala Lys Lys Leu Val
            20                  25                  30
Trp Val Pro Ser Thr Lys Asn Gly Phe Glu Pro Ala Ser Leu Lys Glu
        35                  40                  45
Glu Val Gly Glu Glu Ala Ile Val Glu Leu Val Glu Asn Gly Lys Lys
    50                  55                  60
Val Lys Val Asn Lys Asp Asp Ile Gln Lys Met Asn Pro Pro Lys Phe
65                  70                  75                  80
Ser Lys Val Glu Asp Met Ala Glu Leu Thr Cys Leu Asn Glu Ala Ser
                85                  90                  95
Val Leu His Asn Leu Lys Glu Arg Tyr Tyr Ser Gly Leu Ile Tyr Thr
            100                 105                 110
Tyr Ser Gly Leu Phe Cys Val Val Ile Asn Pro Tyr Lys Asn Leu Pro
        115                 120                 125
Ile Tyr Ser Glu Glu Ile Val Asp Met Tyr Lys Gly Lys Lys Arg His
    130                 135                 140
Glu Met Pro Pro His Ile Tyr Ala Ile Thr Asp Thr Ala Tyr Arg Ser
145                 150                 155                 160
Met Met Gln Asp Arg Glu Asp Gln Ser Ile Leu Cys Thr Gly Glu Ser
                165                 170                 175
Gly Ala Gly Lys Thr Glu Asn Thr Lys Lys Val Ile Gln Tyr Leu Ala
            180                 185                 190
His Val Ala Ser Ser His Lys Ser Lys Lys Asp Gln Gly Glu Leu Glu
        195                 200                 205
Arg Gln Leu Leu Gln Ala Asn Pro Ile Leu Glu Ala Phe Gly Asn Ala
    210                 215                 220
Lys Thr Val Lys Asn Asp Asn Ser Ser Arg Phe Gly Lys Phe Ile Arg
225                 230                 235                 240
Ile Asn Phe Asp Val Asn Gly Tyr Ile Val Gly Ala Asn Ile Glu Thr
                245                 250                 255
Tyr Leu Leu Glu Lys Ser Arg Ala Ile Arg Gln Ala Lys Glu Glu Arg
```

-continued

```
                    260                 265                 270
Thr Phe His Ile Phe Tyr Tyr Leu Leu Ser Gly Ala Gly Glu His Leu
                275                 280                 285

Lys Thr Asp Leu Leu Leu Glu Pro Tyr Asn Lys Tyr Arg Phe Leu Ser
            290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Asp Glu Gln
                325                 330                 335

Met Gly Leu Leu Arg Val Ile Ser Gly Val Leu Gln Leu Gly Asn Ile
                340                 345                 350

Val Phe Lys Lys Glu Arg Asn Thr Asp Gln Ala Ser Met Pro Asp Asn
            355                 360                 365

Thr Ala Ala Gln Lys Val Ser His Leu Leu Gly Ile Asn Val Thr Asp
            370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
                420                 425                 430

Ile Asn Lys Ala Leu Asp Lys Thr Lys Arg Gln Gly Ala Ser Phe Ile
            435                 440                 445

Gly Ile Leu Asp Ile Ala Gly Phe Glu Ile Phe Asp Leu Asn Ser Phe
            450                 455                 460

Glu Gln Leu Cys Ile Asn Tyr Thr Asn Glu Lys Leu Gln Gln Leu Phe
465                 470                 475                 480

Asn His Thr Met Phe Ile Leu Glu Gln Glu Glu Tyr Gln Arg Glu Gly
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
            515                 520                 525

Asp Glu Glu Cys Trp Phe Pro Lys Ala Thr Asp Lys Ser Phe Val Glu
            530                 535                 540

Lys Val Val Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
            595                 600                 605

Ser Glu Leu Trp Lys Asp Val Asp Arg Ile Ile Gly Leu Asp Gln Val
            610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Cys Cys Ile
                660                 665                 670

Ile Pro Asn His Glu Lys Lys Ala Gly Lys Leu Asp Pro His Leu Val
            675                 680                 685
```

-continued

```
Leu Asp Gln Leu Arg Cys Asn Gly Val Leu Glu Gly Ile Arg Ile Cys
690                 695                 700

Arg Gln Gly Phe Pro Asn Arg Val Val Phe Gln Phe Arg Gln Arg
705                 710                 715                 720

Tyr Glu Ile Leu Thr Pro Asn Ser Ile Pro Lys Gly Phe Met Asp Gly
            725                 730                 735

Lys Gln Ala Cys Val Leu Met Ile Lys Ala Leu Glu Leu Asp Ser Asn
                740                 745                 750

Leu Tyr Arg Ile Gly Gln Ser Lys Val Phe Phe Arg Ser Gly Val Leu
        755                 760                 765

Ala His Leu Glu Glu Glu Arg Asp Leu Lys Ile Thr Asp Val Ile Ile
770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Arg Leu Arg Asn Trp Gln Trp Trp Arg Leu Phe Thr
            820                 825                 830

Lys Val Lys Pro Leu Leu Asn Ser Ile Arg His Glu Asp Glu Leu Leu
            835                 840                 845

Ala Lys Glu Ala Glu Leu Thr Lys Val Arg Glu Lys His Leu Ala Ala
850                 855                 860

Glu Asn Arg Leu Thr Glu Met Glu Thr Met Gln Ser Gln Leu Met Ala
865                 870                 875                 880

Glu Lys Leu Gln Leu Gln Glu Gln Leu Gln Ala Lys Thr Glu Leu Cys
                885                 890                 895

Ala Glu Ala Glu Glu Leu Arg Ala Arg Leu Thr Ala Lys Lys Gln Glu
            900                 905                 910

Leu Glu Glu Ile Cys His Asp Leu Glu Ala Arg Val Glu Glu Glu Glu
        915                 920                 925

Glu Arg Cys Gln Tyr Leu Gln Ala Glu Lys Lys Lys Met Gln Gln Asn
930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Lys Leu
                965                 970                 975

Glu Glu Asp Gln Ile Ile Met Glu Asp Gln Asn Cys Lys Leu Ala Lys
            980                 985                 990

Glu Lys Lys Leu Leu Glu Asp Arg Val Ala Glu Phe Thr Thr Asp Leu
        995                 1000                1005

Met Glu Glu Glu Lys Ser Lys Ser Leu Ala Lys Leu Lys Asn
1010                1015                1020

Lys His Glu Ala Met Ile Thr Asp Leu Glu Glu Arg Leu Arg Arg
1025                1030                1035

Glu Glu Lys Gln Arg Gln Glu Leu Glu Lys Thr Arg Arg Lys Leu
        1040                1045                1050

Glu Gly Asp Ser Thr Asp Leu Ser Asp Gln Ile Ala Glu Leu Gln
        1055                1060                1065

Ala Gln Ile Ala Glu Leu Lys Met Gln Leu Ala Lys Lys Glu Glu
        1070                1075                1080

Glu Leu Gln Ala Ala Leu Ala Arg Val Glu Glu Glu Ala Ala Gln
        1085                1090                1095

Lys Asn Met Ala Leu Lys Lys Ile Arg Glu Leu Glu Thr Gln Ile
        1100                1105                1110
```

```
Ser Glu Leu Gln Glu Asp Leu Glu Ser Glu Arg Ala Cys Arg Asn
    1115                1120                1125

Lys Ala Glu Lys Gln Lys Arg Asp Leu Gly Glu Glu Leu Glu Ala
    1130                1135                1140

Leu Lys Thr Glu Leu Glu Asp Thr Leu Asp Ser Thr Ala Ala Gln
    1145                1150                1155

Gln Glu Leu Arg Ser Lys Arg Glu Gln Glu Val Ser Ile Leu Lys
    1160                1165                1170

Lys Thr Leu Glu Asp Glu Ala Lys Thr His Glu Ala Gln Ile Gln
    1175                1180                1185

Glu Met Arg Gln Lys His Ser Gln Ala Val Glu Glu Leu Ala Glu
    1190                1195                1200

Gln Leu Glu Gln Thr Lys Arg Val Lys Ala Thr Leu Glu Lys Ala
    1205                1210                1215

Lys Gln Thr Leu Glu Asn Glu Arg Gly Glu Leu Ala Asn Glu Val
    1220                1225                1230

Lys Ala Leu Leu Gln Gly Lys Gly Asp Ser Glu His Lys Arg Lys
    1235                1240                1245

Lys Val Glu Ala Gln Leu Gln Glu Leu Gln Val Lys Phe Ser Glu
    1250                1255                1260

Gly Glu Arg Val Arg Thr Glu Leu Ala Asp Lys Val Ser Lys Leu
    1265                1270                1275

Gln Val Glu Leu Asp Ser Val Thr Gly Leu Leu Asn Gln Ser Asp
    1280                1285                1290

Ser Lys Ser Ser Lys Leu Thr Lys Asp Phe Ser Ala Leu Glu Ser
    1295                1300                1305

Gln Leu Gln Asp Thr Gln Glu Leu Leu Gln Glu Glu Asn Arg Gln
    1310                1315                1320

Lys Leu Ser Leu Ser Thr Lys Leu Lys Gln Met Glu Asp Glu Lys
    1325                1330                1335

Asn Ser Phe Arg Glu Gln Leu Glu Glu Glu Glu Glu Ala Lys
    1340                1345                1350

Arg Asn Leu Glu Lys Gln Ile Ala Thr Leu His Ala Gln Val Thr
    1355                1360                1365

Asp Met Lys Lys Lys Met Glu Asp Gly Val Gly Cys Leu Glu Thr
    1370                1375                1380

Ala Glu Glu Ala Lys Arg Arg Leu Gln Lys Asp Leu Glu Gly Leu
    1385                1390                1395

Ser Gln Arg Leu Glu Glu Lys Val Ala Ala Tyr Asp Lys Leu Glu
    1400                1405                1410

Lys Thr Lys Thr Arg Leu Gln Gln Glu Leu Asp Asp Leu Leu Val
    1415                1420                1425

Asp Leu Asp His Gln Arg Gln Ser Val Ser Asn Leu Glu Lys Lys
    1430                1435                1440

Gln Lys Lys Phe Asp Gln Leu Leu Ala Glu Glu Lys Thr Ile Ser
    1445                1450                1455

Ala Lys Tyr Ala Glu Glu Arg Asp Arg Ala Glu Ala Glu Ala Arg
    1460                1465                1470

Glu Lys Glu Thr Lys Ala Leu Ser Leu Ala Arg Ala Leu Glu Glu
    1475                1480                1485

Ala Met Glu Gln Lys Ala Glu Leu Glu Arg Leu Asn Lys Gln Phe
    1490                1495                1500

Arg Thr Glu Met Glu Asp Leu Met Ser Ser Lys Asp Asp Val Gly
```

```
            1505                1510                1515

Lys  Ser  Val  His  Glu  Leu  Glu  Lys  Ser  Asn  Arg  Ala  Leu  Glu  Gln
     1520                1525                1530

Gln  Val  Glu  Glu  Met  Lys  Thr  Gln  Leu  Glu  Glu  Leu  Glu  Asp  Glu
     1535                1540                1545

Leu  Gln  Ala  Thr  Glu  Asp  Ala  Lys  Leu  Arg  Leu  Glu  Val  Asn  Leu
     1550                1555                1560

Gln  Ala  Met  Lys  Ala  Gln  Phe  Glu  Arg  Asp  Leu  Gln  Gly  Arg  Asp
     1565                1570                1575

Glu  Gln  Ser  Glu  Glu  Lys  Lys  Lys  Gln  Leu  Val  Arg  Gln  Val  Arg
     1580                1585                1590

Glu  Met  Glu  Ala  Glu  Leu  Glu  Asp  Glu  Arg  Lys  Gln  Arg  Ser  Ile
     1595                1600                1605

Ala  Met  Ala  Ala  Arg  Lys  Lys  Leu  Glu  Met  Asp  Leu  Lys  Asp  Leu
     1610                1615                1620

Glu  Ala  His  Ile  Asp  Thr  Ala  Asn  Lys  Asn  Arg  Glu  Glu  Ala  Ile
     1625                1630                1635

Lys  Gln  Leu  Arg  Lys  Leu  Gln  Ala  Gln  Met  Lys  Asp  Cys  Met  Arg
     1640                1645                1650

Asp  Val  Asp  Asp  Thr  Arg  Ala  Ser  Arg  Glu  Glu  Ile  Leu  Ala  Gln
     1655                1660                1665

Ala  Lys  Glu  Asn  Glu  Lys  Lys  Leu  Lys  Ser  Met  Glu  Ala  Glu  Met
     1670                1675                1680

Ile  Gln  Leu  Gln  Glu  Glu  Leu  Ala  Ala  Ala  Glu  Arg  Ala  Lys  Arg
     1685                1690                1695

Gln  Ala  Gln  Gln  Glu  Arg  Asp  Glu  Leu  Ala  Asp  Glu  Ile  Ala  Asn
     1700                1705                1710

Ser  Ser  Gly  Lys  Gly  Ala  Leu  Ala  Leu  Glu  Glu  Lys  Arg  Arg  Leu
     1715                1720                1725

Glu  Ala  Leu  Ile  Ala  Leu  Leu  Glu  Glu  Glu  Leu  Glu  Glu  Glu  Gln
     1730                1735                1740

Gly  Asn  Thr  Glu  Leu  Ile  Asn  Asp  Arg  Leu  Lys  Lys  Ala  Asn  Leu
     1745                1750                1755

Gln  Ile  Asp  Gln  Ile  Asn  Thr  Asp  Leu  Asn  Leu  Glu  Arg  Ser  His
     1760                1765                1770

Ala  Gln  Lys  Asn  Glu  Asn  Ala  Arg  Gln  Gln  Leu  Glu  Arg  Gln  Asn
     1775                1780                1785

Lys  Glu  Leu  Lys  Ala  Lys  Leu  Gln  Glu  Met  Glu  Ser  Ala  Val  Lys
     1790                1795                1800

Ser  Lys  Tyr  Lys  Ala  Ser  Ile  Ala  Ala  Leu  Glu  Ala  Lys  Ile  Ala
     1805                1810                1815

Gln  Leu  Glu  Glu  Gln  Leu  Asp  Asn  Glu  Thr  Lys  Glu  Arg  Gln  Ala
     1820                1825                1830

Ala  Ser  Lys  Gln  Val  Arg  Arg  Ala  Glu  Lys  Lys  Leu  Lys  Asp  Val
     1835                1840                1845

Leu  Leu  Gln  Val  Glu  Asp  Glu  Arg  Arg  Asn  Ala  Glu  Gln  Phe  Lys
     1850                1855                1860

Asp  Gln  Ala  Asp  Lys  Ala  Ser  Thr  Arg  Leu  Lys  Gln  Leu  Lys  Arg
     1865                1870                1875

Gln  Leu  Glu  Glu  Ala  Glu  Glu  Glu  Ala  Gln  Arg  Ala  Asn  Ala  Ser
     1880                1885                1890

Arg  Arg  Lys  Leu  Gln  Arg  Glu  Leu  Glu  Asp  Ala  Thr  Glu  Thr  Ala
     1895                1900                1905
```

-continued

```
Asp Ala Met Asn Arg Glu Val Ser Ser Leu Lys Asn Lys Leu Arg
    1910                1915                1920
Arg Gly Asp Met Pro Phe Val Val Thr Arg Arg Ile Val Arg Lys
    1925                1930                1935
Gly Thr Gly Asp Cys Ser Glu Glu Val Asp Gly Lys Ala Asp
    1940                1945                1950
Gly Ala Asp Ala Lys Ala Thr Glu
    1955                1960

<210> SEQ ID NO 16
<211> LENGTH: 151
<212> TYPE: PRT
<213> ORGANISM: Rattus sp.

<400> SEQUENCE: 16

Met Cys Asp Phe Thr Glu Asp Gln Thr Ala Glu Phe Lys Glu Ala Phe
1               5                   10                  15
Gln Leu Phe Asp Arg Thr Gly Asp Gly Lys Ile Leu Tyr Ser Gln Cys
            20                  25                  30
Gly Asp Val Met Arg Ala Leu Gly Gln Asn Pro Thr Asn Ala Glu Val
        35                  40                  45
Leu Lys Val Leu Gly Asn Pro Lys Ser Asp Glu Met Asn Val Lys Val
    50                  55                  60
Leu Asp Phe Glu His Phe Leu Pro Met Leu Gln Thr Val Ala Lys Asn
65                  70                  75                  80
Lys Asp Gln Gly Thr Tyr Glu Asp Tyr Val Glu Gly Leu Arg Val Phe
                85                  90                  95
Asp Lys Glu Gly Asn Gly Thr Val Met Gly Ala Glu Ile Arg His Val
            100                 105                 110
Leu Val Thr Leu Gly Glu Lys Met Thr Glu Glu Val Glu Met Leu
        115                 120                 125
Val Ala Gly His Glu Asp Ser Asn Gly Cys Ile Asn Tyr Glu Glu Leu
    130                 135                 140
Leu Arg Met Val Leu Asn Gly
145                 150

<210> SEQ ID NO 17
<211> LENGTH: 554
<212> TYPE: PRT
<213> ORGANISM: Rattus sp.

<400> SEQUENCE: 17

Met Tyr Ala Leu Ala Leu Leu Ala Ser Leu Leu Val Thr Ala Leu Thr
1               5                   10                  15
Ser Pro Val Gln Asp Pro Lys Ile Cys Ser Gly Gly Ser Ala Val Val
            20                  25                  30
Cys Arg Asp Val Lys Thr Ala Val Asp Cys Arg Ala Val Lys His Cys
        35                  40                  45
Gln Gln Met Val Trp Ser Lys Pro Thr Ala Lys Ser Leu Pro Cys Asp
    50                  55                  60
Ile Cys Lys Thr Val Val Thr Glu Ala Gly Asn Leu Leu Lys Asp Asn
65                  70                  75                  80
Ala Thr Glu Glu Glu Ile Leu His Tyr Leu Glu Lys Thr Cys Ala Trp
                85                  90                  95
Ile His Asp Ser Ser Leu Ser Ala Ser Cys Lys Glu Val Val Asp Ser
            100                 105                 110
Tyr Leu Pro Val Ile Leu Asp Met Ile Lys Gly Glu Met Ser Asn Pro
```

```
            115                 120                 125
Gly Glu Val Cys Ser Ala Leu Asn Leu Cys Gln Ser Leu Gln Glu Tyr
            130                 135                 140
Leu Ala Glu Gln Asn Gln Arg Gln Leu Glu Ser Asn Lys Ile Pro Glu
145                 150                 155                 160
Val Asp Leu Ala Arg Val Ala Pro Phe Met Ser Asn Ile Pro Leu
                165                 170                 175
Leu Leu Tyr Pro Gln Asp Arg Pro Arg Ser Gln Pro Gln Pro Lys Ala
            180                 185                 190
Asn Glu Asp Val Cys Gln Asp Cys Met Lys Leu Val Thr Asp Ile Gln
            195                 200                 205
Thr Ala Val Arg Thr Asn Ser Ser Phe Val Gln Gly Leu Val Asp His
210                 215                 220
Val Lys Glu Asp Cys Asp Arg Leu Gly Pro Gly Val Ser Asp Ile Cys
225                 230                 235                 240
Lys Asn Tyr Val Asp Gln Tyr Ser Glu Val Ala Val Gln Met Met Met
                245                 250                 255
His Met Gln Pro Lys Glu Ile Cys Val Met Val Gly Phe Cys Asp Glu
            260                 265                 270
Val Lys Arg Val Pro Met Arg Thr Leu Val Pro Ala Thr Glu Ala Ile
            275                 280                 285
Lys Asn Ile Leu Pro Ala Leu Glu Leu Thr Asp Pro Tyr Glu Gln Asp
            290                 295                 300
Val Ile Gln Ala Gln Asn Val Ile Phe Cys Gln Val Cys Gln Leu Val
305                 310                 315                 320
Met Arg Lys Leu Ser Glu Leu Ile Ile Asn Asn Ala Thr Glu Glu Leu
                325                 330                 335
Leu Ile Lys Gly Leu Ser Lys Ala Cys Ser Leu Leu Pro Ala Pro Ala
            340                 345                 350
Ser Thr Lys Cys Gln Glu Val Leu Val Thr Phe Gly Pro Ser Leu Leu
            355                 360                 365
Asp Val Leu Met His Glu Val Asn Pro Asn Phe Leu Cys Gly Val Ile
            370                 375                 380
Ser Leu Cys Ser Ala Asn Pro Asn Leu Val Gly Thr Leu Glu Gln Pro
385                 390                 395                 400
Ala Ala Ala Ile Val Ser Ala Leu Pro Lys Glu Pro Ala Pro Pro Lys
                405                 410                 415
Gln Pro Glu Glu Pro Lys Gln Ser Ala Leu Arg Ala His Val Pro Pro
            420                 425                 430
Gln Lys Asn Gly Gly Phe Cys Glu Val Cys Lys Lys Leu Val Ile Tyr
            435                 440                 445
Leu Glu His Asn Leu Glu Lys Asn Ser Thr Lys Glu Glu Ile Leu Ala
450                 455                 460
Ala Leu Glu Lys Gly Cys Ser Phe Leu Pro Asp Pro Tyr Gln Lys Gln
465                 470                 475                 480
Cys Asp Glu Phe Val Ala Glu Tyr Glu Pro Leu Leu Leu Glu Ile Leu
                485                 490                 495
Val Glu Val Met Asp Pro Ser Phe Val Cys Ser Lys Ile Gly Val Cys
            500                 505                 510
Pro Ser Ala Tyr Lys Leu Leu Leu Gly Thr Glu Lys Cys Val Trp Gly
            515                 520                 525
Pro Gly Tyr Trp Cys Gln Asn Ser Glu Thr Ala Ala Arg Cys Asn Ala
            530                 535                 540
```

```
Val Asp His Cys Lys Arg His Val Trp Asn
545                 550
```

<210> SEQ ID NO 18
<211> LENGTH: 395
<212> TYPE: PRT
<213> ORGANISM: Rattus sp.

<400> SEQUENCE: 18

```
Met Lys Pro Ala Gln Ser Ser Ile Arg Pro Cys Arg Leu Arg Pro Pro
1               5                   10                  15

Asn Trp Ala Glu Gly Lys Asp Phe Trp Val Ser Asp Pro Lys Lys Gly
            20                  25                  30

Gln Ala Arg Asp Gly Thr Ala Leu Ala Val Ser Arg Ala Gly Ala Leu
        35                  40                  45

Gln Pro Ser Gly Gly Ala Gly Leu Gly Ser Gly Ala Lys Ala Ser His
    50                  55                  60

Val Arg Pro Ala Ala Leu Leu Ser Ser Ile Ser Leu Asn Gly Leu Arg
65                  70                  75                  80

Arg Gly Ser Pro Pro Ile Ser Thr Leu Trp Asn Ala Gly Arg Gly Glu
                85                  90                  95

Leu Gln Asp Arg Arg Asn His Leu Pro Lys Arg Gly Glu Glu Ala Glu
            100                 105                 110

Ser Gln Phe Lys Arg Arg Arg Glu Lys Asp Glu Glu Ser Gly Trp Pro
        115                 120                 125

Ile Glu Ala Ala Glu Asn Gly Arg Gln Ala Ser Phe Arg Phe Ala Ser
    130                 135                 140

Gly Gly Arg Lys Trp Pro Phe Leu Gly Gly Trp Lys Val Arg Lys Phe
145                 150                 155                 160

Val Arg Ala Ala Ala Lys Leu Arg Arg Asp Ala His Ser Trp Phe Ser
                165                 170                 175

Arg Leu Ser Arg Val Ser Gly Ala Gly Arg Arg Ala Gly Val Ala Arg
            180                 185                 190

Pro Gln Glu Val Ser Ser Pro Gly Gly Gly Arg Gly Gly Arg Arg
        195                 200                 205

Glu Pro Arg Leu Gly Ser Ala Pro Gly Gln Asp Leu Thr Ala Thr Met
    210                 215                 220

Ser Ser Lys Arg Ala Lys Thr Lys Thr Thr Lys Lys Arg Pro Gln Arg
225                 230                 235                 240

Ala Thr Ser Asn Val Phe Ala Met Phe Asp Gln Ser Gln Ile Gln Glu
                245                 250                 255

Phe Lys Glu Ala Phe Asn Met Ile Asp Gln Asn Arg Asp Gly Phe Ile
            260                 265                 270

Asp Lys Glu Asp Leu His Asp Met Leu Ala Ser Met Gly Lys Asn Pro
        275                 280                 285

Thr Asp Glu Tyr Leu Asp Ala Met Met Asn Glu Ala Pro Gly Pro Ile
    290                 295                 300

Asn Phe Thr Met Phe Leu Thr Met Phe Gly Glu Lys Leu Asn Gly Thr
305                 310                 315                 320

Asp Pro Glu Asp Val Ile Arg Asn Ala Phe Ala Cys Phe Asp Glu Glu
                325                 330                 335

Ala Ile Gly Thr Ile Gln Glu Asp Tyr Leu Arg Glu Leu Leu Thr Thr
            340                 345                 350

Met Gly Asp Arg Phe Thr Asp Glu Glu Val Asp Glu Leu Tyr Arg Glu
        355                 360                 365
```

```
Ala Pro Ile Asp Lys Lys Gly Asn Phe Asn Tyr Ile Glu Phe Thr Arg
        370                 375                 380

Ile Leu Lys His Gly Ala Lys Asp Lys Asp Asp
385                 390                 395

<210> SEQ ID NO 19
<211> LENGTH: 928
<212> TYPE: PRT
<213> ORGANISM: Rattus sp.

<400> SEQUENCE: 19

Met Gly Asp Met Gln Asp His Glu Lys Val Leu Glu Ile Pro Asp Arg
1               5                   10                  15

Asp Ser Glu Glu Leu Glu His Val Ile Glu Gln Ile Ala Tyr Arg
                20                  25                  30

Asp Leu Asp Ile Pro Val Thr Glu Met Gln Glu Ser Glu Ala Leu Pro
            35                  40                  45

Thr Glu Gln Thr Ala Thr Asp Tyr Ile Pro Thr Ser Thr Ser Thr Ser
    50                  55                  60

His Pro Ser Ser Gln Val Tyr Val Glu Leu Gln Glu Leu Met Met
65                  70                  75                  80

Asp Gln Arg Asn Gln Glu Leu Gln Trp Val Glu Ala Ala His Trp Ile
                85                  90                  95

Gly Leu Glu Glu Asn Leu Arg Glu Asp Gly Val Trp Gly Arg Pro His
            100                 105                 110

Leu Ser Tyr Leu Thr Phe Trp Ser Leu Leu Glu Leu Gln Lys Val Phe
        115                 120                 125

Ser Lys Gly Thr Phe Leu Leu Asp Leu Ala Glu Thr Ser Leu Ala Gly
    130                 135                 140

Val Ala Asn Lys Leu Leu Asp Ser Phe Ile Tyr Glu Asp Gln Ile Arg
145                 150                 155                 160

Pro Gln Asp Arg Asp Glu Leu Leu Arg Ala Leu Leu Lys Arg Ser
                165                 170                 175

His Ala Glu Asp Leu Lys Asp Leu Glu Gly Val Lys Pro Ala Val Leu
            180                 185                 190

Thr Arg Ser Gly Ala Pro Ser Glu Pro Leu Leu Pro His Gln Pro Ser
        195                 200                 205

Leu Glu Thr Lys Leu Tyr Cys Ala Gln Ala Glu Gly Gly Ser Glu Glu
    210                 215                 220

Pro Ser Pro Ser Gly Ile Leu Lys Ile Pro Pro Asn Ser Glu Thr Thr
225                 230                 235                 240

Leu Val Leu Val Gly Arg Ala Ser Phe Leu Val Lys Pro Val Leu Gly
                245                 250                 255

Phe Val Arg Leu Lys Glu Ala Val Pro Leu Glu Asp Leu Val Leu Pro
            260                 265                 270

Glu Pro Val Ser Phe Leu Val Leu Leu Gly Pro Glu Ala Pro His
        275                 280                 285

Ile Asp Tyr Thr Gln Leu Gly Arg Ala Ala Ala Thr Leu Met Thr Glu
    290                 295                 300

Arg Val Phe Arg Val Thr Ala Ser Leu Ala Gln Ser Arg Gly Glu Leu
305                 310                 315                 320

Leu Ser Ser Leu Asp Ser Phe Leu Asp Cys Ser Leu Val Leu Pro Pro
                325                 330                 335

Thr Glu Ala Pro Ser Gly Lys Ala Leu Leu Asn Leu Val Pro Val Gln
            340                 345                 350
```

```
Lys Glu Leu Leu Arg Lys Arg Tyr Leu Pro Arg Pro Ala Lys Pro Asp
            355                 360                 365

Pro Asn Leu Tyr Glu Ala Leu Ala Asp Gly Gly Lys Glu Gly Pro Gly
        370                 375                 380

Asp Glu Asp Asp Pro Leu Arg Arg Thr Gly Arg Ile Phe Gly Gly Leu
385                 390                 395                 400

Ile Arg Asp Ile Arg Arg Arg Tyr Pro Tyr Tyr Leu Ser Asp Ile Thr
                405                 410                 415

Asp Ala Leu Ser Pro Gln Val Leu Ala Ala Val Ile Phe Ile Tyr Phe
                420                 425                 430

Ala Ala Leu Ser Pro Ala Val Thr Phe Gly Gly Leu Leu Gly Glu Lys
            435                 440                 445

Thr Arg Asn Leu Met Gly Val Ser Glu Leu Leu Ile Ser Thr Ala Val
        450                 455                 460

Gln Gly Ile Leu Phe Ala Leu Leu Gly Ala Gln Pro Leu Leu Val Leu
465                 470                 475                 480

Gly Phe Ser Gly Pro Leu Leu Val Phe Glu Glu Ala Phe Tyr Ser Phe
                485                 490                 495

Cys Glu Ser Asn Asn Leu Glu Tyr Ile Val Gly Arg Ala Trp Ile Gly
                500                 505                 510

Phe Trp Leu Ile Leu Leu Val Val Leu Val Val Ala Phe Glu Gly Ser
            515                 520                 525

Phe Leu Val Gln Tyr Ile Ser Arg Tyr Thr Gln Glu Ile Phe Ser Phe
        530                 535                 540

Leu Ile Ser Leu Ile Phe Ile Tyr Glu Thr Phe Ser Lys Leu Ile Lys
545                 550                 555                 560

Ile Phe Gln Asp Tyr Pro Leu Gln Glu Ser Tyr Ala Pro Val Val Met
                565                 570                 575

Lys Pro Lys Pro Gln Gly Pro Val Pro Asn Thr Ala Leu Leu Ser Leu
                580                 585                 590

Val Leu Met Val Gly Thr Phe Leu Leu Ala Met Met Leu Arg Lys Phe
            595                 600                 605

Lys Asn Ser Thr Tyr Phe Pro Gly Lys Leu Arg Arg Val Ile Gly Asp
        610                 615                 620

Phe Gly Val Pro Ile Ser Ile Leu Ile Met Val Leu Val Asp Thr Phe
625                 630                 635                 640

Ile Lys Asn Thr Tyr Thr Gln Lys Leu Ser Val Pro Asp Gly Leu Lys
                645                 650                 655

Val Ser Asn Ser Ser Ala Arg Gly Trp Val Ile His Pro Leu Gly Leu
                660                 665                 670

Tyr Asn His Phe Pro Lys Trp Met Met Phe Ala Ser Val Leu Pro Ala
            675                 680                 685

Leu Leu Val Phe Ile Leu Ile Phe Leu Glu Ser Gln Ile Thr Thr Leu
        690                 695                 700

Ile Val Ser Lys Pro Glu Arg Lys Met Ile Lys Gly Ser Gly Phe His
705                 710                 715                 720

Leu Asp Leu Leu Leu Val Val Gly Met Gly Gly Val Ala Ala Leu Phe
                725                 730                 735

Gly Met Pro Trp Leu Ser Ala Thr Thr Val Arg Ser Val Thr His Ala
                740                 745                 750

Asn Ala Leu Thr Val Met Gly Lys Ala Ser Gly Pro Gly Ala Ala Ala
            755                 760                 765

Gln Ile Gln Glu Val Lys Glu Gln Arg Ile Ser Gly Leu Leu Val Ser
        770                 775                 780
```

```
Val Leu Val Gly Leu Ser Ile Leu Met Glu Pro Ile Leu Ser Arg Ile
785                 790                 795                 800

Pro Leu Ala Val Leu Phe Gly Ile Phe Leu Tyr Met Gly Ile Thr Ser
                805                 810                 815

Leu Ser Gly Ile Gln Leu Phe Asp Arg Ile Leu Leu Phe Lys Pro
            820                 825                 830

Pro Lys Tyr His Pro Asp Val Pro Phe Val Lys Arg Val Lys Thr Trp
            835                 840                 845

Arg Met His Leu Phe Thr Gly Ile Gln Ile Ile Cys Leu Ala Val Leu
            850                 855                 860

Trp Val Val Lys Ser Thr Pro Ala Ser Leu Ala Leu Pro Phe Val Leu
865                 870                 875                 880

Ile Leu Thr Val Pro Leu Arg Arg Leu Leu Pro Leu Ile Phe Arg
                885                 890                 895

Glu Leu Glu Leu Gln Cys Leu Asp Gly Asp Asp Ala Lys Val Thr Phe
                900                 905                 910

Asp Glu Ala Glu Gly Leu Asp Glu Tyr Asp Glu Val Pro Met Pro Val
            915                 920                 925

<210> SEQ ID NO 20
<211> LENGTH: 199
<212> TYPE: PRT
<213> ORGANISM: Rattus sp.

<400> SEQUENCE: 20

Met Ala Asn Arg Gly Pro Ser Tyr Gly Leu Ser Arg Glu Val Gln Gln
1               5                   10                  15

Lys Ile Glu Lys Gln Tyr Asp Pro Asp Leu Glu Gln Ile Leu Ile Gln
            20                  25                  30

Trp Ile Thr Thr Gln Cys Arg Lys Gly Val Ser Gln Pro Gln Pro Gly
        35                  40                  45

Arg Glu Asn Phe Gln Asn Trp Leu Lys Asp Gly Thr Val Leu Cys Glu
    50                  55                  60

Leu Ile Asn Ser Leu Tyr Pro Glu Gly Gln Ala Pro Val Lys Lys Ile
65                  70                  75                  80

Gln Ala Ser Thr Met Ala Phe Lys Gln Met Glu Gln Ile Ser Gln Phe
                85                  90                  95

Leu Gln Ala Ala Glu Arg Tyr Gly Ile Asn Thr Thr Asp Ile Phe Gln
            100                 105                 110

Thr Val Asp Leu Trp Glu Gly Lys Asn Met Ala Cys Val Gln Arg Thr
        115                 120                 125

Leu Met Asn Leu Gly Gly Leu Ala Val Ala Arg Asp Asp Gly Leu Phe
    130                 135                 140

Ser Gly Asp Pro Asn Trp Phe Pro Lys Lys Ser Lys Glu Asn Pro Arg
145                 150                 155                 160

Asn Phe Ser Asp Asn Gln Leu Gln Glu Gly Lys Asn Val Ile Gly Leu
                165                 170                 175

Gln Met Gly Thr Asn Arg Gly Ala Ser Gln Ala Gly Met Thr Gly Tyr
            180                 185                 190

Gly Met Pro Arg Gln Ile Leu
        195

<210> SEQ ID NO 21
<211> LENGTH: 247
<212> TYPE: PRT
<213> ORGANISM: Rattus sp.
```

<400> SEQUENCE: 21

```
Met Ala Gly Ser Thr Thr Ile Glu Ala Val Lys Arg Lys Ile Gln Val
1               5                   10                  15

Leu Gln Gln Ala Asp Asp Ala Glu Glu Arg Ala Glu Arg Leu Gln
            20                  25                  30

Arg Glu Val Glu Gly Glu Arg Ala Arg Glu Gln Ala Glu Ala Glu
            35                  40                  45

Val Ala Ser Leu Asn Arg Arg Ile Gln Leu Val Glu Glu Glu Leu Asp
    50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Leu Lys Asp Glu Glu Lys Met Glu Leu Gln Glu Ile Gln Leu
            100                 105                 110

Lys Glu Ala Lys His Ile Ala Glu Glu Ala Asp Arg Lys Tyr Glu Glu
            115                 120                 125

Val Ala Arg Lys Leu Val Ile Ile Glu Gly Asp Leu Glu Arg Thr Glu
        130                 135                 140

Glu Arg Ala Glu Leu Ala Glu Ser Lys Cys Ser Glu Leu Glu Glu Glu
145                 150                 155                 160

Leu Lys Asn Val Thr Asn Asn Leu Lys Ser Leu Glu Ala Gln Ala Glu
                165                 170                 175

Lys Tyr Ser Gln Lys Glu Asp Lys Tyr Glu Glu Glu Ile Lys Ile Leu
            180                 185                 190

Thr Asp Lys Leu Lys Glu Ala Glu Thr Arg Ala Glu Phe Ala Glu Arg
        195                 200                 205

Ser Val Ala Lys Leu Glu Lys Thr Ile Asp Asp Leu Glu Glu Arg Leu
    210                 215                 220

Tyr Ser Gln Leu Glu Arg Asn Arg Leu Leu Ser Asn Glu Leu Lys Leu
225                 230                 235                 240

Thr Leu His Gly Leu Cys Asp
                245
```

<210> SEQ ID NO 22
<211> LENGTH: 2541
<212> TYPE: PRT
<213> ORGANISM: Rattus sp.

<400> SEQUENCE: 22

```
Met Val Ala Leu Ser Leu Arg Ile Ser Ile Gly Asn Val Val Lys Thr
1               5                   10                  15

Met Gln Phe Glu Pro Ser Thr Met Val Tyr Asp Ala Cys Arg Met Ile
            20                  25                  30

Arg Glu Arg Ile Pro Glu Ala Leu Ala Gly Pro Pro Ser Asp Phe Gly
            35                  40                  45

Leu Phe Leu Ser Asp Asp Asp Pro Lys Lys Gly Ile Trp Leu Glu Ala
    50                  55                  60

Gly Lys Ala Leu Asp Tyr Tyr Met Leu Arg Asn Gly Asp Thr Met Glu
65                  70                  75                  80

Tyr Arg Lys Lys Gln Arg Pro Leu Lys Ile Arg Met Leu Asp Gly Thr
                85                  90                  95

Val Lys Thr Ile Met Val Asp Asp Ser Lys Thr Val Thr Asp Met Leu
            100                 105                 110
```

```
Met Thr Ile Cys Ala Arg Ile Gly Ile Thr Asn His Asp Glu Tyr Ser
            115                 120                 125

Leu Val Arg Glu Leu Met Glu Glu Lys Lys Asp Glu Gly Thr Gly Thr
        130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175

Gly Arg Thr Leu Arg Glu Gln Gly Val Glu Glu His Glu Thr Leu Leu
            180                 185                 190

Leu Arg Arg Lys Phe Phe Tyr Ser Asp Gln Asn Val Asp Ser Arg Asp
        195                 200                 205

Pro Val Gln Leu Asn Leu Leu Tyr Val Gln Ala Arg Asp Asp Ile Leu
210                 215                 220

Asn Gly Ser His Pro Val Ser Phe Asp Lys Ala Cys Glu Phe Ala Gly
225                 230                 235                 240

Phe Gln Cys Gln Ile Gln Phe Gly Pro His Asn Glu Gln Lys His Lys
                245                 250                 255

Ala Gly Phe Leu Asp Leu Lys Asp Phe Leu Pro Lys Glu Tyr Val Lys
            260                 265                 270

Gln Lys Gly Glu Arg Lys Ile Phe Gln Ala His Lys Asn Cys Gly Gln
        275                 280                 285

Met Ser Glu Ile Glu Ala Lys Val Arg Tyr Val Lys Leu Ala Arg Ser
290                 295                 300

Leu Lys Thr Tyr Gly Val Ser Phe Phe Leu Val Lys Glu Lys Met Lys
305                 310                 315                 320

Gly Lys Asn Lys Leu Val Pro Arg Leu Leu Gly Ile Thr Lys Glu Cys
                325                 330                 335

Val Met Arg Val Asp Glu Lys Thr Lys Glu Val Ile Gln Glu Trp Ser
            340                 345                 350

Leu Thr Asn Ile Lys Arg Trp Ala Ala Ser Pro Lys Ser Phe Thr Leu
        355                 360                 365

Asp Phe Gly Asp Tyr Gln Asp Gly Tyr Tyr Ser Val Gln Thr Thr Glu
370                 375                 380

Gly Glu Gln Ile Ala Gln Leu Ile Ala Gly Tyr Ile Asp Ile Ile Leu
385                 390                 395                 400

Lys Lys Lys Lys Ser Lys Asp His Phe Gly Leu Glu Gly Asp Glu Glu
                405                 410                 415

Ser Thr Met Leu Glu Asp Ser Val Ser Pro Lys Lys Ser Thr Val Leu
            420                 425                 430

Gln Gln Gln Tyr Asn Arg Val Gly Lys Ala Glu His Gly Ser Val Ala
        435                 440                 445

Leu Pro Ala Ile Met Arg Ser Gly Ala Ser Gly Pro Glu Asn Phe Gln
450                 455                 460

Val Gly Ser Met Pro Pro Ala Gln Gln Gln Val Thr Ser Gly Gln Met
465                 470                 475                 480

His Arg Gly His Met Pro Pro Leu Thr Ser Ala Gln Gln Ala Leu Thr
                485                 490                 495

Gly Thr Ile Asn Ser Ser Met Gln Ala Val Gln Ala Ala Gln Ala Ala
            500                 505                 510

Leu Asp Asp Phe Asp Ala Leu Pro Pro Leu Gly Gln Asp Ala Ala Ser
        515                 520                 525

Lys Ala Trp Arg Lys Asn Lys Met Asp Glu Ser Lys His Glu Ile His
530                 535                 540
```

```
Ser Gln Val Asp Ala Ile Thr Ala Gly Thr Ala Ser Val Val Asn Leu
545                 550                 555                 560

Thr Ala Gly Asp Pro Ala Glu Thr Asp Tyr Thr Ala Val Gly Cys Ala
                565                 570                 575

Val Thr Thr Ile Ser Ser Asn Leu Thr Glu Met Ser Arg Gly Val Lys
                580                 585                 590

Leu Leu Ala Ala Leu Leu Glu Asp Glu Gly Gly Asn Gly Arg Pro Leu
            595                 600                 605

Leu Gln Ala Ala Lys Gly Leu Ala Gly Ala Val Ser Glu Leu Leu Arg
610                 615                 620

Ser Ala Gln Pro Ala Ser Ala Glu Pro Arg Gln Asn Leu Leu Gln Ala
625                 630                 635                 640

Ala Gly Asn Val Gly Gln Ala Ser Gly Glu Leu Leu Gln Gln Ile Gly
                645                 650                 655

Glu Ser Asp Thr Asp Pro His Phe Gln Asp Ile Leu Met Gln Leu Ala
                660                 665                 670

Lys Ala Val Ala Ser Ala Ala Ala Leu Val Leu Lys Ala Lys Ser
            675                 680                 685

Val Ala Gln Arg Thr Glu Asp Ser Gly Leu Gln Thr Gln Val Ile Ala
                690                 695                 700

Ala Ala Thr Gln Cys Ala Leu Ser Thr Ser Gln Leu Val Ala Cys Thr
705                 710                 715                 720

Lys Val Val Ala Pro Thr Ile Ser Ser Pro Val Cys Gln Glu Gln Leu
                725                 730                 735

Val Glu Ala Gly Arg Leu Val Ala Lys Ala Val Glu Gly Cys Val Ser
                740                 745                 750

Ala Ser Gln Ala Ala Thr Glu Asp Gly Gln Leu Leu Arg Gly Val Gly
            755                 760                 765

Ala Ala Ala Thr Ala Val Thr Gln Ala Leu Asn Glu Leu Leu Gln His
            770                 775                 780

Val Lys Ala His Ala Thr Gly Ala Gly Pro Ala Gly Arg Tyr Asp Gln
785                 790                 795                 800

Ala Thr Asp Thr Ile Leu Thr Val Thr Glu Asn Ile Phe Ser Ser Met
                805                 810                 815

Gly Asp Ala Gly Glu Met Val Arg Gln Ala Arg Ile Leu Ala Gln Ala
                820                 825                 830

Thr Ser Asp Leu Val Asn Ala Ile Lys Ala Asp Ala Glu Gly Glu Ser
            835                 840                 845

Asp Leu Glu Asn Ser Arg Lys Leu Leu Ser Ala Ala Lys Ile Leu Ala
850                 855                 860

Asp Ala Thr Ala Lys Met Val Glu Ala Ala Lys Gly Ala Ala Ala His
865                 870                 875                 880

Pro Asp Ser Glu Glu Gln Gln Gln Arg Leu Arg Glu Ala Ala Glu Gly
                885                 890                 895

Leu Arg Met Ala Thr Asn Ala Ala Gln Asn Ala Ile Lys Lys Lys
            900                 905                 910

Leu Val Gln Arg Leu Glu His Ala Ala Lys Gln Ala Ala Ala Ser Ala
            915                 920                 925

Thr Gln Thr Ile Ala Ala Ala Gln His Ala Ala Ser Ala Pro Lys Ala
            930                 935                 940

Ser Ala Gly Pro Gln Pro Leu Leu Val Gln Ser Cys Lys Ala Val Ala
945                 950                 955                 960

Glu Gln Ile Pro Leu Leu Val Gln Gly Val Arg Gly Ser Gln Ala Gln
```

-continued

```
                 965                 970                 975
Pro Asp Ser Pro Ser Ala Gln Leu Ala Leu Ile Ala Ala Ser Gln Ser
                 980                 985                 990
Phe Leu Gln Pro Gly Gly Lys Met Val Ala Ala Lys Ala Ser Val
             995                1000               1005
Pro Thr Ile Gln Asp Gln Ala Ser Ala Met Gln Leu Ser Gln Cys
    1010                1015                1020
Ala Lys Asn Leu Gly Thr Ala Leu Ala Glu Leu Arg Thr Ala Ala
    1025                1030                1035
Gln Lys Ala Gln Glu Ala Cys Gly Pro Leu Glu Met Asp Ser Ala
    1040                1045                1050
Leu Ser Val Val Gln Asn Leu Glu Lys Asp Leu Gln Glu Ile Lys
    1055                1060                1065
Ala Ala Ala Arg Glu Gly Lys Leu Lys Pro Leu Pro Gly Glu Thr
    1070                1075                1080
Met Glu Lys Cys Thr Gln Asp Leu Gly Asn Ser Thr Lys Ala Val
    1085                1090                1095
Ser Ser Ala Ile Ala Lys Leu Leu Gly Glu Ile Ala Gln Gly Asn
    1100                1105                1110
Glu Asn Tyr Ala Gly Ile Ala Ala Arg Asp Val Ala Gly Gly Leu
    1115                1120                1125
Arg Ser Leu Ala Gln Ala Ala Arg Gly Val Ala Ala Leu Thr Thr
    1130                1135                1140
Asp Pro Ala Val Gln Ala Ile Val Leu Asp Thr Ala Ser Asp Ala
    1145                1150                1155
Leu Asp Lys Ala Ser Ser Leu Ile Glu Glu Ala Lys Lys Ala Ser
    1160                1165                1170
Gly His Pro Gly Asp Pro Glu Ser Gln Gln Arg Leu Ala Gln Val
    1175                1180                1185
Ala Lys Ala Val Thr Gln Ala Leu Asn Arg Cys Val Ser Cys Leu
    1190                1195                1200
Pro Gly Gln Arg Asp Val Asp Asn Ala Leu Arg Ala Val Gly Asp
    1205                1210                1215
Ala Ser Lys Arg Leu Leu Ser Asp Ser Leu Pro Pro Ser Thr Gly
    1220                1225                1230
Thr Phe Gln Glu Ala Gln Ser Arg Leu Asn Glu Ala Ala Ala Gly
    1235                1240                1245
Leu Asn Gln Ala Ala Thr Glu Leu Val Gln Ala Ser Arg Gly Thr
    1250                1255                1260
Pro Gln Asp Leu Ala Arg Ala Ser Gly Arg Phe Gly Gln Asp Phe
    1265                1270                1275
Ser Thr Phe Leu Glu Ala Gly Val Glu Met Ala Gly Gln Ala Pro
    1280                1285                1290
Ser Gln Glu Asp Arg Ala Gln Val Val Ser Asn Leu Lys Gly Ile
    1295                1300                1305
Ser Met Ser Ser Ser Lys Leu Leu Leu Ala Ala Lys Ala Leu Ser
    1310                1315                1320
Thr Asp Pro Ala Ala Pro Asn Leu Lys Ser Gln Leu Ala Ala Ala
    1325                1330                1335
Ala Arg Ala Val Thr Asp Ser Ile Asn Gln Leu Ile Thr Met Cys
    1340                1345                1350
Thr Gln Gln Ala Pro Gly Gln Lys Glu Cys Asp Asn Ala Leu Arg
    1355                1360                1365
```

-continued

```
Gln Leu Glu Thr Val Arg Glu Leu Leu Glu Asn Pro Val Gln Pro
    1370            1375                1380

Ile Asn Asp Met Ser Tyr Phe Gly Cys Leu Asp Ser Val Met Glu
    1385            1390                1395

Asn Ser Lys Val Leu Gly Glu Ala Met Thr Gly Ile Ser Gln Asn
    1400            1405                1410

Ala Lys Asn Gly Asn Leu Pro Glu Phe Gly Asp Ala Ile Ala Thr
    1415            1420                1425

Ala Ser Lys Ala Leu Cys Gly Phe Thr Glu Ala Ala Ala Gln Ala
    1430            1435                1440

Ala Tyr Leu Val Gly Val Ser Asp Pro Asn Ser Gln Ala Gly Gln
    1445            1450                1455

Gln Gly Leu Val Glu Pro Thr Gln Phe Ala Arg Ala Asn Gln Ala
    1460            1465                1470

Ile Gln Met Ala Cys Gln Ser Leu Gly Glu Pro Gly Cys Thr Gln
    1475            1480                1485

Ala Gln Val Leu Ser Ala Ala Thr Ile Val Ala Lys His Thr Ser
    1490            1495                1500

Ala Leu Cys Asn Ser Cys Arg Leu Ala Ser Ala Arg Thr Ala Asn
    1505            1510                1515

Pro Thr Ala Lys Arg Gln Phe Val Gln Ser Ala Lys Glu Val Ala
    1520            1525                1530

Asn Ser Thr Ala Asn Leu Val Lys Thr Ile Lys Ala Leu Asp Gly
    1535            1540                1545

Ala Phe Thr Glu Glu Asn Arg Ala Gln Cys Arg Ala Ala Thr Ala
    1550            1555                1560

Pro Leu Leu Glu Ala Val Asp Asn Leu Ser Ala Phe Ala Ser Asn
    1565            1570                1575

Pro Glu Phe Ser Ser Val Pro Ala Gln Ile Ser Pro Glu Gly Arg
    1580            1585                1590

Ala Ala Met Glu Pro Ile Val Ile Ser Ala Lys Thr Met Leu Glu
    1595            1600                1605

Ser Ala Gly Gly Leu Ile Gln Thr Ala Arg Ala Leu Ala Val Asn
    1610            1615                1620

Pro Arg Asp Pro Pro Arg Trp Ser Val Leu Ala Gly His Ser Arg
    1625            1630                1635

Thr Val Ser Asp Ser Ile Lys Lys Leu Ile Thr Ser Met Arg Asp
    1640            1645                1650

Lys Ala Pro Gly Gln Leu Glu Cys Glu Thr Ala Ile Ala Ala Leu
    1655            1660                1665

Asn Ser Cys Leu Arg Asp Leu Asp Gln Ala Ser Leu Ala Ala Val
    1670            1675                1680

Ser Gln Gln Leu Ala Pro Arg Glu Gly Ile Ser Gln Glu Ala Leu
    1685            1690                1695

His Thr Gln Met Leu Thr Ala Val Gln Glu Ile Ser His Leu Ile
    1700            1705                1710

Glu Pro Leu Ala Ser Ala Ala Arg Ala Glu Ala Ser Gln Leu Gly
    1715            1720                1725

His Lys Val Ser Gln Met Ala Gln Tyr Phe Glu Pro Leu Thr Leu
    1730            1735                1740

Ala Ala Val Gly Ala Ala Ser Lys Thr Leu Ser His Pro Gln Gln
    1745            1750                1755

Met Ala Leu Leu Asp Gln Thr Lys Thr Leu Ala Glu Ser Ala Leu
    1760            1765                1770
```

```
Gln Leu Leu Tyr Thr Ala Lys Glu Ala Gly Gly Asn Pro Lys Gln
    1775                1780                1785

Ala Ala His Thr Gln Glu Ala Leu Glu Glu Ala Val Gln Met Met
    1790                1795                1800

Thr Glu Ala Val Glu Asp Leu Thr Thr Thr Leu Asn Glu Ala Ala
    1805                1810                1815

Ser Ala Ala Gly Val Val Gly Gly Met Val Asp Ser Ile Thr Gln
    1820                1825                1830

Ala Ile Asn Gln Leu Asp Glu Gly Pro Met Gly Glu Pro Glu Gly
    1835                1840                1845

Ser Phe Val Asp Tyr Gln Thr Thr Met Val Arg Thr Ala Lys Ala
    1850                1855                1860

Ile Ala Val Thr Val Gln Glu Met Val Thr Lys Ser Asn Thr Ser
    1865                1870                1875

Pro Glu Glu Leu Gly Pro Leu Ala Asn Gln Leu Thr Ser Asp Tyr
    1880                1885                1890

Gly Arg Leu Ala Ser Gln Ala Lys Pro Ala Ala Val Ala Ala Glu
    1895                1900                1905

Asn Glu Glu Ile Gly Ala His Ile Lys His Arg Val Gln Glu Leu
    1910                1915                1920

Gly His Gly Cys Ser Ala Leu Val Thr Lys Ala Gly Ala Leu Gln
    1925                1930                1935

Cys Ser Pro Ser Asp Val Tyr Thr Lys Lys Glu Leu Ile Glu Cys
    1940                1945                1950

Ala Arg Arg Val Ser Glu Lys Val Ser His Val Leu Ala Ala Leu
    1955                1960                1965

Gln Ala Gly Asn Arg Gly Thr Gln Ala Cys Ile Thr Ala Ala Ser
    1970                1975                1980

Ala Val Ser Gly Ile Ile Ala Asp Leu Asp Thr Thr Ile Met Phe
    1985                1990                1995

Ala Thr Ala Gly Thr Leu Asn Arg Glu Gly Ala Glu Thr Phe Ala
    2000                2005                2010

Asp His Arg Glu Gly Ile Leu Lys Thr Ala Lys Val Leu Val Glu
    2015                2020                2025

Asp Thr Lys Val Leu Val Gln Asn Ala Ala Gly Ser Gln Glu Lys
    2030                2035                2040

Leu Ala Gln Ala Ala Gln Ser Ser Val Ala Thr Ile Thr Arg Leu
    2045                2050                2055

Ala Asp Val Val Lys Leu Gly Ala Ala Ser Leu Gly Ala Glu Asp
    2060                2065                2070

Pro Glu Thr Gln Val Val Leu Ile Asn Ala Val Lys Asp Val Ala
    2075                2080                2085

Lys Ala Leu Gly Asp Leu Ile Ser Ala Thr Lys Ala Ala Ala Gly
    2090                2095                2100

Lys Val Gly Asp Asp Pro Ala Val Trp Gln Leu Lys Asn Ser Ala
    2105                2110                2115

Lys Val Met Val Thr Asn Val Thr Ser Leu Leu Lys Thr Val Lys
    2120                2125                2130

Ala Val Glu Asp Glu Ala Thr Lys Gly Thr Arg Ala Leu Glu Ala
    2135                2140                2145

Thr Thr Glu His Ile Arg Gln Glu Leu Ala Val Phe Cys Ser Pro
    2150                2155                2160

Glu Pro Pro Ala Lys Thr Ser Thr Pro Glu Asp Phe Ile Arg Met
```

```
                    2165                2170                2175

Thr Lys Gly Ile Thr Met Ala Thr Ala Lys Ala Val Ala Ala Gly
        2180                2185                2190

Asn Ser Cys Arg Gln Glu Asp Val Ile Ala Thr Ala Asn Leu Ser
        2195                2200                2205

Arg Arg Ala Ile Ala Asp Met Leu Arg Ala Cys Lys Glu Ala Ala
        2210                2215                2220

Phe His Pro Glu Val Ala Pro Asp Val Arg Leu Arg Ala Leu His
        2225                2230                2235

Phe Gly Arg Glu Cys Ala Asn Gly Tyr Leu Glu Leu Leu Asp His
        2240                2245                2250

Val Leu Leu Thr Leu Gln Lys Pro Asn Pro Glu Leu Lys Gln Gln
        2255                2260                2265

Leu Thr Gly His Ser Lys Arg Val Ala Gly Ser Val Thr Glu Leu
        2270                2275                2280

Ile Gln Ala Ala Glu Ala Met Lys Gly Thr Glu Trp Val Asp Pro
        2285                2290                2295

Glu Asp Pro Thr Val Ile Ala Glu Asn Glu Leu Leu Gly Ala Ala
        2300                2305                2310

Ala Ala Ile Glu Ala Ala Ala Lys Lys Leu Glu Gln Leu Lys Pro
        2315                2320                2325

Arg Ala Lys Pro Lys Glu Ala Asp Glu Ser Leu Asn Phe Glu Glu
        2330                2335                2340

Gln Ile Leu Glu Ala Ala Lys Ser Ile Ala Ala Ala Thr Ser Ala
        2345                2350                2355

Leu Val Lys Ala Ala Ser Ala Ala Gln Arg Glu Leu Val Ala Gln
        2360                2365                2370

Gly Lys Val Gly Ala Ile Pro Ala Asn Ala Leu Asp Asp Gly Gln
        2375                2380                2385

Trp Ser Gln Gly Leu Ile Ser Ala Ala Arg Met Val Ala Ala Ala
        2390                2395                2400

Thr Asn Asn Leu Cys Glu Ala Ala Asn Ala Ala Val Gln Gly His
        2405                2410                2415

Ala Ser Gln Glu Lys Leu Ile Ser Ser Ala Lys Gln Val Ala Ala
        2420                2425                2430

Ser Thr Ala Gln Leu Leu Val Ala Cys Lys Val Lys Ala Asp Gln
        2435                2440                2445

Asp Ser Glu Ala Met Lys Arg Leu Gln Ala Ala Gly Asn Ala Val
        2450                2455                2460

Lys Arg Ala Ser Asp Asn Leu Val Lys Ala Ala Gln Lys Ala Ala
        2465                2470                2475

Ala Phe Glu Asp Gln Glu Asn Glu Thr Val Val Lys Glu Lys
        2480                2485                2490

Met Val Gly Gly Ile Ala Gln Ile Ile Ala Ala Gln Glu Glu Met
        2495                2500                2505

Leu Arg Lys Glu Arg Glu Leu Glu Glu Ala Arg Lys Lys Leu Ala
        2510                2515                2520

Gln Ile Arg Gln Gln Gln Tyr Lys Phe Leu Pro Ser Glu Leu Arg
        2525                2530                2535

Asp Glu His
        2540

<210> SEQ ID NO 23
<211> LENGTH: 191
```

```
<212> TYPE: PRT
<213> ORGANISM: Rattus sp.

<400> SEQUENCE: 23

Met Ser Ala Ala Glu Val Gly Thr Phe Val Gln Arg Leu Arg Gly Leu
1               5                   10                  15

Met Ser Glu Ile Ala Ala Phe Pro Ala Pro Thr Ile Ala Ala Met Asp
            20                  25                  30

Gly Phe Ala Leu Gly Gly Gly Leu Glu Leu Ala Leu Ala Cys Asp Leu
        35                  40                  45

Arg Ile Ala Ala Ser Ser Ala Val Met Gly Leu Ile Glu Thr Thr Arg
50                  55                  60

Gly Leu Leu Pro Gly Ala Gly Gly Thr Gln Arg Leu Pro Arg Cys Leu
65                  70                  75                  80

Gly Val Ala Leu Ala Lys Glu Leu Ile Phe Thr Gly Arg Arg Leu Asn
                85                  90                  95

Gly Val Gln Ala His Glu Leu Gly Leu Val Asn His Ala Val Ala Gln
            100                 105                 110

Asn Glu Glu Gly Asp Ala Ala Tyr His Arg Ala Leu Ala Leu Ala Gln
        115                 120                 125

Glu Ile Leu Pro Gln Ala Pro Ile Ala Val Arg Leu Gly Lys Val Ala
130                 135                 140

Ile Asp Arg Gly Met Glu Val Asp Ile Ala Ser Gly Met Ala Ile Glu
145                 150                 155                 160

His Met Cys Tyr Ala Gln Asn Ile Pro Thr Gln Asp Arg Leu Glu Gly
                165                 170                 175

Met Ala Ala Phe Arg Glu Lys Arg Pro Pro Lys Phe Val Gly Lys
            180                 185                 190

<210> SEQ ID NO 24
<211> LENGTH: 425
<212> TYPE: PRT
<213> ORGANISM: Rattus sp.

<400> SEQUENCE: 24

Met Asn Tyr Ser Arg Phe Leu Thr Ala Thr Ser Leu Ala Arg Lys Thr
1               5                   10                  15

Ser Pro Ile Arg Ala Thr Val Glu Ile Met Ser Arg Ala Pro Lys Asp
            20                  25                  30

Ile Ile Ser Leu Ala Pro Gly Ser Pro Asn Pro Lys Val Phe Pro Phe
        35                  40                  45

Lys Ser Ala Val Phe Thr Val Glu Asn Gly Ser Thr Ile Arg Phe Glu
50                  55                  60

Gly Glu Met Phe Gln Arg Ala Leu Gln Tyr Ser Ser Tyr Gly Ile
65                  70                  75                  80

Pro Glu Leu Leu Ser Trp Leu Lys Gln Leu Gln Ile Lys Leu His Asn
                85                  90                  95

Pro Pro Thr Val Asn Tyr Ser Pro Asn Glu Gly Gln Met Asp Leu Cys
            100                 105                 110

Ile Thr Ser Gly Cys Gln Asp Gly Leu Cys Lys Val Phe Glu Met Leu
        115                 120                 125

Ile Asn Pro Gly Asp Thr Val Leu Val Asn Glu Pro Leu Tyr Ser Gly
130                 135                 140

Ala Leu Phe Ala Met Lys Pro Leu Gly Cys Asn Phe Ile Ser Val Pro
145                 150                 155                 160

Ser Asp Asp Cys Gly Ile Ile Pro Glu Gly Leu Lys Lys Val Leu Ser
```

```
                    165                 170                 175
Gln Trp Lys Pro Glu Asp Ser Lys Asp Pro Thr Lys Arg Thr Pro Lys
            180                 185                 190

Phe Leu Tyr Thr Ile Pro Asn Gly Asn Asn Pro Thr Gly Asn Ser Leu
            195                 200                 205

Thr Gly Asp Arg Lys Lys Glu Ile Tyr Glu Leu Ala Arg Lys Tyr Asp
            210                 215                 220

Phe Leu Ile Ile Glu Asp Pro Tyr Tyr Phe Leu Gln Phe Thr Lys
225                 230                 235                 240

Pro Trp Glu Pro Thr Phe Leu Ser Met Asp Val Asp Gly Arg Val Ile
            245                 250                 255

Arg Ala Asp Ser Leu Ser Lys Val Ile Ser Ser Gly Leu Arg Val Gly
            260                 265                 270

Phe Ile Thr Gly Pro Lys Ser Leu Ile Gln Arg Ile Val Leu His Thr
            275                 280                 285

Gln Ile Ser Ser Leu His Pro Cys Thr Leu Ser Gln Leu Met Ile Ser
            290                 295                 300

Glu Leu Leu Tyr Gln Trp Gly Glu Gly Phe Leu Ala His Val Asp
305                 310                 315                 320

Arg Ala Ile Asp Phe Tyr Lys Asn Gln Arg Asp Phe Ile Leu Ala Ala
            325                 330                 335

Ala Asp Lys Trp Leu Arg Gly Leu Ala Glu Trp His Val Pro Lys Ala
            340                 345                 350

Gly Met Phe Leu Trp Ile Lys Val Asn Gly Ile Ser Asp Ala Lys Lys
            355                 360                 365

Leu Ile Glu Glu Lys Ala Ile Glu Arg Glu Ile Leu Leu Val Pro Gly
            370                 375                 380

Asn Ser Phe Phe Val Asp Asn Ser Ala Pro Ser Ser Phe Arg Ala
385                 390                 395                 400

Ser Phe Ser Gln Val Thr Pro Ala Gln Met Asp Leu Val Phe Gln Arg
            405                 410                 415

Leu Ala Gln Leu Ile Lys Asp Val Ser
            420                 425

<210> SEQ ID NO 25
<211> LENGTH: 699
<212> TYPE: PRT
<213> ORGANISM: Rattus sp.

<400> SEQUENCE: 25

Met Glu Val His Glu Leu Phe Arg Tyr Phe Arg Met Pro Glu Leu Ile
1               5                   10                  15

Asp Ile Arg Gln Tyr Val Arg Thr Leu Pro Thr Asn Thr Leu Met Gly
            20                  25                  30

Phe Gly Ala Phe Ala Ala Leu Thr Thr Phe Trp Tyr Ala Thr Arg Pro
        35                  40                  45

Lys Ala Leu Lys Pro Pro Cys Asp Leu Ser Met Gln Ser Val Glu Val
    50                  55                  60

Thr Gly Thr Thr Glu Gly Val Arg Arg Ser Ala Val Leu Glu Asp Asp
65              70                  75                  80

Lys Leu Leu Leu Tyr Tyr Asp Asp Val Arg Thr Met Tyr Asp Gly
            85                  90                  95

Phe Gln Arg Gly Ile Gln Val Ser Asn Asp Gly Pro Cys Leu Gly Ser
            100                 105                 110

Arg Lys Pro Asn Gln Pro Tyr Glu Trp Ile Ser Tyr Lys Gln Val Ala
```

```
                    115                 120                 125
Glu Met Ala Glu Cys Ile Gly Ser Ala Leu Ile Gln Lys Gly Phe Lys
130                 135                 140
Pro Cys Ser Glu Gln Phe Ile Gly Ile Phe Ser Gln Asn Arg Pro Glu
145                 150                 155                 160
Trp Val Thr Ile Glu Gln Gly Cys Phe Thr Tyr Ser Met Val Val Val
                    165                 170                 175
Pro Leu Tyr Asp Thr Leu Gly Thr Asp Ala Ile Thr Tyr Ile Val Asn
                180                 185                 190
Lys Ala Glu Leu Ser Val Ile Phe Ala Asp Lys Pro Glu Lys Ala Lys
                195                 200                 205
Leu Leu Leu Glu Gly Val Glu Asn Lys Leu Thr Pro Cys Leu Lys Ile
210                 215                 220
Ile Val Ile Met Asp Ser Tyr Asp Asn Asp Leu Val Glu Arg Gly Gln
225                 230                 235                 240
Lys Cys Gly Val Glu Ile Ile Gly Leu Lys Ala Leu Glu Asp Leu Gly
                    245                 250                 255
Arg Val Asn Arg Thr Lys Pro Lys Pro Pro Glu Pro Glu Asp Leu Ala
                260                 265                 270
Ile Ile Cys Phe Thr Ser Gly Thr Thr Gly Asn Pro Lys Gly Ala Met
                275                 280                 285
Val Thr His Gln Asn Ile Met Asn Asp Cys Ser Gly Phe Ile Lys Ala
                290                 295                 300
Thr Glu Ser Ala Phe Ile Ala Ser Pro Glu Asp Val Leu Ile Ser Phe
305                 310                 315                 320
Leu Pro Leu Ala His Met Phe Glu Thr Val Val Glu Cys Val Met Leu
                    325                 330                 335
Cys His Gly Ala Lys Ile Gly Phe Phe Gln Gly Asp Ile Arg Leu Leu
                    340                 345                 350
Met Asp Asp Leu Lys Val Leu Gln Pro Thr Ile Phe Pro Val Val Pro
                355                 360                 365
Arg Leu Leu Asn Arg Met Phe Asp Arg Ile Phe Gly Gln Ala Asn Thr
                370                 375                 380
Ser Val Lys Arg Trp Leu Leu Asp Phe Ala Ser Lys Arg Lys Glu Ala
385                 390                 395                 400
Glu Leu Arg Ser Gly Ile Val Arg Asn Asn Ser Leu Trp Asp Lys Leu
                    405                 410                 415
Ile Phe His Lys Ile Gln Ser Ser Leu Gly Gly Lys Val Arg Leu Met
                    420                 425                 430
Ile Thr Gly Ala Ala Pro Val Ser Ala Thr Val Leu Thr Phe Leu Arg
                435                 440                 445
Ala Ala Leu Gly Cys Gln Phe Tyr Glu Gly Tyr Gly Gln Thr Glu Cys
                450                 455                 460
Thr Ala Gly Cys Cys Leu Ser Leu Pro Gly Asp Trp Thr Ala Gly His
465                 470                 475                 480
Val Gly Ala Pro Met Pro Cys Asn Tyr Ile Lys Leu Val Asp Val Glu
                    485                 490                 495
Asp Met Asn Tyr Gln Ala Ala Lys Gly Glu Gly Glu Val Cys Val Lys
                500                 505                 510
Gly Ala Asn Val Phe Lys Gly Tyr Leu Lys Asp Pro Ala Arg Thr Ala
                515                 520                 525
Glu Ala Leu Asp Lys Asp Gly Trp Leu His Thr Gly Asp Ile Gly Lys
530                 535                 540
```

```
Trp Leu Pro Asn Gly Thr Leu Lys Ile Ile Asp Arg Lys Lys His Ile
545                 550                 555                 560

Phe Lys Leu Ala Gln Gly Glu Tyr Ile Ala Pro Glu Lys Ile Glu Asn
            565                 570                 575

Ile Tyr Leu Arg Ser Glu Ala Val Ala Gln Val Phe Val His Gly Glu
        580                 585                 590

Ser Leu Gln Ala Phe Leu Ile Ala Ile Val Val Pro Asp Val Glu Ile
            595                 600                 605

Leu Pro Ser Trp Ala Gln Lys Arg Gly Phe Gln Gly Ser Phe Glu Glu
    610                 615                 620

Leu Cys Arg Asn Lys Asp Ile Asn Lys Ala Ile Leu Glu Asp Met Val
625                 630                 635                 640

Lys Leu Gly Lys Asn Ala Gly Leu Lys Pro Phe Glu Gln Val Lys Gly
                645                 650                 655

Ile Ala Val His Pro Glu Leu Phe Ser Ile Asp Asn Gly Leu Leu Thr
                660                 665                 670

Pro Thr Leu Lys Ala Lys Arg Pro Glu Leu Arg Asn Tyr Phe Arg Ser
            675                 680                 685

Gln Ile Asp Glu Leu Tyr Ser Thr Ile Lys Ile
    690                 695

<210> SEQ ID NO 26
<211> LENGTH: 902
<212> TYPE: PRT
<213> ORGANISM: Rattus sp.

<400> SEQUENCE: 26

Met Lys Ile Ala Val Ile Gly Gln Ser Leu Phe Gly Gln Glu Val Tyr
1               5                   10                  15

Cys Gln Leu Arg Lys Glu Gly His Glu Val Val Gly Val Phe Thr Ile
            20                  25                  30

Pro Asp Lys Asp Gly Lys Ala Asp Pro Leu Gly Leu Glu Ala Glu Lys
        35                  40                  45

Asp Gly Arg Ala Val Phe Lys Phe Pro Arg Trp Arg Ala Arg Gly Gln
    50                  55                  60

Ala Leu Pro Glu Val Val Ala Lys Tyr Gln Ala Leu Gly Ala Glu Leu
65                  70                  75                  80

Asn Val Leu Pro Phe Cys Ser Gln Phe Ile Pro Met Glu Val Ile Asn
                85                  90                  95

Ala Pro Arg His Gly Ser Ile Ile Tyr His Pro Ser Leu Leu Pro Arg
            100                 105                 110

His Arg Gly Ala Ser Ala Ile Asn Trp Thr Leu Ile His Gly Asp Lys
        115                 120                 125

Lys Gly Gly Phe Thr Ile Phe Trp Ala Asp Asp Gly Leu Asp Thr Gly
    130                 135                 140

Asp Leu Leu Leu Gln Lys Glu Cys Glu Val Leu Pro Asp Asp Thr Val
145                 150                 155                 160

Ser Thr Leu Tyr Asn Arg Phe Leu Phe Pro Glu Gly Ile Lys Gly Met
                165                 170                 175

Val Gln Ala Val Arg Leu Ile Ala Glu Gly Thr Ala Pro Arg Cys Pro
            180                 185                 190

Gln Ser Glu Glu Gly Ala Thr Tyr Glu Gly Ile Gln Lys Lys Glu Thr
        195                 200                 205

Ala Lys Ile Asn Trp Asp Gln Pro Ala Glu Ala Ile His Asn Trp Ile
    210                 215                 220
```

```
Arg Gly Asn Asp Lys Val Pro Gly Ala Trp Thr Glu Ala Cys Gly Gln
225                 230                 235                 240

Lys Leu Thr Phe Phe Asn Ser Thr Leu Asn Thr Ser Gly Leu Ser Thr
                245                 250                 255

Gln Gly Glu Ala Leu Pro Ile Pro Gly Ala His Arg Pro Gly Val Val
            260                 265                 270

Thr Lys Ala Gly Leu Ile Leu Phe Gly Asn Glu His Arg Met Leu Leu
        275                 280                 285

Val Lys Asn Ile Gln Leu Glu Asp Gly Lys Met Met Pro Ala Ser Gln
290                 295                 300

Phe Phe Lys Gly Ser Ala Ser Ser Asp Leu Glu Leu Thr Glu Ala Glu
305                 310                 315                 320

Leu Ala Thr Ala Glu Ala Val Arg Ser Ser Trp Met Arg Ile Leu Pro
                325                 330                 335

Asn Val Pro Glu Val Glu Asp Ser Thr Asp Phe Phe Lys Ser Gly Ala
            340                 345                 350

Ala Ser Val Asp Val Val Arg Leu Val Glu Glu Val Lys Glu Leu Cys
        355                 360                 365

Asp Gly Leu Glu Leu Glu Asn Glu Asp Val Tyr Met Ala Thr Thr Phe
370                 375                 380

Arg Glu Phe Ile Gln Leu Leu Val Arg Lys Leu Arg Gly Glu Asp Asp
385                 390                 395                 400

Glu Ser Glu Cys Val Ile Asn Tyr Val Glu Arg Ala Val Asn Lys Leu
                405                 410                 415

Thr Leu Gln Met Pro Tyr Gln Leu Phe Ile Gly Gly Glu Phe Val Asp
            420                 425                 430

Ala Glu Gly Ser Lys Thr Tyr Asn Thr Ile Asn Pro Thr Asp Gly Ser
        435                 440                 445

Val Ile Cys Gln Val Ser Leu Ala Gln Val Ser Asp Val Asp Lys Ala
450                 455                 460

Val Ala Ala Ala Lys Glu Ala Phe Glu Asn Gly Leu Trp Gly Lys Ile
465                 470                 475                 480

Asn Ala Arg Asp Arg Gly Arg Leu Leu Tyr Arg Leu Ala Asp Val Met
                485                 490                 495

Glu Gln His Gln Glu Glu Leu Ala Thr Ile Glu Ala Leu Asp Arg Gly
            500                 505                 510

Ala Val Tyr Thr Leu Ala Leu Lys Thr His Val Gly Met Ser Ile Gln
        515                 520                 525

Thr Phe Arg Tyr Phe Ala Gly Trp Cys Asp Lys Ile Gln Gly Ala Thr
530                 535                 540

Ile Pro Ile Asn Gln Ala Arg Pro Asn Arg Asn Leu Thr Leu Thr Lys
545                 550                 555                 560

Lys Glu Pro Val Gly Val Cys Gly Ile Val Ile Pro Trp Asn Tyr Pro
                565                 570                 575

Leu Met Met Leu Ser Trp Lys Thr Ala Ala Cys Leu Ala Ala Gly Asn
            580                 585                 590

Thr Val Val Ile Lys Pro Ala Gln Val Thr Pro Leu Thr Ala Leu Lys
        595                 600                 605

Phe Ala Glu Leu Thr Leu Lys Ala Gly Ile Pro Lys Gly Val Val Asn
610                 615                 620

Ile Leu Pro Gly Ser Gly Ser Leu Val Gly Gln Arg Leu Ser Asp His
625                 630                 635                 640

Pro Asp Val Arg Lys Ile Gly Phe Thr Gly Ser Thr Glu Val Gly Lys
                645                 650                 655
```

His Ile Met Lys Ser Cys Ala Leu Ser Asn Val Lys Lys Val Ser Leu
                660                 665                 670

Glu Leu Gly Gly Lys Ser Pro Leu Ile Ile Phe Ala Asp Cys Asp Leu
            675                 680                 685

Asn Lys Ala Val Gln Met Gly Met Ser Ser Val Phe Phe Asn Lys Gly
690                 695                 700

Glu Asn Cys Ile Ala Ala Gly Arg Leu Phe Val Glu Glu Ser Ile His
705                 710                 715                 720

Asn Gln Phe Val Gln Lys Val Val Glu Glu Val Glu Lys Met Lys Ile
                725                 730                 735

Gly Asn Pro Leu Glu Arg Asp Thr Asn His Gly Pro Gln Asn His Glu
            740                 745                 750

Ala His Leu Arg Lys Leu Val Glu Tyr Cys Gln Arg Gly Val Lys Glu
            755                 760                 765

Gly Ala Thr Leu Val Cys Gly Gly Asn Gln Val Pro Arg Pro Gly Phe
770                 775                 780

Phe Phe Gln Pro Thr Val Phe Thr Asp Val Glu Asp His Met Tyr Ile
785                 790                 795                 800

Ala Lys Glu Glu Ser Phe Gly Pro Ile Met Ile Ile Ser Arg Phe Ala
                805                 810                 815

Asp Gly Asp Val Asp Ala Val Leu Ser Arg Ala Asn Ala Thr Glu Phe
            820                 825                 830

Gly Leu Ala Ser Gly Val Phe Thr Arg Asp Ile Asn Lys Ala Leu Tyr
            835                 840                 845

Val Ser Asp Lys Leu Gln Ala Gly Thr Val Phe Ile Asn Thr Tyr Asn
850                 855                 860

Lys Thr Asp Val Ala Ala Pro Phe Gly Gly Phe Lys Gln Ser Gly Phe
865                 870                 875                 880

Gly Lys Asp Leu Gly Glu Ala Ala Leu Asn Glu Tyr Leu Arg Ile Lys
                885                 890                 895

Thr Val Thr Phe Glu Tyr
            900

<210> SEQ ID NO 27
<211> LENGTH: 412
<212> TYPE: PRT
<213> ORGANISM: Rattus sp.

<400> SEQUENCE: 27

Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
                20                  25                  30

Ala Tyr Leu Ala Asn Ile Gly Gln Lys Glu Asp Phe Glu Glu Ala Arg
            35                  40                  45

Lys Lys Ala Leu Lys Leu Gly Ala Lys Lys Val Phe Ile Glu Asp Val
        50                  55                  60

Ser Lys Glu Phe Val Glu Glu Phe Ile Trp Pro Ala Val Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

```
Glu Leu Thr Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Ser Pro Trp Ser Met Asp Glu Asn Leu Met His Ile Ser Tyr Glu Ala
                180                 185                 190

Gly Ile Leu Glu Asn Pro Lys Asn Gln Ala Pro Pro Gly Leu Tyr Thr
            195                 200                 205

Lys Thr Gln Asp Pro Ala Lys Ala Pro Asn Thr Pro Asp Val Leu Glu
    210                 215                 220

Ile Glu Phe Lys Lys Gly Val Pro Val Lys Val Thr Asn Val Lys Asp
225                 230                 235                 240

Gly Thr Thr His Ser Thr Ser Leu Asp Leu Phe Met Tyr Leu Asn Glu
                245                 250                 255

Val Ala Gly Lys His Gly Val Gly Arg Ile Asp Ile Val Glu Asn Arg
                260                 265                 270

Phe Ile Gly Met Lys Ser Arg Gly Ile Tyr Glu Thr Pro Ala Gly Thr
            275                 280                 285

Ile Leu Tyr His Ala His Leu Asp Ile Glu Ala Phe Thr Met Asp Arg
    290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Asp Lys Ser Gln Glu Arg Val Glu Gly Lys Val Gln Val Ser
                340                 345                 350

Val Phe Lys Gly Gln Val Tyr Ile Leu Gly Arg Glu Ser Pro Leu Ser
            355                 360                 365

Leu Tyr Asn Glu Glu Leu Val Ser Met Asn Val Gln Gly Asp Tyr Glu
    370                 375                 380

Pro Ile Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410

<210> SEQ ID NO 28
<211> LENGTH: 857
<212> TYPE: PRT
<213> ORGANISM: Rattus sp.

<400> SEQUENCE: 28

Met Leu Arg Leu Gly Ala Leu Arg Leu Arg Gly Leu Ala Leu Arg Ser
1               5                   10                  15

Ser Gln Gly Arg Pro Ser Ser Ala Gly Leu Arg Glu Gly Gln Glu Ser
                20                  25                  30

Pro Pro Ser Pro Pro Glu Trp Lys Asp Arg Ala Glu Thr Val Ile Ile
            35                  40                  45

Gly Gly Gly Cys Val Gly Val Ser Leu Ala Tyr His Leu Ala Lys Ala
        50                  55                  60

Gly Met Arg Asp Val Val Leu Leu Glu Lys Ser Glu Leu Thr Ala Gly
65                  70                  75                  80

Ser Thr Trp His Ala Ala Gly Leu Thr Thr Tyr Phe His Pro Gly Ile
                85                  90                  95
```

```
Asn Leu Lys Lys Ile His Tyr Asp Ser Ile Lys Leu Tyr Glu Arg Leu
            100                 105                 110

Glu Glu Glu Thr Gly Gln Val Gly Phe His Gln Pro Gly Ser Ile
        115                 120                 125

Arg Leu Ala Thr Thr Pro Glu Arg Val Asp Glu Phe Lys Tyr Gln Met
130                 135                 140

Thr Arg Thr Asn Trp His Ala Thr Glu Gln Tyr Ile Ile Glu Pro Glu
145                 150                 155                 160

Lys Ile His Glu Leu Phe Pro Leu Leu Asn Met Asp Lys Ile Leu Ala
                165                 170                 175

Gly Leu Tyr Asn Pro Gly Asp Gly His Ile Asp Pro Tyr Ser Leu Thr
                180                 185                 190

Met Ala Leu Ala Thr Gly Ala Arg Lys Tyr Gly Ala Leu Leu Lys Tyr
                195                 200                 205

Pro Ala Pro Val Thr Ser Leu Lys Pro Arg Pro Asp Gly Thr Trp Asp
            210                 215                 220

Val Glu Thr Pro Gln Gly Ser Val Arg Ala Asn Arg Ile Val Asn Ala
225                 230                 235                 240

Ala Gly Phe Trp Ala Arg Glu Val Gly Lys Met Ile Gly Leu Asp His
                245                 250                 255

Pro Leu Ile Pro Val Gln His Gln Tyr Val Ile Thr Ser Thr Ile Pro
                260                 265                 270

Glu Val Lys Ala Leu Lys Arg Glu Leu Pro Val Leu Arg Asp Leu Glu
            275                 280                 285

Gly Ser Tyr Tyr Leu Arg Gln Glu Arg Asp Gly Leu Leu Phe Gly Pro
            290                 295                 300

Tyr Glu Ser Gln Glu Lys Met Lys Leu Gln Ala Ser Trp Val Ala His
305                 310                 315                 320

Gly Val Pro Pro Gly Phe Gly Lys Glu Leu Phe Glu Ser Asp Leu Asp
                325                 330                 335

Arg Ile Thr Glu His Val Glu Ala Ala Met Glu Met Val Pro Val Leu
                340                 345                 350

Lys Lys Ala Asp Ile Ile Asn Ile Val Asn Gly Pro Ile Thr Tyr Ser
            355                 360                 365

Pro Asp Ile Leu Pro Met Val Gly Pro His Gln Gly Val Arg Asn Tyr
            370                 375                 380

Trp Val Ala Ile Gly Phe Gly Tyr Gly Ile Ile His Ala Gly Gly Val
385                 390                 395                 400

Gly Thr Tyr Leu Ser Asp Trp Ile Leu His Gly Glu Pro Pro Phe Asp
                405                 410                 415

Leu Ile Glu Leu Asp Pro Asn Arg Tyr Gly Lys Trp Thr Thr Thr Gln
                420                 425                 430

Tyr Thr Glu Ala Lys Ala Arg Glu Ser Tyr Gly Phe Asn Asn Ile Val
            435                 440                 445

Gly Tyr Pro Lys Glu Glu Arg Phe Ala Gly Arg Pro Thr Gln Arg Val
            450                 455                 460

Ser Gly Leu Tyr Lys Ile Leu Glu Ser Lys Cys Ser Met Gly Phe His
465                 470                 475                 480

Ala Gly Trp Glu Gln Pro His Trp Phe Tyr Lys Pro Gly Gln Asp Thr
                485                 490                 495

Gln Tyr Arg Pro Ser Phe Arg Ala Thr Asn Trp Phe Glu Pro Val Gly
            500                 505                 510

Ser Glu Tyr Lys Gln Val Met Gln Arg Val Gly Val Ile Asp Leu Ser
```

```
                515                 520                 525
Pro Phe Gly Lys Phe Asn Ile Lys Gly Gln Asp Ser Thr Gln Leu Leu
530                 535                 540

Asp His Leu Cys Ala Asn Val Ile Pro Lys Val Gly Phe Thr Asn Ile
545                 550                 555                 560

Ser His Met Leu Thr Pro Arg Gly Arg Val Tyr Ala Glu Leu Thr Val
                565                 570                 575

Ser His Gln Ser Pro Gly Glu Phe Leu Leu Ile Thr Gly Ser Gly Ser
                580                 585                 590

Glu Leu His Asp Leu Arg Trp Ile Glu Glu Ala Ala Val Arg Gly Gly
                595                 600                 605

Tyr Asp Val Glu Ile Arg Asn Ile Thr Asp Glu Leu Gly Val Leu Gly
610                 615                 620

Val Ala Gly Pro Tyr Ala Arg Arg Val Leu Gln Lys Leu Thr Ser Glu
625                 630                 635                 640

Asp Leu Ser Asp Asp Val Phe Lys Phe Leu Gln Thr Lys Ser Leu Lys
                645                 650                 655

Ile Ser Asp Ile Pro Val Thr Ala Ile Arg Ile Ser Tyr Thr Gly Glu
                660                 665                 670

Leu Gly Trp Glu Leu Tyr His Arg Arg Glu Asp Ser Ala Ala Leu Tyr
                675                 680                 685

Glu Arg Ile Met Asn Ala Gly Gln Glu Glu Gly Ile Asp Asn Phe Gly
690                 695                 700

Thr Tyr Ala Leu Asn Ala Leu Arg Leu Glu Lys Ala Phe Arg Ala Trp
705                 710                 715                 720

Gly Ser Glu Met Asn Cys Asp Thr Asn Pro Leu Glu Ala Gly Leu Asp
                725                 730                 735

Tyr Phe Ile Lys Leu Asn Lys Pro Ala Asn Phe Thr Gly Lys Gln Ala
                740                 745                 750

Leu Lys Gln Ile Lys Ala Lys Gly Leu Lys Arg Arg Leu Val Cys Leu
                755                 760                 765

Thr Leu Ala Thr Asp Asn Val Asp Pro Glu Gly Asn Glu Ser Val Trp
770                 775                 780

Tyr Lys Gly Lys Val Ile Gly Asn Thr Thr Ser Gly Ser Tyr Ser Tyr
785                 790                 795                 800

Ser Ile Gln Lys Ser Leu Ala Phe Ala Tyr Val Pro Val Glu Leu Ser
                805                 810                 815

Glu Val Gly Gln Gln Val Glu Val Glu Leu Leu Gly Lys Asn Tyr Pro
                820                 825                 830

Ala Thr Ile Ile Gln Glu Pro Leu Val Leu Thr Glu Pro Thr Arg Thr
                835                 840                 845

Arg Leu Gln Lys Asp Gly Arg Lys Ser
    850                 855

<210> SEQ ID NO 29
<211> LENGTH: 519
<212> TYPE: PRT
<213> ORGANISM: Rattus sp.

<400> SEQUENCE: 29

Met Ala Pro Gln Glu Arg Leu Leu Ile Arg Gly Gly Arg Val Val Asn
1               5                   10                  15

Asp Asp Phe Ser Gln Val Ala Asp Val Leu Val Glu Asp Gly Val Val
                20                  25                  30

Arg Ala Leu Gly Arg Asp Leu Leu Pro Pro Gly Asp Thr Ser Arg Gly
```

-continued

```
                35                  40                  45
Leu Arg Ile Leu Asp Ala Ala Gly Lys Leu Val Leu Pro Gly Gly Ile
 50                  55                  60

Asp Thr His Thr His Met Gln Phe Pro Phe Met Gly Ser Gln Ser Val
 65                  70                  75                  80

Asp Asp Phe His Gln Gly Thr Lys Ala Ala Leu Ala Gly Gly Thr Thr
                 85                  90                  95

Met Ile Ile Asp Phe Ala Ile Pro Gln Lys Gly Ser Ser Leu Ile Glu
                100                 105                 110

Ala Phe Glu Thr Trp Arg Asn Trp Ala Asp Pro Lys Val Cys Cys Asp
                115                 120                 125

Tyr Ser Leu His Val Ala Val Thr Trp Trp Ser Asp Lys Val Lys Glu
130                 135                 140

Glu Met Lys Thr Leu Ala Gln Asp Lys Gly Val Asn Ser Phe Lys Met
145                 150                 155                 160

Phe Met Ala Tyr Lys Asp Leu Tyr Met Val Gln Asp Gln Met Tyr
                165                 170                 175

Ala Ala Phe Ser Gln Cys Lys Glu Ile Gly Ala Ile Ala Gln Val His
                180                 185                 190

Ala Glu Asn Gly Asp Leu Ile Ala Glu Gly Ala Lys Lys Met Leu Ala
                195                 200                 205

Leu Gly Ile Thr Gly Pro Glu Gly His Glu Leu Cys Arg Pro Glu Ala
                210                 215                 220

Val Glu Ala Glu Ala Thr Leu Arg Ala Ile Thr Ile Ala Ser Ala Val
225                 230                 235                 240

Asn Cys Pro Leu Tyr Ile Val His Val Met Ser Lys Ser Ala Ala Lys
                245                 250                 255

Val Ile Ala Asp Ala Lys Arg Glu Gly Lys Val Val Tyr Gly Glu Pro
                260                 265                 270

Ile Ala Ala Gly Leu Gly Thr Asp Gly Thr Gln Tyr Trp Asn Lys Glu
                275                 280                 285

Trp Arg His Ala Ala His His Val Met Gly Pro Pro Leu Arg Pro Asp
290                 295                 300

Pro Ser Thr Pro Gly Phe Leu Met Asn Leu Leu Ala Asn Gly Asp Leu
305                 310                 315                 320

Thr Thr Thr Gly Ser Asp Asn Cys Thr Phe Asn Thr Cys Gln Lys Ala
                325                 330                 335

Leu Gly Lys Asp Asp Phe Thr Lys Ile Pro Asn Gly Val Asn Gly Val
                340                 345                 350

Glu Asp Arg Met Ser Val Ile Trp Glu Lys Gly Val His Ser Gly Lys
                355                 360                 365

Met Asp Glu Asn Arg Phe Val Ala Val Thr Ser Thr Asn Ala Ala Lys
370                 375                 380

Ile Phe Asn Leu Tyr Pro Lys Lys Gly Arg Ile Ala Val Gly Ser Asp
385                 390                 395                 400

Ala Asp Met Val Ile Trp Asp Pro Glu Ala Thr Arg Thr Ile Ser Ala
                405                 410                 415

Lys Thr His His Gln Ala Val Asn Phe Asn Ile Phe Glu Gly Met Val
                420                 425                 430

Cys His Gly Val Pro Leu Val Thr Ile Ser Arg Gly Arg Val Val Tyr
                435                 440                 445

Glu Ala Gly Val Phe Asp Val Thr Ala Gly His Gly Lys Phe Ile Pro
                450                 455                 460
```

```
Arg Gln Pro Phe Ala Glu Phe Ile Tyr Lys Arg Val Lys Gln Arg Asp
465                 470                 475                 480

Gln Thr Cys Thr Pro Ile Pro Val Lys Arg Ala Pro Tyr Lys Gly Glu
                485                 490                 495

Val Ile Thr Leu Lys Pro Arg Glu Thr Lys Glu Asp Asp Thr Ala Gly
            500                 505                 510

Thr Arg Met Gln Gly His Ser
        515

<210> SEQ ID NO 30
<211> LENGTH: 885
<212> TYPE: PRT
<213> ORGANISM: Rattus sp.

<400> SEQUENCE: 30

Met Ala Arg Gln Gly Cys Leu Gly Ser Phe Gln Val Ile Ser Leu Phe
1               5                   10                  15

Thr Phe Ala Ile Ser Val Asn Ile Cys Leu Gly Phe Thr Ala Ser Arg
            20                  25                  30

Ile Lys Arg Ala Glu Trp Asp Glu Gly Pro Pro Thr Val Leu Ser Asp
        35                  40                  45

Ser Pro Trp Thr Asn Thr Ser Gly Ser Cys Lys Gly Arg Cys Phe Glu
50                  55                  60

Leu Gln Glu Val Gly Pro Asp Cys Arg Cys Asp Asn Leu Cys Lys
65                  70                  75                  80

Ser Tyr Ser Ser Cys Cys His Asp Phe Asp Glu Leu Cys Leu Lys Thr
                85                  90                  95

Val Arg Gly Trp Glu Cys Thr Lys Asp Arg Ser Gly Glu Val Arg Asn
            100                 105                 110

Glu Glu Asn Ala Cys His Cys Pro Glu Asp Cys Leu Ser Arg Gly Asp
        115                 120                 125

Cys Cys Thr Asn Tyr Gln Val Val Cys Lys Gly Glu Ser His Trp Val
130                 135                 140

Asp Asp Ala Ala Arg Asn Gln Ser Ser Glu Cys Leu Gln Val Cys Pro
145                 150                 155                 160

Pro Pro Leu Ile Ile Phe Ser Val Asp Gly Phe Arg Ala Ser Tyr Met
                165                 170                 175

Lys Lys Gly Ser Lys Val Met Pro Asn Ile Glu Lys Leu Arg Ser Cys
            180                 185                 190

Gly Thr His Val Pro Tyr Thr Arg Pro Val Tyr Pro Thr Lys Thr Phe
        195                 200                 205

Pro Asn Leu Tyr Thr Leu Ala Thr Gly Leu Tyr Pro Glu Ser His Gly
210                 215                 220

Ile Val Gly Asn Ser Met Tyr Asp Pro Val Phe Asp Ala Ser Phe His
225                 230                 235                 240

Leu Arg Gly Arg Glu Lys Phe Asn His Arg Trp Trp Gly Gly Gln Pro
                245                 250                 255

Leu Trp Ile Thr Ala Thr Lys Gln Gly Val Arg Ala Gly Thr Phe Phe
            260                 265                 270

Trp Ser Val Ser Ile Pro His Glu Arg Arg Ile Leu Thr Ile Leu Gln
        275                 280                 285

Trp Leu Ser Leu Pro Asp Asn Glu Arg Pro Ser Val Tyr Ala Phe Tyr
290                 295                 300

Ser Glu Gln Pro Asp Phe Ser Gly His Lys Tyr Gly Pro Phe Gly Pro
305                 310                 315                 320
```

-continued

```
Glu Met Thr Asn Pro Leu Arg Glu Ile Asp Lys Thr Val Gly Gln Leu
                325                 330                 335

Met Asp Gly Leu Lys Gln Leu Arg Leu His Arg Cys Val Asn Val Ile
            340                 345                 350

Phe Val Gly Asp His Gly Met Glu Asp Val Thr Cys Asp Arg Thr Glu
        355                 360                 365

Phe Leu Ser Asn Tyr Leu Thr Asn Val Asp Asp Ile Thr Leu Val Pro
    370                 375                 380

Gly Thr Leu Gly Arg Ile Arg Ala Lys Ser Ile Asn Asn Ser Lys Tyr
385                 390                 395                 400

Asp Pro Lys Thr Ile Ile Ala Asn Leu Thr Cys Lys Lys Pro Asp Gln
                405                 410                 415

His Phe Lys Pro Tyr Met Lys Gln His Leu Pro Lys Arg Leu His Tyr
            420                 425                 430

Ala Asn Asn Arg Arg Ile Glu Asp Ile His Leu Leu Val Asp Arg Arg
        435                 440                 445

Trp His Val Ala Arg Lys Pro Leu Asp Val Tyr Lys Lys Pro Ser Gly
    450                 455                 460

Lys Cys Phe Phe Gln Gly Asp His Gly Phe Asp Asn Lys Val Asn Ser
465                 470                 475                 480

Met Gln Thr Val Phe Val Gly Tyr Gly Pro Thr Phe Lys Tyr Arg Thr
                485                 490                 495

Lys Val Pro Pro Phe Glu Asn Ile Glu Leu Tyr Asn Val Met Cys Asp
            500                 505                 510

Leu Leu Gly Leu Lys Pro Ala Pro Asn Asn Gly Thr His Gly Ser Leu
        515                 520                 525

Asn His Leu Leu Arg Thr Asn Thr Phe Arg Pro Thr Met Pro Asp Glu
    530                 535                 540

Val Ser Arg Pro Asn Tyr Pro Gly Ile Met Tyr Leu Gln Ser Glu Phe
545                 550                 555                 560

Asp Leu Gly Cys Thr Cys Asp Asp Lys Val Glu Pro Lys Asn Lys Leu
                565                 570                 575

Glu Glu Leu Asn Lys Arg Leu His Thr Lys Gly Ser Thr Glu Ala Glu
            580                 585                 590

Thr Gly Lys Phe Arg Gly Ser Lys His Glu Asn Lys Lys Asn Leu Asn
        595                 600                 605

Gly Ser Val Glu Pro Arg Lys Glu Arg His Leu Leu Tyr Gly Arg Pro
    610                 615                 620

Ala Val Leu Tyr Arg Thr Ser Tyr Asp Ile Leu Tyr His Thr Asp Phe
625                 630                 635                 640

Glu Ser Gly Tyr Ser Glu Ile Phe Leu Met Pro Leu Trp Thr Ser Tyr
                645                 650                 655

Thr Ile Ser Lys Gln Ala Glu Val Ser Ser Ile Pro Glu His Leu Thr
            660                 665                 670

Asn Cys Val Arg Pro Asp Val Arg Val Ser Pro Gly Phe Ser Gln Asn
        675                 680                 685

Cys Leu Ala Tyr Lys Asn Asp Lys Gln Met Ser Tyr Gly Phe Leu Phe
    690                 695                 700

Pro Pro Tyr Leu Ser Ser Ser Pro Glu Ala Lys Tyr Asp Ala Phe Leu
705                 710                 715                 720

Val Thr Asn Met Val Pro Met Tyr Pro Ala Phe Lys Arg Val Trp Ala
                725                 730                 735

Tyr Phe Gln Arg Val Leu Val Lys Lys Tyr Ala Ser Glu Arg Asn Gly
            740                 745                 750
```

Val Asn Val Ile Ser Gly Pro Ile Phe Asp Tyr Asn Tyr Asp Gly Leu
            755                 760                 765

Arg Asp Thr Glu Asp Glu Ile Lys Gln Tyr Val Glu Gly Ser Ser Ile
770                 775                 780

Pro Val Pro Thr His Tyr Tyr Ser Ile Ile Thr Ser Cys Leu Asp Phe
785                 790                 795                 800

Thr Gln Pro Ala Asp Lys Cys Asp Gly Pro Leu Ser Val Ser Ser Phe
            805                 810                 815

Ile Leu Pro His Arg Pro Asp Asn Asp Glu Ser Cys Asn Ser Ser Glu
            820                 825                 830

Asp Glu Ser Lys Trp Val Glu Glu Leu Met Lys Met His Thr Ala Arg
            835                 840                 845

Val Arg Asp Ile Glu His Leu Thr Gly Leu Asp Phe Tyr Arg Lys Thr
850                 855                 860

Ser Arg Ser Tyr Ser Glu Ile Leu Thr Leu Lys Thr Tyr Leu His Thr
865                 870                 875                 880

Tyr Glu Ser Glu Ile
            885

<210> SEQ ID NO 31
<211> LENGTH: 579
<212> TYPE: PRT
<213> ORGANISM: Rattus sp.

<400> SEQUENCE: 31

Met Val Leu Ser Glu Val Trp Thr Thr Leu Ser Gly Val Ser Gly Val
1               5                   10                  15

Cys Leu Ala Cys Ser Leu Leu Ser Ala Ala Val Val Leu Arg Trp Thr
            20                  25                  30

Gly Arg Gln Lys Ala Arg Gly Ala Ala Thr Arg Ala Arg Gln Lys Gln
        35                  40                  45

Arg Ala Ser Leu Glu Thr Met Asp Lys Ala Val Gln Arg Phe Arg Leu
    50                  55                  60

Gln Asn Pro Asp Leu Asp Ser Glu Ala Leu Leu Thr Leu Pro Leu Leu
65                  70                  75                  80

Gln Leu Val Gln Lys Leu Gln Ser Gly Glu Leu Ser Pro Glu Ala Val
                85                  90                  95

Phe Phe Thr Tyr Leu Gly Lys Ala Trp Glu Val Asn Lys Gly Thr Asn
            100                 105                 110

Cys Val Thr Ser Tyr Leu Thr Asp Cys Glu Thr Gln Leu Ser Gln Ala
        115                 120                 125

Pro Arg Gln Gly Leu Leu Tyr Gly Val Pro Val Ser Leu Lys Glu Cys
    130                 135                 140

Phe Ser Tyr Lys Gly His Asp Ser Thr Leu Gly Leu Ser Leu Asn Glu
145                 150                 155                 160

Gly Met Pro Ser Glu Ser Asp Cys Val Val Val Gln Val Leu Lys Leu
                165                 170                 175

Gln Gly Ala Val Pro Phe Val His Thr Asn Val Pro Gln Ser Met Leu
            180                 185                 190

Ser Phe Asp Cys Ser Asn Pro Leu Phe Gly Gln Thr Met Asn Pro Trp
        195                 200                 205

Lys Ser Ser Lys Ser Pro Gly Gly Ser Gly Gly Glu Gly Ala Leu
    210                 215                 220

Ile Gly Ser Gly Gly Ser Pro Leu Gly Leu Gly Thr Asp Ile Gly Gly
225                 230                 235                 240

```
Ser Ile Arg Phe Pro Ser Ala Phe Cys Gly Ile Cys Gly Leu Lys Pro
                245                 250                 255

Thr Gly Asn Arg Leu Ser Lys Ser Gly Leu Lys Gly Cys Val Tyr Gly
                260                 265                 270

Gln Thr Ala Val Gln Leu Ser Leu Gly Pro Met Ala Arg Asp Val Glu
                275                 280                 285

Ser Leu Ala Leu Cys Leu Lys Ala Leu Leu Cys Glu His Leu Phe Thr
                290                 295                 300

Leu Asp Pro Thr Val Pro Pro Leu Pro Phe Arg Glu Glu Val Tyr Arg
305                 310                 315                 320

Ser Ser Arg Pro Leu Arg Val Gly Tyr Tyr Glu Thr Asp Asn Tyr Thr
                325                 330                 335

Met Pro Ser Pro Ala Met Arg Arg Ala Leu Ile Glu Thr Lys Gln Arg
                340                 345                 350

Leu Glu Ala Ala Gly His Thr Leu Ile Pro Phe Leu Pro Asn Asn Ile
                355                 360                 365

Pro Tyr Ala Leu Glu Val Leu Ser Ala Gly Gly Leu Phe Ser Asp Gly
                370                 375                 380

Gly Arg Ser Phe Leu Gln Asn Phe Lys Gly Asp Phe Val Asp Pro Cys
385                 390                 395                 400

Leu Gly Asp Leu Ile Leu Ile Leu Arg Leu Pro Ser Trp Phe Lys Arg
                405                 410                 415

Leu Leu Ser Leu Leu Lys Pro Leu Phe Pro Arg Leu Ala Ala Phe
                420                 425                 430

Leu Asn Ser Met Arg Pro Arg Ser Ala Glu Lys Leu Trp Lys Leu Gln
                435                 440                 445

His Glu Ile Glu Met Tyr Arg Gln Ser Val Ile Ala Gln Trp Lys Ala
                450                 455                 460

Met Asn Leu Asp Val Leu Leu Thr Pro Met Leu Gly Pro Ala Leu Asp
465                 470                 475                 480

Leu Asn Thr Pro Gly Arg Ala Thr Gly Ala Ile Ser Tyr Thr Val Leu
                485                 490                 495

Tyr Asn Cys Leu Asp Phe Pro Ala Gly Val Val Pro Val Thr Thr Val
                500                 505                 510

Thr Ala Glu Asp Asp Ala Gln Met Glu Leu Tyr Lys Gly Tyr Phe Gly
                515                 520                 525

Asp Ile Trp Asp Ile Ile Leu Lys Lys Ala Met Lys Asn Ser Val Gly
                530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Gln Leu Met Thr Pro Gln Lys
                565                 570                 575

Gln Pro Ser

<210> SEQ ID NO 32
<211> LENGTH: 236
<212> TYPE: PRT
<213> ORGANISM: Rattus sp.

<400> SEQUENCE: 32

Met Ser Ser Ser Ala Ala Ser Pro Leu Phe Ala Pro Gly Glu Asp Cys
1               5                   10                  15

Gly Pro Ala Trp Arg Ala Ala Pro Ala Ala Tyr Asp Thr Ser Asp Thr
                20                  25                  30
```

-continued

```
His Leu Gln Ile Leu Gly Lys Pro Val Met Glu Arg Trp Glu Thr Pro
            35                  40                  45

Tyr Met His Ser Leu Ala Ala Ala Ala Ser Arg Gly Gly Arg Val
 50                  55                  60

Leu Glu Val Gly Phe Gly Met Ala Ile Ala Ala Ser Arg Val Gln Gln
 65                  70                  75                  80

Ala Pro Ile Lys Glu His Trp Ile Ile Glu Cys Asn Asp Gly Val Phe
                    85                  90                  95

Gln Arg Leu Gln Asn Trp Ala Leu Lys Gln Pro His Lys Val Val Pro
                100                 105                 110

Leu Lys Gly Leu Trp Glu Glu Ala Pro Thr Leu Pro Asp Gly His
                115                 120                 125

Phe Asp Gly Ile Leu Tyr Asp Thr Tyr Pro Leu Ser Glu Glu Thr Trp
130                 135                 140

His Thr His Gln Phe Asn Phe Ile Lys Thr His Ala Phe Arg Leu Leu
145                 150                 155                 160

Lys Pro Gly Gly Ile Leu Thr Tyr Cys Asn Leu Thr Ser Trp Gly Glu
                    165                 170                 175

Leu Met Lys Ser Lys Tyr Thr Asp Ile Thr Ala Met Phe Glu Glu Thr
                180                 185                 190

Gln Val Pro Ala Leu Leu Glu Ala Gly Phe Gln Arg Glu Asn Ile Cys
                195                 200                 205

Thr Glu Val Met Ala Leu Val Pro Ala Asp Cys Arg Tyr Tyr Ala
210                 215                 220

Phe Pro Gln Met Ile Thr Pro Leu Val Thr Lys His
225                 230                 235

<210> SEQ ID NO 33
<211> LENGTH: 440
<212> TYPE: PRT
<213> ORGANISM: Rattus sp.

<400> SEQUENCE: 33

Met Val His Gly Tyr Lys Gly Val Gln Phe Gln Asn Trp Ala Lys Thr
 1               5                  10                  15

Tyr Gly Cys Ser Pro Glu Val Tyr Tyr Gln Pro Thr Ser Val Glu Glu
                20                  25                  30

Val Arg Glu Val Leu Ala Leu Ala Arg Glu Gln Lys Lys Lys Val Lys
            35                  40                  45

Val Val Gly Gly His Ser Pro Ser Asp Ile Ala Cys Thr Asp Gly
 50                  55                  60

Phe Met Ile His Met Gly Lys Met Asn Arg Val Leu Gln Val Asp Lys
 65                  70                  75                  80

Glu Lys Lys Gln Ile Thr Val Glu Ala Gly Ile Leu Leu Ala Asp Leu
                85                  90                  95

His Pro Gln Leu Asp Glu His Gly Leu Ala Met Ser Asn Leu Gly Ala
                100                 105                 110

Val Ser Asp Val Thr Val Ala Gly Val Ile Gly Ser Gly Thr His Asn
                115                 120                 125

Thr Gly Ile Lys His Gly Ile Leu Ala Thr Gln Val Ala Leu Thr
130                 135                 140

Leu Met Thr Ala Asp Gly Glu Val Leu Glu Cys Ser Glu Ser Arg Asn
145                 150                 155                 160

Ala Asp Val Phe Gln Ala Ala Arg Val His Leu Gly Cys Leu Gly Ile
                165                 170                 175
```

-continued

Ile Leu Thr Val Thr Leu Gln Cys Val Pro Gln Phe His Leu Gln Glu
            180                 185                 190

Thr Ser Phe Pro Ser Thr Leu Lys Glu Val Leu Asp Asn Leu Asp Ser
        195                 200                 205

His Leu Lys Arg Ser Glu Tyr Phe Arg Phe Leu Trp Phe Pro His Thr
    210                 215                 220

Glu Asn Val Ser Ile Ile Tyr Gln Asp His Thr Asn Lys Ala Pro Ser
225                 230                 235                 240

Ser Ala Ser Asn Trp Phe Trp Asp Tyr Ala Ile Gly Phe Tyr Leu Leu
                245                 250                 255

Glu Phe Leu Leu Trp Thr Ser Thr Tyr Leu Pro Cys Leu Val Gly Trp
            260                 265                 270

Ile Asn Arg Phe Phe Phe Trp Met Leu Phe Asn Cys Lys Lys Glu Ser
        275                 280                 285

Ser Asn Leu Ser His Lys Ile Phe Thr Tyr Glu Cys Arg Phe Lys Gln
    290                 295                 300

His Val Gln Asp Trp Ala Ile Pro Arg Glu Lys Thr Lys Glu Ala Leu
305                 310                 315                 320

Leu Glu Leu Lys Ala Met Leu Glu Ala His Pro Lys Val Val Ala His
                325                 330                 335

Tyr Pro Val Glu Val Arg Phe Thr Arg Gly Asp Asp Ile Leu Leu Ser
            340                 345                 350

Pro Cys Phe Gln Arg Asp Ser Cys Tyr Met Asn Ile Ile Met Tyr Arg
        355                 360                 365

Pro Tyr Gly Lys Asp Val Pro Arg Leu Asp Tyr Trp Leu Ala Tyr Glu
    370                 375                 380

Thr Ile Met Lys Lys Phe Gly Gly Arg Pro His Trp Ala Lys Ala His
385                 390                 395                 400

Asn Cys Thr Arg Lys Asp Phe Glu Glu Met Tyr Pro Thr Phe His Lys
                405                 410                 415

Phe Cys Asp Ile Arg Glu Lys Leu Asp Pro Thr Gly Met Phe Leu Asn
            420                 425                 430

Ser Tyr Leu Glu Lys Val Phe Tyr
        435                 440

<210> SEQ ID NO 34
<211> LENGTH: 335
<212> TYPE: PRT
<213> ORGANISM: Rattus sp.

<400> SEQUENCE: 34

Met Ala Ala Ser Leu Gly Phe Arg Gly Ala Ser Gly Leu Arg Tyr
1               5                   10                  15

Trp Ser Gly Arg Arg Pro Val Gly Ser Leu Ala Ala Val Cys Ser
                20                  25                  30

Arg Ser Met Ala Ser Lys Thr Pro Val Gly Phe Ile Gly Leu Gly Asn
        35                  40                  45

Met Gly Asn Pro Met Ala Lys Asn Leu Ile Lys His Gly Tyr Pro Leu
    50                  55                  60

Ile Leu Tyr Asp Val Phe Pro Asp Val Cys Lys Glu Phe Lys Glu Ala
65                  70                  75                  80

Gly Glu Gln Val Ala Ser Ser Pro Ala Asp Val Ala Glu Lys Ala Asp
                85                  90                  95

Arg Ile Ile Thr Met Leu Pro Ser Ser Met Asn Ser Ile Glu Val Tyr
            100                 105                 110

```
Ser Gly Ala Asn Gly Ile Leu Lys Lys Val Lys Lys Gly Ser Leu Leu
            115                 120                 125

Ile Asp Ser Ser Thr Ile Asp Pro Ser Val Ser Lys Glu Leu Ala Lys
        130                 135                 140

Glu Val Glu Lys Met Gly Ala Val Phe Met Asp Ala Pro Val Ser Gly
145                 150                 155                 160

Gly Val Gly Ala Ala Arg Ser Gly Asn Leu Thr Phe Met Val Gly Gly
                165                 170                 175

Val Glu Asn Glu Phe Ala Ala Ala Gln Glu Leu Leu Gly Cys Met Gly
            180                 185                 190

Ser Asn Val Leu Tyr Cys Gly Ala Val Gly Ser Gly Gln Ser Ala Lys
        195                 200                 205

Ile Cys Asn Asn Met Leu Leu Ala Ile Ser Met Ile Gly Thr Ala Glu
    210                 215                 220

Ala Met Asn Leu Gly Ile Arg Ser Gly Leu Asp Pro Lys Leu Leu Ala
225                 230                 235                 240

Lys Ile Leu Asn Met Ser Ser Gly Arg Cys Trp Ser Ser Asp Thr Tyr
                245                 250                 255

Asn Pro Val Pro Gly Val Met Asp Gly Val Pro Ser Ser Asn Asn Tyr
            260                 265                 270

Gln Gly Gly Phe Gly Thr Thr Leu Met Ala Lys Asp Leu Gly Leu Ala
        275                 280                 285

Gln Asp Ser Ala Thr Ser Thr Lys Thr Pro Ile Leu Leu Gly Ser Val
    290                 295                 300

Ala His Gln Ile Tyr Arg Met Met Cys Ser Lys Gly Tyr Ser Lys Lys
305                 310                 315                 320

Asp Phe Ser Ser Val Phe Gln Tyr Leu Arg Glu Glu Glu Thr Phe
                325                 330                 335

<210> SEQ ID NO 35
<211> LENGTH: 298
<212> TYPE: PRT
<213> ORGANISM: Rattus sp.

<400> SEQUENCE: 35

Met Glu Glu Lys Gln Ile Leu Cys Val Gly Leu Val Val Leu Asp Ile
1               5                   10                  15

Ile Asn Val Val Asp Lys Tyr Pro Glu Glu Asp Thr Asp Arg Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Arg Cys Ala Phe Met Gly Ser Leu Ala
    50                  55                  60

His Gly His Val Ala Asp Phe Leu Val Ala Asp Phe Arg Arg Arg Gly
65                  70                  75                  80

Val Asp Val Ser Gln Val Ala Trp Gln Ser Gly Asp Thr Pro Cys
                85                  90                  95

Ser Cys Cys Ile Val Asn Asn Ser Asn Gly Ser Arg Thr Ile Ile Leu
            100                 105                 110

Tyr Asp Thr Asn Leu Pro Asp Val Ser Ala Lys Asp Phe Glu Lys Val
        115                 120                 125

Asp Leu Thr Arg Phe Lys Trp Ile His Ile Glu Gly Arg Asn Ala Ser
    130                 135                 140

Glu Gln Val Lys Met Leu Gln Arg Ile Glu Gln Tyr Asn Ala Thr Gln
145                 150                 155                 160
```

```
Pro Leu Gln Gln Lys Val Arg Val Ser Val Glu Ile Glu Lys Pro Arg
            165                 170                 175

Glu Glu Leu Phe Gln Leu Phe Gly Tyr Gly Val Val Phe Val Ser
            180                 185                 190

Lys Asp Val Ala Lys His Leu Gly Phe Arg Ser Ala Gly Glu Ala Leu
            195                 200                 205

Lys Gly Leu Tyr Ser Arg Val Lys Lys Gly Ala Thr Leu Ile Cys Ala
            210                 215                 220

Trp Ala Glu Glu Gly Ala Asp Ala Leu Gly Pro Asp Gly Gln Leu Leu
225                 230                 235                 240

His Ser Asp Ala Phe Pro Pro Arg Val Val Asp Thr Leu Gly Ala
            245                 250                 255

Gly Asp Thr Phe Asn Ala Ser Val Ile Phe Ser Leu Ser Lys Gly Asn
            260                 265                 270

Ser Met Gln Glu Ala Leu Arg Phe Gly Cys Gln Val Ala Gly Lys Lys
            275                 280                 285

Cys Gly Leu Gln Gly Phe Asp Gly Ile Val
            290                 295

<210> SEQ ID NO 36
<211> LENGTH: 464
<212> TYPE: PRT
<213> ORGANISM: Rattus sp.

<400> SEQUENCE: 36

Met Glu Pro Ser Pro Leu Glu Leu Pro Val Asp Ala Val Arg Arg Ile
1               5                   10                  15

Ala Ala Glu Leu Asn Cys Asp Pro Thr Asp Glu Arg Val Ala Leu Arg
            20                  25                  30

Leu Asp Glu Glu Asp Lys Leu Lys Arg Phe Lys Asp Cys Phe Tyr Ile
            35                  40                  45

Pro Lys Met Arg Asp Leu Pro Ser Ile Asp Leu Ser Leu Val Asn Glu
        50                  55                  60

Asp Asp Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
            85                  90                  95

Ile Gly Ala Tyr Gly His Glu Val Gly Lys Arg Pro Trp Ile Ile Gly
            100                 105                 110

Asp Glu Ser Ile Val Thr Leu Met Lys Asp Ile Val Gly Ala His Glu
            115                 120                 125

Lys Glu Ile Ala Leu Met Asn Ala Leu Thr Val Asn Leu His Leu Leu
            130                 135                 140

Leu Leu Ser Phe Phe Lys Pro Thr Pro Lys Arg His Lys Ile Leu Leu
145                 150                 155                 160

Glu Ala Lys Ala Phe Pro Ser Asp His Tyr Ala Ile Glu Ser Gln Ile
            165                 170                 175

Gln Leu His Gly Leu Asp Val Glu Lys Ser Met Arg Met Ile Lys Pro
            180                 185                 190

Arg Glu Gly Glu Glu Thr Leu Arg Met Glu Asp Ile Leu Glu Val Ile
            195                 200                 205

Glu Lys Glu Gly Asp Ser Ile Ala Val Val Leu Phe Ser Gly Leu His
            210                 215                 220

Phe Tyr Thr Gly Gln Leu Phe Asn Ile Pro Ala Ile Thr Gln Ala Gly
225                 230                 235                 240
```

-continued

```
His Ala Lys Gly Cys Phe Val Gly Phe Asp Leu Ala His Ala Val Gly
            245                 250                 255

Asn Val Glu Leu His Leu His Asp Trp Asp Val Asp Phe Ala Cys Trp
        260                 265                 270

Cys Ser Tyr Lys Tyr Leu Asn Ser Gly Ala Gly Gly Leu Ala Gly Ala
    275                 280                 285

Phe Ile His Glu Lys His Ala His Thr Ile Lys Pro Ala Leu Val Gly
290                 295                 300

Trp Phe Gly His Glu Leu Ser Thr Arg Phe Asn Met Asp Asn Lys Leu
305                 310                 315                 320

Gln Leu Ile Pro Gly Val Asn Gly Phe Arg Ile Ser Asn Pro Pro Ile
            325                 330                 335

Leu Leu Val Cys Ser Leu His Ala Ser Leu Glu Ile Phe Gln Gln Ala
        340                 345                 350

Thr Met Thr Ala Leu Arg Arg Lys Ser Ile Leu Leu Thr Gly Tyr Leu
    355                 360                 365

Glu Tyr Leu Leu Lys His Tyr His Gly Gly Asn Asp Thr Glu Asn Lys
370                 375                 380

Arg Pro Val Val Asn Ile Ile Thr Pro Ser Arg Ala Glu Glu Arg Gly
385                 390                 395                 400

Cys Gln Leu Thr Leu Thr Phe Ser Ile Ser Lys Lys Gly Val Phe Lys
            405                 410                 415

Glu Leu Glu Lys Arg Gly Val Val Cys Asp Lys Arg Glu Pro Glu Gly
        420                 425                 430

Ile Arg Val Ala Pro Val Pro Leu Tyr Asn Ser Phe His Asp Val Tyr
    435                 440                 445

Lys Phe Ile Arg Leu Leu Thr Ala Ile Leu Asp Ser Thr Glu Arg Asn
450                 455                 460

<210> SEQ ID NO 37
<211> LENGTH: 1178
<212> TYPE: PRT
<213> ORGANISM: Rattus sp.

<400> SEQUENCE: 37

Met Leu Lys Phe Gln Thr Val Arg Gly Gly Leu Arg Leu Leu Gly Val
1               5                   10                  15

Arg Arg Ser Ser Thr Ala Pro Val Ala Ser Pro Asn Val Arg Arg Leu
            20                  25                  30

Glu Tyr Lys Pro Ile Lys Lys Val Met Val Ala Asn Arg Gly Glu Ile
        35                  40                  45

Ala Ile Arg Val Phe Arg Ala Cys Thr Glu Leu Gly Ile Arg Thr Val
    50                  55                  60

Ala Val Tyr Ser Glu Gln Asp Thr Gly Gln Met His Arg Gln Lys Ala
65                  70                  75                  80

Asp Glu Ala Tyr Leu Ile Gly Arg Gly Leu Ala Pro Val Gln Ala Tyr
            85                  90                  95

Leu His Ile Pro Asp Ile Ile Lys Val Ala Lys Glu Asn Gly Val Asp
        100                 105                 110

Ala Val His Pro Gly Tyr Gly Phe Leu Ser Glu Arg Ala Asp Phe Ala
    115                 120                 125

Gln Ala Cys Gln Asp Ala Gly Val Arg Phe Ile Gly Pro Ser Pro Glu
130                 135                 140

Val Val Arg Lys Met Gly Asp Lys Val Glu Ala Arg Ala Ile Ala Ile
145                 150                 155                 160
```

```
Ala Ala Gly Val Pro Val Pro Gly Thr Asn Ser Pro Ile Asn Ser
            165                 170                 175

Leu His Glu Ala His Glu Phe Ser Asn Thr Tyr Gly Phe Pro Ile Ile
                180                 185                 190

Phe Lys Ala Ala Tyr Gly Gly Gly Arg Gly Met Arg Val Val His
            195                 200                 205

Ser Tyr Glu Glu Leu Glu Glu Asn Tyr Thr Arg Ala Tyr Ser Glu Ala
    210                 215                 220

Leu Ala Ala Phe Gly Asn Gly Ala Leu Phe Val Glu Lys Phe Ile Glu
225                 230                 235                 240

Lys Pro Arg His Ile Glu Val Gln Ile Leu Gly Asp Gln Tyr Gly Asn
                245                 250                 255

Ile Leu His Leu Tyr Glu Arg Asp Cys Ser Ile Gln Arg Arg His Gln
            260                 265                 270

Lys Val Val Glu Ile Ala Pro Ala Thr His Leu Asp Pro Gln Leu Arg
            275                 280                 285

Ser Arg Leu Thr Ser Asp Ser Val Lys Leu Ala Lys Gln Val Gly Tyr
    290                 295                 300

Glu Asn Ala Gly Thr Val Glu Phe Leu Val Asp Lys His Gly Lys His
305                 310                 315                 320

Tyr Phe Ile Glu Val Asn Ser Arg Leu Gln Val Glu His Thr Val Thr
                325                 330                 335

Glu Glu Ile Thr Asp Val Asp Leu Val His Ala Gln Ile His Val Ser
            340                 345                 350

Glu Gly Arg Ser Leu Pro Asp Leu Gly Leu Arg Gln Glu Asn Ile Arg
            355                 360                 365

Ile Asn Gly Cys Ala Ile Gln Cys Arg Val Thr Thr Glu Asp Pro Ala
370                 375                 380

Arg Ser Phe Gln Pro Asp Thr Gly Arg Ile Glu Val Phe Arg Ser Gly
385                 390                 395                 400

Glu Gly Met Gly Ile Arg Leu Asp Asn Ala Ser Ala Phe Gln Gly Ala
                405                 410                 415

Val Ile Ser Pro His Tyr Asp Ser Leu Leu Val Lys Val Ile Ala His
            420                 425                 430

Gly Lys Asp His Pro Thr Ala Ala Thr Lys Met Ser Arg Ala Leu Ala
            435                 440                 445

Glu Phe Arg Val Arg Gly Val Lys Thr Asn Ile Pro Phe Leu Gln Asn
    450                 455                 460

Val Leu Asn Asn Gln Gln Phe Leu Ala Gly Ile Val Asp Thr Gln Phe
465                 470                 475                 480

Ile Asp Glu Asn Pro Glu Leu Phe Gln Leu Arg Pro Ala Gln Asn Arg
                485                 490                 495

Ala Gln Lys Leu Leu His Tyr Leu Gly His Val Met Val Asn Gly Pro
            500                 505                 510

Thr Thr Pro Ile Pro Val Lys Val Ser Pro Ser Pro Val Asp Pro Ile
            515                 520                 525

Val Pro Val Val Pro Ile Gly Pro Pro Ala Gly Phe Arg Asp Ile
            530                 535                 540

Leu Leu Arg Glu Gly Pro Glu Gly Phe Ala Arg Ala Val Arg Asn His
545                 550                 555                 560

Gln Gly Leu Leu Leu Met Asp Thr Thr Phe Arg Asp Ala His Gln Ser
                565                 570                 575

Leu Leu Ala Thr Arg Val Arg Thr His Asp Leu Lys Lys Ile Ala Pro
            580                 585                 590
```

```
Tyr Val Ala His Asn Phe Asn Asn Leu Phe Ser Ile Glu Asn Trp Gly
             595                 600                 605

Gly Ala Thr Phe Asp Val Ala Met Arg Phe Leu Tyr Glu Cys Pro Trp
             610                 615                 620

Arg Arg Leu Gln Glu Leu Arg Glu Leu Ile Pro Asn Ile Pro Phe Gln
625                 630                 635                 640

Met Leu Leu Arg Gly Ala Asn Ala Val Gly Tyr Thr Asn Tyr Pro Asp
             645                 650                 655

Asn Val Val Phe Lys Phe Cys Glu Val Ala Lys Glu Asn Gly Met Asp
             660                 665                 670

Val Phe Arg Ile Phe Asp Ser Leu Asn Tyr Leu Pro Asn Met Leu Leu
             675                 680                 685

Gly Met Glu Ala Ala Gly Ser Ala Gly Gly Val Glu Ala Ala Ile
             690                 695                 700

Ser Tyr Thr Gly Asp Val Ala Asp Pro Ser Arg Thr Lys Tyr Ser Leu
705                 710                 715                 720

Glu Tyr Tyr Met Gly Leu Ala Glu Glu Leu Val Arg Ala Gly Thr His
             725                 730                 735

Ile Leu Cys Ile Lys Asp Met Ala Gly Leu Leu Lys Pro Ala Ala Cys
             740                 745                 750

Thr Met Leu Val Ser Ser Leu Arg Asp Arg Phe Pro Asp Leu Pro Leu
             755                 760                 765

His Ile His Thr His Asp Thr Ser Gly Ser Gly Val Ala Ala Met Leu
             770                 775                 780

Ala Cys Ala Gln Ala Gly Ala Asp Val Val Asp Val Ala Val Asp Ser
785                 790                 795                 800

Met Ser Gly Met Thr Ser Gln Pro Ser Met Gly Ala Leu Val Ala Cys
             805                 810                 815

Thr Lys Gly Thr Pro Leu Asp Thr Glu Val Pro Leu Glu Arg Val Phe
             820                 825                 830

Asp Tyr Ser Glu Tyr Trp Glu Gly Ala Arg Gly Leu Tyr Ala Ala Phe
             835                 840                 845

Asp Cys Thr Ala Thr Met Lys Ser Gly Asn Ser Asp Val Tyr Glu Asn
             850                 855                 860

Glu Ile Pro Gly Gly Gln Tyr Thr Asn Leu His Phe Gln Ala His Ser
865                 870                 875                 880

Met Gly Leu Gly Ser Lys Phe Lys Glu Val Lys Lys Ala Tyr Val Glu
             885                 890                 895

Ala Asn Gln Met Leu Gly Asp Leu Ile Lys Val Thr Pro Ser Ser Lys
             900                 905                 910

Ile Val Gly Asp Leu Ala Gln Phe Met Val Gln Asn Gly Leu Ser Arg
             915                 920                 925

Ala Glu Ala Glu Ala Gln Ala Glu Glu Leu Ser Phe Pro Arg Ser Val
930                 935                 940

Val Glu Phe Leu Gln Gly Tyr Ile Gly Ile Pro His Gly Gly Phe Pro
945                 950                 955                 960

Glu Pro Phe Arg Ser Lys Val Leu Lys Asp Leu Pro Arg Ile Glu Gly
             965                 970                 975

Arg Pro Gly Ala Ser Leu Pro Pro Leu Asn Leu Lys Glu Leu Glu Lys
             980                 985                 990

Asp Leu Ile Asp Arg His Gly Glu  Glu Val Thr Pro Glu  Asp Val Leu
             995                 1000                1005

Ser Ala  Ala Met Tyr Pro Asp  Val Phe Ala Gln Phe  Lys Asp Phe
```

-continued

```
                1010                1015                1020

Thr Ala Thr Phe Gly Pro Leu Asp Ser Leu Asn Thr Arg Leu Phe
    1025                1030                1035

Leu Gln Gly Pro Lys Ile Ala Glu Glu Phe Glu Val Glu Leu Glu
    1040                1045                1050

Arg Gly Lys Thr Leu His Ile Lys Ala Leu Ala Val Ser Asp Leu
    1055                1060                1065

Asn Arg Ala Gly Gln Arg Gln Val Phe Phe Glu Leu Asn Gly Gln
    1070                1075                1080

Leu Arg Ser Ile Leu Val Lys Asp Thr Gln Ala Met Lys Glu Met
    1085                1090                1095

His Phe His Pro Lys Ala Leu Lys Asp Val Lys Gly Gln Ile Gly
    1100                1105                1110

Ala Pro Met Pro Gly Lys Val Ile Asp Val Lys Val Ala Ala Gly
    1115                1120                1125

Ala Lys Val Val Lys Gly Gln Pro Leu Cys Val Leu Ser Ala Met
    1130                1135                1140

Lys Met Glu Thr Val Val Thr Ser Pro Met Glu Gly Thr Ile Arg
    1145                1150                1155

Lys Val His Val Thr Lys Asp Met Thr Leu Glu Gly Asp Asp Leu
    1160                1165                1170

Ile Leu Glu Ile Glu
    1175

<210> SEQ ID NO 38
<211> LENGTH: 407
<212> TYPE: PRT
<213> ORGANISM: Rattus sp.

<400> SEQUENCE: 38

Met Arg Trp Phe Arg Ala Leu Leu Lys Asn Ala Ser Leu Ala Gly Ala
1               5                   10                  15

Pro Lys Tyr Ile Glu His Phe Ser Lys Phe Ser Pro Ser Pro Leu Ser
                20                  25                  30

Met Lys Gln Phe Leu Asp Phe Gly Ser Ser Asn Ala Cys Glu Lys Thr
            35                  40                  45

Ser Phe Thr Phe Leu Arg Gln Glu Leu Pro Val Arg Leu Ala Asn Ile
        50                  55                  60

Met Lys Glu Ile Asn Leu Leu Pro Asp Arg Val Leu Ser Thr Pro Ser
65                  70                  75                  80

Val Gln Leu Val Gln Ser Trp Tyr Val Gln Ser Leu Leu Asp Ile Met
                85                  90                  95

Glu Phe Leu Asp Lys Asp Pro Glu Asp His Arg Thr Leu Ser Gln Phe
                100                 105                 110

Thr Asp Ala Leu Val Thr Ile Arg Asn Arg His Asn Asp Val Val Pro
            115                 120                 125

Thr Met Ala Gln Gly Val Leu Glu Tyr Lys Asp Thr Tyr Gly Asp Asp
        130                 135                 140

Pro Val Ser Asn Gln Asn Ile Gln Tyr Phe Leu Asp Arg Phe Tyr Leu
145                 150                 155                 160

Ser Arg Ile Ser Ile Arg Met Leu Ile Asn Gln His Thr Leu Ile Phe
                165                 170                 175

Asp Gly Ser Thr Asn Pro Ala His Pro Lys His Ile Gly Ser Ile Asp
            180                 185                 190

Pro Asn Cys Ser Val Ser Asp Val Val Lys Asp Ala Tyr Asp Met Ala
```

```
                    195                 200                 205
Lys Leu Leu Cys Asp Lys Tyr Tyr Met Ala Ser Pro Asp Leu Glu Ile
    210                 215                 220

Gln Glu Val Asn Ala Thr Asn Ala Thr Gln Pro Ile His Met Val Tyr
225                 230                 235                 240

Val Pro Ser His Leu Tyr His Met Leu Phe Glu Leu Phe Lys Asn Ala
                245                 250                 255

Met Arg Ala Thr Val Glu Ser His Glu Ser Ser Leu Thr Leu Pro Pro
            260                 265                 270

Ile Lys Ile Met Val Ala Leu Gly Glu Glu Asp Leu Ser Ile Lys Met
        275                 280                 285

Ser Asp Arg Gly Gly Gly Val Pro Leu Arg Lys Ile Glu Arg Leu Phe
    290                 295                 300

Ser Tyr Met Tyr Ser Thr Ala Pro Thr Pro Gln Pro Gly Thr Gly Gly
305                 310                 315                 320

Thr Pro Leu Ala Gly Phe Gly Tyr Gly Leu Pro Ile Ser Arg Leu Tyr
                325                 330                 335

Ala Lys Tyr Phe Gln Gly Asp Leu Gln Leu Phe Ser Met Glu Gly Phe
            340                 345                 350

Gly Thr Asp Ala Val Ile Tyr Leu Lys Ala Leu Ser Thr Asp Ser Val
        355                 360                 365

Glu Arg Leu Pro Val Tyr Asn Lys Ser Ala Trp Arg His Tyr Gln Thr
    370                 375                 380

Ile Gln Glu Ala Gly Asp Trp Cys Val Pro Ser Thr Glu Pro Lys Asn
385                 390                 395                 400

Thr Ser Thr Tyr Arg Val Ser
                405

<210> SEQ ID NO 39
<211> LENGTH: 362
<212> TYPE: PRT
<213> ORGANISM: Rattus sp.

<400> SEQUENCE: 39

Met Glu Val His Asn Val Ser Ala Pro Phe Asn Phe Ser Leu Pro Pro
1               5                   10                  15

Gly Phe Gly His Arg Ala Thr Asp Lys Ala Leu Ser Ile Ile Leu Val
            20                  25                  30

Leu Met Leu Leu Leu Ile Met Leu Ser Leu Gly Cys Thr Met Glu Phe
        35                  40                  45

Ser Lys Ile Lys Ala His Leu Trp Lys Pro Lys Gly Val Ile Val Ala
    50                  55                  60

Leu Val Ala Gln Phe Gly Ile Met Pro Leu Ala Ala Phe Leu Leu Gly
65                  70                  75                  80

Lys Ile Phe His Leu Ser Asn Ile Glu Ala Leu Ala Ile Leu Ile Cys
                85                  90                  95

Gly Cys Ser Pro Gly Gly Asn Leu Ser Asn Leu Phe Thr Leu Ala Met
            100                 105                 110

Lys Gly Asp Met Asn Leu Ser Ile Val Met Thr Thr Cys Ser Ser Phe
        115                 120                 125

Ser Ala Leu Gly Met Met Pro Leu Leu Leu Tyr Val Tyr Ser Lys Gly
    130                 135                 140

Ile Tyr Asp Gly Asp Leu Lys Asp Lys Val Pro Tyr Lys Gly Ile Met
145                 150                 155                 160

Ile Ser Leu Val Ile Val Leu Ile Pro Cys Thr Ile Gly Ile Val Leu
```

```
                    165                 170                 175
Lys Ser Lys Arg Pro His Tyr Val Pro Tyr Ile Leu Lys Gly Gly Met
            180                 185                 190

Ile Ile Thr Phe Leu Leu Ser Val Ala Val Thr Ala Leu Ser Val Ile
            195                 200                 205

Asn Val Gly Asn Ser Ile Met Phe Val Met Thr Pro His Leu Leu Ala
            210                 215                 220

Thr Ser Ser Leu Met Pro Phe Ser Gly Phe Leu Met Gly Tyr Ile Leu
225                 230                 235                 240

Ser Ala Leu Phe Gln Leu Asn Pro Ser Cys Arg Arg Thr Ile Ser Met
            245                 250                 255

Glu Thr Gly Phe Gln Asn Ile Gln Leu Cys Ser Thr Ile Leu Asn Val
            260                 265                 270

Thr Phe Pro Pro Glu Val Ile Gly Pro Leu Phe Phe Phe Pro Leu Leu
            275                 280                 285

Tyr Met Ile Phe Gln Leu Ala Glu Gly Leu Leu Ile Ile Ile Ile Phe
            290                 295                 300

Arg Cys Tyr Glu Lys Ile Lys Pro Pro Lys Asp Gln Thr Lys Ile Thr
305                 310                 315                 320

Tyr Lys Ala Ala Ala Thr Glu Asp Ala Thr Pro Ala Ala Leu Glu Lys
            325                 330                 335

Gly Thr His Asn Gly Asn Ile Pro Pro Leu Gln Pro Gly Pro Ser Pro
            340                 345                 350

Asn Gly Leu Asn Ser Gly Gln Met Ala Asn
            355                 360

<210> SEQ ID NO 40
<211> LENGTH: 429
<212> TYPE: PRT
<213> ORGANISM: Rattus sp.

<400> SEQUENCE: 40

Met Ala Ala Gln Gly Tyr Gly Tyr Tyr Arg Thr Val Ile Phe Thr Ala
1               5                   10                  15

Met Phe Gly Gly Tyr Ser Leu Tyr Tyr Phe Asn Arg Lys Thr Phe Ser
            20                  25                  30

Phe Val Met Pro Ser Leu Val Asp Glu Ile Ala Leu Asp Lys Asp Asp
        35                  40                  45

Leu Gly Leu Ile Thr Ser Ser Gln Ser Ala Ala Tyr Ala Ile Ser Lys
    50                  55                  60

Phe Val Ser Gly Val Leu Ser Asp Gln Met Ser Ala Arg Trp Leu Phe
65                  70                  75                  80

Ser Ser Gly Leu Leu Leu Val Gly Leu Val Asn Val Val Phe Ser Trp
                85                  90                  95

Ser Ser Thr Val Thr Ala Phe Ala Ala Leu Trp Phe Leu Asn Gly Leu
            100                 105                 110

Ala Gln Gly Leu Gly Trp Pro Pro Cys Gly Lys Ile Leu Arg Lys Trp
            115                 120                 125

Phe Glu Pro Ser Gln Phe Gly Thr Trp Trp Ala Val Leu Ser Thr Ser
        130                 135                 140

Met Asn Leu Ala Gly Ser Leu Gly Pro Ile Leu Ala Thr Ile Leu Ala
145                 150                 155                 160

Gln Ser Tyr Ser Trp Arg Ser Thr Leu Ala Leu Ser Gly Ser Leu Cys
                165                 170                 175

Val Val Val Ser Phe Phe Cys Leu Leu Leu Ile His Asn Glu Pro Ala
```

```
                    180                 185                 190
Asp Val Gly Leu Arg Asn Leu Asp Pro Ala Pro Ser Lys Gly Lys Lys
            195                 200                 205

Gly Ser Ser Lys Glu Glu Ser Thr Leu Gln Asp Leu Leu Ser Pro
    210                 215                 220

Tyr Leu Trp Val Leu Ser Thr Gly Tyr Leu Val Val Phe Gly Val Lys
225                 230                 235                 240

Thr Cys Cys Thr Asp Trp Gly Gln Phe Phe Leu Ile Gln Glu Arg Gly
                245                 250                 255

Gln Ser Ala Leu Val Gly Ser Ser Tyr Ile Ser Ala Leu Glu Val Gly
            260                 265                 270

Gly Leu Val Gly Ser Ile Ala Ala Gly Tyr Leu Ser Asp Arg Ala Met
        275                 280                 285

Ala Lys Ala Gly Leu Ser Val Tyr Gly Asn Pro Arg His Ser Leu Leu
        290                 295                 300

Leu Leu Met Met Ala Gly Met Ala Ala Ser Met Phe Leu Phe Arg Val
305                 310                 315                 320

Thr Val Thr Ser Asp Ser Pro Lys Ile Trp Ile Leu Val Leu Gly Ala
                325                 330                 335

Val Phe Gly Phe Ser Ser Tyr Gly Pro Ile Ala Leu Phe Gly Val Ile
                340                 345                 350

Ala Asn Glu Ser Ala Pro Pro Asn Leu Cys Gly Thr Ser His Ala Ile
                355                 360                 365

Val Gly Leu Met Ala Asn Val Gly Gly Phe Leu Ala Gly Leu Pro Phe
            370                 375                 380

Ser Thr Ile Ala Lys His Tyr Ser Trp Ser Thr Ala Phe Trp Val Ala
385                 390                 395                 400

Glu Val Ile Cys Ile Ala Ser Thr Val Val Phe Leu Leu Arg Asn
                405                 410                 415

Ile Arg Thr Lys Met Gly Arg Val Ser Lys Lys Ala Glu
                420                 425

<210> SEQ ID NO 41
<211> LENGTH: 463
<212> TYPE: PRT
<213> ORGANISM: Rattus sp.

<400> SEQUENCE: 41

Met Leu Cys Ser Glu Leu Glu Thr Gly Ala Trp Gly Ala Leu Ala Ala
1               5                   10                  15

Glu Leu Gly Ala Ser Glu Ala Ala Ser Val Ser Val Asp Gln Gly Ala
            20                  25                  30

Gly Ser Ala Leu Leu Gly Leu Glu Ser Glu Ala Ala Trp Ala Ala Ser
        35                  40                  45

Leu Phe Ala Ser Arg Pro Ala Leu Gly Ala Ser Val Phe Leu Ala Ser
    50                  55                  60

Pro Pro Ser Trp Gly Ala Arg Ser Gly Ala Arg Val Pro Ser Ala Leu
65                  70                  75                  80

Gly Ala Arg Leu Ala Gly Leu Gly Gly Leu Val Ala His Arg Gly Pro
                85                  90                  95

Gly Pro Gly Arg Leu Leu Leu Arg His Trp Pro Gly Leu Gly Leu Leu
            100                 105                 110

Leu Arg Gly Ala Leu Ala Leu Leu Gly Leu Gly Leu Gly Arg Leu Leu
        115                 120                 125

Leu Thr Gly Arg Leu Leu Val Gly Leu Leu Phe Leu Ser Pro Cys Leu
```

```
                130                 135                 140
Pro Ile Trp Ser Val Leu Gly Leu Leu Cys Ala Leu Leu Asp Leu Ser
145                 150                 155                 160

Gly Val Gly Gly Arg Leu Gly Phe Ser Leu Leu Trp Gly Pro Leu Phe
                165                 170                 175

Leu Gly Ala Arg Ala Phe Ser Leu Leu Val Phe Val Leu Gly Leu Leu
                180                 185                 190

Leu Ile His Ile Val Thr Leu Leu Ala Gln Leu Ala Ser His His Gly
                195                 200                 205

Val Pro Leu Leu Arg Gly Ala Asp Glu Lys Ser Ser Leu His Phe Phe
210                 215                 220

Lys Leu Tyr Leu Leu Pro Leu Pro His Asn Lys Leu Trp Ala Thr Asn
225                 230                 235                 240

Gln Thr Pro Ile Asn Glu Arg Thr Glu Met Val Tyr Ser Phe Arg Gln
                245                 250                 255

Leu Lys Gln Ala Ala Arg Ile Gln Gly Lys Arg Trp Thr His Pro Glu
                260                 265                 270

Gly Gln Leu Gly Ser Ser Asn Ile Cys Val Pro Leu Thr His Leu Ser
                275                 280                 285

Ser Ser Pro Lys Tyr Leu Tyr Val Ala Arg Asn Ala Lys Asp Cys Met
290                 295                 300

Val Ser Tyr Tyr His Phe Tyr Arg Met Ser Gln Val Leu Pro Asn Pro
305                 310                 315                 320

Gly Thr Trp Asn Glu Tyr Phe Glu Thr Phe Ile Asn Gly Lys Val Ser
                325                 330                 335

Cys Gly Ser Trp Phe Asp His Val Lys Gly Trp Trp Glu Ile Arg Asp
                340                 345                 350

Arg Tyr Gln Ile Leu Phe Leu Phe Tyr Glu Asp Met Lys Arg Asp Pro
                355                 360                 365

Lys Arg Glu Ile Gln Lys Val Met Gln Phe Met Gly Lys Asn Leu Asp
370                 375                 380

Glu Glu Val Val Asp Lys Ile Val Leu Glu Thr Ser Phe Glu Lys Met
385                 390                 395                 400

Lys Asp Asn Pro Leu Thr Asn Phe Ser Thr Ile Pro Lys Thr Ile Met
                405                 410                 415

Asp Gln Ser Ile Ser Pro Phe Met Arg Lys Gly Ile Val Gly Asp Trp
                420                 425                 430

Lys Asn His Phe Thr Val Ala Gln Asn Glu Arg Phe Asp Glu Ile Tyr
                435                 440                 445

Glu Gln Lys Met Asp Gly Thr Ser Leu Asn Phe Cys Met Glu Leu
450                 455                 460

<210> SEQ ID NO 42
<211> LENGTH: 161
<212> TYPE: PRT
<213> ORGANISM: Rattus sp.

<400> SEQUENCE: 42

Met Asp Gln Glu Ala Val Gly Asn Val Val Leu Leu Ala Ile Val Thr
1               5                   10                  15

Leu Ile Ser Val Val Gln Asn Ala Phe Phe Ala His Lys Val Glu Leu
                20                  25                  30

Glu Ser Lys Ala Gln Ser Gly Arg Ser Phe Gln Arg Thr Gly Thr Leu
                35                  40                  45

Ala Phe Glu Arg Val Tyr Thr Ala Asn Gln Asn Cys Val Asp Ala Tyr
```

```
            50                  55                  60
Pro Thr Phe Leu Val Val Leu Trp Thr Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Thr Gln Ser Thr Pro Gly Tyr
            100                 105                 110

Ile Phe Gly Lys Arg Ile Ile Leu Phe Leu Phe Leu Met Ser Leu Ala
            115                 120                 125

Gly Ile Leu Asn His Tyr Leu Ile Phe Phe Phe Gly Ser Asp Phe Glu
            130                 135                 140

Asn Tyr Ile Arg Thr Ile Thr Thr Thr Ile Ser Pro Leu Leu Leu Ile
145                 150                 155                 160

Pro

<210> SEQ ID NO 43
<211> LENGTH: 180
<212> TYPE: PRT
<213> ORGANISM: Rattus sp.

<400> SEQUENCE: 43

Met Ser Glu Ser Glu Leu Gln Leu Val Ala Arg Arg Ile Arg Ser Phe
1               5                   10                  15

Pro Asp Phe Pro Ile Pro Gly Val Leu Phe Arg Asp Ile Ser Pro Leu
                20                  25                  30

Leu Lys Asp Pro Asp Ser Phe Arg Ala Ser Ile Arg Leu Leu Ala Gly
            35                  40                  45

His Leu Lys Ser Thr His Gly Gly Lys Ile Asp Tyr Ile Ala Gly Leu
        50                  55                  60

Asp Ser Arg Gly Phe Leu Phe Gly Pro Ser Leu Ala Gln Glu Leu Gly
65                  70                  75                  80

Val Gly Cys Val Leu Ile Arg Lys Arg Gly Lys Leu Pro Gly Pro Thr
                85                  90                  95

Val Ser Ala Ser Tyr Ser Leu Glu Tyr Gly Lys Ala Glu Leu Glu Ile
            100                 105                 110

Gln Lys Asp Ala Leu Glu Pro Gly Gln Lys Val Val Ile Val Asp Asp
        115                 120                 125

Leu Leu Ala Thr Gly Gly Thr Met Cys Ala Ala Cys Glu Leu Leu Ser
130                 135                 140

Gln Leu Arg Ala Glu Val Val Glu Cys Val Ser Leu Val Glu Leu Thr
145                 150                 155                 160

Ser Leu Lys Gly Arg Glu Lys Leu Gly Pro Val Pro Phe Phe Ser Leu
                165                 170                 175

Leu Gln Tyr Glu
            180

<210> SEQ ID NO 44
<211> LENGTH: 220
<212> TYPE: PRT
<213> ORGANISM: Rattus sp.

<400> SEQUENCE: 44

Met Gly Ser Lys Leu Ser Lys Lys Lys Gly Tyr Asn Val Asn Asp
1               5                   10                  15

Glu Lys Ala Lys Asp Lys Asp Lys Lys Ala Glu Gly Ala Gly Thr Glu
                20                  25                  30
```

```
Glu Gly Thr Gln Lys Ser Glu Pro Gln Ala Ala Asp Ala
    35              40              45

Thr Glu Val Lys Glu Ser Ala Glu Glu Lys Pro Lys Asp Ala Ala Asp
    50              55              60

Gly Glu Ala Lys Ala Glu Lys Glu Ala Asp Lys Ala Ala Ala Lys
65              70              75              80

Glu Glu Ala Pro Lys Ala Glu Pro Glu Lys Ser Glu Gly Ala Ala Glu
                85              90              95

Glu Gln Pro Glu Pro Ala Pro Ala Pro Glu Gln Glu Ala Ala Ala Pro
            100             105             110

Gly Pro Ala Ala Gly Gly Glu Ala Pro Lys Ala Gly Glu Ala Ser Ala
            115             120             125

Glu Ser Thr Gly Ala Ala Asp Gly Ala Pro Gln Glu Glu Gly Glu Ala
        130             135             140

Lys Lys Thr Glu Ala Pro Ala Ala Gly Pro Glu Ala Lys Ser Asp Ala
145             150             155             160

Ala Pro Ala Ala Ser Asp Ser Lys Pro Ser Thr Glu Pro Ala Pro Ser
                165             170             175

Ser Lys Glu Thr Pro Ala Ala Ser Glu Ala Pro Ser Ser Ala Ala Lys
            180             185             190

Ala Pro Ala Pro Ala Ala Pro Ala Glu Pro Gln Ala Glu Ala Pro
            195             200             205

Val Ala Ser Ser Glu Gln Ser Val Ala Val Lys Glu
        210             215             220

<210> SEQ ID NO 45
<211> LENGTH: 169
<212> TYPE: PRT
<213> ORGANISM: Rattus sp.

<400> SEQUENCE: 45

Met Ser Gln Ser Trp Val Pro Ala Val Gly Leu Thr Leu Val Pro Ser
1               5                   10                  15

Leu Gly Gly Phe Met Gly Ala Tyr Phe Val Arg Gly Glu Gly Leu Arg
                20                  25                  30

Trp Tyr Ala Ser Leu Gln Lys Pro Ser Trp His Pro Pro Arg Trp Thr
            35                  40                  45

Leu Ala Pro Ile Trp Gly Thr Leu Tyr Ser Ala Met Gly Tyr Gly Ser
        50                  55                  60

Tyr Ile Ile Trp Lys Glu Leu Gly Gly Phe Thr Glu Glu Ala Met Val
65                  70                  75                  80

Pro Leu Gly Leu Tyr Thr Gly Gln Leu Ala Leu Asn Trp Ala Trp Pro
                85                  90                  95

Pro Ile Phe Phe Gly Ala Arg Gln Met Gly Trp Ala Leu Val Asp Leu
                100                 105                 110

Met Leu Val Ser Gly Val Ala Thr Ala Thr Leu Ala Trp His Arg
            115                 120                 125

Val Ser Pro Pro Ala Ala Arg Leu Leu Tyr Pro Tyr Leu Ala Trp Leu
        130                 135                 140

Ala Phe Ala Thr Met Leu Asn Tyr Tyr Val Trp Arg Asp Asn Ser Gly
145                 150                 155                 160

Arg Arg Gly Gly Ser Arg Leu Thr Glu
                165

<210> SEQ ID NO 46
<211> LENGTH: 277
```

```
<212> TYPE: PRT
<213> ORGANISM: Rattus sp.

<400> SEQUENCE: 46

Met Ser Ser Asp Arg Pro Val Ala Leu Val Thr Gly Ala Asn Lys Gly
1               5                   10                  15

Ile Gly Phe Ala Ile Val Arg Asp Leu Cys Arg Lys Phe Leu Gly Asp
            20                  25                  30

Val Val Leu Thr Ala Arg Asp Glu Ser Arg Gly His Glu Ala Val Lys
        35                  40                  45

Gln Leu Gln Thr Glu Gly Leu Ser Pro Arg Phe His Gln Leu Asp Ile
    50                  55                  60

Asp Asn Pro Gln Ser Ile Arg Ala Leu Arg Asp Phe Leu Leu Gln Glu
65                  70                  75                  80

Tyr Gly Gly Leu Asn Val Leu Val Asn Asn Ala Gly Ile Ala Phe Lys
                85                  90                  95

Val Val Asp Pro Thr Pro Phe His Ile Gln Ala Glu Val Thr Met Lys
            100                 105                 110

Thr Asn Phe Phe Gly Thr Gln Asp Val Cys Lys Glu Leu Leu Pro Ile
        115                 120                 125

Ile Lys Pro Gln Gly Arg Val Val Asn Val Ser Ser Val Ser Leu
    130                 135                 140

Arg Ala Leu Lys Ser Cys Ser Pro Glu Leu Gln Gln Lys Phe Arg Ser
145                 150                 155                 160

Glu Thr Ile Thr Glu Glu Leu Val Gly Leu Met Asn Lys Phe Ile
                165                 170                 175

Glu Asp Ala Lys Lys Gly Val His Ala Lys Glu Gly Trp Pro Asn Ser
            180                 185                 190

Ala Tyr Gly Val Thr Lys Ile Gly Val Thr Val Leu Ser Arg Ile Tyr
        195                 200                 205

Ala Arg Lys Leu Asn Glu Glu Arg Arg Glu Asp Lys Ile Leu Leu Asn
    210                 215                 220

Ala Cys Cys Pro Gly Trp Val Arg Thr Asp Met Ala Gly Pro Lys Ala
225                 230                 235                 240

Thr Lys Ser Pro Glu Glu Gly Ala Glu Thr Pro Val Tyr Leu Ala Leu
                245                 250                 255

Leu Pro Pro Gly Ala Glu Gly Pro His Gly Gln Phe Val Gln Asp Lys
            260                 265                 270

Lys Val Glu Pro Trp
        275

<210> SEQ ID NO 47
<211> LENGTH: 303
<212> TYPE: PRT
<213> ORGANISM: Rattus sp.

<400> SEQUENCE: 47

Met Trp Pro Leu Ala Ala Ala Leu Leu Leu Gly Ser Cys Cys Cys Gly
1               5                   10                  15

Ser Ala Gln Leu Leu Leu Ser Lys Val Lys Ser Val Glu Phe Thr Ser
            20                  25                  30

Cys Asn Asp Thr Val Val Ile Pro Cys Lys Val Leu Asn Val Glu Ala
        35                  40                  45

Gln Ser Thr Asp Glu Met Phe Val Lys Trp Lys Leu Asn Lys Ser Tyr
    50                  55                  60

Ile Phe Ile Tyr Asp Gly Asn Lys Asn Ser Thr Thr Arg Glu Gln Asn
```

```
            65                  70                  75                  80
Phe Thr Ser Ala Lys Ile Ser Val Ser Asp Leu Leu Lys Gly Ile Ala
                85                  90                  95
Ser Leu Thr Met Asp Thr His Glu Ala Val Val Gly Asn Tyr Thr Cys
               100                 105                 110
Glu Val Thr Glu Leu Ser Arg Glu Gly Lys Thr Val Ile Glu Leu Lys
               115                 120                 125
Asn Arg Pro Val Ser Trp Phe Ser Thr Asn Lys Ile Leu Ile Val
           130                 135                 140
Ile Phe Pro Ile Leu Ala Ile Leu Leu Phe Trp Gly Lys Phe Gly Ile
145                 150                 155                 160
Leu Thr Leu Lys Tyr Lys Ser Ser His Thr Asn Lys Arg Ile Ile Leu
               165                 170                 175
Leu Leu Val Ala Gly Leu Ala Leu Thr Leu Ile Val Val Gly Ala
           180                 185                 190
Ile Leu Phe Ile Pro Gly Glu Lys Pro Val Lys Asn Ala Ser Gly Leu
           195                 200                 205
Gly Leu Ile Val Ile Ser Thr Gly Ile Leu Ile Leu Gln Tyr Asn
       210                 215                 220
Val Phe Met Thr Ala Phe Gly Met Thr Ser Phe Thr Ile Ala Ile Leu
225                 230                 235                 240
Ile Thr Gln Val Leu Gly Tyr Val Leu Ala Val Val Gly Met Cys Leu
               245                 250                 255
Cys Ile Met Ala Cys Glu Pro Val His Gly Pro Leu Leu Ile Ser Gly
           260                 265                 270
Leu Gly Ile Ile Ala Leu Ala Glu Leu Leu Gly Leu Val Tyr Met Lys
           275                 280                 285
Phe Val Ala Ser Asn Gln Arg Thr Ile Gln Pro Pro Arg Asn Asn
           290                 295                 300

<210> SEQ ID NO 48
<211> LENGTH: 328
<212> TYPE: PRT
<213> ORGANISM: Rattus sp.

<400> SEQUENCE: 48

Met Arg Ser His Thr Gly Leu Arg Ala Leu Val Ala Pro Gly Cys Ser
1               5                  10                  15
Leu Leu Leu Leu Tyr Leu Leu Ala Ala Thr Arg Pro Asp Arg Ala Val
               20                  25                  30
Gly Asp Pro Ala Asp Ser Ala Phe Thr Ser Leu Pro Val Arg Glu Glu
           35                  40                  45
Met Met Ala Lys Tyr Ala Asn Leu Ser Leu Glu Thr Tyr Asn Ile Ser
       50                  55                  60
Leu Thr Glu Gln Thr Arg Val Ser Glu Gln Asn Ile Thr Leu Glu Arg
65                  70                  75                  80
Pro Ser His Leu Glu Leu Glu Cys Thr Phe Thr Ala Thr Glu Asp Val
               85                  90                  95
Met Ser Met Asn Val Thr Trp Lys Lys Asp Asp Ala Leu Leu Glu Thr
               100                 105                 110
Thr Asp Gly Phe Asn Thr Thr Lys Met Gly Asp Thr Leu Tyr Ser Gln
           115                 120                 125
Tyr Arg Phe Thr Val Phe Asn Ser Lys Gln Met Gly Lys Tyr Ser Cys
       130                 135                 140
Phe Leu Gly Glu Glu Leu Arg Gly Thr Phe Asn Ile Arg Val Pro Lys
```

```
                145                 150                 155                 160
Val His Gly Lys Asn Lys Pro Leu Ile Thr Tyr Val Gly Asp Ser Thr
            165                 170                 175

Val Leu Lys Cys Glu Cys Gln Asn Cys Leu Pro Leu Asn Trp Thr Trp
        180                 185                 190

Tyr Met Ser Asn Gly Thr Ala Gln Val Pro Ile Asp Val His Val Asn
        195                 200                 205

Asp Lys Phe Asp Ile Asn Gly Ser Tyr Ala Asn Glu Thr Lys Leu Lys
        210                 215                 220

Val Lys His Leu Leu Glu Glu Asp Gly Gly Ser Tyr Trp Cys Arg Ala
225                 230                 235                 240

Ala Phe Pro Leu Gly Glu Ser Glu His Ile Lys Leu Val Val Leu
            245                 250                 255

Ser Phe Met Val Pro Leu Lys Pro Phe Leu Ala Ile Ile Ala Glu Val
            260                 265                 270

Ile Leu Leu Val Ala Ile Ile Leu Leu Cys Glu Val Tyr Thr Gln Lys
            275                 280                 285

Lys Lys Asn Asp Pro Asp Asp Gly Lys Glu Phe Glu Gln Ile Glu Gln
        290                 295                 300

Leu Lys Ser Asp Asp Ser Asn Gly Ile Glu Asn Asn Val Pro Arg Tyr
305                 310                 315                 320

Arg Lys Thr Asp Ser Gly Asp Gln
                325

<210> SEQ ID NO 49
<211> LENGTH: 578
<212> TYPE: PRT
<213> ORGANISM: Rattus sp.

<400> SEQUENCE: 49

Met Ala Pro Ser Pro Arg Pro Gln His Val Leu His Trp Lys Glu Ala
1               5                   10                  15

His Ser Phe Tyr Leu Leu Ser Pro Leu Met Gly Phe Leu Ser Arg Ala
            20                  25                  30

Trp Ser Arg Leu Arg Gly Pro Glu Val Ser Glu Ala Trp Leu Ala Glu
        35                  40                  45

Thr Val Ala Gly Ala Asn Gln Ile Glu Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
        115                 120                 125

Glu His Thr Ala Gly Leu Pro Thr Leu Gln Pro Leu His Leu Gln Gly
    130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Gly Pro Ala Glu Asp
                165                 170                 175

Glu Glu Asp Thr Glu Thr Val Lys Lys Ala His Gln Ala Ser Ala Ala
            180                 185                 190

Ser Ile Ala Pro Gly Tyr Lys Pro Ser Thr Ser Val Tyr Cys Pro Gly
```

```
                195                 200                 205
Glu Ala Glu His Arg Ala Thr Glu Glu Lys Gly Thr Asp Asn Lys Ala
210                 215                 220
Glu Pro Ser Gly Ser His Ser Arg Val Trp Glu Tyr His Thr Arg Glu
225                 230                 235                 240
Arg Pro Lys Gln Glu Gly Glu Thr Lys Pro Glu Gln His Arg Ala Gly
                245                 250                 255
Gln Ser His Pro Cys Gln Asn Ala Glu Ala Glu Gly Gly Pro Glu
    260                 265                 270
Thr Ser Val Cys Ser Gly Ser Ala Phe Leu Lys Ala Trp Val Tyr Arg
        275                 280                 285
Pro Gly Glu Asp Thr Glu Glu Glu Asp Ser Asp Leu Asp Ser Ala
290                 295                 300
Glu Glu Asp Thr Ala His Thr Cys Thr Thr Pro His Thr Ser Ala Phe
305                 310                 315                 320
Leu Lys Ala Trp Val Tyr Arg Pro Gly Glu Asp Thr Glu Glu Glu Asp
                325                 330                 335
Asp Gly Asp Trp Asp Ser Ala Glu Glu Asp Thr Ala Gln Ser Cys Thr
                340                 345                 350
Thr Pro His Thr Ser Ala Phe Leu Lys Ala Trp Val Tyr Arg Pro Gly
            355                 360                 365
Glu Asp Thr Glu Glu Asp Ser Glu Asn Val Ala Pro Val Asp
370                 375                 380
Ser Glu Thr Val Asp Ser Cys Gln Ser Thr Gln His Cys Leu Pro Val
385                 390                 395                 400
Glu Lys Thr Lys Gly Cys Gly Glu Ala Glu Pro Pro Phe Gln Val
                405                 410                 415
Ala Phe Tyr Leu Pro Gly Gln Lys Pro Ala Pro Trp Ala Ala Pro
                420                 425                 430
Lys Leu Pro Leu Arg Leu Gln Lys Arg Leu Arg Ser Phe Lys Ala Pro
            435                 440                 445
Ala Arg Asn Gln Asp Pro Glu Ile Pro Leu Lys Gly Arg Lys Val His
450                 455                 460
Phe Ser Glu Lys Val Thr Val His Phe Leu Ala Val Trp Ala Gly Pro
465                 470                 475                 480
Ala Gln Ala Ala Arg Gly Pro Trp Glu Gln Phe Ala Arg Asp Arg
                485                 490                 495
Ser Arg Phe Ala Arg Arg Ile Ala Gln Ala Glu Glu Gln Leu Gly Pro
            500                 505                 510
Tyr Leu Thr Pro Ala Phe Arg Ala Arg Ala Trp Thr Arg Leu Arg Asn
            515                 520                 525
Leu Pro Leu Pro Leu Ser Ser Ser Leu Pro Leu Pro Glu Pro Cys
530                 535                 540
Ser Ser Thr Glu Ala Thr Pro Leu Ser Gln Asp Val Thr Thr Pro Ser
545                 550                 555                 560
Pro Leu Pro Ser Glu Ile Pro Pro Ser Leu Asp Leu Gly Gly Arg
                565                 570                 575
Arg Gly

<210> SEQ ID NO 50
<211> LENGTH: 357
<212> TYPE: PRT
<213> ORGANISM: Rattus sp.

<400> SEQUENCE: 50
```

```
Met Ala Glu Leu Gln Glu Val Gln Ile Thr Glu Glu Lys Pro Leu Leu
1               5                   10                  15

Pro Gly Gln Thr Pro Glu Ala Ala Lys Thr His Ser Val Glu Thr Pro
                20                  25                  30

Tyr Gly Ser Val Thr Phe Thr Tyr Gly Thr Pro Lys Pro Lys Arg
            35                  40                  45

Pro Ala Ile Phe Thr Tyr His Asp Val Gly Leu Asn Tyr Lys Ser Cys
            50                  55                  60

Phe Gln Pro Leu Phe Gln Phe Gly Asp Met Gln Glu Ile Ile Gln Asn
65                      70                  75                  80

Phe Val Arg Val His Val Asp Ala Pro Gly Met Glu Glu Gly Ala Pro
                85                  90                  95

Val Phe Pro Leu Gly Tyr Gln Tyr Pro Ser Gln Asp Gln Leu Ala Asp
                100                 105                 110

Met Ile Pro Cys Ile Leu Gln Tyr Leu Asn Phe Ser Thr Ile Ile Gly
            115                 120                 125

Val Gly Val Gly Ala Gly Ala Tyr Ile Leu Ser Arg Tyr Ala Leu Asn
130                 135                 140

His Pro Asp Thr Val Glu Gly Leu Val Leu Ile Asn Ile Asp Pro Asn
145                 150                 155                 160

Ala Lys Gly Trp Met Asp Trp Ala Ala His Lys Leu Thr Gly Leu Thr
                165                 170                 175

Ser Ser Ile Pro Glu Met Ile Leu Gly His Leu Phe Ser Gln Glu Glu
            180                 185                 190

Leu Ser Gly Asn Ser Glu Leu Ile Gln Lys Tyr Arg Ser Leu Ile Thr
        195                 200                 205

His Ala Pro Asn Leu Glu Asn Ile Glu Leu Tyr Trp Asn Ser Tyr Asn
    210                 215                 220

Asn Arg Arg Asp Leu Asn Phe Glu Arg Gly Gly Glu Met Thr Leu Lys
225                 230                 235                 240

Cys Pro Val Met Leu Val Val Gly Asp Gln Ala Pro His Glu Asp Ala
                245                 250                 255

Val Val Glu Cys Asn Ser Lys Leu Asp Pro Thr Gln Thr Ser Phe Leu
            260                 265                 270

Lys Met Ala Asp Ser Gly Gly Gln Pro Gln Leu Thr Gln Pro Gly Lys
        275                 280                 285

Leu Thr Glu Ala Phe Lys Tyr Phe Val Gln Gly Met Gly Tyr Met Ala
    290                 295                 300

Ser Ser Cys Met Thr Arg Leu Ser Arg Ser Arg Thr Ala Ser Leu Thr
305                 310                 315                 320

Ser Ala Ala Ser Ile Asp Gly Ser Arg Ser Arg Ser Arg Thr Leu Ser
                325                 330                 335

Gln Ser Ser Glu Ser Gly Thr Leu Pro Ser Gly Pro Pro Gly His Thr
            340                 345                 350

Met Glu Val Ser Cys
            355

<210> SEQ ID NO 51
<211> LENGTH: 152
<212> TYPE: PRT
<213> ORGANISM: Rattus sp.

<400> SEQUENCE: 51

Met Ala Asn Ser Glu Arg Thr Phe Ile Ala Ile Lys Pro Asp Gly Val
1               5                   10                  15
```

Gln Arg Gly Leu Val Gly Glu Ile Ile Lys Arg Phe Glu Gln Lys Gly
            20                  25                  30

Phe Arg Leu Val Gly Leu Lys Phe Ile Gln Ala Ser Glu Asp Leu Leu
        35                  40                  45

Lys Glu His Tyr Ile Asp Leu Lys Asp Arg Pro Phe Phe Ser Gly Leu
    50                  55                  60

Val Lys Tyr Met His Ser Gly Pro Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Ser Leu Trp Phe Gln Pro Glu Glu Leu Val Asp Tyr Lys Ser
130                 135                 140

Cys Ala Gln Asn Trp Ile Tyr Glu
145                 150

<210> SEQ ID NO 52
<211> LENGTH: 636
<212> TYPE: PRT
<213> ORGANISM: Rattus sp.

<400> SEQUENCE: 52

Met Ser Glu Arg Lys Glu Gly Arg Gly Lys Gly Lys Gly Lys Lys Lys
1               5                   10                  15

Asp Arg Gly Ser Arg Gly Lys Pro Gly Pro Ala Glu Gly Asp Pro Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Glu Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Phe Ile Thr Gly Met Pro Ala Ser Thr Glu
130                 135                 140

Thr Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Ile Lys Cys Ala Glu Lys Glu Lys Thr Phe Cys Val Asn
            180                 185                 190

Gly Gly Glu Cys Phe Thr Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
            245                 250                 255

Cys Val Val Ala Tyr Cys Lys Thr Lys Lys Gln Arg Gln Lys Leu His
                260                 265                 270

Asp Arg Leu Arg Gln Ser Leu Arg Ser Glu Arg Ser Asn Leu Val Asn
            275                 280                 285

Ile Ala Asn Gly Pro His His Pro Asn Pro Pro Glu Asn Val Gln
        290                 295                 300

Leu Val Asn Gln Tyr Val Ser Lys Asn Val Ile Ser Ser Glu His Ile
305                 310                 315                 320

Val Glu Arg Glu Val Glu Thr Ser Phe Ser Thr Ser His Tyr Thr Ser
                325                 330                 335

Thr Ala His His Ser Thr Thr Val Thr Gln Thr Pro Ser His Ser Trp
            340                 345                 350

Ser Asn Gly His Thr Glu Ser Val Ile Ser Glu Ser Asn Ser Val Ile
            355                 360                 365

Met Met Ser Ser Val Glu Asn Ser Arg His Ser Ser Pro Ala Gly Gly
        370                 375                 380

Pro Arg Gly Arg Leu His Gly Leu Gly Gly Pro Arg Asp Asn Ser Phe
385                 390                 395                 400

Leu Arg His Ala Arg Glu Thr Pro Asp Ser Tyr Arg Asp Ser Pro His
                405                 410                 415

Ser Glu Arg Tyr Val Ser Ala Met Thr Thr Pro Ala Arg Met Ser Pro
            420                 425                 430

Val Asp Phe His Thr Pro Ser Ser Pro Lys Ser Pro Pro Ser Glu Met
        435                 440                 445

Ser Pro Pro Val Ser Ser Met Thr Val Ser Met Pro Ser Val Ala Val
450                 455                 460

Ser Pro Phe Val Glu Glu Glu Arg Pro Leu Leu Leu Val Thr Pro Pro
465                 470                 475                 480

Arg Leu Arg Glu Lys Lys Tyr Asp His His Pro Gln Gln Leu Asn Ser
                485                 490                 495

Phe His His Asn Pro Ala His Gln Ser Thr Ser Leu Pro Pro Ser Pro
            500                 505                 510

Leu Arg Ile Val Glu Asp Glu Glu Tyr Glu Thr Thr Gln Glu Tyr Glu
        515                 520                 525

Ser Val Gln Glu Pro Val Lys Lys Val Thr Asn Ser Arg Arg Ala Lys
530                 535                 540

Arg Thr Lys Pro Asn Gly His Ile Ala Asn Arg Leu Glu Met Asp Ser
545                 550                 555                 560

Asn Thr Ser Ser Val Ser Ser Asn Ser Glu Ser Glu Thr Glu Asp Glu
                565                 570                 575

Arg Val Gly Glu Asp Thr Pro Phe Leu Gly Ile Gln Asn Pro Leu Ala
            580                 585                 590

Ala Ser Leu Glu Val Ala Pro Ala Phe Arg Leu Ala Glu Ser Arg Thr
        595                 600                 605

Asn Pro Ala Gly Arg Phe Ser Thr Gln Glu Glu Leu Gln Ala Arg Leu
        610                 615                 620

Ser Ser Val Ile Ala Asn Gln Asp Pro Ile Ala Val
625                 630                 635

<210> SEQ ID NO 53
<211> LENGTH: 364
<212> TYPE: PRT

<213> ORGANISM: Rattus sp.

<400> SEQUENCE: 53

Met Ala Phe Asp Asp Lys Met Lys Pro Val Asn Gly Gln Pro Asp Gln
1               5                   10                  15

Lys Ser Cys Gly Lys Lys Pro Lys Gly Leu His Leu Leu Ser Ser Thr
            20                  25                  30

Trp Trp Cys Pro Ala Ala Val Thr Leu Ala Ile Leu Cys Leu Val Leu
        35                  40                  45

Ser Val Thr Leu Ile Val Gln Gln Thr Gln Leu Leu Gln Val Ser Asp
    50                  55                  60

Leu Leu Lys Gln Tyr Gln Ala Asn Leu Thr Gln Gln Asp His Ile Leu
65                  70                  75                  80

Glu Gly Gln Met Ser Ala Gln Lys Lys Ala Glu Asn Ala Ser Gln Glu
                85                  90                  95

Ser Lys Arg Glu Leu Lys Glu Gln Ile Asp Thr Leu Thr Trp Lys Leu
            100                 105                 110

Asn Glu Lys Ser Lys Glu Gln Glu Lys Leu Leu Gln Gln Asn Gln Asn
        115                 120                 125

Leu Gln Glu Ala Leu Gln Arg Ala Val Asn Ala Ser Glu Glu Ser Lys
130                 135                 140

Trp Glu Leu Lys Glu Gln Ile Asp Ile Leu Asn Trp Lys Leu Asn Gly
145                 150                 155                 160

Ile Ser Lys Glu Gln Lys Glu Leu Leu Gln Gln Asn Gln Asn Leu Gln
                165                 170                 175

Glu Ala Leu Gln Lys Ala Glu Lys Tyr Ser Glu Glu Ser Gln Arg Glu
            180                 185                 190

Leu Lys Glu Gln Ile Asp Thr Leu Ser Trp Lys Leu Asn Glu Lys Ser
        195                 200                 205

Lys Glu Gln Glu Glu Leu Leu Gln Gln Asn Gln Asn Leu Gln Glu Ala
    210                 215                 220

Leu Gln Arg Ala Ala Asn Ser Ser Gly Pro Cys Pro Gln Asp Trp Ile
225                 230                 235                 240

Trp His Lys Glu Asn Cys Tyr Leu Phe His Gly Pro Phe Asn Trp Glu
                245                 250                 255

Lys Ser Arg Glu Asn Cys Leu Ser Leu Asp Ala Gln Leu Leu Gln Ile
            260                 265                 270

Ser Thr Thr Asp Asp Leu Asn Phe Val Leu Gln Ala Thr Ser His Ser
        275                 280                 285

Thr Ser Pro Phe Trp Met Gly Leu His Arg Lys Asn Pro Asn His Pro
290                 295                 300

Trp Leu Trp Glu Asn Gly Ser Pro Leu Ser Phe Gln Phe Phe Arg Thr
305                 310                 315                 320

Arg Gly Val Ser Leu Gln Met Tyr Ser Ser Gly Thr Cys Ala Tyr Ile
                325                 330                 335

Gln Gly Gly Val Val Phe Ala Glu Asn Cys Ile Leu Thr Ala Phe Ser
            340                 345                 350

Ile Cys Gln Lys Lys Ala Asn Leu Leu Thr Gln
        355                 360

<210> SEQ ID NO 54
<211> LENGTH: 350
<212> TYPE: PRT
<213> ORGANISM: Rattus sp.

<400> SEQUENCE: 54

```
Met Ser His Gln Thr Gly Ile Gln Ala Ser Glu Asp Val Lys Glu Ile
1               5                   10                  15

Phe Ala Arg Ala Arg Asn Gly Lys Tyr Arg Leu Leu Lys Ile Ser Ile
                20                  25                  30

Glu Asn Glu Gln Leu Val Val Gly Ser Cys Ser Pro Pro Ser Asp Ser
            35                  40                  45

Trp Glu Gln Asp Tyr Asp Pro Phe Val Leu Pro Leu Leu Glu Asp Lys
    50                  55                  60

Gln Pro Cys Tyr Val Leu Phe Arg Leu Asp Ser Gln Asn Ala Gln Gly
65              70                  75                  80

Tyr Glu Trp Ile Phe Ile Ala Trp Ser Pro Asp His Ser His Val Arg
                85                  90                  95

Gln Lys Met Leu Tyr Ala Ala Thr Arg Ala Thr Leu Lys Lys Glu Phe
                100                 105                 110

Gly Gly Gly His Ile Lys Asp Glu Val Phe Gly Thr Val Lys Glu Asp
            115                 120                 125

Val Ser Leu His Gly Tyr Arg Lys Tyr Leu Leu Ser Gln Ser Ser Pro
            130                 135                 140

Ala Pro Leu Thr Ala Ala Glu Glu Leu Arg Gln Ile Lys Ile Ser
145                 150                 155                 160

Glu Val Gln Thr Asp Val Ser Val Asp Thr Lys His Gln Thr Leu Gln
                165                 170                 175

Gly Val Ala Phe Pro Ile Ser Arg Asp Ala Phe Gln Ala Leu Glu Lys
                180                 185                 190

Leu Ser Lys Arg Gln Leu Asn Tyr Val Gln Leu Glu Ile Asp Ile Lys
            195                 200                 205

Asn Glu Thr Ile Ile Leu Ala Asn Thr Glu Asn Thr Glu Leu Lys Asp
            210                 215                 220

Leu Pro Lys Arg Ile Pro Lys Asp Ser Ala Arg Tyr His Phe Phe Leu
225                 230                 235                 240

Tyr Lys His Ser His Glu Gly Asp Tyr Leu Glu Ser Ile Val Phe Ile
                245                 250                 255

Tyr Ser Met Pro Gly Tyr Thr Cys Ser Ile Arg Glu Arg Met Leu Tyr
                260                 265                 270

Ser Ser Cys Lys Ser Pro Leu Leu Asp Ile Val Glu Arg Gln Leu Gln
            275                 280                 285

Met Asp Val Ile Arg Lys Ile Glu Ile Asp Asn Gly Asp Glu Leu Thr
            290                 295                 300

Ala Asp Phe Leu Tyr Asp Glu Val His Pro Lys Gln His Ala His Lys
305                 310                 315                 320

Gln Ser Phe Ala Lys Pro Lys Gly Pro Ala Gly Lys Arg Gly Ile Arg
                325                 330                 335

Arg Leu Ile Arg Gly Pro Ala Glu Ala Glu Ala Thr Thr Asp
            340                 345                 350

<210> SEQ ID NO 55
<211> LENGTH: 300
<212> TYPE: PRT
<213> ORGANISM: Rattus sp.

<400> SEQUENCE: 55

Met Ser Leu Tyr Pro Ser Leu Glu Asp Leu Lys Val Asp Lys Val Ile
1               5                   10                  15

Gln Ala Gln Thr Ala Ser Ser Ala Asn Pro Ala Ser Gln Ala Phe Phe
                20                  25                  30
```

```
Leu Asn Val Val Asp Ser Ala Ala Phe Pro Pro Gly Gly Asn Leu Tyr
        35                  40                  45

Pro Lys Leu Tyr Pro Glu Leu Ser Gln Tyr Met Gly Leu Ser Leu Ser
 50                  55                  60

Glu Ala Glu Ile Cys Glu Asn Met Pro Val Val Ser Gly Ala Pro Thr
 65                  70                  75                  80

Gln Gly Gln Leu Val Ala Arg Pro Ser Ser Val Asn Tyr Met Val Ala
                 85                  90                  95

Pro Val Thr Gly Asn Asp Ala Gly Ile Arg Arg Ala Glu Ile Lys Gln
                100                 105                 110

Gly Ile Arg Glu Val Ile Leu Cys Lys Asp Gln Asp Gly Lys Ile Gly
            115                 120                 125

Leu Arg Leu Lys Ser Val Asp Asn Gly Ile Phe Val Gln Leu Val Gln
130                 135                 140

Ala Asn Ser Pro Ala Ser Leu Val Gly Leu Arg Phe Gly Asp Gln Val
145                 150                 155                 160

Leu Gln Ile Asn Gly Glu Asn Cys Ala Gly Trp Ser Ser Asp Lys Ala
                165                 170                 175

His Lys Val Leu Lys Gln Ala Phe Gly Glu Lys Ile Thr Met Thr Ile
            180                 185                 190

Arg Asp Arg Pro Phe Glu Arg Thr Val Thr Met His Lys Asp Ser Ser
        195                 200                 205

Gly His Val Gly Phe Ile Phe Lys Ser Gly Lys Ile Thr Ser Ile Val
210                 215                 220

Lys Asp Ser Ser Ala Ala Arg Asn Gly Leu Leu Thr Asp His His Ile
225                 230                 235                 240

Cys Glu Ile Asn Gly Gln Asn Val Ile Gly Leu Lys Asp Ala Gln Ile
                245                 250                 255

Ala Asp Ile Leu Ser Thr Ala Gly Thr Val Val Thr Ile Thr Ile Met
            260                 265                 270

Pro Ala Phe Ile Phe Glu His Ile Ile Lys Arg Met Ala Pro Ser Ile
        275                 280                 285

Met Lys Ser Leu Met Asp His Thr Ile Pro Glu Val
        290                 295                 300

<210> SEQ ID NO 56
<211> LENGTH: 79
<212> TYPE: PRT
<213> ORGANISM: Rattus sp.

<400> SEQUENCE: 56

Met Lys Val Ala Ile Ile Phe Leu Leu Ser Ala Leu Ala Leu Leu Ser
1               5                   10                  15

Leu Ala Gly Asn Pro Pro Ala Glu Val Asn Gly Lys Thr Pro Asn Cys
            20                  25                  30

Pro Lys Gln Ile Met Gly Cys Pro Arg Ile Tyr Asp Pro Val Cys Gly
        35                  40                  45

Thr Asn Gly Ile Thr Tyr Pro Ser Glu Cys Ser Leu Cys Phe Glu Asn
    50                  55                  60

Arg Lys Phe Gly Thr Ser Ile His Ile Gln Arg Arg Gly Thr Cys
65                  70                  75

<210> SEQ ID NO 57
<211> LENGTH: 246
<212> TYPE: PRT
<213> ORGANISM: Rattus sp.
```

```
<400> SEQUENCE: 57

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
                20                  25                  30

Leu Asn Glu Pro Leu Ser Asn Glu Asp Arg Asn Leu Leu Ser Val Ala
            35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ala Leu Leu Asp Lys Phe Leu Ile Lys Asn Cys
                100                 105                 110

Asn Asp Phe Gln Tyr Glu Ser Lys Val Phe Tyr Leu Lys Met Lys Gly
            115                 120                 125

Asp Tyr Tyr Arg Tyr Leu Ala Glu Val Ala Ser Gly Glu Lys Lys Asn
130                 135                 140

Ser Val Val Glu Ala Ser Glu Ala Ala Tyr Lys Glu Ala Phe Glu Ile
145                 150                 155                 160

Ser Lys Glu His Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

<210> SEQ ID NO 58
<211> LENGTH: 95
<212> TYPE: PRT
<213> ORGANISM: Rattus sp.

<400> SEQUENCE: 58

Met Pro Ser Gln Met Glu His Ala Met Glu Thr Met Met Leu Thr Phe
1               5                   10                  15

His Arg Phe Ala Gly Glu Lys Asn Tyr Leu Thr Lys Glu Asp Leu Arg
                20                  25                  30

Val Leu Met Glu Arg Glu Phe Pro Gly Phe Leu Glu Asn Gln Lys Asp
            35                  40                  45

Pro Leu Ala Val Asp Lys Ile Met Lys Asp Leu Asp Gln Cys Arg Asp
    50                  55                  60

Gly Lys Val Gly Phe Gln Ser Phe Leu Ser Leu Val Ala Gly Leu Ile
65                  70                  75                  80

Ile Ala Cys Asn Asp Tyr Phe Val Val His Met Lys Gln Lys Lys
                85                  90                  95

<210> SEQ ID NO 59
<211> LENGTH: 158
```

```
<212> TYPE: PRT
<213> ORGANISM: Rattus sp.

<400> SEQUENCE: 59

Met Ser His Gly Lys Arg Thr Asp Met Leu Pro Glu Ile Ala Ala Ala
1               5                   10                  15

Val Gly Phe Leu Thr Ser Leu Leu Arg Thr Arg Gly Cys Val Ser Glu
            20                  25                  30

Gln Arg Leu Lys Val Phe Ser Arg Ala Leu Gln Asp Ala Leu Thr Asp
        35                  40                  45

His Tyr Lys His His Trp Phe Pro Glu Lys Pro Ser Lys Gly Ser Gly
    50                  55                  60

Tyr Arg Cys Ile Arg Ile Asn His Lys Met Asp Pro Ile Ile Ser Lys
65                  70                  75                  80

Val Ala Ser Gln Ile Gly Leu Ser Gln Pro Gln Leu His Gln Leu Leu
                85                  90                  95

Pro Ser Glu Leu Thr Leu Trp Val Asp Pro Tyr Glu Val Ser Tyr Arg
            100                 105                 110

Ile Gly Glu Asp Gly Ser Ile Cys Val Leu Tyr Glu Glu Ala Pro Val
        115                 120                 125

Ala Thr Ser Tyr Gly Leu Leu Thr Cys Lys Asn Gln Met Met Leu Gly
    130                 135                 140

Arg Ser Pro Ser Lys Asn Tyr Val Met Thr Val Ser Ser
145                 150                 155

<210> SEQ ID NO 60
<211> LENGTH: 875
<212> TYPE: PRT
<213> ORGANISM: Rattus sp.

<400> SEQUENCE: 60

Met Lys Ser Thr Asp Ile Val Leu Lys Ala Asn Gly Leu Leu Leu Asp
1               5                   10                  15

Leu Lys Gln Gly Lys Ser Leu Thr Leu Pro Val Asn Asp Asn Asp Glu
            20                  25                  30

Arg His Lys Ile Gln Phe Glu Arg Cys Gln Gly Ser Ser Gln Glu Gln
        35                  40                  45

Leu Thr Asn Arg Gly Arg Met Ile Arg Val Ser Asp Lys Leu Ile Ala
    50                  55                  60

Phe Lys Arg Arg Val Lys Cys Val Arg Met Thr Pro Pro Arg Met Ile
65                  70                  75                  80

Ser Ser Leu Thr Thr Arg Leu Glu Leu Thr Val Lys Tyr Pro Val Gly
                85                  90                  95

Ser Asn Arg Thr Lys Gly Glu Arg Met Ala Leu Arg Phe Phe Lys Ala
            100                 105                 110

Arg Val Val Ala Glu Lys Ser Val Arg Arg Thr Leu Pro Cys Ser Gln
        115                 120                 125

Glu His Val Pro Ala Arg Glu Gln Gln Glu Cys Gly Glu Ile Pro Val
    130                 135                 140

Pro Val Lys Phe Lys Ser Gln Trp Val Val Phe Gln Gly Cys Cys Gly
145                 150                 155                 160

Val Arg Leu His Cys Ala Gly Thr Ala Asn Gly Arg Lys Gly Ser Ile
                165                 170                 175

Arg Arg Gly Thr Gly Arg Leu Gly Cys Asp Gln Gln Lys Ser Thr Asn
            180                 185                 190

Val Val Tyr Gln Ala His His Val Ser Arg Asn Lys Arg Gly Gln Val
```

-continued

```
            195                 200                 205
Val Gly Thr Arg Gly Gly Phe Arg Gly Cys Leu Ser Gly Ala Gly Lys
210                     215                 220

Thr Thr Ile Ser Phe Ala Leu Glu Glu Tyr Leu Val Ser His Ala Ile
225                 230                 235                 240

Pro Cys Tyr Ser Leu Asp Gly Asp Asn Val Arg His Gly Leu Asn Lys
                245                 250                 255

Asn Leu Gly Phe Ser Ala Gly Asp Arg Glu Asn Ile Arg Arg Ile
            260                 265                 270

Ala Glu Val Ala Lys Leu Phe Ala Asp Ala Gly Leu Val Cys Ile Thr
        275                 280                 285

Ser Phe Ile Ser Pro Phe Ala Lys Gly Pro Leu Ile Ser Ser Ile Gly
    290                 295                 300

Tyr Val Lys Arg Val Ala Ser Val Pro Glu Ala Ser Ala Pro Val Asp
305                 310                 315                 320

Arg Lys Leu Leu Trp Asp Arg Glu Asn Ala Arg Lys Ile His Glu Ser
                325                 330                 335

Ala Gly Leu Pro Phe Phe Glu Ile Phe Val Asp Ala Pro Leu Asn Ile
            340                 345                 350

Cys Glu Ser Arg Asp Val Lys Gly Leu Tyr Lys Arg Ala Arg Ala Gly
        355                 360                 365

Glu Ile Lys Gly Phe Thr Gly Ile Asp Ser Asn Tyr Glu Lys Pro Glu
    370                 375                 380

Thr Pro Glu Cys Val Leu Lys Thr Asn Leu Ser Ser Val Ser Asp Cys
385                 390                 395                 400

Val Gln Gln Val Val Glu Leu Leu Gln Glu Gln Ser Ile Val Pro His
                405                 410                 415

Thr Thr Ile Lys Gly Ile His Glu Leu Phe Val Pro Glu Asn Lys Ile
            420                 425                 430

Asp Gln Ile Arg Ala Glu Leu Glu Thr Leu Pro Ser Leu Pro Ile Thr
        435                 440                 445

Lys Leu Asp Leu Gln Trp Val Gln Ile Leu Ser Glu Gly Trp Ala Thr
450                 455                 460

Pro Leu Lys Gly Phe Met Arg Glu Lys Glu Tyr Leu Gln Thr Leu His
465                 470                 475                 480

Phe Asp Thr Leu Leu Asp Asp Gly Val Ile Asn Met Ser Ile Pro Ile
                485                 490                 495

Val Leu Pro Val Ser Gly Asp Asp Lys Ala Arg Leu Glu Gly Cys Ser
            500                 505                 510

Lys Phe Ala Leu Met Tyr Glu Gly Arg Arg Val Ala Leu Leu Gln Asp
        515                 520                 525

Pro Glu Phe Tyr Glu His Arg Lys Glu Glu Arg Cys Ser Arg Val Trp
    530                 535                 540

Gly Thr Ala Ser Ala Lys His Pro His Ile Lys Ala Asp Ser Cys Ser
545                 550                 555                 560

Met Pro Tyr Val Ser Thr Gly Ile Val Pro Leu Val Asp Ile Arg Ile
                565                 570                 575

Ala Met Asn Thr Gly Val Gln Ile Ser Leu Gln Asp Met Val Met Glu
            580                 585                 590

Gly Gly Asp Trp Leu Val Gly Asp Leu Gln Val Leu Glu Arg Ile
        595                 600                 605

Arg Trp Asn Asp Gly Leu Asp Gln Tyr Arg Leu Thr Pro Leu Glu Leu
    610                 615                 620
```

```
Lys Gln Lys Cys Lys Asp Met Asp Ala Gly Ser His Lys Gly Glu Pro
625                 630                 635                 640

Ala Ala Gly Thr Arg Glu Gln Gly Gln Ala Ile Leu Leu Thr Pro Asn
            645                 650                 655

Leu Gly Ser Pro Phe Leu Asp Ala Val Phe Ala Phe Gln Leu Arg Asn
            660                 665                 670

Pro Val His Asn Gly His Ala Leu Leu Met Gln Asp Thr Arg Arg Arg
            675                 680                 685

Leu Leu Glu Arg Gly Tyr Lys His Pro Val Leu Leu Leu His Pro Leu
            690                 695                 700

Gly Gly Trp Thr Lys Asp Asp Val Pro Leu Asp Trp Arg Met Lys
705                 710                 715                 720

Gln His Ala Ala Val Leu Glu Glu Gly Ile Leu Asp Pro Lys Ser Thr
                725                 730                 735

Ile Val Ala Ile Phe Pro Ser Pro Met Leu Tyr Ala Gly Pro Thr Glu
                740                 745                 750

Val Gln Trp His Cys Arg Cys Arg Met Ile Ala Gly Ala Asn Phe Tyr
                755                 760                 765

Ile Val Gly Arg Asp Pro Ala Gly Met Pro His Pro Glu Thr Lys Lys
                770                 775                 780

Asp Leu Tyr Glu Pro Thr His Gly Gly Lys Val Leu Ser Met Ala Pro
785                 790                 795                 800

Gly Leu Thr Ser Val Glu Ile Ile Pro Phe Arg Val Ala Ala Tyr Asn
                805                 810                 815

Lys Ile Lys Lys Ala Met Asp Phe Tyr Asp Pro Ala Arg His Asp Glu
                820                 825                 830

Phe Asp Phe Ile Ser Gly Thr Arg Met Arg Lys Leu Ala Arg Glu Gly
            835                 840                 845

Glu Asp Pro Pro Asp Gly Phe Met Ala Pro Lys Ala Trp Lys Val Leu
            850                 855                 860

Thr Asp Tyr Tyr Arg Ser Leu Glu Lys Ile Asn
865                 870                 875

<210> SEQ ID NO 61
<211> LENGTH: 142
<212> TYPE: PRT
<213> ORGANISM: Rattus sp.

<400> SEQUENCE: 61

Met Ala Ala Ala Ala Glu Gly Val Pro Ala Thr Arg Arg Glu Pro
1               5                   10                  15

Pro Arg Asp Asp Ala Ala Val Glu Thr Ala Glu Glu Ala Lys Glu Pro
                20                  25                  30

Ala Glu Ala Asp Ile Asn Glu Leu Cys Arg Asp Met Phe Ser Lys Met
            35                  40                  45

Ala Thr Tyr Leu Thr Gly Glu Leu Thr Ala Thr Ser Glu Asp Tyr Lys
        50                  55                  60

Leu Leu Glu Asn Met Asn Lys Leu Thr Ser Leu Lys Tyr Leu Glu Met
65                  70                  75                  80

Lys Asp Ile Ala Ile Asn Ile Ser Arg Asn Leu Lys Asp Leu Asn Gln
                85                  90                  95

Lys Tyr Ala Gly Leu Gln Pro Tyr Leu Asp Gln Ile Asn Val Ile Glu
            100                 105                 110

Glu Gln Val Ala Ala Leu Glu Gln Ala Ala Tyr Lys Leu Asp Ala Tyr
        115                 120                 125
```

```
Ser Lys Lys Leu Glu Ala Lys Tyr Lys Lys Leu Glu Lys Arg
    130                 135                 140
```

<210> SEQ ID NO 62
<211> LENGTH: 351
<212> TYPE: PRT
<213> ORGANISM: Rattus sp.

<400> SEQUENCE: 62

```
Met Pro Ser Gly Leu Pro Cys Pro Ser Leu Asp Arg Gly Ala Arg
1               5                   10                  15

Arg Val Ala Thr Glu Thr Pro Asp Arg Ser Gly Gly Ala Pro Gly Ala
            20                  25                  30

Leu Ser Ala Pro Gly Gly Ser Gly Val Ser Cys Ser Arg Ala Pro
        35                  40                  45

Trp Arg Pro Gly Ala Ala Leu Val Gly Leu Pro Ser Arg Val Pro Gly
    50                  55                  60

Gly Ala Lys Gly Lys Met Leu Arg Asn Leu Asp Asp Arg Asp Ala
65              70                  75                  80

Gln Thr Lys Gln Leu Gln Asp Ala Val Thr Asn Val Glu Lys His Phe
                85                  90                  95

Gly Glu Leu Cys Gln Ile Phe Ala Ala Tyr Val Arg Lys Thr Ala Arg
            100                 105                 110

Leu Arg Asp Lys Ala Asp Leu Leu Val Asn Glu Ile Asn Leu Tyr Ala
        115                 120                 125

Ser Thr Glu Thr Pro Asn Leu Lys Gln Gly Leu Lys Asp Phe Ala Asp
130                 135                 140

Glu Phe Ala Lys Leu Gln Asp Tyr Arg Gln Ala Glu Val Glu Arg Leu
145                 150                 155                 160

Glu Ala Lys Val Val Glu Pro Leu Lys Ala Tyr Gly Thr Ile Val Lys
                165                 170                 175

Met Lys Arg Asp Asp Leu Lys Ala Thr Leu Thr Ala Arg Asn Arg Glu
            180                 185                 190

Ala Lys Gln Leu Ser Gln Leu Glu Arg Thr Arg Gln Arg Asn Pro Ser
        195                 200                 205

Asp Arg His Ala Glu Thr Glu Leu Gln Arg Ala Thr Ile Asp Ala Thr
    210                 215                 220

Arg Thr Thr Arg His Leu Glu Glu Thr Ile Asp Asn Phe Glu Lys Gln
225                 230                 235                 240

Lys Ile Lys Asp Ile Lys Asn Ile Leu Ser Glu Phe Ile Thr Ile Glu
                245                 250                 255

Met Leu Phe His Gly Lys Ala Leu Glu Val Leu Thr Ala Ala Tyr Gln
            260                 265                 270

Asn Ile Gln Lys Ile Asp Glu Asp Glu Asp Leu Glu Val Phe Arg Asn
        275                 280                 285

Ser Leu Tyr Leu Ser Asp Tyr Pro Ser Arg Leu Asp Ile Val Arg Ala
    290                 295                 300

Asn Ser Lys Ser Pro Leu Gln Arg Pro Leu Ser Thr Lys Cys Thr Ser
305                 310                 315                 320

Gly Thr Gly Gln Val Ala Thr Cys Arg Thr Lys Lys Asp Gln His Val
                325                 330                 335

Glu Asp Glu Asp Asp Glu Leu Val Thr Glu Asp Glu Asn
            340                 345                 350
```

<210> SEQ ID NO 63
<211> LENGTH: 676

<212> TYPE: PRT
<213> ORGANISM: Rattus sp.

<400> SEQUENCE: 63

```
Met Asn Leu Phe Gly Phe Ala Ser Cys Gln Leu Ile Leu Val Pro Ser
1               5                   10                  15

Gln Gly Arg Thr Ala Gly Gly His Asp His Ser Arg Ser Asn Leu Asp
            20                  25                  30

Glu Lys Asp Ser Gly Ser Ala Gly Ser Gly Phe Ser Pro Ser Pro Thr
        35                  40                  45

Ser Leu Val Pro Thr Gly Trp Phe Arg Ser Pro Asn Thr Val Leu Leu
    50                  55                  60

Leu Ser Asn Val Phe His Ser Pro Arg Asp Pro Ile Met Thr Val Val
65                  70                  75                  80

Leu Leu Leu Pro Leu Arg Phe Glu Cys Lys His Asn Arg Ala Ala Arg
                85                  90                  95

Tyr Arg Asp Pro Ser Pro Leu Pro Pro Arg Ser Ser Thr Ala Arg Pro
            100                 105                 110

Leu Ser Pro Ala Gln Gly Pro Pro Ser Pro Ile Gly Ser Gly Gly
        115                 120                 125

Gly Ala Gly Arg Ala Arg Ser Asp Ala Arg Met Ala Leu Gly Phe Arg
130                 135                 140

Pro Arg Arg Leu Ala Gly Ser Arg Gly Asp Gly Leu Leu Ala Pro Gly
145                 150                 155                 160

His Asp Ala Leu Ile His Gln Ala Val Cys Arg Arg Ala Glu Thr Asp
                165                 170                 175

Thr Pro Gly Thr Ser Pro Thr Thr Val Leu Leu Arg Ala Ser Arg
            180                 185                 190

Pro Met Cys Asn Thr Asn Met Ser Val Ser Thr Glu Gly Ala Ala Gly
        195                 200                 205

Thr Ser Gln Ile Pro Ala Ser Glu Gln Glu Thr Leu Val Arg Pro Lys
210                 215                 220

Pro Leu Leu Leu Lys Leu Leu Lys Ser Val Gly Ala Gln Lys Asp Ile
225                 230                 235                 240

Tyr Thr Met Lys Glu Ile Ile Phe Tyr Ile Gly Gln Tyr Ile Met Thr
                245                 250                 255

Lys Arg Leu Tyr Asp Glu Lys Gln Gln His Ile Val Tyr Cys Ser Asn
            260                 265                 270

Asp Leu Leu Gly Asp Val Phe Gly Val Pro Ser Phe Ser Val Lys Glu
        275                 280                 285

His Arg Lys Ile Tyr Ala Met Ile Tyr Arg Asn Leu Val Val Ser
290                 295                 300

Gln Gln Asp Ser Gly Thr Ser Pro Ser Glu Ser Arg Cys Gln Pro Glu
305                 310                 315                 320

Gly Gly Ser Asp Leu Lys Asp Pro Val Gln Ala Ser Gln Glu Glu Lys
                325                 330                 335

Pro Ser Ser Ser Asp Val Val Ser Arg Pro Ser Thr Ser Ser Arg Arg
            340                 345                 350

Arg Ala Ile Ser Glu Thr Glu Glu Asn Thr Asp Glu Leu Pro Gly Glu
        355                 360                 365

Arg Gln Arg Lys Arg His Arg Ala Leu Ser Phe Asp Glu Ser Leu Gly
370                 375                 380

Leu Cys Val Leu Arg Glu Ile Cys Cys Glu Arg Ser Ser Ser Ser Glu
385                 390                 395                 400
```

```
Ala Thr Asp Thr Pro Ser His Gln Asp Leu Asp Asp Gly Val Ser Asp
                405                 410                 415
His Ser Ala Asp Cys Leu Asp Gln Asp Ser Val Ser Asp Gln Phe Ser
            420                 425                 430
Val Glu Phe Glu Val Glu Ser Leu Asp Ser Glu Asp Tyr Ser Leu Ser
        435                 440                 445
Asp Glu Gly His Glu Leu Ser Asp Glu Asp Asp Glu Val Tyr Arg Val
    450                 455                 460
Thr Val Tyr Gln Ala Gly Glu Ser Asp Ala Asp Ser Phe Glu Gly Asp
465                 470                 475                 480
Pro Glu Ile Ser Leu Ala Asp Tyr Trp Lys Cys Thr Cys Asn Glu
                485                 490                 495
Met Asn Pro Pro Leu Pro Ser His Cys Asn Arg Cys Trp Thr Leu Arg
                500                 505                 510
Glu Asn Trp Leu Pro Asp Asp Lys Gly Lys Asp Lys Val Glu Ile Ser
                515                 520                 525
Glu Lys Ala Lys Leu Glu Ser Ser Asp Gln Ala Glu Gly Leu Asp
            530                 535                 540
Val Pro Asp Gly Lys Lys Val Thr Glu Asp Ala Lys Glu Ser Ser
545                 550                 555                 560
Ala Glu Asp Ser Glu Gly Lys Val Ala Gln Met Leu Leu Ser Gln Glu
                565                 570                 575
Ser Asp Asp Tyr Ser Gln Pro Ser Thr Ser Ser Ser Ile Val Tyr Ser
                580                 585                 590
Ser Gln Glu Ser Gly Lys Glu Leu Lys Glu Asp Thr Gln Asp Lys Glu
                595                 600                 605
Glu Ser Met Glu Ser Ser Phe Ser Leu Asn Ala Ile Glu Pro Cys Val
                610                 615                 620
Ile Cys Gln Gly Arg Pro Lys Asn Gly Cys Ile Val His Gly Lys Thr
625                 630                 635                 640
Gly His Leu Met Ser Cys Phe Thr Cys Ala Lys Lys Leu Lys Lys Arg
                645                 650                 655
Asn Lys Pro Cys Pro Val Cys Arg Gln Pro Ile Gln Met Ile Val Leu
                660                 665                 670
Thr Tyr Phe Asn
        675

<210> SEQ ID NO 64
<211> LENGTH: 2511
<212> TYPE: PRT
<213> ORGANISM: Homo sapiens

<400> SEQUENCE: 64

Met Glu Glu Val Val Ile Ala Gly Met Ser Gly Lys Leu Pro Glu Ser
1               5                   10                  15
Glu Asn Leu Gln Glu Phe Trp Asp Asn Leu Ile Gly Gly Val Asp Met
                20                  25                  30
Val Thr Asp Asp Asp Arg Arg Trp Lys Ala Gly Leu Tyr Gly Leu Pro
            35                  40                  45
Arg Arg Ser Gly Lys Leu Lys Asp Leu Ser Arg Phe Asp Ala Ser Phe
    50                  55                  60
Phe Gly Val His Pro Lys Gln Ala His Thr Met Asp Pro Gln Leu Arg
65                  70                  75                  80
Leu Leu Leu Glu Val Thr Tyr Glu Ala Ile Val Asp Gly Gly Ile Asn
                85                  90                  95
```

```
Pro Asp Ser Leu Arg Gly Thr His Thr Gly Val Trp Val Gly Val Ser
            100                 105                 110

Gly Ser Glu Thr Ser Glu Ala Leu Ser Arg Asp Pro Glu Thr Leu Val
            115                 120                 125

Gly Tyr Ser Met Val Gly Cys Gln Arg Ala Met Met Ala Asn Arg Leu
130                 135                 140

Ser Phe Phe Phe Asp Phe Arg Gly Pro Ser Ile Ala Leu Asp Thr Ala
145                 150                 155                 160

Cys Ser Ser Ser Leu Met Ala Leu Gln Asn Ala Tyr Gln Ala Ile His
                165                 170                 175

Ser Gly Gln Cys Pro Ala Ala Ile Val Gly Gly Ile Asn Val Leu Leu
            180                 185                 190

Lys Pro Asn Thr Ser Val Gln Phe Leu Arg Leu Gly Met Leu Ser Pro
            195                 200                 205

Glu Gly Thr Cys Lys Ala Phe Asp Thr Ala Gly Asn Gly Tyr Cys Arg
            210                 215                 220

Ser Glu Gly Val Val Ala Val Leu Leu Thr Lys Lys Ser Leu Ala Arg
225                 230                 235                 240

Arg Val Tyr Ala Thr Ile Leu Asn Ala Gly Thr Asn Thr Asp Gly Phe
                245                 250                 255

Lys Glu Gln Gly Val Thr Phe Pro Ser Gly Asp Ile Gln Glu Gln Leu
            260                 265                 270

Ile Arg Ser Leu Tyr Gln Ser Ala Gly Val Ala Pro Glu Ser Phe Glu
            275                 280                 285

Tyr Ile Glu Ala His Gly Thr Gly Thr Lys Val Gly Asp Pro Gln Glu
290                 295                 300

Leu Asn Gly Ile Thr Arg Ala Leu Cys Ala Thr Arg Gln Glu Pro Leu
305                 310                 315                 320

Leu Ile Gly Ser Thr Lys Ser Asn Met Gly His Pro Glu Pro Ala Ser
                325                 330                 335

Gly Leu Ala Ala Leu Ala Lys Val Leu Leu Ser Leu Glu His Gly Leu
            340                 345                 350

Trp Ala Pro Asn Leu His Phe His Ser Pro Asn Pro Glu Ile Pro Ala
            355                 360                 365

Leu Leu Asp Gly Arg Leu Gln Val Val Asp Gln Pro Leu Pro Val Arg
            370                 375                 380

Gly Gly Asn Val Gly Ile Asn Ser Phe Gly Phe Gly Gly Ser Asn Val
385                 390                 395                 400

His Ile Ile Leu Arg Pro Asn Thr Gln Pro Pro Ala Pro Ala Pro
                405                 410                 415

His Ala Thr Leu Pro Arg Leu Leu Arg Ala Ser Gly Arg Thr Pro Glu
            420                 425                 430

Ala Val Gln Lys Leu Leu Glu Gln Gly Leu Arg His Ser Gln Asp Leu
            435                 440                 445

Ala Phe Leu Ser Met Leu Asn Asp Ile Ala Ala Val Pro Ala Thr Ala
450                 455                 460

Met Pro Phe Arg Gly Tyr Ala Val Leu Gly Gly Glu Arg Gly Gly Pro
465                 470                 475                 480

Glu Val Gln Gln Val Pro Ala Gly Glu Arg Pro Leu Trp Phe Ile Cys
                485                 490                 495

Ser Gly Met Gly Thr Gln Trp Arg Gly Met Gly Leu Ser Leu Met Arg
            500                 505                 510

Leu Asp Arg Phe Arg Asp Ser Ile Leu Arg Ser Asp Glu Ala Val Lys
            515                 520                 525
```

```
Pro Phe Gly Leu Lys Val Ser Gln Leu Leu Ser Thr Asp Glu Ser
    530             535                 540

Thr Phe Asp Asp Ile Val His Ser Phe Val Ser Leu Thr Ala Ile Gln
545                 550                 555                 560

Ile Gly Leu Ile Asp Leu Leu Ser Cys Met Gly Leu Arg Pro Asp Gly
                565                 570                 575

Ile Val Gly His Ser Leu Gly Glu Val Ala Cys Gly Tyr Ala Asp Gly
                580                 585                 590

Cys Leu Ser Gln Glu Glu Ala Val Leu Ala Ala Tyr Trp Arg Gly Gln
            595                 600                 605

Cys Ile Lys Glu Ala His Leu Pro Pro Gly Ala Met Ala Ala Val Gly
    610                 615                 620

Leu Ser Trp Glu Glu Cys Lys Gln Arg Cys Pro Pro Gly Val Val Pro
625                 630                 635                 640

Ala Cys His Asn Ser Lys Asp Thr Val Thr Ile Ser Gly Pro Gln Ala
                645                 650                 655

Pro Val Phe Glu Phe Val Glu Gln Leu Arg Lys Glu Gly Val Phe Ala
                660                 665                 670

Lys Glu Val Arg Thr Gly Gly Met Ala Phe His Ser Tyr Phe Met Glu
            675                 680                 685

Ala Ile Ala Pro Pro Leu Leu Gln Glu Leu Lys Lys Val Ile Arg Glu
    690                 695                 700

Pro Lys Pro Arg Ser Ala Arg Trp Leu Ser Thr Ser Ile Pro Glu Ala
705                 710                 715                 720

Gln Trp His Ser Ser Leu Ala Arg Thr Ser Ser Ala Glu Tyr Asn Val
                725                 730                 735

Asn Asn Leu Val Ser Pro Val Leu Phe Gln Glu Ala Leu Trp His Val
                740                 745                 750

Pro Glu His Ala Val Val Leu Glu Ile Ala Pro His Ala Leu Leu Gln
            755                 760                 765

Ala Val Leu Lys Arg Gly Leu Lys Pro Ser Cys Thr Ile Ile Pro Leu
    770                 775                 780

Met Lys Lys Asp His Arg Asp Asn Leu Glu Phe Phe Leu Ala Gly Ile
785                 790                 795                 800

Gly Arg Leu His Leu Ser Gly Ile Asp Ala Asn Pro Asn Ala Leu Phe
                805                 810                 815

Pro Pro Val Glu Phe Pro Ala Pro Arg Gly Thr Pro Leu Ile Ser Pro
                820                 825                 830

Leu Ile Lys Trp Asp His Ser Leu Ala Trp Asp Val Pro Ala Ala Glu
    835                 840                 845

Asp Phe Pro Asn Gly Ser Gly Ser Pro Ser Ala Ala Ile Tyr Asn Ile
    850                 855                 860

Asp Thr Ser Ser Glu Ser Pro Asp His Tyr Leu Val Asp His Thr Leu
865                 870                 875                 880

Asp Gly Arg Val Leu Phe Pro Ala Thr Gly Tyr Leu Ser Ile Val Trp
                885                 890                 895

Lys Thr Leu Ala Arg Ala Leu Gly Leu Gly Val Glu Gln Leu Pro Val
            900                 905                 910

Val Phe Glu Asp Val Val Leu His Gln Ala Thr Ile Leu Pro Lys Thr
    915                 920                 925

Gly Thr Val Ser Leu Glu Val Arg Leu Leu Glu Ala Ser Arg Ala Phe
    930                 935                 940

Glu Val Ser Glu Asn Gly Asn Leu Val Val Ser Gly Lys Val Tyr Gln
```

```
        945                 950                 955                 960
Trp Asp Asp Pro Asp Pro Arg Leu Phe Asp His Pro Glu Ser Pro Thr
                    965                 970                 975
Pro Asn Pro Thr Glu Pro Leu Phe Leu Ala Gln Ala Glu Val Tyr Lys
                    980                 985                 990
Glu Leu Arg Leu Arg Gly Tyr Asp Tyr Gly Pro His Phe Gln Gly Ile
            995                 1000                1005
Leu Glu Ala Ser Leu Glu Gly Asp Ser Gly Arg Leu Leu Trp Lys
        1010                1015                1020
Asp Asn Trp Val Ser Phe Met Asp Thr Met Leu Gln Met Ser Ile
        1025                1030                1035
Leu Gly Ser Ala Lys His Gly Leu Tyr Leu Pro Thr Arg Val Thr
        1040                1045                1050
Ala Ile His Ile Asp Pro Ala Thr His Arg Gln Lys Leu Tyr Thr
        1055                1060                1065
Leu Gln Asp Lys Ala Gln Val Ala Asp Val Val Ser Arg Trp
        1070                1075                1080
Leu Arg Val Thr Val Ala Gly Gly Val His Ile Ser Gly Leu His
        1085                1090                1095
Thr Glu Ser Ala Pro Arg Arg Gln Gln Glu Gln Val Pro Ile
        1100                1105                1110
Leu Glu Lys Phe Cys Phe Thr Pro His Thr Glu Glu Gly Cys Leu
        1115                1120                1125
Ser Glu Arg Ala Ala Leu Gln Glu Glu Leu Gln Leu Cys Lys Gly
        1130                1135                1140
Leu Val Gln Ala Leu Gln Thr Lys Val Thr Gln Gln Gly Leu Lys
        1145                1150                1155
Met Val Val Pro Gly Leu Asp Gly Ala Gln Ile Pro Arg Asp Pro
        1160                1165                1170
Ser Gln Gln Glu Leu Pro Arg Leu Leu Ser Ala Ala Cys Arg Leu
        1175                1180                1185
Gln Leu Asn Gly Asn Leu Gln Leu Glu Leu Ala Gln Val Leu Ala
        1190                1195                1200
Gln Glu Arg Pro Lys Leu Pro Glu Asp Pro Leu Leu Ser Gly Leu
        1205                1210                1215
Leu Asp Ser Pro Ala Leu Lys Ala Cys Leu Asp Thr Ala Val Glu
        1220                1225                1230
Asn Met Pro Ser Leu Lys Met Lys Val Val Glu Val Leu Ala Gly
        1235                1240                1245
His Gly His Leu Tyr Ser Arg Ile Pro Gly Leu Leu Ser Pro His
        1250                1255                1260
Pro Leu Leu Gln Leu Ser Tyr Thr Ala Thr Asp Arg His Pro Gln
        1265                1270                1275
Ala Leu Glu Ala Ala Gln Ala Glu Leu Gly Gln His Asp Val Ala
        1280                1285                1290
Gln Gly Gln Trp Asp Pro Ala Asp Pro Ala Pro Ser Ala Leu Gly
        1295                1300                1305
Ser Ala Asp Leu Leu Val Cys Asn Cys Ala Val Ala Ala Leu Gly
        1310                1315                1320
Asp Pro Ala Ser Ala Leu Ser Asn Met Val Ala Ala Leu Arg Glu
        1325                1330                1335
Gly Gly Phe Leu Leu Leu His Thr Leu Leu Arg Gly His Pro Leu
        1340                1345                1350
```

```
Gly Asp Ile Val Ala Phe Leu Thr Ser Thr Glu Pro Gln Tyr Gly
1355                1360                1365

Gln Gly Ile Leu Ser Gln Asp Ala Trp Glu Ser Leu Phe Ser Arg
1370                1375                1380

Val Ser Leu Arg Leu Val Gly Leu Lys Lys Ser Phe Tyr Gly Ser
1385                1390                1395

Thr Leu Phe Leu Cys Arg Arg Pro Thr Pro Gln Asp Ser Pro Ile
1400                1405                1410

Phe Leu Pro Val Asp Asp Thr Ser Phe Arg Trp Val Glu Ser Leu
1415                1420                1425

Lys Gly Ile Leu Ala Asp Glu Asp Ser Ser Arg Pro Val Trp Leu
1430                1435                1440

Lys Ala Ile Asn Cys Ala Thr Ser Gly Val Val Gly Leu Val Asn
1445                1450                1455

Cys Leu Arg Arg Glu Pro Gly Gly Asn Arg Leu Arg Cys Val Leu
1460                1465                1470

Leu Ser Asn Leu Ser Ser Thr Ser His Val Pro Glu Val Asp Pro
1475                1480                1485

Gly Ser Ala Glu Leu Gln Lys Val Leu Gln Gly Asp Leu Val Met
1490                1495                1500

Asn Val Tyr Arg Asp Gly Ala Trp Gly Ala Phe Arg His Phe Leu
1505                1510                1515

Leu Glu Glu Asp Lys Pro Glu Glu Pro Thr Ala His Ala Phe Val
1520                1525                1530

Ser Thr Leu Thr Arg Gly Asp Leu Ser Ser Ile Arg Trp Val Cys
1535                1540                1545

Ser Ser Leu Arg His Ala Gln Pro Thr Cys Pro Gly Ala Gln Leu
1550                1555                1560

Cys Thr Val Tyr Tyr Ala Ser Leu Asn Phe Arg Asp Ile Met Leu
1565                1570                1575

Ala Thr Gly Lys Leu Ser Pro Asp Ala Ile Pro Gly Lys Trp Thr
1580                1585                1590

Ser Gln Asp Ser Leu Leu Gly Met Glu Phe Ser Gly Arg Asp Ala
1595                1600                1605

Ser Gly Lys Arg Val Met Gly Leu Val Pro Ala Lys Gly Leu Ala
1610                1615                1620

Thr Ser Val Leu Leu Ser Pro Asp Phe Leu Trp Asp Val Pro Ser
1625                1630                1635

Asn Trp Thr Leu Glu Glu Ala Ala Ser Val Pro Val Val Tyr Ser
1640                1645                1650

Thr Ala Tyr Tyr Ala Leu Val Val Arg Gly Arg Val Arg Pro Gly
1655                1660                1665

Glu Thr Leu Leu Ile His Ser Gly Ser Gly Gly Val Gly Gln Ala
1670                1675                1680

Ala Ile Ala Ile Ala Leu Ser Leu Gly Cys Arg Val Phe Thr Thr
1685                1690                1695

Val Gly Ser Ala Glu Lys Arg Ala Tyr Leu Gln Ala Arg Phe Pro
1700                1705                1710

Gln Leu Asp Ser Thr Ser Phe Ala Asn Ser Arg Asp Thr Ser Phe
1715                1720                1725

Glu Gln His Val Leu Trp His Thr Gly Gly Lys Gly Val Asp Leu
1730                1735                1740

Val Leu Asn Ser Leu Ala Glu Glu Lys Leu Gln Ala Ser Val Arg
1745                1750                1755
```

```
Cys Leu Ala Thr His Gly Arg Phe Leu Glu Ile Gly Lys Phe Asp
    1760            1765                1770

Leu Ser Gln Asn His Pro Leu Gly Met Ala Ile Phe Leu Lys Asn
    1775            1780                1785

Val Thr Phe His Gly Val Leu Leu Asp Ala Phe Phe Asn Glu Ser
    1790            1795                1800

Ser Ala Asp Trp Arg Glu Val Trp Ala Leu Val Gln Ala Gly Ile
    1805            1810                1815

Arg Asp Gly Val Val Arg Pro Leu Lys Cys Thr Val Phe His Gly
    1820            1825                1830

Ala Gln Val Glu Asp Ala Phe Arg Tyr Met Ala Gln Gly Lys His
    1835            1840                1845

Ile Gly Lys Val Val Val Gln Val Leu Ala Glu Glu Pro Glu Ala
    1850            1855                1860

Val Leu Lys Gly Ala Lys Pro Lys Leu Met Ser Ala Ile Ser Lys
    1865            1870                1875

Thr Phe Cys Pro Ala His Lys Ser Tyr Ile Ile Ala Gly Gly Leu
    1880            1885                1890

Gly Gly Phe Gly Leu Glu Leu Ala Gln Trp Leu Ile Gln Arg Gly
    1895            1900                1905

Val Gln Lys Leu Val Leu Thr Ser Arg Ser Gly Ile Arg Thr Gly
    1910            1915                1920

Tyr Gln Ala Lys Gln Val Arg Arg Trp Arg Arg Gln Gly Val Gln
    1925            1930                1935

Val Gln Val Ser Thr Ser Asn Ile Ser Ser Leu Glu Gly Ala Arg
    1940            1945                1950

Gly Leu Ile Ala Glu Ala Ala Gln Leu Gly Pro Val Gly Gly Val
    1955            1960                1965

Phe Asn Leu Ala Val Val Leu Arg Asp Gly Leu Leu Glu Asn Gln
    1970            1975                1980

Thr Pro Glu Phe Phe Gln Asp Val Cys Lys Pro Lys Tyr Ser Gly
    1985            1990                1995

Thr Leu Asn Leu Asp Arg Val Thr Arg Glu Ala Cys Pro Glu Leu
    2000            2005                2010

Asp Tyr Phe Val Val Phe Ser Ser Val Ser Cys Gly Arg Gly Asn
    2015            2020                2025

Ala Gly Gln Ser Asn Tyr Gly Phe Ala Asn Ser Ala Met Glu Arg
    2030            2035                2040

Ile Cys Glu Lys Arg Arg His Glu Gly Leu Pro Gly Leu Ala Val
    2045            2050                2055

Gln Trp Gly Ala Ile Gly Asp Val Gly Ile Leu Val Glu Thr Met
    2060            2065                2070

Ser Thr Asn Asp Thr Ile Val Ser Gly Thr Leu Pro Gln Arg Met
    2075            2080                2085

Ala Ser Cys Leu Glu Val Leu Asp Leu Phe Leu Asn Gln Pro His
    2090            2095                2100

Met Val Leu Ser Ser Phe Val Leu Ala Glu Lys Ala Ala Ala Tyr
    2105            2110                2115

Arg Asp Arg Asp Ser Gln Arg Asp Leu Val Glu Ala Val Ala His
    2120            2125                2130

Ile Leu Gly Ile Arg Asp Leu Ala Ala Val Asn Leu Asp Ser Ser
    2135            2140                2145

Leu Ala Asp Leu Gly Leu Asp Ser Leu Met Ser Val Glu Val Arg
```

```
                    2150                2155                2160
Gln Thr Leu Glu Arg Glu Leu Asn Leu Val Leu Ser Val Arg Glu
    2165                2170                2175
Val Arg Gln Leu Thr Leu Arg Lys Leu Gln Glu Leu Ser Ser Lys
    2180                2185                2190
Ala Asp Glu Ala Ser Glu Leu Ala Cys Pro Thr Pro Lys Glu Asp
    2195                2200                2205
Gly Leu Ala Gln Gln Gln Thr Gln Leu Asn Leu Arg Ser Leu Leu
    2210                2215                2220
Val Asn Pro Glu Gly Pro Thr Leu Met Arg Leu Asn Ser Val Gln
    2225                2230                2235
Ser Ser Glu Arg Pro Leu Phe Leu Val His Pro Ile Glu Gly Ser
    2240                2245                2250
Thr Thr Val Phe His Ser Leu Ala Ser Arg Leu Ser Ile Pro Thr
    2255                2260                2265
Tyr Gly Leu Gln Cys Thr Arg Ala Ala Pro Leu Asp Ser Ile His
    2270                2275                2280
Ser Leu Ala Ala Tyr Tyr Ile Asp Cys Ile Arg Gln Val Gln Pro
    2285                2290                2295
Glu Gly Pro Tyr Arg Val Ala Gly Tyr Ser Tyr Gly Ala Cys Val
    2300                2305                2310
Ala Phe Glu Met Cys Ser Gln Leu Gln Ala Gln Gln Ser Pro Ala
    2315                2320                2325
Pro Thr His Asn Ser Leu Phe Leu Phe Asp Gly Ser Pro Thr Tyr
    2330                2335                2340
Val Leu Ala Tyr Thr Gln Ser Tyr Arg Ala Lys Leu Thr Pro Gly
    2345                2350                2355
Cys Glu Ala Glu Ala Glu Thr Glu Ala Ile Cys Phe Phe Val Gln
    2360                2365                2370
Gln Phe Thr Asp Met Glu His Asn Arg Val Leu Glu Ala Leu Leu
    2375                2380                2385
Pro Leu Lys Gly Leu Glu Glu Arg Val Ala Ala Ala Val Asp Leu
    2390                2395                2400
Ile Ile Lys Ser His Gln Gly Leu Asp Arg Gln Glu Leu Ser Phe
    2405                2410                2415
Ala Ala Arg Ser Phe Tyr Tyr Lys Leu Arg Ala Ala Glu Gln Tyr
    2420                2425                2430
Thr Pro Lys Ala Lys Tyr His Gly Asn Val Met Leu Leu Arg Ala
    2435                2440                2445
Lys Thr Gly Gly Ala Tyr Gly Glu Asp Leu Gly Ala Asp Tyr Asn
    2450                2455                2460
Leu Ser Gln Val Cys Asp Gly Lys Val Ser Val His Val Ile Glu
    2465                2470                2475
Gly Asp His Arg Thr Leu Leu Glu Gly Ser Gly Leu Glu Ser Ile
    2480                2485                2490
Ile Ser Ile Ile His Ser Ser Leu Ala Glu Pro Arg Val Ser Val
    2495                2500                2505
Arg Glu Gly
    2510

<210> SEQ ID NO 65
<211> LENGTH: 387
<212> TYPE: PRT
<213> ORGANISM: Homo sapiens
```

<400> SEQUENCE: 65

```
Met Ser Thr Phe Phe Ser Asp Thr Ala Trp Ile Cys Leu Ala Val Pro
1               5                   10                  15

Thr Val Leu Cys Gly Thr Val Phe Cys Lys Tyr Lys Ser Ser Gly
            20                  25                  30

Gln Leu Trp Ser Trp Met Val Cys Leu Ala Gly Leu Cys Ala Val Cys
            35                  40                  45

Leu Leu Ile Leu Ser Pro Phe Trp Gly Leu Ile Leu Phe Ser Val Ser
50                  55                  60

Cys Phe Leu Met Tyr Thr Tyr Leu Ser Gly Gln Glu Leu Leu Pro Val
65                  70                  75                  80

Asp Gln Lys Ala Val Leu Val Thr Gly Gly Asp Cys Gly Leu Gly His
                85                  90                  95

Ala Leu Cys Lys Tyr Leu Asp Glu Leu Gly Phe Thr Val Phe Ala Gly
                100                 105                 110

Val Leu Asn Glu Asn Gly Pro Gly Ala Glu Glu Leu Arg Arg Thr Cys
            115                 120                 125

Ser Pro Arg Leu Ser Val Leu Gln Met Asp Ile Thr Lys Pro Val Gln
130                 135                 140

Ile Lys Asp Ala Tyr Ser Lys Val Ala Ala Met Leu Gln Asp Arg Gly
145                 150                 155                 160

Leu Trp Ala Val Ile Asn Asn Ala Gly Val Leu Gly Phe Pro Thr Asp
                165                 170                 175

Gly Glu Leu Leu Leu Met Thr Asp Tyr Lys Gln Cys Met Ala Val Asn
            180                 185                 190

Phe Phe Gly Thr Val Glu Val Thr Lys Thr Phe Leu Pro Leu Leu Arg
        195                 200                 205

Lys Ser Lys Gly Arg Leu Val Asn Val Ser Ser Met Gly Gly Gly Ala
210                 215                 220

Pro Met Glu Arg Leu Ala Ser Tyr Gly Ser Ser Lys Ala Ala Val Thr
225                 230                 235                 240

Met Phe Ser Ser Val Met Arg Leu Glu Leu Ser Lys Trp Gly Ile Lys
                245                 250                 255

Val Ala Ser Ile Gln Pro Gly Gly Phe Leu Thr Asn Ile Ala Gly Thr
            260                 265                 270

Ser Asp Lys Trp Glu Lys Leu Glu Lys Asp Ile Leu Asp His Leu Pro
            275                 280                 285

Ala Glu Val Gln Glu Asp Tyr Gly Gln Asp Tyr Ile Leu Ala Gln Arg
290                 295                 300

Asn Phe Leu Leu Leu Ile Asn Ser Leu Ala Ser Lys Asp Phe Ser Pro
305                 310                 315                 320

Val Leu Arg Asp Ile Gln His Ala Ile Leu Ala Lys Ser Pro Phe Ala
                325                 330                 335

Tyr Tyr Thr Pro Gly Lys Gly Ala Tyr Leu Trp Ile Cys Leu Ala His
                340                 345                 350

Tyr Leu Pro Ile Gly Ile Tyr Asp Tyr Phe Ala Lys Arg His Phe Gly
            355                 360                 365

Gln Asp Lys Pro Met Pro Arg Ala Leu Arg Met Pro Asn Tyr Lys Lys
        370                 375                 380

Lys Ala Thr
385
```

<210> SEQ ID NO 66
<211> LENGTH: 294

```
<212> TYPE: PRT
<213> ORGANISM: Homo sapiens

<400> SEQUENCE: 66

Met Asn Ser Glu Leu Asp Tyr Tyr Glu Lys Phe Glu Val His Gly
1               5                   10                  15

Ile Leu Met Tyr Lys Asp Phe Val Lys Tyr Trp Asp Asn Val Glu Ala
            20                  25                  30

Phe Gln Ala Arg Pro Asp Asp Leu Val Ile Ala Thr Tyr Pro Lys Ser
                35                  40                  45

Gly Thr Thr Trp Val Ser Glu Ile Val Tyr Met Ile Tyr Lys Glu Gly
        50                  55                  60

Asp Val Glu Lys Cys Lys Glu Asp Val Ile Phe Asn Arg Ile Pro Phe
65                  70                  75                  80

Leu Glu Cys Arg Lys Glu Asn Leu Met Asn Gly Val Lys Gln Leu Asp
                85                  90                  95

Glu Met Asn Ser Pro Arg Ile Val Lys Thr His Leu Pro Pro Glu Leu
            100                 105                 110

Leu Pro Ala Ser Phe Trp Glu Lys Asp Cys Lys Ile Ile Tyr Leu Cys
            115                 120                 125

Arg Asn Ala Lys Asp Val Ala Val Ser Phe Tyr Tyr Phe Phe Leu Met
        130                 135                 140

Val Ala Gly His Pro Asn Pro Gly Ser Phe Pro Glu Phe Val Glu Lys
145                 150                 155                 160

Phe Met Gln Gly Gln Val Pro Tyr Gly Ser Trp Tyr Lys His Val Lys
                165                 170                 175

Ser Trp Trp Glu Lys Gly Lys Ser Pro Arg Val Leu Phe Leu Phe Tyr
            180                 185                 190

Glu Asp Leu Lys Glu Asp Ile Arg Lys Glu Val Ile Lys Leu Ile His
        195                 200                 205

Phe Leu Glu Arg Lys Pro Ser Glu Glu Leu Val Asp Arg Ile Ile His
    210                 215                 220

His Thr Ser Phe Gln Glu Met Lys Asn Asn Pro Ser Thr Asn Tyr Thr
225                 230                 235                 240

Thr Leu Pro Asp Glu Ile Met Asn Gln Lys Leu Ser Pro Phe Met Arg
                245                 250                 255

Lys Gly Ile Thr Gly Asp Trp Lys Asn His Phe Thr Val Ala Leu Asn
            260                 265                 270

Glu Lys Phe Asp Lys His Tyr Glu Gln Gln Met Lys Glu Ser Thr Leu
        275                 280                 285

Lys Phe Arg Thr Glu Ile
    290

<210> SEQ ID NO 67
<211> LENGTH: 487
<212> TYPE: PRT
<213> ORGANISM: Homo sapiens

<400> SEQUENCE: 67

Met Ser Lys Leu Leu Arg His Arg Arg Lys His Asp Asp Arg Arg
1               5                   10                  15

Phe Thr Cys Pro Val Glu Gly Cys Gly Lys Ser Phe Thr Arg Ala Glu
            20                  25                  30

His Leu Lys Gly His Ser Ile Thr His Leu Gly Thr Lys Pro Phe Glu
        35                  40                  45

Cys Pro Val Glu Gly Cys Cys Ala Arg Phe Ser Ala Arg Ser Ser Leu
```

```
              50                  55                  60
Tyr Ile His Ser Lys Lys His Val Gln Asp Val Gly Ala Pro Lys Ser
 65                  70                  75                  80

Arg Cys Pro Val Ser Thr Cys Asn Arg Leu Phe Thr Ser Lys His Ser
                     85                  90                  95

Met Lys Ala His Met Val Arg Gln His Ser Arg Arg Gln Asp Leu Leu
                    100                 105                 110

Pro Gln Leu Glu Ala Pro Ser Ser Leu Thr Pro Ser Ser Glu Leu Ser
                115                 120                 125

Ser Pro Gly Gln Ser Glu Leu Thr Asn Met Asp Leu Ala Ala Leu Phe
                130                 135                 140

Ser Asp Thr Pro Ala Asn Ala Ser Gly Ser Ala Gly Gly Ser Asp Glu
145                 150                 155                 160

Ala Leu Asn Ser Gly Ile Leu Thr Ile Asp Val Thr Ser Val Ser Ser
                    165                 170                 175

Ser Leu Gly Gly Asn Leu Pro Ala Asn Asn Ser Ser Leu Gly Pro Met
                180                 185                 190

Glu Pro Leu Val Leu Val Ala His Ser Asp Ile Pro Pro Ser Leu Asp
                195                 200                 205

Ser Pro Leu Val Leu Gly Thr Ala Ala Thr Val Leu Gln Gln Gly Ser
210                 215                 220

Phe Ser Val Asp Asp Val Gln Thr Val Ser Ala Gly Ala Leu Gly Cys
225                 230                 235                 240

Leu Val Ala Leu Pro Met Lys Asn Leu Ser Asp Asp Pro Leu Ala Leu
                    245                 250                 255

Thr Ser Asn Ser Asn Leu Ala Ala His Ile Thr Thr Pro Thr Ser Ser
                260                 265                 270

Ser Thr Pro Arg Glu Asn Ala Ser Val Pro Glu Leu Leu Ala Pro Ile
                275                 280                 285

Lys Val Glu Pro Asp Ser Pro Ser Arg Pro Gly Ala Val Gly Gln Gln
                290                 295                 300

Glu Gly Ser His Gly Leu Pro Gln Ser Thr Leu Pro Ser Pro Ala Glu
305                 310                 315                 320

Gln His Gly Ala Gln Asp Thr Glu Leu Ser Ala Gly Thr Gly Asn Phe
                    325                 330                 335

Tyr Leu Glu Ser Gly Gly Ser Ala Arg Thr Asp Tyr Arg Ala Ile Gln
                340                 345                 350

Leu Ala Lys Glu Lys Lys Gln Arg Gly Ala Gly Ser Asn Ala Gly Ala
                355                 360                 365

Ser Gln Ser Thr Gln Arg Lys Ile Lys Glu Gly Lys Met Ser Pro Pro
370                 375                 380

His Phe His Ala Ser Gln Asn Ser Trp Leu Cys Gly Ser Leu Val Val
385                 390                 395                 400

Pro Ser Gly Gly Arg Pro Gly Pro Ala Pro Ala Gly Val Gln Cys
                    405                 410                 415

Gly Ala Gln Gly Val Gln Val Gln Leu Val Gln Asp Asp Pro Ser Gly
                420                 425                 430

Glu Gly Val Leu Pro Ser Ala Arg Gly Pro Ala Thr Phe Leu Pro Phe
                435                 440                 445

Leu Thr Val Asp Leu Pro Val Tyr Val Leu Gln Glu Val Leu Pro Ser
                450                 455                 460

Ser Gly Gly Pro Ala Gly Pro Glu Ala Thr Gln Phe Pro Gly Ser Thr
465                 470                 475                 480
```

Ile Asn Leu Gln Asp Leu Gln
                485

<210> SEQ ID NO 68
<211> LENGTH: 114
<212> TYPE: PRT
<213> ORGANISM: Homo sapiens

<400> SEQUENCE: 68

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 69
<211> LENGTH: 501
<212> TYPE: PRT
<213> ORGANISM: Homo sapiens

<400> SEQUENCE: 69

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 70
<211> LENGTH: 204
<212> TYPE: PRT
<213> ORGANISM: Homo sapiens

<400> SEQUENCE: 70

Met Ala Glu Gln Glu Pro Thr Ala Glu Gln Leu Ala Gln Ile Ala Ala
1               5                   10                  15

Glu Asn Glu Glu Asp Glu His Ser Val Asn Tyr Lys Pro Pro Ala Gln
            20                  25                  30

Lys Ser Ile Gln Glu Ile Gln Glu Leu Asp Lys Asp Asp Glu Ser Leu
        35                  40                  45

Arg Lys Tyr Lys Glu Ala Leu Leu Gly Arg Val Ala Val Ser Ala Asp
    50                  55                  60

Pro Asn Val Pro Asn Val Val Val Thr Gly Leu Thr Leu Val Cys Ser
65                  70                  75                  80

Ser Ala Pro Gly Pro Leu Glu Leu Asp Leu Thr Gly Asp Leu Glu Ser
            85                  90                  95

Phe Lys Lys Gln Ser Phe Val Leu Lys Glu Gly Val Glu Tyr Arg Ile
        100                 105                 110

Lys Ile Ser Phe Arg Val Asn Arg Glu Ile Val Ser Gly Met Lys Tyr
            115                 120                 125

Ile Gln His Thr Tyr Arg Lys Gly Val Lys Ile Asp Lys Thr Asp Tyr
    130                 135                 140

Met Val Gly Ser Tyr Gly Pro Arg Ala Glu Glu Tyr Glu Phe Leu Thr
145                 150                 155                 160

Pro Val Glu Glu Ala Pro Lys Gly Met Leu Ala Arg Gly Ser Tyr Ser
                165                 170                 175

Ile Lys Ser Arg Phe Thr Asp Asp Lys Thr Asp His Leu Ser Trp
            180                 185                 190

Glu Trp Asn Leu Thr Ile Lys Lys Asp Trp Lys Asp
        195                 200

<210> SEQ ID NO 71
<211> LENGTH: 261
<212> TYPE: PRT
<213> ORGANISM: Homo sapiens

<400> SEQUENCE: 71

Met Ala Ser Pro Asp Trp Gly Tyr Asp Asp Lys Asn Gly Pro Glu Gln
1               5                   10                  15

Trp Ser Lys Leu Tyr Pro Ile Ala Asn Gly Asn Asn Gln Ser Pro Val
            20                  25                  30

Asp Ile Lys Thr Ser Glu Thr Lys His Asp Thr Ser Leu Lys Pro Ile
        35                  40                  45

Ser Val Ser Tyr Asn Pro Ala Thr Ala Lys Glu Ile Ile Asn Val Gly
    50                  55                  60

His Ser Phe His Val Asn Phe Glu Asp Asn Asp Asn Arg Ser Val Leu
65                  70                  75                  80

Lys Gly Gly Pro Phe Ser Asp Ser Tyr Arg Leu Phe Gln Phe His Phe
            85                  90                  95

His Trp Gly Ser Thr Asn Glu His Gly Ser Glu His Thr Val Asp Gly
        100                 105                 110

Val Lys Tyr Ser Ala Glu Leu His Val Ala His Trp Asn Ser Ala Lys
    115                 120                 125

Tyr Ser Ser Leu Ala Glu Ala Ala Ser Lys Ala Asp Gly Leu Ala Val
130                 135                 140

Ile Gly Val Leu Met Lys Val Gly Glu Ala Asn Pro Lys Leu Gln Lys
145                 150                 155                 160

Val Leu Asp Ala Leu Gln Ala Ile Lys Thr Lys Gly Lys Arg Ala Pro
                165                 170                 175

Phe Thr Asn Phe Asp Pro Ser Thr Leu Leu Pro Ser Ser Leu Asp Phe
            180                 185                 190

Trp Thr Tyr Pro Gly Ser Leu Thr His Pro Pro Leu Tyr Glu Ser Val
        195                 200                 205

Thr Trp Ile Ile Cys Lys Glu Ser Ile Ser Val Ser Ser Glu Gln Leu
    210                 215                 220

Ala Gln Phe Arg Ser Leu Leu Ser Asn Val Glu Gly Asp Asn Ala Val
225                 230                 235                 240

Pro Met Gln His Asn Asn Arg Pro Thr Gln Pro Leu Lys Gly Arg Thr
                245                 250                 255

```
Val Arg Ala Ser Phe
            260

<210> SEQ ID NO 72
<211> LENGTH: 260
<212> TYPE: PRT
<213> ORGANISM: Homo sapiens

<400> SEQUENCE: 72

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260

<210> SEQ ID NO 73
<211> LENGTH: 609
<212> TYPE: PRT
<213> ORGANISM: Homo sapiens

<400> SEQUENCE: 73

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45
```

```
Phe Glu Ser Gln Ser Glu Asp Glu Leu Thr Pro Phe Asp Met Ser Ile
 50                  55                  60

Gln Cys Ile Gln Ser Val Tyr Ile Ser Lys Ile Ser Ser Asp Arg
 65                  70                  75                  80

Asp Leu Leu Ala Val Val Phe Tyr Gly Thr Glu Lys Asp Lys Asn Ser
                 85                  90                  95

Val Asn Phe Lys Asn Ile Tyr Val Leu Gln Glu Leu Asp Asn Pro Gly
                100                 105                 110

Ala Lys Arg Ile Leu Glu Leu Asp Gln Phe Lys Gly Gln Gln Gly Gln
            115                 120                 125

Lys Arg Phe Gln Asp Met Met Gly His Gly Ser Asp Tyr Ser Leu Ser
            130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
                180                 185                 190

Leu Arg Asp Thr Gly Ile Phe Leu Asp Leu Met His Leu Lys Lys Pro
            195                 200                 205

Gly Gly Phe Asp Ile Ser Leu Phe Tyr Arg Asp Ile Ile Ser Ile Ala
            210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
                260                 265                 270

Ile Tyr Asn Leu Val Gln Lys Ala Leu Lys Pro Pro Ile Lys Leu
            275                 280                 285

Tyr Arg Glu Thr Asn Glu Pro Val Lys Thr Lys Thr Arg Thr Phe Asn
            290                 295                 300

Thr Ser Thr Gly Gly Leu Leu Pro Ser Asp Thr Lys Arg Ser Gln
305                 310                 315                 320

Ile Tyr Gly Ser Arg Gln Ile Ile Leu Glu Lys Glu Thr Glu Glu
            325                 330                 335

Leu Lys Arg Phe Asp Asp Pro Gly Leu Met Leu Met Gly Phe Lys Pro
            340                 345                 350

Leu Val Leu Leu Lys Lys His His Tyr Leu Arg Pro Ser Leu Phe Val
            355                 360                 365

Tyr Pro Glu Glu Ser Leu Val Ile Gly Ser Ser Thr Leu Phe Ser Ala
            370                 375                 380

Leu Leu Ile Lys Cys Leu Glu Lys Val Ala Ala Leu Cys Arg Tyr
385                 390                 395                 400

Thr Pro Arg Arg Asn Ile Pro Pro Tyr Phe Val Ala Leu Val Pro Gln
                405                 410                 415

Glu Glu Glu Leu Asp Asp Gln Lys Ile Gln Val Thr Pro Pro Gly Phe
            420                 425                 430

Gln Leu Val Phe Leu Pro Phe Ala Asp Asp Lys Arg Lys Met Pro Phe
            435                 440                 445

Thr Glu Lys Ile Met Ala Thr Pro Glu Gln Val Gly Lys Met Lys Ala
            450                 455                 460

Ile Val Glu Lys Leu Arg Phe Thr Arg Ser Asp Ser Phe Glu Asn
465                 470                 475                 480
```

```
Pro Val Leu Gln Gln His Phe Arg Asn Leu Glu Ala Leu Ala Leu Asp
                485                 490                 495

Leu Met Glu Pro Glu Gln Ala Val Asp Leu Thr Leu Pro Lys Val Glu
            500                 505                 510

Ala Met Asn Lys Arg Leu Gly Ser Leu Val Asp Glu Phe Lys Glu Leu
            515                 520                 525

Val Tyr Pro Pro Asp Tyr Asn Pro Gly Lys Val Thr Lys Arg Lys
530                 535                 540

His Asp Asn Glu Gly Ser Gly Ser Lys Arg Pro Lys Val Glu Tyr Ser
545                 550                 555                 560

Glu Glu Glu Leu Lys Thr His Ile Ser Lys Gly Thr Leu Gly Lys Phe
                565                 570                 575

Thr Val Pro Met Leu Lys Glu Ala Cys Arg Ala Tyr Gly Leu Lys Ser
            580                 585                 590

Gly Leu Lys Lys Gln Glu Leu Leu Glu Ala Leu Thr Lys His Phe Gln
            595                 600                 605

Asp

<210> SEQ ID NO 74
<211> LENGTH: 1960
<212> TYPE: PRT
<213> ORGANISM: Homo sapiens

<400> SEQUENCE: 74

Met Ala Gln Gln Ala Ala Asp Lys Tyr Leu Tyr Val Asp Lys Asn Phe
1               5                   10                  15

Ile Asn Asn Pro Leu Ala Gln Ala Asp Trp Ala Ala Lys Lys Leu Val
                20                  25                  30

Trp Val Pro Ser Asp Lys Ser Gly Phe Glu Pro Ala Ser Leu Lys Glu
            35                  40                  45

Glu Val Gly Glu Glu Ala Ile Val Glu Leu Val Glu Asn Gly Lys Lys
        50                  55                  60

Val Lys Val Asn Lys Asp Asp Ile Gln Lys Met Asn Pro Pro Lys Phe
65                  70                  75                  80

Ser Lys Val Glu Asp Met Ala Glu Leu Thr Cys Leu Asn Glu Ala Ser
                85                  90                  95

Val Leu His Asn Leu Lys Glu Arg Tyr Tyr Ser Gly Leu Ile Tyr Thr
                100                 105                 110

Tyr Ser Gly Leu Phe Cys Val Val Ile Asn Pro Tyr Lys Asn Leu Pro
            115                 120                 125

Ile Tyr Ser Glu Glu Ile Val Glu Met Tyr Lys Gly Lys Lys Arg His
130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240
```

```
Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu
        275                 280                 285

Lys Thr Asp Leu Leu Leu Glu Pro Tyr Asn Lys Tyr Arg Phe Leu Ser
    290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Glu Gln
                325                 330                 335

Met Gly Leu Leu Arg Val Ile Ser Gly Val Leu Gln Leu Gly Asn Ile
            340                 345                 350

Val Phe Lys Lys Glu Arg Asn Thr Asp Gln Ala Ser Met Pro Asp Asn
        355                 360                 365

Thr Ala Ala Gln Lys Val Ser His Leu Leu Gly Ile Asn Val Thr Asp
    370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
            420                 425                 430

Ile Asn Lys Ala Leu Asp Lys Thr Lys Arg Gln Gly Ala Ser Phe Ile
        435                 440                 445

Gly Ile Leu Asp Ile Ala Gly Phe Glu Ile Phe Asp Leu Asn Ser Phe
    450                 455                 460

Glu Gln Leu Cys Ile Asn Tyr Thr Asn Glu Lys Leu Gln Gln Leu Phe
465                 470                 475                 480

Asn His Thr Met Phe Ile Leu Glu Gln Glu Glu Tyr Gln Arg Glu Gly
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
        515                 520                 525

Asp Glu Glu Cys Trp Phe Pro Lys Ala Thr Asp Lys Ser Phe Val Glu
    530                 535                 540

Lys Val Met Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
        595                 600                 605

Ser Glu Leu Trp Lys Asp Val Asp Arg Ile Ile Gly Leu Asp Gln Val
    610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Arg Cys Ile
            660                 665                 670
```

```
Ile Pro Asn His Glu Lys Lys Ala Gly Lys Leu Asp Pro His Leu Val
        675                 680                 685

Leu Asp Gln Leu Arg Cys Asn Gly Val Leu Glu Gly Ile Arg Ile Cys
        690                 695                 700

Arg Gln Gly Phe Pro Asn Arg Val Val Phe Gln Glu Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765

Ala His Leu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Met Met
        835                 840                 845

Ala Lys Glu Glu Glu Leu Val Lys Val Arg Glu Lys Gln Leu Ala Ala
850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
                885                 890                 895

Ala Glu Ala Glu Glu Leu Arg Ala Arg Leu Thr Ala Lys Lys Gln Glu
                900                 905                 910

Leu Glu Glu Ile Cys His Asp Leu Glu Ala Arg Val Glu Glu Glu Glu
        915                 920                 925

Glu Arg Cys Gln His Leu Gln Ala Glu Lys Lys Lys Met Gln Gln Asn
    930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Lys Leu
                965                 970                 975

Glu Glu Glu Gln Ile Ile Leu Glu Asp Gln Asn Cys Lys Leu Ala Lys
            980                 985                 990

Glu Lys Lys Leu Leu Glu Asp Arg Ile Ala Glu Phe Thr Thr Asn Leu
            995                 1000                1005

Thr Glu Glu Glu Glu Lys Ser Lys Ser Leu Ala Lys Leu Lys Asn
    1010                1015                1020

Lys His Glu Ala Met Ile Thr Asp Leu Glu Glu Arg Leu Arg Arg
    1025                1030                1035

Glu Glu Lys Gln Arg Gln Glu Leu Glu Lys Thr Arg Arg Lys Leu
    1040                1045                1050

Glu Gly Asp Ser Thr Asp Leu Ser Asp Gln Ile Ala Glu Leu Gln
    1055                1060                1065

Ala Gln Ile Ala Glu Leu Lys Met Gln Leu Ala Lys Lys Glu Glu
    1070                1075                1080

Glu Leu Gln Ala Ala Leu Ala Arg Val Glu Glu Glu Ala Ala Gln
```

-continued

```
               1085                1090                1095

Lys Asn Met Ala Leu Lys Lys Ile Arg Glu Leu Glu Ser Gln Ile
        1100                1105                1110

Ser Glu Leu Gln Glu Asp Leu Glu Ser Glu Arg Ala Ser Arg Asn
        1115                1120                1125

Lys Ala Glu Lys Gln Lys Arg Asp Leu Gly Glu Glu Leu Glu Ala
        1130                1135                1140

Leu Lys Thr Glu Leu Glu Asp Thr Leu Asp Ser Thr Ala Ala Gln
        1145                1150                1155

Gln Glu Leu Arg Ser Lys Arg Glu Gln Glu Val Asn Ile Leu Lys
        1160                1165                1170

Lys Thr Leu Glu Glu Glu Ala Lys Thr His Glu Ala Gln Ile Gln
        1175                1180                1185

Glu Met Arg Gln Lys His Ser Gln Ala Val Glu Glu Leu Ala Glu
        1190                1195                1200

Gln Leu Glu Gln Thr Lys Arg Val Lys Ala Asn Leu Glu Lys Ala
        1205                1210                1215

Lys Gln Thr Leu Glu Asn Glu Arg Gly Glu Leu Ala Asn Glu Val
        1220                1225                1230

Lys Val Leu Leu Gln Gly Lys Gly Asp Ser Glu His Lys Arg Lys
        1235                1240                1245

Lys Val Glu Ala Gln Leu Gln Glu Leu Gln Val Lys Phe Asn Glu
        1250                1255                1260

Gly Glu Arg Val Arg Thr Glu Leu Ala Asp Lys Val Thr Lys Leu
        1265                1270                1275

Gln Val Glu Leu Asp Asn Val Thr Gly Leu Leu Ser Gln Ser Asp
        1280                1285                1290

Ser Lys Ser Ser Lys Leu Thr Lys Asp Phe Ser Ala Leu Glu Ser
        1295                1300                1305

Gln Leu Gln Asp Thr Gln Glu Leu Leu Gln Glu Glu Asn Arg Gln
        1310                1315                1320

Lys Leu Ser Leu Ser Thr Lys Leu Lys Gln Val Glu Asp Glu Lys
        1325                1330                1335

Asn Ser Phe Arg Glu Gln Leu Glu Glu Glu Glu Ala Lys His
        1340                1345                1350

Asn Leu Glu Lys Gln Ile Ala Thr Leu His Ala Gln Val Ala Asp
        1355                1360                1365

Met Lys Lys Lys Met Glu Asp Ser Val Gly Cys Leu Glu Thr Ala
        1370                1375                1380

Glu Glu Val Lys Arg Lys Leu Gln Lys Asp Leu Glu Gly Leu Ser
        1385                1390                1395

Gln Arg His Glu Glu Lys Val Ala Ala Tyr Asp Lys Leu Glu Lys
        1400                1405                1410

Thr Lys Thr Arg Leu Gln Gln Glu Leu Asp Asp Leu Leu Val Asp
        1415                1420                1425

Leu Asp His Gln Arg Gln Ser Ala Cys Asn Leu Glu Lys Lys Gln
        1430                1435                1440

Lys Lys Phe Asp Gln Leu Leu Ala Glu Glu Lys Thr Ile Ser Ala
        1445                1450                1455

Lys Tyr Ala Glu Glu Arg Asp Arg Ala Glu Ala Glu Ala Arg Glu
        1460                1465                1470

Lys Glu Thr Lys Ala Leu Ser Leu Ala Arg Ala Leu Glu Glu Ala
        1475                1480                1485
```

```
Met Glu Gln Lys Ala Glu Leu Glu Arg Leu Asn Lys Gln Phe Arg
    1490                1495                1500

Thr Glu Met Glu Asp Leu Met Ser Ser Lys Asp Asp Val Gly Lys
    1505                1510                1515

Ser Val His Glu Leu Glu Lys Ser Lys Arg Ala Leu Glu Gln Gln
    1520                1525                1530

Val Glu Glu Met Lys Thr Gln Leu Glu Glu Leu Glu Asp Glu Leu
    1535                1540                1545

Gln Ala Thr Glu Asp Ala Lys Leu Arg Leu Glu Val Asn Leu Gln
    1550                1555                1560

Ala Met Lys Ala Gln Phe Glu Arg Asp Leu Gln Gly Arg Asp Glu
    1565                1570                1575

Gln Ser Glu Glu Lys Lys Lys Gln Leu Val Arg Gln Val Arg Glu
    1580                1585                1590

Met Glu Ala Glu Leu Glu Asp Glu Arg Lys Gln Arg Ser Met Ala
    1595                1600                1605

Val Ala Ala Arg Lys Lys Leu Glu Met Asp Leu Lys Asp Leu Glu
    1610                1615                1620

Ala His Ile Asp Ser Ala Asn Lys Asn Arg Asp Glu Ala Ile Lys
    1625                1630                1635

Gln Leu Arg Lys Leu Gln Ala Gln Met Lys Asp Cys Met Arg Glu
    1640                1645                1650

Leu Asp Asp Thr Arg Ala Ser Arg Glu Glu Ile Leu Ala Gln Ala
    1655                1660                1665

Lys Glu Asn Glu Lys Lys Leu Lys Ser Met Glu Ala Glu Met Ile
    1670                1675                1680

Gln Leu Gln Glu Glu Leu Ala Ala Ala Glu Arg Ala Lys Arg Gln
    1685                1690                1695

Ala Gln Gln Glu Arg Asp Glu Leu Ala Asp Glu Ile Ala Asn Ser
    1700                1705                1710

Ser Gly Lys Gly Ala Leu Ala Leu Glu Glu Lys Arg Arg Leu Glu
    1715                1720                1725

Ala Arg Ile Ala Gln Leu Glu Glu Glu Leu Glu Glu Glu Gln Gly
    1730                1735                1740

Asn Thr Glu Leu Ile Asn Asp Arg Leu Lys Lys Ala Asn Leu Gln
    1745                1750                1755

Ile Asp Gln Ile Asn Thr Asp Leu Asn Leu Glu Arg Ser His Ala
    1760                1765                1770

Gln Lys Asn Glu Asn Ala Arg Gln Gln Leu Glu Arg Gln Asn Lys
    1775                1780                1785

Glu Leu Lys Val Lys Leu Gln Glu Met Glu Gly Thr Val Lys Ser
    1790                1795                1800

Lys Tyr Lys Ala Ser Ile Thr Ala Leu Glu Ala Lys Ile Ala Gln
    1805                1810                1815

Leu Glu Glu Gln Leu Asp Asn Glu Thr Lys Glu Arg Gln Ala Ala
    1820                1825                1830

Cys Lys Gln Val Arg Arg Thr Glu Lys Lys Leu Lys Asp Val Leu
    1835                1840                1845

Leu Gln Val Asp Asp Glu Arg Arg Asn Ala Glu Gln Tyr Lys Asp
    1850                1855                1860

Gln Ala Asp Lys Ala Ser Thr Arg Leu Lys Gln Leu Lys Arg Gln
    1865                1870                1875

Leu Glu Glu Ala Glu Glu Glu Ala Gln Arg Ala Asn Ala Ser Arg
    1880                1885                1890
```

```
Arg Lys Leu Gln Arg Glu Leu Glu Asp Ala Thr Glu Thr Ala Asp
    1895                1900                1905

Ala Met Asn Arg Glu Val Ser Ser Leu Lys Asn Lys Leu Arg Arg
    1910                1915                1920

Gly Asp Leu Pro Phe Val Val Pro Arg Arg Met Ala Arg Lys Gly
    1925                1930                1935

Ala Gly Asp Gly Ser Asp Glu Val Asp Gly Lys Ala Asp Gly
    1940                1945                1950

Ala Glu Ala Lys Pro Ala Glu
    1955            1960

<210> SEQ ID NO 75
<211> LENGTH: 152
<212> TYPE: PRT
<213> ORGANISM: Homo sapiens

<400> SEQUENCE: 75

Met Met Cys Asp Phe Thr Glu Asp Gln Thr Thr Glu Phe Lys Glu Ala
1               5                   10                  15

Phe Gln Leu Phe Asp Arg Thr Gly Asp Gly Lys Ile Leu Tyr Asn Gln
            20                  25                  30

Cys Gly Asp Val Met Arg Pro Leu Gly Gln Asn Pro Thr Asn Thr Glu
        35                  40                  45

Val Val Lys Val Leu Arg Asn Pro Lys Ser Asn Glu Met Asn Val Lys
    50                  55                  60

Leu Leu Asp Phe Glu His Phe Leu Pro Met Leu Gln Met Val Ala Lys
65                  70                  75                  80

Asn Lys Asp Gln Gly Thr Tyr Glu Asp Tyr Val Glu Gly Leu Gln Val
                85                  90                  95

Phe Asp Lys Glu Gly Asn Gly Thr Ile Met Gly Val Glu Phe Trp His
            100                 105                 110

Val Leu Val Thr Leu Gly Glu Lys Ile Thr Glu Glu Glu Val Glu Val
        115                 120                 125

Leu Val Ala Gly Asn Glu Gly Ser Asn Gly Cys Ile Asp Tyr Glu Ala
    130                 135                 140

Phe Val Arg His Ile Leu Ser Gly
145                 150

<210> SEQ ID NO 76
<211> LENGTH: 524
<212> TYPE: PRT
<213> ORGANISM: Homo sapiens

<400> SEQUENCE: 76

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95
```

```
Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
            115                 120                 125

Gly Glu Val Cys Ser Ala Leu Asn Leu Cys Glu Ser Leu Gln Lys His
            130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
            195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
            275                 280                 285

Ser Lys Asn Val Ile Pro Ala Leu Glu Leu Val Glu Pro Ile Lys Lys
            290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
            355                 360                 365

Leu Ser Ile Leu Leu Glu Glu Val Ser Pro Glu Leu Val Cys Ser Met
370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
            405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
            435                 440                 445

Lys Gln Cys Asp Gln Phe Val Ala Glu Tyr Glu Pro Val Leu Ile Glu
            450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
            515                 520
```

<210> SEQ ID NO 77
<211> LENGTH: 171
<212> TYPE: PRT
<213> ORGANISM: Homo sapiens

<400> SEQUENCE: 77

Met Ser Ser Lys Arg Thr Lys Thr Lys Lys Arg Pro Gln Arg
1               5                   10                  15

Ala Thr Ser Asn Val Phe Ala Met Phe Asp Gln Ser Gln Ile Gln Glu
            20                  25                  30

Phe Lys Glu Ala Phe Asn Met Ile Asp Gln Asn Arg Asp Gly Phe Ile
        35                  40                  45

Asp Lys Glu Asp Leu His Asp Met Leu Ala Ser Leu Gly Lys Asn Pro
    50                  55                  60

Thr Asp Glu Tyr Leu Asp Ala Met Met Asn Glu Ala Pro Gly Pro Ile
65                  70                  75                  80

Asn Phe Thr Met Phe Leu Thr Met Phe Gly Glu Lys Leu Asn Gly Thr
                85                  90                  95

Asp Pro Glu Asp Val Ile Arg Asn Ala Phe Ala Cys Phe Asp Glu Glu
            100                 105                 110

Ala Thr Gly Thr Ile Gln Glu Asp Tyr Leu Arg Glu Leu Leu Thr Thr
        115                 120                 125

Met Gly Asp Arg Phe Thr Asp Glu Val Asp Glu Leu Tyr Arg Glu
    130                 135                 140

Ala Pro Ile Asp Lys Lys Gly Asn Phe Asn Tyr Ile Glu Phe Thr Arg
145                 150                 155                 160

Ile Leu Lys His Gly Ala Lys Asp Lys Asp Asp
                165                 170

<210> SEQ ID NO 78
<211> LENGTH: 911
<212> TYPE: PRT
<213> ORGANISM: Homo sapiens

<400> SEQUENCE: 78

Met Glu Glu Leu Gln Asp Asp Tyr Glu Asp Met Met Glu Glu Asn Leu
1               5                   10                  15

Glu Gln Glu Glu Tyr Glu Asp Pro Asp Ile Pro Glu Ser Gln Met Glu
            20                  25                  30

Glu Pro Ala Ala His Asp Thr Glu Ala Thr Ala Thr Asp Tyr His Thr
        35                  40                  45

Thr Ser His Pro Gly Thr His Lys Val Tyr Val Glu Leu Gln Glu Leu
    50                  55                  60

Val Met Asp Glu Lys Asn Gln Glu Leu Arg Trp Met Glu Ala Ala Arg
65                  70                  75                  80

Trp Val Gln Leu Glu Glu Asn Leu Gly Glu Asn Gly Ala Trp Gly Arg
                85                  90                  95

Pro His Leu Ser His Leu Thr Phe Trp Ser Leu Leu Glu Leu Arg Arg
            100                 105                 110

Val Phe Thr Lys Gly Thr Val Leu Leu Asp Leu Gln Glu Thr Ser Leu
        115                 120                 125

Ala Gly Val Ala Asn Gln Leu Leu Asp Arg Phe Ile Phe Glu Asp Gln
    130                 135                 140

Ile Arg Pro Gln Asp Arg Glu Glu Leu Leu Arg Ala Leu Leu Leu Lys
145                 150                 155                 160

-continued

```
His Ser His Ala Gly Glu Leu Glu Ala Leu Gly Gly Val Lys Pro Ala
            165                 170                 175

Val Leu Thr Arg Ser Gly Asp Pro Ser Gln Pro Leu Leu Pro Gln His
        180                 185                 190

Ser Ser Leu Glu Thr Gln Leu Phe Cys Glu Gln Gly Asp Gly Gly Thr
        195                 200                 205

Glu Gly His Ser Pro Ser Gly Ile Leu Glu Lys Ile Pro Pro Asp Ser
    210                 215                 220

Glu Ala Thr Leu Val Leu Val Gly Arg Ala Asp Phe Leu Glu Gln Pro
225                 230                 235                 240

Val Leu Gly Phe Val Arg Leu Gln Glu Ala Ala Glu Leu Glu Ala Val
                245                 250                 255

Glu Leu Pro Val Pro Ile Arg Phe Leu Phe Val Leu Leu Gly Pro Glu
            260                 265                 270

Ala Pro His Ile Asp Tyr Thr Gln Leu Gly Arg Ala Ala Ala Thr Leu
        275                 280                 285

Met Ser Glu Arg Val Phe Arg Ile Asp Ala Tyr Met Ala Gln Ser Arg
    290                 295                 300

Gly Glu Leu Leu His Ser Leu Glu Gly Phe Leu Asp Cys Ser Leu Val
305                 310                 315                 320

Leu Pro Pro Thr Asp Ala Pro Ser Glu Gln Ala Leu Leu Ser Leu Val
                325                 330                 335

Pro Val Gln Arg Glu Leu Leu Arg Arg Arg Tyr Gln Ser Ser Pro Ala
            340                 345                 350

Lys Pro Asp Ser Ser Phe Tyr Lys Gly Leu Asp Leu Asn Gly Gly Pro
        355                 360                 365

Asp Asp Pro Leu Gln Gln Thr Gly Gln Leu Phe Gly Gly Leu Val Arg
    370                 375                 380

Asp Ile Arg Arg Arg Tyr Pro Tyr Tyr Leu Ser Asp Ile Thr Asp Ala
385                 390                 395                 400

Phe Ser Pro Gln Val Leu Ala Ala Val Ile Phe Ile Tyr Phe Ala Ala
                405                 410                 415

Leu Ser Pro Ala Ile Thr Phe Gly Gly Leu Leu Gly Glu Lys Thr Arg
            420                 425                 430

Asn Gln Met Gly Val Ser Glu Leu Leu Ile Ser Thr Ala Val Gln Gly
        435                 440                 445

Ile Leu Phe Ala Leu Leu Gly Ala Gln Pro Leu Leu Val Val Gly Phe
    450                 455                 460

Ser Gly Pro Leu Leu Val Phe Glu Glu Ala Phe Ser Phe Cys Glu
465                 470                 475                 480

Thr Asn Gly Leu Glu Tyr Ile Val Gly Arg Val Trp Ile Gly Phe Trp
                485                 490                 495

Leu Ile Leu Leu Val Val Leu Val Ala Phe Glu Gly Ser Phe Leu
            500                 505                 510

Val Arg Phe Ile Ser Arg Tyr Thr Gln Glu Ile Phe Ser Phe Leu Ile
        515                 520                 525

Ser Leu Ile Phe Ile Tyr Glu Thr Phe Ser Lys Leu Ile Lys Ile Phe
    530                 535                 540

Gln Asp His Pro Leu Gln Lys Thr Tyr Asn Tyr Asn Val Leu Met Val
545                 550                 555                 560

Pro Lys Pro Gln Gly Pro Leu Pro Asn Thr Ala Leu Leu Ser Leu Val
                565                 570                 575

Leu Met Ala Gly Thr Phe Phe Ala Met Met Leu Arg Lys Phe Lys
            580                 585                 590
```

Asn Ser Ser Tyr Phe Pro Gly Lys Leu Arg Arg Val Ile Gly Asp Phe
            595                 600                 605

Gly Val Pro Ile Ser Ile Leu Ile Met Val Leu Val Asp Phe Phe Ile
610                 615                 620

Gln Asp Thr Tyr Thr Gln Lys Leu Ser Val Pro Asp Gly Phe Lys Val
625                 630                 635                 640

Ser Asn Ser Ser Ala Arg Gly Trp Val Ile His Pro Leu Gly Leu Arg
                645                 650                 655

Ser Glu Phe Pro Ile Trp Met Met Phe Ala Ser Ala Leu Pro Ala Leu
                660                 665                 670

Leu Val Phe Ile Leu Ile Phe Leu Glu Ser Gln Ile Thr Thr Leu Ile
            675                 680                 685

Val Ser Lys Pro Glu Arg Lys Met Val Lys Gly Ser Gly Phe His Leu
            690                 695                 700

Asp Leu Leu Val Val Gly Met Gly Gly Val Ala Ala Leu Phe Gly
705                 710                 715                 720

Met Pro Trp Leu Ser Ala Thr Thr Val Arg Ser Val Thr His Ala Asn
                725                 730                 735

Ala Leu Thr Val Met Gly Lys Ala Ser Thr Pro Gly Ala Ala Ala Gln
                740                 745                 750

Ile Gln Glu Val Lys Glu Gln Arg Ile Ser Gly Leu Leu Val Ala Val
            755                 760                 765

Leu Val Gly Leu Ser Ile Leu Met Glu Pro Ile Leu Ser Arg Ile Pro
770                 775                 780

Leu Ala Val Leu Phe Gly Ile Phe Leu Tyr Met Gly Val Thr Ser Leu
785                 790                 795                 800

Ser Gly Ile Gln Leu Phe Asp Arg Ile Leu Leu Leu Phe Lys Pro Pro
                805                 810                 815

Lys Tyr His Pro Asp Val Pro Tyr Val Lys Arg Val Lys Thr Trp Arg
                820                 825                 830

Met His Leu Phe Thr Gly Ile Gln Ile Ile Cys Leu Ala Val Leu Trp
            835                 840                 845

Val Val Lys Ser Thr Pro Ala Ser Leu Ala Leu Pro Phe Val Leu Ile
            850                 855                 860

Leu Thr Val Pro Leu Arg Arg Val Leu Leu Pro Leu Ile Phe Arg Asn
865                 870                 875                 880

Val Glu Leu Gln Cys Leu Asp Ala Asp Ala Lys Ala Thr Phe Asp
                885                 890                 895

Glu Glu Glu Gly Arg Asp Glu Tyr Asp Glu Val Ala Met Pro Val
                900                 905                 910

<210> SEQ ID NO 79
<211> LENGTH: 199
<212> TYPE: PRT
<213> ORGANISM: Homo sapiens

<400> SEQUENCE: 79

Met Ala Asn Arg Gly Pro Ala Tyr Gly Leu Ser Arg Glu Val Gln Gln
1               5                   10                  15

Lys Ile Glu Lys Gln Tyr Asp Ala Asp Leu Glu Gln Ile Leu Ile Gln
                20                  25                  30

Trp Ile Thr Thr Gln Cys Arg Lys Asp Val Gly Arg Pro Gln Pro Gly
            35                  40                  45

Arg Glu Asn Phe Gln Asn Trp Leu Lys Asp Gly Thr Val Leu Cys Glu
        50                  55                  60

Leu Ile Asn Ala Leu Tyr Pro Glu Gly Gln Ala Pro Val Lys Lys Ile
65                  70                  75                  80

Gln Ala Ser Thr Met Ala Phe Lys Gln Met Glu Gln Ile Ser Gln Phe
                85                  90                  95

Leu Gln Ala Ala Glu Arg Tyr Gly Ile Asn Thr Thr Asp Ile Phe Gln
            100                 105                 110

Thr Val Asp Leu Trp Glu Gly Lys Asn Met Ala Cys Val Gln Arg Thr
        115                 120                 125

Leu Met Asn Leu Gly Gly Leu Ala Val Ala Arg Asp Asp Gly Leu Phe
    130                 135                 140

Ser Gly Asp Pro Asn Trp Phe Pro Lys Lys Ser Lys Glu Asn Pro Arg
145                 150                 155                 160

Asn Phe Ser Asp Asn Gln Leu Gln Glu Gly Lys Asn Val Ile Gly Leu
                165                 170                 175

Gln Met Gly Thr Asn Arg Gly Ala Ser Gln Ala Gly Met Thr Gly Tyr
            180                 185                 190

Gly Met Pro Arg Gln Ile Leu
        195

<210> SEQ ID NO 80
<211> LENGTH: 243
<212> TYPE: PRT
<213> ORGANISM: Homo sapiens

<400> SEQUENCE: 80

Met Met Glu Ala Ile Lys Lys Lys Met Gln Met Leu Lys Leu Asp Lys
1               5                   10                  15

Glu Asn Ala Leu Asp Arg Ala Glu Gln Ala Glu Ala Glu Gln Lys Gln
            20                  25                  30

Ala Glu Glu Arg Ser Lys Gln Leu Glu Asp Glu Leu Ala Ala Met Gln
        35                  40                  45

Lys Lys Leu Lys Gly Thr Glu Asp Glu Leu Asp Arg Ala Gln Glu Arg
    50                  55                  60

Leu Ala Thr Ala Leu Gln Lys Leu Glu Glu Ala Glu Lys Ala Ala Asp
65                  70                  75                  80

Glu Ser Glu Arg Gly Met Lys Val Ile Glu Asn Arg Ala Leu Lys Asp
                85                  90                  95

Glu Glu Lys Met Glu Leu Gln Glu Ile Gln Leu Lys Glu Ala Lys His
            100                 105                 110

Ile Ala Glu Glu Ala Asp Arg Lys Tyr Glu Glu Val Ala Arg Lys Leu
        115                 120                 125

Val Ile Ile Glu Gly Asp Leu Glu Arg Thr Glu Glu Arg Ala Glu Leu
    130                 135                 140

Ala Glu Ser Lys Cys Ser Glu Leu Glu Glu Glu Leu Lys Asn Val Thr
145                 150                 155                 160

Asn Asn Leu Lys Ser Leu Glu Ala Gln Ala Glu Lys Tyr Ser Gln Lys
                165                 170                 175

Glu Asp Lys Tyr Glu Glu Glu Ile Lys Ile Leu Thr Asp Lys Leu Lys
            180                 185                 190

Glu Ala Glu Thr Arg Ala Glu Phe Ala Glu Arg Ser Val Ala Lys Leu
        195                 200                 205

Glu Lys Thr Ile Asp Asp Leu Glu Asp Glu Leu Tyr Ala Gln Lys Leu
    210                 215                 220

Lys Tyr Lys Ala Ile Ser Glu Glu Leu Asp His Ala Leu Asn Asp Met
225                 230                 235                 240

Thr Ser Ile

<210> SEQ ID NO 81
<211> LENGTH: 2541
<212> TYPE: PRT
<213> ORGANISM: Homo sapiens

<400> SEQUENCE: 81

```
Met Val Ala Leu Ser Leu Lys Ile Ser Ile Gly Asn Val Val Lys Thr
1               5                   10                  15

Met Gln Phe Glu Pro Ser Thr Met Val Tyr Asp Ala Cys Arg Ile Ile
            20                  25                  30

Arg Glu Arg Ile Pro Glu Ala Pro Ala Gly Pro Pro Ser Asp Phe Gly
        35                  40                  45

Leu Phe Leu Ser Asp Asp Pro Lys Lys Gly Ile Trp Leu Glu Ala
    50                  55                  60

Gly Lys Ala Leu Asp Tyr Tyr Met Leu Arg Asn Gly Asp Thr Met Glu
65                  70                  75                  80

Tyr Arg Lys Lys Gln Arg Pro Leu Lys Ile Arg Met Leu Asp Gly Thr
                85                  90                  95

Val Lys Thr Ile Met Val Asp Asp Ser Lys Thr Val Thr Asp Met Leu
            100                 105                 110

Met Thr Ile Cys Ala Arg Ile Gly Ile Thr Asn His Asp Glu Tyr Ser
        115                 120                 125

Leu Val Arg Glu Leu Met Glu Glu Lys Lys Glu Glu Ile Thr Gly Thr
    130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175

Gly Arg Thr Leu Arg Glu Gln Gly Val Glu Glu His Glu Thr Leu Leu
            180                 185                 190

Leu Arg Arg Lys Phe Phe Tyr Ser Asp Gln Asn Val Asp Ser Arg Asp
        195                 200                 205

Pro Val Gln Leu Asn Leu Leu Tyr Val Gln Ala Arg Asp Asp Ile Leu
    210                 215                 220

Asn Gly Ser His Pro Val Ser Phe Asp Lys Ala Cys Glu Phe Ala Gly
225                 230                 235                 240

Phe Gln Cys Gln Ile Gln Phe Gly Pro His Asn Glu Gln Lys His Lys
                245                 250                 255

Ala Gly Phe Leu Asp Leu Lys Asp Phe Leu Pro Lys Glu Tyr Val Lys
            260                 265                 270

Gln Lys Gly Glu Arg Lys Ile Phe Gln Ala His Lys Asn Cys Gly Gln
        275                 280                 285

Met Ser Glu Ile Glu Ala Lys Val Arg Tyr Val Lys Leu Ala Arg Ser
    290                 295                 300

Leu Lys Thr Tyr Gly Val Ser Phe Phe Leu Val Lys Glu Lys Met Lys
305                 310                 315                 320

Gly Lys Asn Lys Leu Val Pro Arg Leu Leu Gly Ile Thr Lys Glu Cys
                325                 330                 335

Val Met Arg Val Asp Glu Lys Thr Lys Glu Val Ile Gln Glu Trp Asn
            340                 345                 350

Leu Thr Asn Ile Lys Arg Trp Ala Ala Ser Pro Lys Ser Phe Thr Leu
        355                 360                 365
```

```
Asp Phe Gly Asp Tyr Gln Asp Gly Tyr Tyr Ser Val Gln Thr Thr Glu
    370                 375                 380

Gly Glu Gln Ile Ala Gln Leu Ile Ala Gly Tyr Ile Asp Ile Ile Leu
385                 390                 395                 400

Lys Lys Lys Lys Ser Lys Asp His Phe Gly Leu Glu Gly Asp Glu Glu
                    405                 410                 415

Ser Thr Met Leu Glu Asp Ser Val Ser Pro Lys Lys Ser Thr Val Leu
            420                 425                 430

Gln Gln Gln Tyr Asn Arg Val Gly Lys Val Glu His Gly Ser Val Ala
        435                 440                 445

Leu Pro Ala Ile Met Arg Ser Gly Ala Ser Gly Pro Glu Asn Phe Gln
    450                 455                 460

Val Gly Ser Met Pro Pro Ala Gln Gln Gln Ile Thr Ser Gly Gln Met
465                 470                 475                 480

His Arg Gly His Met Pro Pro Leu Thr Ser Ala Gln Gln Ala Leu Thr
                485                 490                 495

Gly Thr Ile Asn Ser Ser Met Gln Ala Val Gln Ala Ala Gln Ala Thr
            500                 505                 510

Leu Asp Asp Phe Asp Thr Leu Pro Pro Leu Gly Gln Asp Ala Ala Ser
        515                 520                 525

Lys Ala Trp Arg Lys Asn Lys Met Asp Glu Ser Lys His Glu Ile His
    530                 535                 540

Ser Gln Val Asp Ala Ile Thr Ala Gly Thr Ala Ser Val Val Asn Leu
545                 550                 555                 560

Thr Ala Gly Asp Pro Ala Glu Thr Asp Tyr Thr Ala Val Gly Cys Ala
                565                 570                 575

Val Thr Thr Ile Ser Ser Asn Leu Thr Glu Met Ser Arg Gly Val Lys
            580                 585                 590

Leu Leu Ala Ala Leu Leu Glu Asp Glu Gly Gly Ser Gly Arg Pro Leu
        595                 600                 605

Leu Gln Ala Ala Lys Gly Leu Ala Gly Ala Val Ser Glu Leu Leu Arg
    610                 615                 620

Ser Ala Gln Pro Ala Ser Ala Glu Pro Arg Gln Asn Leu Leu Gln Ala
625                 630                 635                 640

Ala Gly Asn Val Gly Gln Ala Ser Gly Glu Leu Leu Gln Gln Ile Gly
                645                 650                 655

Glu Ser Asp Thr Asp Pro His Phe Gln Asp Ala Leu Met Gln Leu Ala
            660                 665                 670

Lys Ala Val Ala Ser Ala Ala Ala Ala Leu Val Leu Lys Ala Lys Ser
        675                 680                 685

Val Ala Gln Arg Thr Glu Asp Ser Gly Leu Gln Thr Gln Val Ile Ala
    690                 695                 700

Ala Ala Thr Gln Cys Ala Leu Ser Thr Ser Gln Leu Val Ala Cys Thr
705                 710                 715                 720

Lys Val Val Ala Pro Thr Ile Ser Ser Pro Val Cys Gln Glu Gln Leu
                725                 730                 735

Val Glu Ala Gly Arg Leu Val Ala Lys Ala Val Glu Gly Cys Val Ser
            740                 745                 750

Ala Ser Gln Ala Ala Thr Glu Asp Gly Gln Leu Leu Arg Gly Val Gly
        755                 760                 765

Ala Ala Ala Thr Ala Val Thr Gln Ala Leu Asn Glu Leu Leu Gln His
    770                 775                 780

Val Lys Ala His Ala Thr Gly Ala Gly Pro Ala Gly Arg Tyr Asp Gln
785                 790                 795                 800
```

```
Ala Thr Asp Thr Ile Leu Thr Val Thr Glu Asn Ile Phe Ser Ser Met
            805                 810                 815
Gly Asp Ala Gly Glu Met Val Gly Gln Ala Arg Ile Leu Ala Gln Ala
            820                 825                 830
Thr Ser Asp Leu Val Asn Ala Ile Lys Ala Asp Ala Glu Gly Glu Ser
            835                 840                 845
Asp Leu Glu Asn Ser Arg Lys Leu Leu Ser Ala Ala Lys Ile Leu Ala
            850                 855                 860
Asp Ala Thr Ala Lys Met Val Glu Ala Ala Lys Gly Ala Ala Ala His
865                 870                 875                 880
Pro Asp Ser Glu Glu Gln Gln Arg Leu Arg Glu Ala Ala Glu Gly
            885                 890                 895
Leu Arg Met Ala Thr Asn Ala Ala Ala Gln Asn Ala Ile Lys Lys Lys
            900                 905                 910
Leu Val Gln Arg Leu Glu His Ala Ala Lys Gln Ala Ala Ala Ser Ala
            915                 920                 925
Thr Gln Thr Ile Ala Ala Ala Gln His Ala Ala Ser Thr Pro Lys Ala
            930                 935                 940
Ser Ala Gly Pro Gln Pro Leu Leu Val Gln Ser Cys Lys Ala Val Ala
945                 950                 955                 960
Glu Gln Ile Pro Leu Leu Val Gln Gly Val Arg Gly Ser Gln Ala Gln
            965                 970                 975
Pro Asp Ser Pro Ser Ala Gln Leu Ala Leu Ile Ala Ala Ser Gln Ser
            980                 985                 990
Phe Leu Gln Pro Gly Gly Lys Met Val Ala Ala Lys Ala Ser Val
            995                 1000                1005
Pro Thr Ile Gln Asp Gln Ala Ser Ala Met Gln Leu Ser Gln Cys
            1010                1015                1020
Ala Lys Asn Leu Gly Thr Ala Leu Ala Glu Leu Arg Thr Ala Ala
            1025                1030                1035
Gln Lys Ala Gln Glu Ala Cys Gly Pro Leu Glu Met Asp Ser Ala
            1040                1045                1050
Leu Ser Val Val Gln Asn Leu Glu Lys Asp Leu Gln Glu Val Lys
            1055                1060                1065
Ala Ala Ala Arg Asp Gly Lys Leu Lys Pro Leu Pro Gly Glu Thr
            1070                1075                1080
Met Glu Lys Cys Thr Gln Asp Leu Gly Asn Ser Thr Lys Ala Val
            1085                1090                1095
Ser Ser Ala Ile Ala Gln Leu Leu Gly Glu Val Ala Gln Gly Asn
            1100                1105                1110
Glu Asn Tyr Ala Gly Ile Ala Ala Arg Asp Val Ala Gly Gly Leu
            1115                1120                1125
Arg Ser Leu Ala Gln Ala Ala Arg Gly Val Ala Ala Leu Thr Ser
            1130                1135                1140
Asp Pro Ala Val Gln Ala Ile Val Leu Asp Thr Ala Ser Asp Val
            1145                1150                1155
Leu Asp Lys Ala Ser Ser Leu Ile Glu Glu Ala Lys Lys Ala Ala
            1160                1165                1170
Gly His Pro Gly Asp Pro Glu Ser Gln Gln Arg Leu Ala Gln Val
            1175                1180                1185
Ala Lys Ala Val Thr Gln Ala Leu Asn Arg Cys Val Ser Cys Leu
            1190                1195                1200
Pro Gly Gln Arg Asp Val Asp Asn Ala Leu Arg Ala Val Gly Asp
```

```
              1205                1210                1215
Ala Ser Lys Arg Leu Leu Ser Asp Ser Leu Pro Pro Ser Thr Gly
    1220                1225                1230

Thr Phe Gln Glu Ala Gln Ser Arg Leu Asn Glu Ala Ala Ala Gly
    1235                1240                1245

Leu Asn Gln Ala Ala Thr Glu Leu Val Gln Ala Ser Arg Gly Thr
    1250                1255                1260

Pro Gln Asp Leu Ala Arg Ala Ser Gly Arg Phe Gly Gln Asp Phe
    1265                1270                1275

Ser Thr Phe Leu Glu Ala Gly Val Glu Met Ala Gly Gln Ala Pro
    1280                1285                1290

Ser Gln Glu Asp Arg Ala Gln Val Val Ser Asn Leu Lys Gly Ile
    1295                1300                1305

Ser Met Ser Ser Ser Lys Leu Leu Leu Ala Ala Lys Ala Leu Ser
    1310                1315                1320

Thr Asp Pro Ala Ala Pro Asn Leu Lys Ser Gln Leu Ala Ala Ala
    1325                1330                1335

Ala Arg Ala Val Thr Asp Ser Ile Asn Gln Leu Ile Thr Met Cys
    1340                1345                1350

Thr Gln Gln Ala Pro Gly Gln Lys Glu Cys Asp Asn Ala Leu Arg
    1355                1360                1365

Glu Leu Glu Thr Val Arg Glu Leu Leu Glu Asn Pro Val Gln Pro
    1370                1375                1380

Ile Asn Asp Met Ser Tyr Phe Gly Cys Leu Asp Ser Val Met Glu
    1385                1390                1395

Asn Ser Lys Val Leu Gly Glu Ala Met Thr Gly Ile Ser Gln Asn
    1400                1405                1410

Ala Lys Asn Gly Asn Leu Pro Glu Phe Gly Asp Ala Ile Ser Thr
    1415                1420                1425

Ala Ser Lys Ala Leu Cys Gly Phe Thr Glu Ala Ala Ala Gln Ala
    1430                1435                1440

Ala Tyr Leu Val Gly Val Ser Asp Pro Asn Ser Gln Ala Gly Gln
    1445                1450                1455

Gln Gly Leu Val Glu Pro Thr Gln Phe Ala Arg Ala Asn Gln Ala
    1460                1465                1470

Ile Gln Met Ala Cys Gln Ser Leu Gly Glu Pro Gly Cys Thr Gln
    1475                1480                1485

Ala Gln Val Leu Ser Ala Ala Thr Ile Val Ala Lys His Thr Ser
    1490                1495                1500

Ala Leu Cys Asn Ser Cys Arg Leu Ala Ser Ala Arg Thr Thr Asn
    1505                1510                1515

Pro Thr Ala Lys Arg Gln Phe Val Gln Ser Ala Lys Glu Val Ala
    1520                1525                1530

Asn Ser Thr Ala Asn Leu Val Lys Thr Ile Lys Ala Leu Asp Gly
    1535                1540                1545

Ala Phe Thr Glu Glu Asn Arg Ala Gln Cys Arg Ala Ala Thr Ala
    1550                1555                1560

Pro Leu Leu Glu Ala Val Asp Asn Leu Ser Ala Phe Ala Ser Asn
    1565                1570                1575

Pro Glu Phe Ser Ser Ile Pro Ala Gln Ile Ser Pro Glu Gly Arg
    1580                1585                1590

Ala Ala Met Glu Pro Ile Val Ile Ser Ala Lys Thr Met Leu Glu
    1595                1600                1605
```

```
Ser Ala Gly Gly Leu Ile Gln Thr Ala Arg Ala Leu Ala Val Asn
    1610                1615                1620

Pro Arg Asp Pro Pro Ser Trp Ser Val Leu Ala Gly His Ser Arg
    1625                1630                1635

Thr Val Ser Asp Ser Ile Lys Lys Leu Ile Thr Ser Met Arg Asp
    1640                1645                1650

Lys Ala Pro Gly Gln Leu Glu Cys Glu Thr Ala Ile Ala Ala Leu
    1655                1660                1665

Asn Ser Cys Leu Arg Asp Leu Asp Gln Ala Ser Leu Ala Ala Val
    1670                1675                1680

Ser Gln Gln Leu Ala Pro Arg Glu Gly Ile Ser Gln Glu Ala Leu
    1685                1690                1695

His Thr Gln Met Leu Thr Ala Val Gln Glu Ile Ser His Leu Ile
    1700                1705                1710

Glu Pro Leu Ala Asn Ala Ala Arg Ala Glu Ala Ser Gln Leu Gly
    1715                1720                1725

His Lys Val Ser Gln Met Ala Gln Tyr Phe Glu Pro Leu Thr Leu
    1730                1735                1740

Ala Ala Val Gly Ala Ala Ser Lys Thr Leu Ser His Pro Gln Gln
    1745                1750                1755

Met Ala Leu Leu Asp Gln Thr Lys Thr Leu Ala Glu Ser Ala Leu
    1760                1765                1770

Gln Leu Leu Tyr Thr Ala Lys Glu Ala Gly Gly Asn Pro Lys Gln
    1775                1780                1785

Ala Ala His Thr Gln Glu Ala Leu Glu Glu Ala Val Gln Met Met
    1790                1795                1800

Thr Glu Ala Val Glu Asp Leu Thr Thr Thr Leu Asn Glu Ala Ala
    1805                1810                1815

Ser Ala Ala Gly Val Val Gly Gly Met Val Asp Ser Ile Thr Gln
    1820                1825                1830

Ala Ile Asn Gln Leu Asp Glu Gly Pro Met Gly Glu Pro Glu Gly
    1835                1840                1845

Ser Phe Val Asp Tyr Gln Thr Thr Met Val Arg Thr Ala Lys Ala
    1850                1855                1860

Ile Ala Val Thr Val Gln Glu Met Val Thr Lys Ser Asn Thr Ser
    1865                1870                1875

Pro Glu Glu Leu Gly Pro Leu Ala Asn Gln Leu Thr Ser Asp Tyr
    1880                1885                1890

Gly Arg Leu Ala Ser Glu Ala Lys Pro Ala Ala Val Ala Ala Glu
    1895                1900                1905

Asn Glu Glu Ile Gly Ser His Ile Lys His Arg Val Gln Glu Leu
    1910                1915                1920

Gly His Gly Cys Ala Ala Leu Val Thr Lys Ala Gly Ala Leu Gln
    1925                1930                1935

Cys Ser Pro Ser Asp Ala Tyr Thr Lys Lys Glu Leu Ile Glu Cys
    1940                1945                1950

Ala Arg Arg Val Ser Glu Lys Val Ser His Val Leu Ala Ala Leu
    1955                1960                1965

Gln Ala Gly Asn Arg Gly Thr Gln Ala Cys Ile Thr Ala Ala Ser
    1970                1975                1980

Ala Val Ser Gly Ile Ile Ala Asp Leu Asp Thr Thr Ile Met Phe
    1985                1990                1995

Ala Thr Ala Gly Thr Leu Asn Arg Glu Gly Thr Glu Thr Phe Ala
    2000                2005                2010
```

-continued

```
Asp His Arg Glu Gly Ile Leu Lys Thr Ala Lys Val Leu Val Glu
    2015                2020                2025

Asp Thr Lys Val Leu Val Gln Asn Ala Ala Gly Ser Gln Glu Lys
    2030                2035                2040

Leu Ala Gln Ala Ala Gln Ser Ser Val Ala Thr Ile Thr Arg Leu
    2045                2050                2055

Ala Asp Val Val Lys Leu Gly Ala Ala Ser Leu Gly Ala Glu Asp
    2060                2065                2070

Pro Glu Thr Gln Val Val Leu Ile Asn Ala Val Lys Asp Val Ala
    2075                2080                2085

Lys Ala Leu Gly Asp Leu Ile Ser Ala Thr Lys Ala Ala Ala Gly
    2090                2095                2100

Lys Val Gly Asp Asp Pro Ala Val Trp Gln Leu Lys Asn Ser Ala
    2105                2110                2115

Lys Val Met Val Thr Asn Val Thr Ser Leu Leu Lys Thr Val Lys
    2120                2125                2130

Ala Val Glu Asp Glu Ala Thr Lys Gly Thr Arg Ala Leu Glu Ala
    2135                2140                2145

Thr Thr Glu His Ile Arg Gln Glu Leu Ala Val Phe Cys Ser Pro
    2150                2155                2160

Glu Pro Pro Ala Lys Thr Ser Thr Pro Glu Asp Phe Ile Arg Met
    2165                2170                2175

Thr Lys Gly Ile Thr Met Ala Thr Ala Lys Ala Val Ala Ala Gly
    2180                2185                2190

Asn Ser Cys Arg Gln Glu Asp Val Ile Ala Thr Ala Asn Leu Ser
    2195                2200                2205

Arg Arg Ala Ile Ala Asp Met Leu Arg Ala Cys Lys Glu Ala Ala
    2210                2215                2220

Tyr His Pro Glu Val Ala Pro Asp Val Arg Leu Arg Ala Leu His
    2225                2230                2235

Tyr Gly Arg Glu Cys Ala Asn Gly Tyr Leu Glu Leu Leu Asp His
    2240                2245                2250

Val Leu Leu Thr Leu Gln Lys Pro Ser Pro Glu Leu Lys Gln Gln
    2255                2260                2265

Leu Thr Gly His Ser Lys Arg Val Ala Gly Ser Val Thr Glu Leu
    2270                2275                2280

Ile Gln Ala Ala Glu Ala Met Lys Gly Thr Glu Trp Val Asp Pro
    2285                2290                2295

Glu Asp Pro Thr Val Ile Ala Glu Asn Glu Leu Leu Gly Ala Ala
    2300                2305                2310

Ala Ala Ile Glu Ala Ala Ala Lys Lys Leu Glu Gln Leu Lys Pro
    2315                2320                2325

Arg Ala Lys Pro Lys Glu Ala Asp Glu Ser Leu Asn Phe Glu Glu
    2330                2335                2340

Gln Ile Leu Glu Ala Ala Lys Ser Ile Ala Ala Ala Thr Ser Ala
    2345                2350                2355

Leu Val Lys Ala Ala Ser Ala Ala Gln Arg Glu Leu Val Ala Gln
    2360                2365                2370

Gly Lys Val Gly Ala Ile Pro Ala Asn Ala Leu Asp Asp Gly Gln
    2375                2380                2385

Trp Ser Gln Gly Leu Ile Ser Ala Ala Arg Met Val Ala Ala Ala
    2390                2395                2400

Thr Asn Asn Leu Cys Glu Ala Ala Asn Ala Ala Val Gln Gly His
```

```
                   2405                  2410                 2415

Ala Ser Gln Glu Lys Leu Ile  Ser Ser Ala Lys Gln  Val Ala Ala
    2420             2425                2430

Ser Thr Ala Gln Leu Leu Val  Ala Cys Lys Val Lys  Ala Asp Gln
    2435             2440                2445

Asp Ser Glu Ala Met Lys Arg  Leu Gln Ala Ala Gly  Asn Ala Val
    2450             2455                2460

Lys Arg Ala Ser Asp Asn Leu  Val Lys Ala Ala Gln  Lys Ala Ala
    2465             2470                2475

Ala Phe Glu Glu Gln Glu Asn  Glu Thr Val Val Val  Lys Glu Lys
    2480             2485                2490

Met Val Gly Gly Ile Ala Gln  Ile Ile Ala Ala Gln  Glu Glu Met
    2495             2500                2505

Leu Arg Lys Glu Arg Glu Leu  Glu Glu Ala Arg Lys  Lys Leu Ala
    2510             2515                2520

Gln Ile Arg Gln Gln Gln Tyr  Lys Phe Leu Pro Ser  Glu Leu Arg
    2525             2530                2535

Asp Glu His
    2540

<210> SEQ ID NO 82
<211> LENGTH: 261
<212> TYPE: PRT
<213> ORGANISM: Homo sapiens

<400> SEQUENCE: 82

Met Leu Arg Val Leu Cys Leu Leu Arg Pro Trp Arg Pro Leu Arg Ala
1               5                   10                  15

Arg Gly Cys Ala Ser Asp Gly Ala Ala Gly Gly Ser Glu Ile Gln Val
            20                  25                  30

Arg Ala Leu Ala Gly Pro Asp Gln Gly Ile Thr Glu Ile Leu Met Asn
        35                  40                  45

Arg Pro Ser Ala Arg Asn Ala Leu Gly Asn Val Phe Val Ser Glu Leu
    50                  55                  60

Leu Glu Thr Leu Ala Gln Leu Arg Glu Asp Arg Gln Val Arg Val Leu
65                  70                  75                  80

Leu Phe Arg Ser Gly Val Lys Gly Ala Phe Cys Ala Gly Ala Asp Leu
                85                  90                  95

Lys Glu Arg Glu Gln Met Ser Glu Ala Glu Val Gly Val Phe Val Gln
            100                 105                 110

Arg Leu Arg Gly Leu Met Asn Asp Ile Ala Ser Ser Ala Val Met Gly
        115                 120                 125

Leu Ile Glu Thr Thr Arg Gly Leu Leu Pro Gly Ala Gly Gly Thr Gln
    130                 135                 140

Arg Leu Pro Arg Cys Leu Gly Val Ala Leu Ala Lys Glu Leu Ile Phe
145                 150                 155                 160

Thr Gly Arg Arg Leu Ser Gly Thr Glu Ala His Val Leu Gly Leu Val
                165                 170                 175

Asn His Ala Val Ala Gln Asn Glu Glu Gly Asp Ala Ala Tyr Gln Arg
            180                 185                 190

Ala Arg Ala Leu Ala Gln Glu Ile Leu Pro Gln Ala Pro Ile Ala Val
        195                 200                 205

Arg Leu Gly Lys Val Ala Ile Asn Arg Gly Thr Glu Val Asp Ile Ala
    210                 215                 220

Ser Gly Met Ala Ile Glu Gly Met Cys Tyr Ala Gln Asn Ile Pro Thr
```

```
                225                 230                 235                 240
Arg Asp Arg Leu Glu Gly Met Ala Ala Phe Arg Glu Lys Arg Thr Pro
                    245                 250                 255
Lys Phe Val Gly Lys
            260

<210> SEQ ID NO 83
<211> LENGTH: 425
<212> TYPE: PRT
<213> ORGANISM: Homo sapiens

<400> SEQUENCE: 83

Met Asn Tyr Ala Arg Phe Ile Thr Ala Ala Ser Ala Ala Arg Asn Pro
1               5                   10                  15

Ser Pro Ile Arg Thr Met Thr Asp Ile Leu Ser Arg Gly Pro Lys Ser
            20                  25                  30

Met Ile Ser Leu Ala Gly Gly Leu Pro Asn Pro Asn Met Phe Pro Phe
        35                  40                  45

Lys Thr Ala Val Ile Thr Val Glu Asn Gly Lys Thr Ile Gln Phe Gly
50                  55                  60

Glu Glu Met Met Lys Arg Ala Leu Gln Tyr Ser Pro Ser Ala Gly Ile
65                  70                  75                  80

Pro Glu Leu Leu Ser Trp Leu Lys Gln Leu Gln Ile Lys Leu His Asn
                85                  90                  95

Pro Pro Thr Ile His Tyr Pro Pro Ser Gln Gly Gln Met Asp Leu Cys
            100                 105                 110

Val Thr Ser Gly Ser Gln Gln Gly Leu Cys Lys Val Phe Glu Met Ile
        115                 120                 125

Ile Asn Pro Gly Asp Asn Val Leu Leu Asp Glu Pro Ala Tyr Ser Gly
130                 135                 140

Thr Leu Gln Ser Leu His Pro Leu Gly Cys Asn Ile Ile Asn Val Ala
145                 150                 155                 160

Ser Asp Glu Ser Gly Ile Val Pro Asp Ser Leu Arg Asp Ile Leu Ser
                165                 170                 175

Arg Trp Lys Pro Glu Asp Ala Lys Asn Pro Gln Lys Asn Thr Pro Lys
            180                 185                 190

Phe Leu Tyr Thr Val Pro Asn Gly Asn Asn Pro Thr Gly Asn Ser Leu
        195                 200                 205

Thr Ser Glu Arg Lys Lys Glu Ile Tyr Glu Leu Ala Arg Lys Tyr Asp
210                 215                 220

Phe Leu Ile Ile Glu Asp Asp Pro Tyr Tyr Phe Leu Gln Phe Asn Lys
225                 230                 235                 240

Phe Arg Val Pro Thr Phe Leu Ser Met Asp Val Asp Gly Arg Val Ile
                245                 250                 255

Arg Ala Asp Ser Phe Ser Lys Ile Ile Ser Ser Gly Leu Arg Ile Gly
            260                 265                 270

Phe Leu Thr Gly Pro Lys Pro Leu Ile Glu Arg Val Ile Leu His Ile
        275                 280                 285

Gln Val Ser Thr Leu His Pro Ser Thr Phe Asn Gln Leu Met Ile Ser
        290                 295                 300

Gln Leu Leu His Glu Trp Gly Glu Glu Gly Phe Met Ala His Val Asp
305                 310                 315                 320

Arg Val Ile Asp Phe Tyr Ser Asn Gln Lys Asp Ala Ile Leu Ala Ala
                325                 330                 335

Ala Asp Lys Trp Leu Thr Gly Leu Ala Glu Trp His Val Pro Ala Ala
```

```
                340             345             350
Gly Met Phe Leu Trp Ile Lys Val Lys Gly Ile Asn Asp Val Lys Glu
        355             360             365

Leu Ile Glu Glu Lys Ala Val Lys Met Gly Val Leu Met Leu Pro Gly
    370             375             380

Asn Ala Phe Tyr Val Asp Ser Ser Ala Pro Ser Pro Tyr Leu Arg Ala
385             390             395             400

Ser Phe Ser Ser Ala Ser Pro Glu Gln Met Asp Val Ala Phe Gln Val
        405             410             415

Leu Ala Gln Leu Ile Lys Glu Ser Leu
        420             425

<210> SEQ ID NO 84
<211> LENGTH: 698
<212> TYPE: PRT
<213> ORGANISM: Homo sapiens

<400> SEQUENCE: 84

Met Gln Ala His Glu Leu Phe Arg Tyr Phe Arg Met Pro Glu Leu Val
1               5                   10                  15

Asp Phe Arg Gln Tyr Val Arg Thr Leu Pro Thr Asn Thr Leu Met Gly
                20                  25                  30

Phe Gly Ala Phe Ala Ala Leu Thr Thr Phe Trp Tyr Ala Thr Arg Pro
            35                  40                  45

Lys Pro Leu Lys Pro Pro Cys Asp Leu Ser Met Gln Ser Val Glu Val
    50                  55                  60

Ala Gly Ser Gly Gly Ala Arg Arg Ser Ala Leu Leu Asp Ser Asp Glu
65                  70                  75                  80

Pro Leu Val Tyr Phe Tyr Asp Asp Val Thr Thr Leu Tyr Glu Gly Phe
                85                  90                  95

Gln Arg Gly Ile Gln Val Ser Asn Asn Gly Pro Cys Leu Gly Ser Arg
            100                 105                 110

Lys Pro Asp Gln Pro Tyr Glu Trp Leu Ser Tyr Lys Gln Val Ala Glu
        115                 120                 125

Leu Ser Glu Cys Ile Gly Ser Ala Leu Ile Gln Lys Gly Phe Lys Thr
    130                 135                 140

Ala Pro Asp Gln Phe Ile Gly Ile Phe Ala Gln Asn Arg Pro Glu Trp
145                 150                 155                 160

Val Ile Ile Glu Gln Gly Cys Phe Ala Tyr Ser Met Val Ile Val Pro
                165                 170                 175

Leu Tyr Asp Thr Leu Gly Asn Glu Ala Ile Thr Tyr Ile Val Asn Lys
            180                 185                 190

Ala Glu Leu Ser Leu Val Phe Val Asp Lys Pro Glu Lys Ala Lys Leu
        195                 200                 205

Leu Leu Glu Gly Val Glu Asn Lys Leu Ile Pro Gly Leu Lys Ile Ile
    210                 215                 220

Val Val Met Asp Ala Tyr Gly Ser Glu Leu Val Glu Arg Gly Gln Arg
225                 230                 235                 240

Cys Gly Val Glu Val Thr Ser Met Lys Ala Met Glu Asp Leu Gly Arg
                245                 250                 255

Ala Asn Arg Arg Lys Pro Lys Pro Pro Ala Pro Glu Asp Leu Ala Val
            260                 265                 270

Ile Cys Phe Thr Ser Gly Thr Thr Gly Asn Pro Lys Gly Ala Met Val
        275                 280                 285

Thr His Arg Asn Ile Val Ser Asp Cys Ser Ala Phe Val Lys Ala Thr
```

```
                290               295               300
Glu Asn Thr Val Asn Pro Cys Pro Asp Asp Thr Leu Ile Ser Phe Leu
305                 310                 315                 320

Pro Leu Ala His Met Phe Glu Arg Val Val Glu Cys Val Met Leu Cys
                    325                 330                 335

His Gly Ala Lys Ile Gly Phe Phe Gln Gly Asp Ile Arg Leu Leu Met
                    340                 345                 350

Asp Asp Leu Lys Val Leu Gln Pro Thr Val Phe Pro Val Val Pro Arg
                355                 360                 365

Leu Leu Asn Arg Met Phe Asp Arg Ile Phe Gly Gln Ala Asn Thr Thr
                370                 375                 380

Leu Lys Arg Trp Leu Leu Asp Phe Ala Ser Lys Arg Lys Glu Ala Glu
385                 390                 395                 400

Leu Arg Ser Gly Ile Ile Arg Asn Asn Ser Leu Trp Asp Arg Leu Ile
                    405                 410                 415

Phe His Lys Val Gln Ser Ser Leu Gly Gly Arg Val Arg Leu Met Val
                420                 425                 430

Thr Gly Ala Ala Pro Val Ser Ala Thr Val Leu Thr Phe Leu Arg Ala
                435                 440                 445

Ala Leu Gly Cys Gln Phe Tyr Glu Gly Tyr Gly Gln Thr Glu Cys Thr
450                 455                 460

Ala Gly Cys Cys Leu Thr Met Pro Gly Asp Trp Thr Ala Gly His Val
465                 470                 475                 480

Gly Ala Pro Met Pro Cys Asn Leu Ile Lys Leu Val Asp Val Glu Glu
                    485                 490                 495

Met Asn Tyr Met Ala Ala Glu Gly Glu Gly Glu Val Cys Val Lys Gly
                500                 505                 510

Pro Asn Val Phe Gln Gly Tyr Leu Lys Asp Pro Ala Lys Thr Ala Glu
                515                 520                 525

Ala Leu Asp Lys Asp Gly Trp Leu His Thr Gly Asp Ile Gly Lys Trp
                530                 535                 540

Leu Pro Asn Gly Thr Leu Lys Ile Ile Asp Arg Lys Lys His Ile Phe
545                 550                 555                 560

Lys Leu Ala Gln Gly Glu Tyr Ile Ala Pro Glu Lys Ile Glu Asn Ile
                    565                 570                 575

Tyr Met Arg Ser Glu Pro Val Ala Gln Val Phe Val His Gly Glu Ser
                580                 585                 590

Leu Gln Ala Phe Leu Ile Ala Ile Val Val Pro Asp Val Glu Thr Leu
                595                 600                 605

Cys Ser Trp Ala Gln Lys Arg Gly Phe Glu Gly Ser Phe Glu Glu Leu
610                 615                 620

Cys Arg Asn Lys Asp Val Lys Lys Ala Ile Leu Glu Asp Met Val Arg
625                 630                 635                 640

Leu Gly Lys Asp Ser Gly Leu Lys Pro Phe Glu Gln Val Lys Gly Ile
                    645                 650                 655

Thr Leu His Pro Glu Leu Phe Ser Ile Asp Asn Gly Leu Leu Thr Pro
                    660                 665                 670

Thr Met Lys Ala Lys Arg Pro Glu Leu Arg Asn Tyr Phe Arg Ser Gln
                    675                 680                 685

Ile Asp Asp Leu Tyr Ser Thr Ile Lys Val
                    690                 695

<210> SEQ ID NO 85
<211> LENGTH: 902
```

<212> TYPE: PRT
<213> ORGANISM: Homo sapiens

<400> SEQUENCE: 85

```
Met Lys Ile Ala Val Ile Gly Gln Ser Leu Phe Gly Gln Glu Val Tyr
1               5                   10                  15

Cys His Leu Arg Lys Glu Gly His Glu Val Val Gly Val Phe Thr Val
                20                  25                  30

Pro Asp Lys Asp Gly Lys Ala Asp Pro Leu Gly Leu Ala Glu Lys
            35                  40                  45

Asp Gly Val Pro Val Phe Lys Tyr Ser Arg Trp Arg Ala Lys Gly Gln
        50                  55                  60

Ala Leu Pro Asp Val Val Ala Lys Tyr Gln Ala Leu Gly Ala Glu Leu
65                  70                  75                  80

Asn Val Leu Pro Phe Cys Ser Gln Phe Ile Pro Met Glu Ile Ile Ser
                85                  90                  95

Ala Pro Arg His Gly Ser Ile Ile Tyr His Pro Ser Leu Leu Pro Arg
            100                 105                 110

His Arg Gly Ala Ser Ala Ile Asn Trp Thr Leu Ile His Gly Asp Lys
        115                 120                 125

Lys Gly Gly Phe Ser Ile Phe Trp Ala Asp Asp Gly Leu Asp Thr Gly
    130                 135                 140

Asp Leu Leu Leu Gln Lys Glu Cys Glu Val Leu Pro Asp Asp Thr Val
145                 150                 155                 160

Ser Thr Leu Tyr Asn Arg Phe Leu Phe Pro Glu Gly Ile Lys Gly Met
                165                 170                 175

Val Gln Ala Val Arg Leu Ile Ala Glu Gly Lys Ala Pro Arg Leu Pro
            180                 185                 190

Gln Pro Glu Glu Gly Ala Thr Tyr Glu Gly Ile Gln Lys Lys Glu Thr
        195                 200                 205

Ala Lys Ile Asn Trp Asp Gln Pro Ala Glu Ala Ile His Asn Trp Ile
    210                 215                 220

Arg Gly Asn Asp Lys Val Pro Gly Ala Trp Thr Glu Ala Cys Glu Gln
225                 230                 235                 240

Lys Leu Thr Phe Phe Asn Ser Thr Leu Asn Thr Ser Gly Leu Val Pro
                245                 250                 255

Glu Gly Asp Ala Leu Pro Ile Pro Gly Ala His Arg Pro Gly Val Val
            260                 265                 270

Thr Lys Ala Gly Leu Ile Leu Phe Gly Asn Asp Asp Lys Met Leu Leu
        275                 280                 285

Val Lys Asn Ile Gln Leu Glu Asp Gly Lys Met Ile Leu Ala Ser Asn
    290                 295                 300

Phe Phe Lys Gly Ala Ala Ser Ser Val Leu Glu Leu Thr Glu Ala Glu
305                 310                 315                 320

Leu Val Thr Ala Glu Ala Val Arg Ser Val Trp Gln Arg Ile Leu Pro
                325                 330                 335

Lys Val Leu Glu Val Glu Asp Ser Thr Asp Phe Phe Lys Ser Gly Ala
            340                 345                 350

Ala Ser Val Asp Val Val Arg Leu Val Glu Glu Val Lys Glu Leu Cys
        355                 360                 365

Asp Gly Leu Glu Leu Glu Asn Glu Asp Val Tyr Met Ala Ser Thr Phe
    370                 375                 380

Gly Asp Phe Ile Gln Leu Leu Val Arg Lys Leu Arg Gly Asp Asp Glu
385                 390                 395                 400
```

-continued

Glu Gly Glu Cys Ser Ile Asp Tyr Val Glu Met Ala Val Asn Lys Arg
            405                 410                 415

Thr Val Arg Met Pro His Gln Leu Phe Ile Gly Gly Glu Phe Val Asp
            420                 425                 430

Ala Glu Gly Ala Lys Thr Ser Glu Thr Ile Asn Pro Thr Asp Gly Ser
            435                 440                 445

Val Ile Cys Gln Val Ser Leu Ala Gln Val Thr Asp Val Asp Lys Ala
            450                 455                 460

Val Ala Ala Ala Lys Asp Ala Phe Glu Asn Gly Arg Trp Gly Lys Ile
465                 470                 475                 480

Ser Ala Arg Asp Arg Gly Arg Leu Met Tyr Arg Leu Ala Asp Leu Met
            485                 490                 495

Glu Gln His Gln Glu Glu Leu Ala Thr Ile Glu Ala Leu Asp Ala Gly
            500                 505                 510

Ala Val Tyr Thr Leu Ala Leu Lys Thr His Val Gly Met Ser Ile Gln
            515                 520                 525

Thr Phe Arg Tyr Phe Ala Gly Trp Cys Asp Lys Ile Gln Gly Ser Thr
            530                 535                 540

Ile Pro Ile Asn Gln Ala Arg Pro Asn Arg Asn Leu Thr Leu Thr Arg
545                 550                 555                 560

Lys Glu Pro Val Gly Val Cys Gly Ile Ile Pro Trp Asn Tyr Pro
            565                 570                 575

Leu Met Met Leu Ser Trp Lys Thr Ala Ala Cys Leu Ala Ala Gly Asn
            580                 585                 590

Thr Val Val Ile Lys Pro Ala Gln Val Thr Pro Leu Thr Ala Leu Lys
            595                 600                 605

Phe Ala Glu Leu Thr Leu Lys Ala Gly Ile Pro Lys Gly Val Val Asn
610                 615                 620

Val Leu Pro Gly Ser Gly Ser Leu Val Gly Gln Arg Leu Ser Asp His
625                 630                 635                 640

Pro Asp Val Arg Lys Ile Gly Phe Thr Gly Ser Thr Glu Val Gly Lys
            645                 650                 655

His Ile Met Lys Ser Cys Ala Ile Ser Asn Val Lys Lys Val Ser Leu
            660                 665                 670

Glu Leu Gly Gly Lys Ser Pro Leu Ile Ile Phe Ala Asp Cys Asp Leu
            675                 680                 685

Asn Lys Ala Val Gln Met Gly Met Ser Ser Val Phe Phe Asn Lys Gly
            690                 695                 700

Glu Asn Cys Ile Ala Ala Gly Arg Leu Phe Val Glu Asp Ser Ile His
705                 710                 715                 720

Asp Glu Phe Val Arg Arg Val Val Glu Glu Val Arg Lys Met Lys Val
            725                 730                 735

Gly Asn Pro Leu Asp Arg Asp Thr Asp His Gly Pro Gln Asn His His
            740                 745                 750

Ala His Leu Val Lys Leu Met Glu Tyr Cys Gln His Gly Val Lys Glu
            755                 760                 765

Gly Ala Thr Leu Val Cys Gly Gly Asn Gln Val Pro Arg Pro Gly Phe
            770                 775                 780

Phe Phe Glu Pro Thr Val Phe Thr Asp Val Glu Asp His Met Phe Ile
785                 790                 795                 800

Ala Lys Glu Glu Ser Phe Gly Pro Val Met Ile Ile Ser Arg Phe Ala
            805                 810                 815

Asp Gly Asp Leu Asp Ala Val Leu Ser Arg Ala Asn Ala Thr Glu Phe
            820                 825                 830

```
Gly Leu Ala Ser Gly Val Phe Thr Arg Asp Ile Asn Lys Ala Leu Tyr
            835                 840                 845
Val Ser Asp Lys Leu Gln Ala Gly Thr Val Phe Val Asn Thr Tyr Asn
        850                 855                 860
Lys Thr Asp Val Ala Ala Pro Phe Gly Phe Lys Gln Ser Gly Phe
865                 870                 875                 880
Gly Lys Asp Leu Gly Glu Ala Ala Leu Asn Glu Tyr Leu Arg Val Lys
            885                 890                 895
Thr Val Thr Phe Glu Tyr
            900

<210> SEQ ID NO 86
<211> LENGTH: 412
<212> TYPE: PRT
<213> ORGANISM: Homo sapiens

<400> SEQUENCE: 86

Met Ser Ser Lys Gly Ser Val Val Leu Ala Tyr Ser Gly Gly Leu Asp
1               5                  10                  15
Thr Ser Cys Ile Leu Val Trp Leu Lys Glu Gln Gly Tyr Asp Val Ile
            20                  25                  30
Ala Tyr Leu Ala Asn Ile Gly Gln Lys Glu Asp Phe Glu Glu Ala Arg
        35                  40                  45
Lys Lys Ala Leu Lys Leu Gly Ala Lys Lys Val Phe Ile Glu Asp Val
    50                  55                  60
Ser Arg Glu Phe Val Glu Glu Phe Ile Trp Pro Ala Ile Gln Ser Ser
65                  70                  75                  80
Ala Leu Tyr Glu Asp Arg Tyr Leu Leu Gly Thr Ser Leu Ala Arg Pro
                85                  90                  95
Cys Ile Ala Arg Lys Gln Val Glu Ile Ala Gln Arg Glu Gly Ala Lys
            100                 105                 110
Tyr Val Ser His Gly Ala Thr Gly Lys Gly Asn Asp Gln Val Arg Phe
        115                 120                 125
Glu Leu Ser Cys Tyr Ser Leu Ala Pro Gln Ile Lys Val Ile Ala Pro
    130                 135                 140
Trp Arg Met Pro Glu Phe Tyr Asn Arg Phe Lys Gly Arg Asn Asp Leu
145                 150                 155                 160
Met Glu Tyr Ala Lys Gln His Gly Ile Pro Ile Pro Val Thr Pro Lys
                165                 170                 175
Asn Pro Trp Ser Met Asp Glu Asn Leu Met His Ile Ser Tyr Glu Ala
            180                 185                 190
Gly Ile Leu Glu Asn Pro Lys Asn Gln Ala Pro Pro Gly Leu Tyr Thr
        195                 200                 205
Lys Thr Gln Asp Pro Ala Lys Ala Pro Asn Thr Pro Asp Ile Leu Glu
    210                 215                 220
Ile Glu Phe Lys Lys Gly Val Pro Val Lys Val Thr Asn Val Lys Asp
225                 230                 235                 240
Gly Thr Thr His Gln Thr Ser Leu Glu Leu Phe Met Tyr Leu Asn Glu
                245                 250                 255
Val Ala Gly Lys His Gly Val Gly Arg Ile Asp Ile Val Glu Asn Arg
            260                 265                 270
Phe Ile Gly Met Lys Ser Arg Gly Ile Tyr Glu Thr Pro Ala Gly Thr
        275                 280                 285
Ile Leu Tyr His Ala His Leu Asp Ile Glu Ala Phe Thr Met Asp Arg
    290                 295                 300
```

-continued

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410

<210> SEQ ID NO 87
<211> LENGTH: 866
<212> TYPE: PRT
<213> ORGANISM: Homo sapiens

<400> SEQUENCE: 87

Met Leu Arg Pro Gly Ala Gln Leu Leu Arg Gly Leu Leu Arg Ser
1               5                   10                  15

Cys Pro Leu Gln Gly Ser Pro Gly Arg Pro Arg Ser Val Cys Gly Arg
            20                  25                  30

Glu Gly Glu Glu Lys Pro Pro Leu Ser Ala Glu Thr Gln Trp Lys Asp
        35                  40                  45

Arg Ala Glu Thr Val Ile Ile Gly Gly Gly Cys Val Gly Val Ser Leu
50                  55                  60

Ala Tyr His Leu Ala Lys Ala Gly Met Lys Asp Val Val Leu Leu Glu
65                  70                  75                  80

Lys Ser Glu Leu Thr Ala Gly Ser Thr Trp His Ala Ala Gly Leu Thr
                85                  90                  95

Thr Tyr Phe His Pro Gly Ile Asn Leu Lys Lys Ile His Tyr Asp Ser
            100                 105                 110

Ile Lys Leu Tyr Glu Lys Leu Glu Glu Glu Thr Gly Gln Val Val Gly
        115                 120                 125

Phe His Gln Pro Gly Ser Ile Arg Leu Ala Thr Thr Pro Val Arg Val
    130                 135                 140

Asp Glu Phe Lys Tyr Gln Met Thr Arg Thr Gly Trp His Ala Thr Glu
145                 150                 155                 160

Gln Tyr Leu Ile Glu Pro Glu Lys Ile Gln Glu Met Phe Pro Leu Leu
                165                 170                 175

Asn Met Asn Lys Val Leu Ala Gly Leu Tyr Asn Pro Gly Asp Gly His
            180                 185                 190

Ile Asp Pro Tyr Ser Leu Thr Met Ala Leu Ala Gly Ala Arg Lys
        195                 200                 205

Cys Gly Ala Leu Leu Lys Tyr Pro Ala Pro Val Thr Ser Leu Lys Ala
    210                 215                 220

Arg Ser Asp Gly Thr Trp Asp Val Glu Thr Pro Gln Gly Ser Met Arg
225                 230                 235                 240

Ala Asn Arg Ile Val Asn Ala Ala Gly Phe Trp Ala Arg Glu Val Gly
                245                 250                 255

Lys Met Ile Gly Leu Glu His Pro Leu Ile Pro Val Gln His Gln Tyr
            260                 265                 270

```
Val Val Thr Ser Thr Ile Ser Glu Val Lys Ala Leu Lys Arg Glu Leu
            275                 280                 285

Pro Val Leu Arg Asp Leu Glu Gly Ser Tyr Tyr Leu Arg Gln Glu Arg
        290                 295                 300

Asp Gly Leu Leu Phe Gly Pro Tyr Glu Ser Gln Glu Lys Met Lys Val
305                 310                 315                 320

Gln Asp Ser Trp Val Thr Asn Gly Val Pro Pro Gly Phe Gly Lys Glu
                325                 330                 335

Leu Phe Glu Ser Asp Leu Asp Arg Ile Met Glu His Ile Lys Ala Ala
            340                 345                 350

Met Glu Met Val Pro Val Leu Lys Lys Ala Asp Ile Ile Asn Val Val
        355                 360                 365

Asn Gly Pro Ile Thr Tyr Ser Pro Asp Ile Leu Pro Met Val Gly Pro
370                 375                 380

His Gln Gly Val Arg Asn Tyr Trp Val Ala Ile Gly Phe Gly Tyr Gly
385                 390                 395                 400

Ile Ile His Ala Gly Gly Val Gly Lys Tyr Leu Ser Asp Trp Ile Leu
                405                 410                 415

His Gly Glu Pro Pro Phe Asp Leu Ile Glu Leu Asp Pro Asn Arg Tyr
            420                 425                 430

Gly Lys Trp Thr Thr Thr Gln Tyr Thr Glu Ala Lys Ala Arg Glu Ser
        435                 440                 445

Tyr Gly Phe Asn Asn Ile Val Gly Tyr Pro Lys Glu Glu Arg Phe Ala
450                 455                 460

Gly Arg Pro Thr Gln Arg Val Ser Gly Leu Tyr Gln Arg Leu Glu Ser
465                 470                 475                 480

Lys Cys Ser Met Gly Phe His Ala Gly Trp Glu Gln Pro His Trp Phe
                485                 490                 495

Tyr Lys Pro Gly Gln Asp Thr Gln Tyr Arg Pro Ser Phe Arg Arg Thr
            500                 505                 510

Asn Trp Phe Glu Pro Val Gly Ser Glu Tyr Lys Gln Val Met Gln Arg
        515                 520                 525

Val Ala Val Thr Asp Leu Ser Pro Phe Gly Lys Phe Asn Ile Lys Gly
        530                 535                 540

Gln Asp Ser Ile Arg Leu Leu Asp His Leu Phe Ala Asn Val Ile Pro
545                 550                 555                 560

Lys Val Gly Phe Thr Asn Ile Ser His Met Leu Thr Pro Lys Gly Arg
                565                 570                 575

Val Tyr Ala Glu Leu Thr Val Ser His Gln Ser Pro Gly Glu Phe Leu
            580                 585                 590

Leu Ile Thr Gly Ser Gly Ser Glu Leu His Asp Leu Arg Trp Ile Glu
        595                 600                 605

Glu Glu Ala Val Lys Gly Gly Tyr Asp Val Glu Ile Lys Asn Ile Thr
610                 615                 620

Asp Glu Leu Gly Val Leu Gly Val Ala Gly Pro Gln Ala Arg Lys Val
625                 630                 635                 640

Leu Gln Lys Leu Thr Ser Glu Asp Leu Ser Asp Val Phe Lys Phe
                645                 650                 655

Leu Gln Thr Lys Ser Leu Lys Val Ser Asn Ile Pro Val Thr Ala Ile
            660                 665                 670

Arg Ile Ser Tyr Thr Gly Glu Leu Gly Trp Glu Leu Tyr His Arg Arg
        675                 680                 685

Glu Asp Ser Val Ala Leu Tyr Asp Ala Ile Met Asn Ala Gly Gln Glu
```

```
            690                 695                 700
Glu Gly Ile Asp Asn Phe Gly Thr Tyr Ala Met Asn Ala Leu Arg Leu
705                 710                 715                 720

Glu Lys Ala Phe Arg Ala Trp Gly Leu Glu Met Asn Cys Asp Thr Asn
                725                 730                 735

Pro Leu Glu Ala Gly Leu Glu Tyr Phe Val Lys Leu Asn Lys Pro Ala
                    740                 745                 750

Asp Phe Ile Gly Lys Gln Ala Leu Lys Gln Ile Lys Ala Lys Gly Leu
                        755                 760                 765

Lys Arg Arg Leu Val Cys Leu Thr Leu Ala Thr Asp Asp Val Asp Pro
                770                 775                 780

Glu Gly Asn Glu Ser Ile Trp Tyr Asn Gly Lys Val Val Gly Asn Thr
785                 790                 795                 800

Thr Ser Gly Ser Tyr Ser Tyr Ser Ile Gln Lys Ser Leu Ala Phe Ala
                    805                 810                 815

Tyr Val Pro Val Gln Leu Ser Glu Val Gly Gln Gln Val Glu Val Glu
                820                 825                 830

Leu Leu Gly Lys Asn Tyr Pro Ala Val Ile Ile Gln Glu Pro Leu Val
                835                 840                 845

Leu Thr Glu Pro Thr Arg Asn Arg Leu Gln Lys Gly Gly Lys Asp
                850                 855                 860

Lys Thr
865

<210> SEQ ID NO 88
<211> LENGTH: 519
<212> TYPE: PRT
<213> ORGANISM: Homo sapiens

<400> SEQUENCE: 88

Met Ala Ala Pro Ser Arg Leu Leu Ile Arg Gly Gly Arg Val Val Asn
1               5                   10                  15

Asp Asp Phe Ser Glu Val Ala Asp Val Leu Val Glu Asp Gly Val Val
                20                  25                  30

Arg Ala Leu Gly His Asp Leu Leu Pro Pro Gly Gly Ala Pro Ala Gly
            35                  40                  45

Leu Arg Val Leu Asp Ala Ala Gly Lys Leu Val Leu Pro Gly Gly Ile
        50                  55                  60

Asp Thr His Thr His Met Gln Phe Pro Phe Met Gly Ser Arg Ser Ile
65                  70                  75                  80

Asp Asp Phe His Gln Gly Thr Lys Ala Ala Leu Ser Gly Gly Thr Thr
                85                  90                  95

Met Ile Ile Asp Phe Ala Ile Pro Gln Lys Gly Gly Ser Leu Ile Glu
                100                 105                 110

Ala Phe Glu Thr Trp Arg Ser Trp Ala Asp Pro Lys Val Cys Cys Asp
            115                 120                 125

Tyr Ser Leu His Val Ala Val Thr Trp Trp Ser Asp Gln Val Lys Glu
        130                 135                 140

Glu Met Lys Ile Leu Val Gln Asp Lys Gly Val Asn Ser Phe Lys Met
145                 150                 155                 160

Phe Met Ala Tyr Lys Asp Leu Tyr Met Val Thr Asp Leu Glu Leu Tyr
                165                 170                 175

Glu Ala Phe Ser Arg Cys Lys Glu Ile Gly Ala Ile Ala Gln Val His
                180                 185                 190

Ala Glu Asn Gly Asp Leu Ile Ala Glu Gly Ala Lys Lys Met Leu Ala
```

-continued

```
                195                 200                 205
Leu Gly Ile Thr Gly Pro Glu Gly His Glu Leu Cys Arg Pro Glu Ala
        210                 215                 220

Val Glu Ala Glu Ala Thr Leu Arg Ala Ile Thr Ile Ala Ser Ala Val
225                 230                 235                 240

Asn Cys Pro Leu Tyr Ile Val His Val Met Ser Lys Ser Ala Ala Lys
                245                 250                 255

Val Ile Ala Asp Ala Arg Arg Asp Gly Lys Val Val Tyr Gly Glu Pro
    260                 265                 270

Ile Ala Ala Ser Leu Gly Thr Asp Gly Thr His Tyr Trp Asn Lys Glu
        275                 280                 285

Trp His His Ala Ala His His Val Met Gly Pro Pro Leu Arg Pro Asp
    290                 295                 300

Pro Ser Thr Pro Asp Phe Leu Met Asn Leu Leu Ala Asn Asp Asp Leu
305                 310                 315                 320

Thr Thr Thr Gly Thr Asp Asn Cys Thr Phe Asn Thr Cys Gln Lys Ala
                325                 330                 335

Leu Gly Lys Asp Asp Phe Thr Lys Ile Pro Asn Gly Val Asn Gly Val
            340                 345                 350

Glu Asp Arg Met Ser Val Ile Trp Glu Lys Val His Ser Gly Lys
        355                 360                 365

Met Asp Glu Asn Arg Phe Val Ala Val Thr Ser Thr Asn Ala Ala Lys
    370                 375                 380

Ile Phe Asn Leu Tyr Pro Arg Lys Gly Arg Ile Ala Val Gly Ser Asp
385                 390                 395                 400

Ala Asp Ile Val Ile Trp Asp Pro Lys Gly Thr Arg Thr Ile Ser Ala
                405                 410                 415

Lys Thr His His Gln Ala Val Asn Phe Asn Ile Phe Glu Gly Met Val
            420                 425                 430

Cys His Gly Val Pro Leu Val Thr Ile Ser Arg Gly Lys Val Val Tyr
        435                 440                 445

Glu Ala Gly Val Phe Ser Val Thr Ala Gly Asp Gly Lys Phe Ile Pro
    450                 455                 460

Arg Lys Pro Phe Ala Glu Tyr Ile Tyr Lys Arg Ile Lys Gln Arg Asp
465                 470                 475                 480

Arg Thr Cys Thr Pro Thr Pro Val Glu Arg Ala Pro Tyr Lys Gly Glu
                485                 490                 495

Val Ala Thr Leu Lys Ser Arg Val Thr Lys Glu Asp Ala Thr Ala Gly
            500                 505                 510

Thr Arg Lys Gln Ala His Pro
        515

<210> SEQ ID NO 89
<211> LENGTH: 915
<212> TYPE: PRT
<213> ORGANISM: Homo sapiens

<400> SEQUENCE: 89

Met Ala Arg Arg Ser Ser Phe Gln Ser Cys Gln Ile Ile Ser Leu Phe
1               5                   10                  15

Thr Phe Ala Val Gly Val Ser Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
```

```
                50                  55                  60
Glu Leu Gln Glu Ala Gly Pro Pro Asp Cys Arg Cys Asp Asn Leu Cys
 65                  70                  75                  80

Lys Ser Tyr Thr Ser Cys Cys His Asp Phe Asp Glu Leu Cys Leu Lys
                 85                  90                  95

Thr Ala Arg Gly Trp Glu Cys Thr Lys Asp Arg Cys Gly Glu Val Arg
                100                 105                 110

Asn Glu Glu Asn Ala Cys His Cys Ser Glu Asp Cys Leu Ala Arg Gly
                115                 120                 125

Asp Cys Cys Thr Asn Tyr Gln Val Val Cys Lys Gly Glu Ser His Trp
130                 135                 140

Val Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
                180                 185                 190

Arg Ser Cys Gly Thr His Ser Pro Tyr Met Arg Pro Val Tyr Pro Thr
                195                 200                 205

Lys Thr Phe Pro Asn Leu Tyr Thr Leu Ala Thr Gly Leu Tyr Pro Glu
210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
                260                 265                 270

Thr Phe Phe Trp Ser Val Val Ile Pro His Glu Arg Arg Ile Leu Thr
                275                 280                 285

Ile Leu Arg Trp Leu Thr Leu Pro Asp His Glu Arg Pro Ser Val Tyr
                290                 295                 300

Ala Phe Tyr Ser Glu Gln Pro Asp Phe Ser Gly His Lys Tyr Gly Pro
305                 310                 315                 320

Phe Gly Pro Glu Glu Ser Ser Tyr Gly Ser Pro Phe Thr Pro Ala Lys
                325                 330                 335

Arg Pro Lys Arg Lys Val Ala Pro Lys Arg Arg Gln Glu Arg Pro Val
                340                 345                 350

Ala Pro Pro Lys Lys Arg Arg Lys Ile His Arg Met Asp His Tyr
                355                 360                 365

Ala Ala Glu Thr Arg Gln Asp Lys Met Thr Asn Pro Leu Arg Glu Ile
370                 375                 380

Asp Lys Ile Val Gly Gln Leu Met Asp Gly Leu Lys Gln Leu Lys Leu
385                 390                 395                 400

Arg Arg Cys Val Asn Val Ile Phe Val Gly Asp His Gly Met Glu Asp
                405                 410                 415

Val Thr Cys Asp Arg Thr Glu Phe Leu Ser Asn Tyr Leu Thr Asn Val
                420                 425                 430

Asp Asp Ile Thr Leu Val Pro Gly Thr Leu Gly Arg Ile Arg Ser Lys
                435                 440                 445

Phe Ser Asn Asn Ala Lys Tyr Asp Pro Lys Ala Ile Ile Ala Asn Leu
                450                 455                 460

Thr Cys Lys Lys Pro Asp Gln His Phe Lys Pro Tyr Leu Lys Gln His
465                 470                 475                 480
```

-continued

Leu Pro Lys Arg Leu His Tyr Ala Asn Asn Arg Arg Ile Glu Asp Ile
            485                 490                 495

His Leu Leu Val Glu Arg Arg Trp His Val Ala Arg Lys Pro Leu Asp
        500                 505                 510

Val Tyr Lys Lys Pro Ser Gly Lys Cys Phe Phe Gln Gly Asp His Gly
        515                 520                 525

Phe Asp Asn Lys Val Asn Ser Met Gln Thr Val Phe Val Gly Tyr Gly
    530                 535                 540

Pro Thr Phe Lys Tyr Lys Thr Lys Val Pro Pro Phe Glu Asn Ile Glu
545                 550                 555                 560

Leu Tyr Asn Val Met Cys Asp Leu Leu Gly Leu Lys Pro Ala Pro Asn
                565                 570                 575

Asn Gly Thr His Gly Ser Leu Asn His Leu Leu Arg Thr Asn Thr Phe
            580                 585                 590

Arg Pro Thr Met Pro Glu Glu Val Thr Arg Pro Asn Tyr Pro Gly Ile
        595                 600                 605

Met Tyr Leu Gln Ser Asp Phe Asp Leu Gly Cys Thr Cys Asp Asp Lys
        610                 615                 620

Val Glu Pro Lys Asn Lys Leu Asp Glu Leu Asn Lys Arg Leu His Thr
625                 630                 635                 640

Lys Gly Ser Thr Glu Glu Arg His Leu Leu Tyr Gly Arg Pro Ala Val
                645                 650                 655

Leu Tyr Arg Thr Arg Tyr Asp Ile Leu Tyr His Thr Asp Phe Glu Ser
            660                 665                 670

Gly Tyr Ser Glu Ile Phe Leu Met Leu Leu Trp Thr Ser Tyr Thr Val
        675                 680                 685

Ser Lys Gln Ala Glu Val Ser Ser Val Pro Asp His Leu Thr Ser Cys
    690                 695                 700

Val Arg Pro Asp Val Arg Val Ser Pro Ser Phe Ser Gln Asn Cys Leu
705                 710                 715                 720

Ala Tyr Lys Asn Asp Lys Gln Met Ser Tyr Gly Phe Leu Phe Pro Pro
                725                 730                 735

Tyr Leu Ser Ser Ser Pro Glu Ala Lys Tyr Asp Ala Phe Leu Val Thr
            740                 745                 750

Asn Met Val Pro Met Tyr Pro Ala Phe Lys Arg Val Trp Asn Tyr Phe
        755                 760                 765

Gln Arg Val Leu Val Lys Lys Tyr Ala Ser Glu Arg Asn Gly Val Asn
    770                 775                 780

Val Ile Ser Gly Pro Ile Phe Asp Tyr Asp Tyr Asp Gly Leu His Asp
785                 790                 795                 800

Thr Glu Asp Lys Ile Lys Gln Tyr Val Glu Gly Ser Ser Ile Pro Val
                805                 810                 815

Pro Thr His Tyr Tyr Ser Ile Ile Thr Ser Cys Leu Asp Phe Thr Gln
            820                 825                 830

Pro Ala Asp Lys Cys Asp Gly Pro Leu Ser Val Ser Ser Phe Ile Leu
        835                 840                 845

Pro His Arg Pro Asp Asn Glu Glu Ser Cys Asn Ser Ser Glu Asp Glu
    850                 855                 860

Ser Lys Trp Val Glu Glu Leu Met Lys Met His Thr Ala Arg Val Arg
865                 870                 875                 880

Asp Ile Glu His Leu Thr Ser Leu Asp Phe Phe Arg Lys Thr Ser Arg
                885                 890                 895

Ser Tyr Pro Glu Ile Leu Thr Leu Lys Thr Tyr Leu His Thr Tyr Glu
            900                 905                 910

```
Ser Glu Ile
        915

<210> SEQ ID NO 90
<211> LENGTH: 579
<212> TYPE: PRT
<213> ORGANISM: Homo sapiens

<400> SEQUENCE: 90

Met Val Gln Tyr Glu Leu Trp Ala Ala Leu Pro Gly Ala Ser Gly Val
1               5                   10                  15

Ala Leu Ala Cys Cys Phe Val Ala Ala Val Ala Leu Arg Trp Ser
            20                  25                  30

Gly Arg Arg Thr Ala Arg Gly Ala Val Val Arg Ala Arg Gln Lys Gln
        35                  40                  45

Arg Ala Gly Leu Glu Asn Met Asp Arg Ala Ala Gln Arg Phe Arg Leu
    50                  55                  60

Gln Asn Pro Asp Leu Asp Ser Glu Ala Leu Leu Ala Leu Pro Leu Pro
65                  70                  75                  80

Gln Leu Val Gln Lys Leu His Ser Arg Glu Leu Ala Pro Glu Ala Val
                85                  90                  95

Leu Phe Thr Tyr Val Gly Lys Ala Trp Glu Val Asn Lys Gly Thr Asn
            100                 105                 110

Cys Val Thr Ser Tyr Leu Ala Asp Cys Glu Thr Gln Leu Ser Gln Ala
        115                 120                 125

Pro Arg Gln Gly Leu Leu Tyr Gly Val Pro Val Ser Leu Lys Glu Cys
    130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
            180                 185                 190

Ser Tyr Asp Cys Ser Asn Pro Leu Phe Gly Gln Thr Val Asn Pro Trp
        195                 200                 205

Lys Ser Ser Lys Ser Pro Gly Gly Ser Ser Gly Glu Gly Ala Leu
    210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
                245                 250                 255

Thr Gly Asn Arg Leu Ser Lys Ser Gly Leu Lys Gly Cys Val Tyr Gly
            260                 265                 270

Gln Glu Ala Val Arg Leu Ser Val Gly Pro Met Ala Arg Asp Val Glu
        275                 280                 285

Ser Leu Ala Leu Cys Leu Arg Ala Leu Leu Cys Glu Asp Met Phe Arg
    290                 295                 300

Leu Asp Pro Thr Val Pro Pro Leu Pro Phe Arg Glu Glu Val Tyr Thr
305                 310                 315                 320

Ser Ser Gln Pro Leu Arg Val Gly Tyr Tyr Glu Thr Asp Asn Tyr Thr
                325                 330                 335

Met Pro Ser Pro Ala Met Arg Arg Ala Val Leu Glu Thr Lys Gln Ser
            340                 345                 350

Leu Glu Ala Ala Gly His Thr Leu Val Pro Phe Leu Pro Ser Asn Ile
        355                 360                 365
```

```
Pro His Ala Leu Glu Thr Leu Ser Thr Gly Gly Leu Phe Ser Asp Gly
    370                 375                 380

Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
                405                 410                 415

Leu Leu Ala Phe Leu Val Lys Pro Leu Leu Pro Arg Leu Ser Ala Phe
            420                 425                 430

Leu Ser Asn Met Lys Ser Arg Ser Ala Gly Lys Leu Trp Glu Leu Gln
        435                 440                 445

His Glu Ile Glu Val Tyr Arg Lys Thr Val Ile Ala Gln Trp Arg Ala
    450                 455                 460

Leu Asp Leu Asp Val Val Leu Thr Pro Met Leu Ala Pro Ala Leu Asp
465                 470                 475                 480

Leu Asn Ala Pro Gly Arg Ala Thr Gly Ala Val Ser Tyr Thr Met Leu
                485                 490                 495

Tyr Asn Cys Leu Asp Phe Pro Ala Gly Val Val Pro Val Thr Thr Val
            500                 505                 510

Thr Ala Glu Asp Glu Ala Gln Met Glu His Tyr Arg Gly Tyr Phe Gly
        515                 520                 525

Asp Ile Trp Asp Lys Met Leu Gln Lys Gly Met Lys Lys Ser Val Gly
    530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
                565                 570                 575

Gln Ser Ser

<210> SEQ ID NO 91
<211> LENGTH: 236
<212> TYPE: PRT
<213> ORGANISM: Homo sapiens

<400> SEQUENCE: 91

Met Ser Ala Pro Ser Ala Thr Pro Ile Phe Ala Pro Gly Glu Asn Cys
1               5                   10                  15

Ser Pro Ala Trp Gly Ala Ala Pro Ala Ala Tyr Asp Ala Ala Asp Thr
            20                  25                  30

His Leu Arg Ile Leu Gly Lys Pro Val Met Glu Arg Trp Glu Thr Pro
        35                  40                  45

Tyr Met His Ala Leu Ala Ala Ala Ser Ser Lys Gly Gly Arg Val
    50                  55                  60

Leu Glu Val Gly Phe Gly Met Ala Ile Ala Ala Ser Lys Val Gln Glu
65                  70                  75                  80

Ala Pro Ile Asp Glu His Trp Ile Ile Glu Cys Asn Asp Gly Val Phe
                85                  90                  95

Gln Arg Leu Arg Asp Trp Ala Pro Arg Gln Thr His Lys Val Ile Pro
            100                 105                 110

Leu Lys Gly Leu Trp Glu Asp Val Ala Pro Thr Leu Pro Asp Gly His
        115                 120                 125

Phe Asp Gly Ile Leu Tyr Asp Thr Tyr Pro Leu Ser Glu Glu Thr Trp
    130                 135                 140

His Thr His Gln Phe Asn Phe Ile Lys Asn His Ala Phe Arg Leu Leu
145                 150                 155                 160
```

```
Lys Pro Gly Gly Val Leu Thr Tyr Cys Asn Leu Thr Ser Trp Gly Glu
                165                 170                 175

Leu Met Lys Ser Lys Tyr Ser Asp Ile Thr Ile Met Phe Glu Glu Thr
            180                 185                 190

Gln Val Pro Ala Leu Leu Glu Ala Gly Phe Arg Arg Glu Asn Ile Arg
        195                 200                 205

Thr Glu Val Met Ala Leu Val Pro Pro Ala Asp Cys Arg Tyr Tyr Ala
    210                 215                 220

Phe Pro Gln Met Ile Thr Pro Leu Val Thr Lys Gly
225                 230                 235

<210> SEQ ID NO 92
<211> LENGTH: 336
<212> TYPE: PRT
<213> ORGANISM: Homo sapiens

<400> SEQUENCE: 92

Met Ala Ala Ser Leu Arg Leu Leu Gly Ala Ala Ser Gly Leu Arg Tyr
1               5                   10                  15

Trp Ser Arg Arg Leu Arg Pro Ala Ala Gly Ser Phe Ala Ala Val Cys
            20                  25                  30

Ser Arg Ser Val Ala Ser Lys Thr Pro Val Gly Phe Ile Gly Leu Gly
        35                  40                  45

Asn Met Gly Asn Pro Met Ala Lys Asn Leu Met Lys His Gly Tyr Pro
    50                  55                  60

Leu Ile Ile Tyr Asp Val Phe Pro Asp Ala Cys Lys Glu Phe Gln Asp
65                  70                  75                  80

Ala Gly Glu Gln Val Val Ser Ser Pro Ala Asp Val Ala Glu Lys Ala
                85                  90                  95

Asp Arg Ile Ile Thr Met Leu Pro Thr Ser Ile Asn Ala Ile Glu Ala
            100                 105                 110

Tyr Ser Gly Ala Asn Gly Ile Leu Lys Lys Val Lys Lys Gly Ser Leu
        115                 120                 125

Leu Ile Asp Ser Ser Thr Ile Asp Pro Ala Val Ser Lys Glu Leu Ala
    130                 135                 140

Lys Glu Val Glu Lys Met Gly Ala Val Phe Met Asp Ala Pro Val Ser
145                 150                 155                 160

Gly Gly Val Gly Ala Arg Ser Gly Asn Leu Thr Phe Met Val Gly
                165                 170                 175

Gly Val Glu Asp Glu Phe Ala Ala Gln Glu Leu Leu Gly Cys Met
            180                 185                 190

Gly Ser Asn Val Val Tyr Cys Gly Ala Val Gly Thr Gly Gln Ala Ala
        195                 200                 205

Lys Ile Cys Asn Asn Met Leu Leu Ala Ile Ser Met Ile Gly Thr Ala
    210                 215                 220

Glu Ala Met Asn Leu Gly Ile Arg Leu Gly Leu Asp Pro Lys Leu Leu
225                 230                 235                 240

Ala Lys Ile Leu Asn Met Ser Ser Gly Arg Cys Trp Ser Ser Asp Thr
                245                 250                 255

Tyr Asn Pro Val Pro Gly Val Met Asp Gly Val Pro Ser Ala Asn Asn
            260                 265                 270

Tyr Gln Gly Gly Phe Gly Thr Thr Leu Met Ala Lys Asp Leu Gly Leu
        275                 280                 285

Ala Gln Asp Ser Ala Thr Ser Thr Lys Ser Pro Ile Leu Leu Gly Ser
    290                 295                 300
```

```
Leu Ala His Gln Ile Tyr Arg Met Met Cys Ala Lys Gly Tyr Ser Lys
305                 310                 315                 320

Lys Asp Phe Ser Ser Val Phe Gln Phe Leu Arg Glu Glu Glu Thr Phe
                325                 330                 335

<210> SEQ ID NO 93
<211> LENGTH: 298
<212> TYPE: PRT
<213> ORGANISM: Homo sapiens

<400> SEQUENCE: 93

Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
                20                  25                  30

Leu Ser Gln Arg Trp Gln Arg Gly Gly Asn Ala Ser Asn Ser Cys Thr
            35                  40                  45

Val Leu Ser Leu Leu Gly Ala Pro Cys Ala Phe Met Gly Ser Met Ala
        50                  55                  60

Pro Gly His Val Ala Asp Phe Val Leu Asp Asp Leu Arg Arg Tyr Ser
65                  70                  75                  80

Val Asp Leu Arg Tyr Thr Val Phe Gln Thr Thr Gly Ser Val Pro Ile
                85                  90                  95

Ala Thr Val Ile Ile Asn Glu Ala Ser Gly Ser Arg Thr Ile Leu Tyr
                100                 105                 110

Tyr Asp Arg Ser Leu Pro Asp Val Ser Ala Thr Asp Phe Glu Lys Val
            115                 120                 125

Asp Leu Thr Gln Phe Lys Trp Ile His Ile Glu Gly Arg Asn Ala Ser
        130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
210                 215                 220

Trp Ala Glu Glu Gly Ala Asp Ala Leu Gly Pro Asp Gly Lys Leu Leu
225                 230                 235                 240

His Ser Asp Ala Phe Pro Pro Arg Val Val Asp Thr Leu Gly Ala
                245                 250                 255

Gly Asp Thr Phe Asn Ala Ser Val Ile Phe Ser Leu Ser Gln Gly Arg
                260                 265                 270

Ser Val Gln Glu Ala Leu Arg Phe Gly Cys Gln Val Ala Gly Lys Lys
            275                 280                 285

Cys Gly Leu Gln Gly Phe Asp Gly Ile Val
        290                 295

<210> SEQ ID NO 94
<211> LENGTH: 307
<212> TYPE: PRT
<213> ORGANISM: Homo sapiens

<400> SEQUENCE: 94

Met Glu Pro Ser Ser Leu Glu Leu Pro Ala Asp Thr Val Gln Arg Ile
```

|  | 1 |  |  |  | 5 |  |  |  |  | 10 |  |  |  |  | 15 |  |
|---|---|---|---|---|---|---|---|---|---|---|---|---|---|---|---|---|

Ala Ala Glu Leu Lys Cys His Pro Thr Asp Glu Arg Val Ala Leu His
                    20                  25                  30

Leu Asp Glu Glu Asp Lys Leu Arg His Phe Arg Glu Cys Phe Tyr Ile
                35                  40                  45

Pro Lys Ile Gln Asp Leu Pro Pro Val Asp Leu Ser Leu Val Asn Lys
            50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                    85                  90                  95

Ile Ala Ala Tyr Gly His Glu Val Gly Lys Arg Pro Trp Ile Thr Gly
                    100                 105                 110

Asp Glu Ser Ile Val Gly Leu Met Lys Asp Ile Val Gly Ala Asn Glu
                115                 120                 125

Lys Glu Ile Ala Leu Met Asn Ala Leu Thr Val Asn Leu His Leu Leu
            130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                    165                 170                 175

Gln Leu His Gly Leu Asn Ile Glu Glu Ser Met Arg Met Ile Lys Pro
                180                 185                 190

Arg Glu Gly Glu Glu Thr Leu Arg Ile Glu Asp Ile Leu Glu Val Ile
            195                 200                 205

Glu Lys Glu Gly Asp Ser Ile Ala Val Ile Leu Phe Ser Gly Val His
210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                    245                 250                 255

Asn Val Glu Leu Tyr Leu His Asp Trp Gly Val Asp Phe Ala Cys Trp
                260                 265                 270

Cys Ser Tyr Lys Tyr Leu Asn Ala Gly Ala Gly Gly Ile Ala Gly Ala
            275                 280                 285

Phe Ile His Glu Lys His Ala His Thr Ile Lys Pro Ala Arg Ser Glu
290                 295                 300

Phe Phe Asn
305

<210> SEQ ID NO 95
<211> LENGTH: 1178
<212> TYPE: PRT
<213> ORGANISM: Homo sapiens

<400> SEQUENCE: 95

Met Leu Lys Phe Arg Thr Val His Gly Gly Leu Arg Leu Leu Gly Ile
1               5                   10                  15

Arg Arg Thr Ser Thr Ala Pro Ala Ala Ser Pro Asn Val Arg Arg Leu
                20                  25                  30

Glu Tyr Lys Pro Ile Lys Lys Val Met Val Ala Asn Arg Gly Glu Ile
                35                  40                  45

Ala Ile Arg Val Phe Arg Ala Cys Thr Glu Leu Gly Ile Arg Thr Val
            50                  55                  60

Ala Ile Tyr Ser Glu Gln Asp Thr Gly Gln Met His Arg Gln Lys Ala

-continued

```
                65                  70                  75                  80
Asp Glu Ala Tyr Leu Ile Gly Arg Gly Leu Ala Pro Val Gln Ala Tyr
                        85                  90                  95

Leu His Ile Pro Asp Ile Ile Lys Val Ala Lys Glu Asn Asn Val Asp
                100                 105                 110

Ala Val His Pro Gly Tyr Gly Phe Leu Ser Glu Arg Ala Asp Phe Ala
                115                 120                 125

Gln Ala Cys Gln Asp Ala Gly Val Arg Phe Ile Gly Pro Ser Pro Glu
                130                 135                 140

Val Val Arg Lys Met Gly Asp Lys Val Glu Ala Arg Ala Ile Ala Ile
145                 150                 155                 160

Ala Ala Gly Val Pro Val Pro Gly Thr Asp Ala Pro Ile Thr Ser
                165                 170                 175

Leu His Glu Ala His Glu Phe Ser Asn Thr Tyr Gly Phe Pro Ile Ile
                180                 185                 190

Phe Lys Ala Ala Tyr Gly Gly Gly Arg Gly Met Arg Val Val His
            195                 200                 205

Ser Tyr Glu Glu Leu Glu Glu Asn Tyr Thr Arg Ala Tyr Ser Glu Ala
            210                 215                 220

Leu Ala Ala Phe Gly Asn Gly Ala Leu Phe Val Glu Lys Phe Ile Glu
225                 230                 235                 240

Lys Pro Arg His Ile Glu Val Gln Ile Leu Gly Asp Gln Tyr Gly Asn
                245                 250                 255

Ile Leu His Leu Tyr Glu Arg Asp Cys Ser Ile Gln Arg Arg His Gln
                260                 265                 270

Lys Val Val Glu Ile Ala Pro Ala Ala His Leu Asp Pro Gln Leu Arg
            275                 280                 285

Thr Arg Leu Thr Ser Asp Ser Val Lys Leu Ala Lys Gln Val Gly Tyr
            290                 295                 300

Glu Asn Ala Gly Thr Val Glu Phe Leu Val Asp Arg His Gly Lys His
305                 310                 315                 320

Tyr Phe Ile Glu Val Asn Ser Arg Leu Gln Val Glu His Thr Val Thr
                325                 330                 335

Glu Glu Ile Thr Asp Val Asp Leu Val His Ala Gln Ile His Val Ser
                340                 345                 350

Glu Gly Arg Ser Leu Pro Asp Leu Gly Leu Arg Gln Glu Asn Ile Arg
            355                 360                 365

Ile Asn Gly Cys Ala Ile Gln Cys Arg Val Thr Thr Glu Asp Pro Ala
370                 375                 380

Arg Ser Phe Gln Pro Asp Thr Gly Arg Ile Glu Val Phe Arg Ser Gly
385                 390                 395                 400

Glu Gly Met Gly Ile Arg Leu Asp Asn Ala Ser Ala Phe Gln Gly Ala
                405                 410                 415

Val Ile Ser Pro His Tyr Asp Ser Leu Leu Val Lys Val Ile Ala His
                420                 425                 430

Gly Lys Asp His Pro Thr Ala Ala Thr Lys Met Ser Arg Ala Leu Ala
            435                 440                 445

Glu Phe Arg Val Arg Gly Val Lys Thr Asn Ile Ala Phe Leu Gln Asn
            450                 455                 460

Val Leu Asn Asn Gln Gln Phe Leu Ala Gly Thr Val Asp Thr Gln Phe
465                 470                 475                 480

Ile Asp Glu Asn Pro Glu Leu Phe Gln Leu Arg Pro Ala Gln Asn Arg
                485                 490                 495
```

```
Ala Gln Lys Leu Leu His Tyr Leu Gly His Val Met Val Asn Gly Pro
            500                 505                 510

Thr Thr Pro Ile Pro Val Lys Ala Ser Pro Ser Pro Thr Asp Pro Val
            515                 520                 525

Val Pro Ala Val Pro Ile Gly Pro Pro Ala Gly Phe Arg Asp Ile
            530                 535                 540

Leu Leu Arg Glu Gly Pro Glu Gly Phe Ala Arg Ala Val Arg Asn His
545                 550                 555                 560

Pro Gly Leu Leu Leu Met Asp Thr Thr Phe Arg Asp Ala His Gln Ser
                565                 570                 575

Leu Leu Ala Thr Arg Val Arg Thr His Asp Leu Lys Lys Ile Ala Pro
            580                 585                 590

Tyr Val Ala His Asn Phe Ser Lys Leu Phe Ser Met Glu Asn Trp Gly
            595                 600                 605

Gly Ala Thr Phe Asp Val Ala Met Arg Phe Leu Tyr Glu Cys Pro Trp
            610                 615                 620

Arg Arg Leu Gln Glu Leu Arg Glu Leu Ile Pro Asn Ile Pro Phe Gln
625                 630                 635                 640

Met Leu Leu Arg Gly Ala Asn Ala Val Gly Tyr Thr Asn Tyr Pro Asp
                645                 650                 655

Asn Val Val Phe Lys Phe Cys Glu Val Ala Lys Glu Asn Gly Met Asp
                660                 665                 670

Val Phe Arg Val Phe Asp Ser Leu Asn Tyr Leu Pro Asn Met Leu Leu
            675                 680                 685

Gly Met Glu Ala Ala Gly Ser Ala Gly Gly Val Val Glu Ala Ala Ile
            690                 695                 700

Ser Tyr Thr Gly Asp Val Ala Asp Pro Ser Arg Thr Lys Tyr Ser Leu
705                 710                 715                 720

Gln Tyr Tyr Met Gly Leu Ala Glu Glu Leu Val Arg Ala Gly Thr His
                725                 730                 735

Ile Leu Cys Ile Lys Asp Met Ala Gly Leu Leu Lys Pro Thr Ala Cys
                740                 745                 750

Thr Met Leu Val Ser Ser Leu Arg Asp Arg Phe Pro Asp Leu Pro Leu
            755                 760                 765

His Ile His Thr His Asp Thr Ser Gly Ala Gly Val Ala Ala Met Leu
            770                 775                 780

Ala Cys Ala Gln Ala Gly Ala Asp Val Val Asp Val Ala Ala Asp Ser
785                 790                 795                 800

Met Ser Gly Met Thr Ser Gln Pro Ser Met Gly Ala Leu Val Ala Cys
                805                 810                 815

Thr Arg Gly Thr Pro Leu Asp Thr Glu Val Pro Met Glu Arg Val Phe
                820                 825                 830

Asp Tyr Ser Glu Tyr Trp Glu Gly Ala Arg Gly Leu Tyr Ala Ala Phe
            835                 840                 845

Asp Cys Thr Ala Thr Met Lys Ser Gly Asn Ser Asp Val Tyr Glu Asn
            850                 855                 860

Glu Ile Pro Gly Gly Gln Tyr Thr Asn Leu His Phe Gln Ala His Ser
865                 870                 875                 880

Met Gly Leu Gly Ser Lys Phe Lys Glu Val Lys Lys Ala Tyr Val Glu
                885                 890                 895

Ala Asn Gln Met Leu Gly Asp Leu Ile Lys Val Thr Pro Ser Ser Lys
            900                 905                 910

Ile Val Gly Asp Leu Ala Gln Phe Met Val Gln Asn Gly Leu Ser Arg
            915                 920                 925
```

```
Ala Glu Ala Glu Ala Gln Ala Glu Glu Leu Ser Phe Pro Arg Ser Val
        930                 935                 940

Val Glu Phe Leu Gln Gly Tyr Ile Gly Val Pro His Gly Gly Phe Pro
945                 950                 955                 960

Glu Pro Phe Arg Ser Lys Val Leu Lys Asp Leu Pro Arg Val Glu Gly
                965                 970                 975

Arg Pro Gly Ala Ser Leu Pro Pro Leu Asp Leu Gln Ala Leu Glu Lys
            980                 985                 990

Glu Leu Val Asp Arg His Gly Glu Glu Val Thr Pro Glu Asp Val Leu
        995                 1000                1005

Ser Ala Ala Met Tyr Pro Asp Val Phe Ala His Phe Lys Asp Phe
    1010                1015                1020

Thr Ala Thr Phe Gly Pro Leu Asp Ser Leu Asn Thr Arg Leu Phe
    1025                1030                1035

Leu Gln Gly Pro Lys Ile Ala Glu Glu Phe Glu Val Glu Leu Glu
    1040                1045                1050

Arg Gly Lys Thr Leu His Ile Lys Ala Leu Ala Val Ser Asp Leu
    1055                1060                1065

Asn Arg Ala Gly Gln Arg Gln Val Phe Phe Glu Leu Asn Gly Gln
    1070                1075                1080

Leu Arg Ser Ile Leu Val Lys Asp Thr Gln Ala Met Lys Glu Met
    1085                1090                1095

His Phe His Pro Lys Ala Leu Lys Asp Val Lys Gly Gln Ile Gly
    1100                1105                1110

Ala Pro Met Pro Gly Lys Val Ile Asp Ile Lys Val Val Ala Gly
    1115                1120                1125

Ala Lys Val Ala Lys Gly Gln Pro Leu Cys Val Leu Ser Ala Met
    1130                1135                1140

Lys Met Glu Thr Val Val Thr Ser Pro Met Glu Gly Thr Val Arg
    1145                1150                1155

Lys Val His Val Thr Lys Asp Met Thr Leu Glu Gly Asp Asp Leu
    1160                1165                1170

Ile Leu Glu Ile Glu
    1175

<210> SEQ ID NO 96
<211> LENGTH: 407
<212> TYPE: PRT
<213> ORGANISM: Homo sapiens

<400> SEQUENCE: 96

Met Arg Trp Val Trp Ala Leu Leu Lys Asn Ala Ser Leu Ala Gly Ala
1               5                   10                  15

Pro Lys Tyr Ile Glu His Phe Ser Lys Phe Ser Pro Ser Pro Leu Ser
            20                  25                  30

Met Lys Gln Phe Leu Asp Phe Gly Ser Ser Asn Ala Cys Glu Lys Thr
        35                  40                  45

Ser Phe Thr Phe Leu Arg Gln Glu Leu Pro Val Arg Leu Ala Asn Ile
    50                  55                  60

Met Lys Glu Ile Asn Leu Leu Pro Asp Arg Val Leu Ser Thr Pro Ser
65                  70                  75                  80

Val Gln Leu Val Gln Ser Trp Tyr Val Gln Ser Leu Leu Asp Ile Met
                85                  90                  95

Glu Phe Leu Asp Lys Asp Pro Glu Asp His Arg Thr Leu Ser Gln Phe
            100                 105                 110
```

```
Thr Asp Ala Leu Val Thr Ile Arg Asn Arg His Asn Asp Val Val Pro
            115                 120                 125

Thr Met Ala Gln Gly Val Leu Glu Tyr Lys Asp Thr Tyr Gly Asp Asp
        130                 135                 140

Pro Val Ser Asn Gln Asn Ile Gln Tyr Phe Leu Asp Arg Phe Tyr Leu
145                 150                 155                 160

Ser Arg Ile Ser Ile Arg Met Leu Ile Asn Gln His Thr Leu Ile Phe
                165                 170                 175

Asp Gly Ser Thr Asn Pro Ala His Pro Lys His Ile Gly Ser Ile Asp
            180                 185                 190

Pro Asn Cys Asn Val Ser Glu Val Val Lys Asp Ala Tyr Asp Met Ala
        195                 200                 205

Lys Leu Leu Cys Asp Lys Tyr Tyr Met Ala Ser Pro Asp Leu Glu Ile
210                 215                 220

Gln Glu Ile Asn Ala Ala Asn Ser Lys Gln Pro Ile His Met Val Tyr
225                 230                 235                 240

Val Pro Ser His Leu Tyr His Met Leu Phe Glu Leu Phe Lys Asn Ala
                245                 250                 255

Met Arg Ala Thr Val Glu Ser His Glu Ser Ser Leu Ile Leu Pro Pro
            260                 265                 270

Ile Lys Val Met Val Ala Leu Gly Glu Glu Asp Leu Ser Ile Lys Met
        275                 280                 285

Ser Asp Arg Gly Gly Gly Val Pro Leu Arg Lys Ile Glu Arg Leu Phe
290                 295                 300

Ser Tyr Met Tyr Ser Thr Ala Pro Thr Pro Gln Pro Gly Thr Gly Gly
305                 310                 315                 320

Thr Pro Leu Ala Gly Phe Gly Tyr Gly Leu Pro Ile Ser Arg Leu Tyr
                325                 330                 335

Ala Lys Tyr Phe Gln Gly Asp Leu Gln Leu Phe Ser Met Glu Gly Phe
            340                 345                 350

Gly Thr Asp Ala Val Ile Tyr Leu Lys Ala Leu Ser Thr Asp Ser Val
        355                 360                 365

Glu Arg Leu Pro Val Tyr Asn Lys Ser Ala Trp Arg His Tyr Gln Thr
    370                 375                 380

Ile Gln Glu Ala Gly Asp Trp Cys Val Pro Ser Thr Glu Pro Lys Asn
385                 390                 395                 400

Thr Ser Thr Tyr Arg Val Ser
                405

<210> SEQ ID NO 97
<211> LENGTH: 349
<212> TYPE: PRT
<213> ORGANISM: Homo sapiens

<400> SEQUENCE: 97

Met Glu Ala His Asn Ala Ser Ala Pro Phe Asn Phe Thr Leu Pro Pro
1               5                   10                  15

Asn Phe Gly Lys Arg Pro Thr Asp Leu Ala Leu Ser Val Ile Leu Val
            20                  25                  30

Phe Met Leu Phe Phe Ile Met Leu Ser Leu Gly Cys Thr Met Glu Phe
        35                  40                  45

Ser Lys Ile Lys Ala His Leu Trp Lys Pro Lys Gly Leu Ala Ile Ala
    50                  55                  60

Leu Val Ala Gln Tyr Gly Ile Met Pro Leu Thr Ala Phe Val Leu Gly
65                  70                  75                  80
```

Lys Val Phe Arg Leu Lys Asn Ile Glu Ala Leu Ala Ile Leu Val Cys
                85                  90                  95

Gly Cys Ser Pro Gly Asn Leu Ser Asn Val Phe Ser Leu Ala Met
            100                 105                 110

Lys Gly Asp Met Asn Leu Ser Ile Val Met Thr Thr Cys Ser Thr Phe
            115                 120                 125

Cys Ala Leu Gly Met Met Pro Leu Leu Leu Tyr Ile Tyr Ser Arg Gly
130                 135                 140

Ile Tyr Asp Gly Asp Leu Lys Asp Lys Val Pro Tyr Lys Gly Ile Val
145                 150                 155                 160

Ile Ser Leu Val Leu Val Leu Ile Pro Cys Thr Gly Ile Val Leu
                165                 170                 175

Lys Ser Lys Arg Pro Gln Tyr Met Arg Tyr Val Ile Lys Gly Gly Met
            180                 185                 190

Ile Ile Ile Leu Leu Cys Ser Val Ala Val Thr Val Leu Ser Ala Ile
                195                 200                 205

Asn Val Gly Lys Ser Ile Met Phe Ala Met Thr Pro Leu Leu Ile Ala
            210                 215                 220

Thr Ser Ser Leu Met Pro Phe Ile Gly Phe Leu Leu Gly Tyr Val Leu
225                 230                 235                 240

Ser Ala Leu Phe Cys Leu Asn Gly Arg Cys Arg Arg Thr Val Ser Met
                245                 250                 255

Glu Thr Gly Cys Gln Asn Val Gln Leu Cys Ser Thr Ile Leu Asn Val
            260                 265                 270

Ala Phe Pro Pro Glu Val Ile Gly Pro Leu Phe Phe Phe Pro Leu Leu
            275                 280                 285

Tyr Met Ile Phe Gln Leu Gly Glu Gly Leu Leu Leu Ile Ala Ile Phe
            290                 295                 300

Trp Cys Tyr Glu Lys Phe Lys Thr Pro Lys Asp Lys Thr Lys Met Ile
305                 310                 315                 320

Tyr Thr Ala Ala Thr Thr Glu Glu Thr Ile Pro Gly Ala Leu Gly Asn
                325                 330                 335

Gly Thr Tyr Lys Gly Glu Asp Cys Ser Pro Cys Thr Ala
            340                 345

<210> SEQ ID NO 98
<211> LENGTH: 429
<212> TYPE: PRT
<213> ORGANISM: Homo sapiens

<400> SEQUENCE: 98

Met Ala Ala Gln Gly Tyr Gly Tyr Tyr Arg Thr Val Ile Phe Ser Ala
1               5                   10                  15

Met Phe Gly Gly Tyr Ser Leu Tyr Tyr Phe Asn Arg Lys Thr Phe Ser
                20                  25                  30

Phe Val Met Pro Ser Leu Val Glu Glu Ile Pro Leu Asp Lys Asp Asp
            35                  40                  45

Leu Gly Phe Ile Thr Ser Ser Gln Ser Ala Ala Tyr Ala Ile Ser Lys
        50                  55                  60

Phe Val Ser Gly Val Leu Ser Asp Gln Met Ser Ala Arg Trp Leu Phe
65                  70                  75                  80

Ser Ser Gly Leu Leu Leu Val Gly Leu Val Asn Ile Phe Phe Ala Trp
                85                  90                  95

Ser Ser Thr Val Pro Val Phe Ala Ala Leu Trp Phe Leu Asn Gly Leu
            100                 105                 110

```
Ala Gln Gly Leu Gly Trp Pro Pro Cys Gly Lys Val Leu Arg Lys Trp
        115                 120                 125

Phe Glu Pro Ser Gln Phe Gly Thr Trp Trp Ala Ile Leu Ser Thr Ser
        130                 135                 140

Met Asn Leu Ala Gly Leu Gly Pro Ile Leu Ala Thr Ile Leu Ala
145                 150                 155                 160

Gln Ser Tyr Ser Trp Arg Ser Thr Leu Ala Leu Ser Gly Ala Leu Cys
        165                 170                 175

Val Val Val Ser Phe Leu Cys Leu Leu Leu Ile His Asn Glu Pro Ala
        180                 185                 190

Asp Val Gly Leu Arg Asn Leu Asp Pro Met Pro Ser Glu Gly Lys Lys
        195                 200                 205

Gly Ser Leu Lys Glu Glu Ser Thr Leu Gln Glu Leu Leu Leu Ser Pro
        210                 215                 220

Tyr Leu Trp Val Leu Ser Thr Gly Tyr Leu Val Val Phe Gly Val Lys
225                 230                 235                 240

Thr Cys Cys Thr Asp Trp Gly Gln Phe Phe Leu Ile Gln Glu Lys Gly
        245                 250                 255

Gln Ser Ala Leu Val Gly Ser Ser Tyr Met Ser Ala Leu Glu Val Gly
        260                 265                 270

Gly Leu Val Gly Ser Ile Ala Ala Gly Tyr Leu Ser Asp Arg Ala Met
        275                 280                 285

Ala Lys Ala Gly Leu Ser Asn Tyr Gly Asn Pro Arg His Gly Leu Leu
        290                 295                 300

Leu Phe Met Met Ala Gly Met Thr Val Ser Met Tyr Leu Phe Arg Val
305                 310                 315                 320

Thr Val Thr Ser Asp Ser Pro Lys Leu Trp Ile Leu Val Leu Gly Ala
        325                 330                 335

Val Phe Gly Phe Ser Ser Tyr Gly Pro Ile Ala Leu Phe Gly Val Ile
        340                 345                 350

Ala Asn Glu Ser Ala Pro Pro Asn Leu Cys Gly Thr Ser His Ala Ile
        355                 360                 365

Val Gly Leu Met Ala Asn Val Gly Gly Phe Leu Ala Gly Leu Pro Phe
        370                 375                 380

Ser Thr Ile Ala Lys His Tyr Ser Trp Ser Thr Ala Phe Trp Val Ala
385                 390                 395                 400

Glu Val Ile Cys Ala Ala Ser Thr Ala Ala Phe Phe Leu Leu Arg Asn
                405                 410                 415

Ile Arg Thr Lys Met Gly Arg Val Ser Lys Lys Ala Glu
        420                 425

<210> SEQ ID NO 99
<211> LENGTH: 296
<212> TYPE: PRT
<213> ORGANISM: Homo sapiens

<400> SEQUENCE: 99

Met Ala Leu Thr Ser Asp Leu Gly Lys Gln Ile Lys Leu Lys Glu Val
1               5                   10                  15

Glu Gly Thr Leu Leu Gln Pro Ala Thr Val Asp Asn Trp Ser Gln Ile
        20                  25                  30

Gln Ser Phe Glu Ala Lys Pro Asp Asp Leu Leu Ile Cys Thr Tyr Pro
        35                  40                  45

Lys Ala Gly Thr Thr Trp Ile Gln Glu Ile Val Asp Met Ile Glu Gln
        50                  55                  60
```

```
Asn Gly Asp Val Glu Lys Cys Gln Arg Ala Ile Ile Gln His Arg His
 65                  70                  75                  80

Pro Phe Ile Glu Trp Ala Arg Pro Gln Pro Ser Gly Val Glu Lys
             85                  90                  95

Ala Lys Ala Met Pro Ser Pro Arg Ile Leu Lys Thr His Leu Ser Thr
            100                 105                 110

Gln Leu Leu Pro Pro Ser Phe Trp Glu Asn Asn Cys Lys Phe Leu Tyr
            115                 120                 125

Val Ala Arg Asn Ala Lys Asp Cys Met Val Ser Tyr Tyr His Phe Gln
            130                 135                 140

Arg Met Asn His Met Leu Pro Asp Pro Gly Thr Trp Glu Glu Tyr Phe
145                 150                 155                 160

Glu Thr Phe Ile Asn Gly Lys Val Val Trp Gly Ser Trp Phe Asp His
                165                 170                 175

Val Lys Gly Trp Trp Glu Met Lys Asp Arg His Gln Ile Leu Phe Leu
            180                 185                 190

Phe Tyr Glu Asp Ile Lys Arg Asp Pro Lys His Glu Ile Arg Lys Val
        195                 200                 205

Met Gln Phe Met Gly Lys Lys Val Asp Glu Thr Val Leu Asp Lys Ile
    210                 215                 220

Val Gln Glu Thr Ser Phe Glu Lys Met Lys Glu Asn Pro Met Thr Asn
225                 230                 235                 240

Arg Ser Thr Val Ser Lys Ser Ile Leu Asp Gln Ser Ile Ser Ser Phe
                245                 250                 255

Met Arg Lys Gly Thr Val Gly Asp Trp Lys Asn His Phe Thr Val Ala
            260                 265                 270

Gln Asn Glu Arg Phe Asp Glu Ile Tyr Arg Arg Lys Met Glu Gly Thr
        275                 280                 285

Ser Ile Asn Phe Cys Met Glu Leu
    290                 295

<210> SEQ ID NO 100
<211> LENGTH: 161
<212> TYPE: PRT
<213> ORGANISM: Homo sapiens

<400> SEQUENCE: 100

Met Asp Gln Glu Thr Val Gly Asn Val Val Leu Leu Ala Ile Val Thr
  1               5                  10                  15

Leu Ile Ser Val Val Gln Asn Gly Phe Phe Ala His Lys Val Glu His
                 20                  25                  30

Glu Ser Arg Thr Gln Asn Gly Arg Ser Phe Gln Arg Thr Gly Thr Leu
             35                  40                  45

Ala Phe Glu Arg Val Tyr Thr Ala Asn Gln Asn Cys Val Asp Ala Tyr
         50                  55                  60

Pro Thr Phe Leu Ala Val Leu Trp Ser Ala Gly Leu Leu Cys Ser Gln
 65                  70                  75                  80

Val Pro Ala Ala Phe Ala Gly Leu Met Tyr Leu Phe Val Arg Gln Lys
             85                  90                  95

Tyr Phe Val Gly Tyr Leu Gly Glu Arg Thr Gln Ser Thr Pro Gly Tyr
            100                 105                 110

Ile Phe Gly Lys Arg Ile Ile Leu Phe Leu Phe Leu Met Ser Val Ala
            115                 120                 125

Gly Ile Phe Asn Tyr Tyr Leu Ile Phe Phe Gly Ser Asp Phe Glu
            130                 135                 140
```

Asn Tyr Ile Lys Thr Ile Ser Thr Thr Ile Ser Pro Leu Leu Leu Ile
145                 150                 155                 160

Pro

<210> SEQ ID NO 101
<211> LENGTH: 180
<212> TYPE: PRT
<213> ORGANISM: Homo sapiens

<400> SEQUENCE: 101

Met Ala Asp Ser Glu Leu Gln Leu Val Glu Gln Arg Ile Arg Ser Phe
1               5                   10                  15

Pro Asp Phe Pro Thr Pro Gly Val Val Phe Arg Asp Ile Ser Pro Val
                20                  25                  30

Leu Lys Asp Pro Ala Ser Phe Arg Ala Ala Ile Gly Leu Leu Ala Arg
            35                  40                  45

His Leu Lys Ala Thr His Gly Gly Arg Ile Asp Tyr Ile Ala Gly Leu
        50                  55                  60

Asp Ser Arg Gly Phe Leu Phe Gly Pro Ser Leu Ala Gln Glu Leu Gly
65                  70                  75                  80

Leu Gly Cys Val Leu Ile Arg Lys Arg Gly Lys Leu Pro Gly Pro Thr
                85                  90                  95

Leu Trp Ala Ser Tyr Ser Leu Glu Tyr Gly Lys Ala Glu Leu Glu Ile
            100                 105                 110

Gln Lys Asp Ala Leu Glu Pro Gly Gln Arg Val Val Val Asp Asp
        115                 120                 125

Leu Leu Ala Thr Gly Gly Thr Met Asn Ala Ala Cys Glu Leu Leu Gly
130                 135                 140

Arg Leu Gln Ala Glu Val Leu Glu Cys Val Ser Leu Val Glu Leu Thr
145                 150                 155                 160

Ser Leu Lys Gly Arg Glu Lys Leu Ala Pro Val Pro Phe Phe Ser Leu
                165                 170                 175

Leu Gln Tyr Glu
        180

<210> SEQ ID NO 102
<211> LENGTH: 227
<212> TYPE: PRT
<213> ORGANISM: Homo sapiens

<400> SEQUENCE: 102

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
                20                  25                  30

Glu Glu Gly Thr Pro Lys Glu Ser Glu Pro Gln Ala Ala Ala Glu Pro
            35                  40                  45

Ala Glu Ala Lys Glu Gly Lys Glu Lys Pro Asp Gln Asp Ala Glu Gly
        50                  55                  60

Lys Ala Glu Glu Lys Glu Gly Glu Lys Asp Ala Ala Ala Lys Glu
65                  70                  75                  80

Glu Ala Pro Lys Ala Gly Pro Gly Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala Ala

-continued

```
            115                 120                 125
Pro Ala Glu Ser Ala Ala Pro Ala Ala Gly Glu Glu Pro Ser Lys Glu
        130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
    210                 215                 220

Val Lys Glu
225

<210> SEQ ID NO 103
<211> LENGTH: 169
<212> TYPE: PRT
<213> ORGANISM: Homo sapiens

<400> SEQUENCE: 103

Met Ala Pro Pro Trp Val Pro Ala Met Gly Phe Thr Leu Ala Pro Ser
1               5                   10                  15

Leu Gly Cys Phe Val Gly Ser Arg Phe Val His Gly Glu Gly Leu Arg
            20                  25                  30

Trp Tyr Ala Gly Leu Gln Lys Pro Ser Trp His Pro Pro His Trp Val
        35                  40                  45

Leu Gly Pro Val Trp Gly Thr Leu Tyr Ser Ala Met Gly Tyr Gly Ser
    50                  55                  60

Tyr Leu Val Trp Lys Glu Leu Gly Gly Phe Thr Glu Lys Ala Val Val
65                  70                  75                  80

Pro Leu Gly Leu Tyr Thr Gly Gln Leu Ala Leu Asn Trp Ala Trp Pro
                85                  90                  95

Pro Ile Phe Phe Gly Ala Arg Gln Met Gly Trp Ala Leu Val Asp Leu
            100                 105                 110

Leu Leu Val Ser Gly Ala Ala Ala Thr Thr Val Ala Trp Tyr Gln
        115                 120                 125

Val Ser Pro Leu Ala Ala Arg Leu Leu Tyr Pro Tyr Leu Ala Trp Leu
    130                 135                 140

Ala Phe Thr Thr Thr Leu Asn Tyr Cys Val Trp Arg Asp Asn His Gly
145                 150                 155                 160

Trp Arg Gly Gly Arg Leu Pro Glu
                165

<210> SEQ ID NO 104
<211> LENGTH: 277
<212> TYPE: PRT
<213> ORGANISM: Homo sapiens

<400> SEQUENCE: 104

Met Ser Ser Gly Ile His Val Ala Leu Val Thr Gly Gly Asn Lys Gly
1               5                   10                  15

Ile Gly Leu Ala Ile Val Arg Asp Leu Cys Arg Leu Phe Ser Gly Asp
            20                  25                  30

Val Val Leu Thr Ala Arg Asp Val Thr Arg Gly Gln Ala Ala Val Gln
        35                  40                  45
```

```
Gln Leu Gln Ala Glu Gly Leu Ser Pro Arg Phe His Gln Leu Asp Ile
 50                  55                  60

Asp Asp Leu Gln Ser Ile Arg Ala Leu Arg Asp Phe Leu Arg Lys Glu
 65                  70                  75                  80

Tyr Gly Gly Leu Asp Val Leu Val Asn Asn Ala Gly Ile Ala Phe Lys
                 85                  90                  95

Val Ala Asp Pro Thr Pro Phe His Ile Gln Ala Glu Val Thr Met Lys
            100                 105                 110

Thr Asn Phe Phe Gly Thr Arg Asp Val Cys Thr Glu Leu Leu Pro Leu
        115                 120                 125

Ile Lys Pro Gln Gly Arg Val Val Asn Val Ser Ser Ile Met Ser Val
    130                 135                 140

Arg Ala Leu Lys Ser Cys Ser Pro Glu Leu Gln Gln Lys Phe Arg Ser
145                 150                 155                 160

Glu Thr Ile Thr Glu Glu Leu Val Gly Leu Met Asn Lys Phe Val
                165                 170                 175

Glu Asp Thr Lys Lys Gly Val His Gln Lys Glu Gly Trp Pro Ser Ser
                180                 185                 190

Ala Tyr Gly Val Thr Lys Ile Gly Val Thr Val Leu Ser Arg Ile His
                195                 200                 205

Ala Arg Lys Leu Ser Glu Gln Arg Lys Gly Asp Lys Ile Leu Leu Asn
    210                 215                 220

Ala Cys Cys Pro Gly Trp Val Arg Thr Asp Met Ala Gly Pro Lys Ala
225                 230                 235                 240

Thr Lys Ser Pro Glu Glu Gly Ala Glu Thr Pro Val Tyr Leu Ala Leu
                245                 250                 255

Leu Pro Pro Asp Ala Glu Gly Pro His Gly Gln Phe Val Ser Glu Lys
            260                 265                 270

Arg Val Glu Gln Trp
        275

<210> SEQ ID NO 105
<211> LENGTH: 312
<212> TYPE: PRT
<213> ORGANISM: Homo sapiens

<400> SEQUENCE: 105

Met Trp Pro Leu Val Ala Ala Leu Leu Leu Gly Ser Ala Cys Cys Gly
 1                   5                  10                  15

Ser Ala Gln Leu Leu Phe Asn Lys Thr Lys Ser Val Glu Phe Thr Phe
                 20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
 50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140
```

```
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Met Asp Glu Lys Thr
            165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys
            290                 295                 300

Ala Val Glu Glu Pro Leu Asn Glu
305                 310

<210> SEQ ID NO 106
<211> LENGTH: 327
<212> TYPE: PRT
<213> ORGANISM: Homo sapiens

<400> SEQUENCE: 106

Met Arg Ala Leu Pro Gly Leu Leu Glu Ala Arg Ala Arg Thr Pro Arg
1               5                   10                  15

Leu Leu Leu Leu Gln Cys Leu Leu Ala Ala Ala Arg Pro Ser Ser Ala
                20                  25                  30

Asp Gly Ser Ala Pro Asp Ser Pro Phe Thr Ser Pro Pro Leu Arg Glu
            35                  40                  45

Glu Ile Met Ala Asn Asn Phe Ser Leu Glu Ser His Asn Ile Ser Leu
        50                  55                  60

Thr Glu His Ser Ser Met Pro Val Glu Lys Asn Ile Thr Leu Glu Arg
65                  70                  75                  80

Pro Ser Asn Val Asn Leu Thr Cys Gln Phe Thr Thr Ser Gly Asp Leu
                85                  90                  95

Asn Ala Val Asn Val Thr Trp Lys Lys Asp Gly Glu Gln Leu Glu Asn
            100                 105                 110

Asn Tyr Leu Val Ser Ala Thr Gly Ser Thr Leu Tyr Thr Gln Tyr Arg
        115                 120                 125

Phe Thr Ile Ile Asn Ser Lys Gln Met Gly Ser Tyr Ser Cys Phe Phe
    130                 135                 140

Arg Glu Glu Lys Glu Gln Arg Gly Thr Phe Asn Phe Lys Val Pro Glu
145                 150                 155                 160

Leu His Gly Lys Asn Lys Pro Leu Ile Ser Tyr Val Gly Asp Ser Thr
                165                 170                 175

Val Leu Thr Cys Lys Cys Gln Asn Cys Phe Pro Leu Asn Trp Thr Trp
            180                 185                 190

Tyr Ser Ser Asn Gly Ser Val Lys Val Pro Val Gly Val Gln Met Asn
        195                 200                 205
```

```
Lys Tyr Val Ile Asn Gly Thr Tyr Ala Asn Glu Thr Lys Leu Lys Ile
    210                 215                 220

Thr Gln Leu Leu Glu Glu Asp Gly Glu Ser Tyr Trp Cys Arg Ala Leu
225                 230                 235                 240

Phe Gln Leu Gly Glu Ser Glu His Ile Glu Leu Val Val Leu Ser
                    245                 250                 255

Tyr Leu Val Pro Leu Lys Pro Phe Leu Val Ile Val Ala Glu Val Ile
                260                 265                 270

Leu Leu Val Ala Thr Ile Leu Leu Cys Glu Lys Tyr Thr Gln Lys Lys
                275                 280                 285

Lys Lys His Ser Asp Glu Gly Lys Glu Phe Glu Gln Ile Glu Gln Leu
            290                 295                 300

Lys Ser Asp Asp Ser Asn Gly Ile Glu Asn Asn Val Pro Arg His Arg
305                 310                 315                 320

Lys Asn Glu Ser Leu Gly Gln
                325

<210> SEQ ID NO 107
<211> LENGTH: 674
<212> TYPE: PRT
<213> ORGANISM: Homo sapiens

<400> SEQUENCE: 107

Met Ala Pro Gly Gln Ala Pro His Gln Ala Thr Pro Trp Arg Asp Ala
1               5                   10                  15

His Pro Phe Phe Leu Leu Ser Pro Val Met Gly Leu Leu Ser Arg Ala
                20                  25                  30

Trp Ser Arg Leu Arg Gly Leu Gly Pro Leu Glu Pro Trp Leu Val Glu
            35                  40                  45

Ala Val Lys Gly Ala Ala Leu Val Glu Ala Gly Leu Glu Gly Glu Ala
        50                  55                  60

Arg Thr Pro Leu Ala Ile Pro His Thr Pro Trp Gly Arg Arg Pro Gly
65                  70                  75                  80

Glu Glu Ala Glu Asp Ser Gly Gly Pro Gly Glu Asp Arg Glu Thr Leu
                85                  90                  95

Gly Leu Lys Thr Ser Ser Leu Pro Glu Ala Trp Gly Leu Leu Asp
                100                 105                 110

Asp Asp Asp Gly Met Tyr Gly Glu Arg Glu Ala Thr Ser Val Pro Arg
            115                 120                 125

Gly Gln Gly Ser Gln Phe Ala Asp Gly Gln Arg Ala Pro Leu Ser Pro
        130                 135                 140

Ser Leu Leu Ile Arg Thr Leu Gln Gly Ser Asp Lys Asn Pro Gly Glu
145                 150                 155                 160

Glu Lys Ala Glu Glu Glu Gly Val Ala Glu Glu Gly Val Asn Lys
                165                 170                 175

Phe Ser Tyr Pro Pro Ser His Arg Glu Cys Cys Pro Ala Val Glu Glu
            180                 185                 190

Glu Asp Asp Glu Glu Ala Val Lys Lys Glu Ala His Arg Thr Ser Thr
        195                 200                 205

Ser Ala Leu Ser Pro Gly Ser Lys Pro Ser Thr Trp Val Ser Cys Pro
210                 215                 220

Gly Glu Glu Glu Asn Gln Ala Thr Glu Asp Lys Arg Thr Glu Arg Ser
225                 230                 235                 240

Lys Gly Ala Arg Lys Thr Ser Val Ser Pro Arg Ser Ser Gly Ser Asp
                245                 250                 255
```

```
Pro Arg Ser Trp Glu Tyr Arg Ser Gly Glu Ala Ser Glu Lys Glu
        260                 265                 270

Glu Lys Ala His Glu Glu Thr Gly Lys Gly Glu Ala Ala Pro Gly Pro
        275                 280                 285

Gln Ser Ser Ala Pro Ala Gln Arg Pro Gln Leu Lys Ser Trp Trp Cys
        290                 295                 300

Gln Pro Ser Asp Glu Glu Ser Glu Val Lys Pro Leu Gly Ala Ala
305                 310                 315                 320

Glu Lys Asp Gly Glu Ala Glu Cys Pro Pro Cys Ile Pro Pro Ser
            325                 330                 335

Ala Phe Leu Lys Ala Trp Val Tyr Trp Pro Gly Glu Asp Thr Glu Glu
        340                 345                 350

Glu Glu Asp Glu Glu Glu Asp Glu Asp Ser Asp Ser Gly Ser Asp Glu
        355                 360                 365

Glu Glu Gly Glu Ala Glu Ala Ser Ser Ser Thr Pro Ala Thr Gly Val
        370                 375                 380

Phe Leu Lys Ser Trp Val Tyr Gln Pro Gly Glu Asp Thr Glu Glu Glu
385                 390                 395                 400

Glu Asp Glu Asp Ser Asp Thr Gly Ser Ala Glu Asp Glu Arg Glu Ala
                405                 410                 415

Glu Thr Ser Ala Ser Thr Pro Pro Ala Ser Ala Phe Leu Lys Ala Trp
        420                 425                 430

Val Tyr Arg Pro Gly Glu Asp Thr Glu Glu Glu Glu Asp Glu Asp Val
        435                 440                 445

Asp Ser Glu Asp Lys Glu Asp Asp Ser Glu Ala Ala Leu Gly Glu Ala
        450                 455                 460

Glu Ser Asp Pro His Pro Ser His Pro Asp Gln Ser Ala His Phe Arg
465                 470                 475                 480

Gly Trp Gly Tyr Arg Pro Gly Lys Glu Thr Glu Glu Glu Glu Ala Ala
                485                 490                 495

Glu Asp Trp Gly Glu Ala Glu Pro Cys Pro Phe Arg Val Ala Ile Tyr
            500                 505                 510

Val Pro Gly Glu Lys Pro Pro Pro Trp Ala Pro Pro Arg Leu Pro
        515                 520                 525

Leu Arg Leu Gln Arg Arg Leu Lys Arg Pro Glu Thr Pro Thr His Asp
        530                 535                 540

Pro Asp Pro Glu Thr Pro Leu Lys Ala Arg Lys Val Arg Phe Ser Glu
545                 550                 555                 560

Lys Val Thr Val His Phe Leu Ala Val Trp Ala Gly Pro Ala Gln Ala
                565                 570                 575

Ala Arg Gln Gly Pro Trp Glu Gln Leu Ala Arg Asp Ser Arg Phe
        580                 585                 590

Ala Arg Arg Ile Ala Gln Ala Gln Glu Glu Leu Ser Pro Cys Leu Thr
        595                 600                 605

Pro Ala Ala Arg Ala Arg Ala Trp Ala Arg Leu Arg Asn Pro Leu
610                 615                 620

Ala Pro Ile Pro Ala Leu Thr Gln Thr Leu Pro Ser Ser Val Pro
625                 630                 635                 640

Ser Ser Pro Val Gln Thr Thr Pro Leu Ser Gln Ala Val Ala Thr Pro
                645                 650                 655

Ser Arg Ser Ser Ala Ala Ala Ala Ala Leu Asp Leu Ser Gly Arg
        660                 665                 670

Arg Gly
```

<210> SEQ ID NO 108
<211> LENGTH: 357
<212> TYPE: PRT
<213> ORGANISM: Homo sapiens

<400> SEQUENCE: 108

Met Ala Glu Leu Gln Glu Val Gln Ile Thr Glu Glu Lys Pro Leu Leu
1               5                   10                  15

Pro Gly Gln Thr Pro Glu Ala Ala Lys Thr His Ser Val Glu Thr Pro
            20                  25                  30

Tyr Gly Ser Val Thr Phe Thr Val Tyr Gly Thr Pro Lys Pro Lys Arg
        35                  40                  45

Pro Ala Ile Leu Thr Tyr His Asp Val Gly Leu Asn Tyr Lys Ser Cys
    50                  55                  60

Phe Gln Pro Leu Phe Gln Phe Glu Asp Met Gln Glu Ile Ile Gln Asn
65                  70                  75                  80

Phe Val Arg Val His Val Asp Ala Pro Gly Met Glu Glu Gly Ala Pro
                85                  90                  95

Val Phe Pro Leu Gly Tyr Gln Tyr Pro Ser Leu Asp Gln Leu Ala Asp
            100                 105                 110

Met Ile Pro Cys Val Leu Gln Tyr Leu Asn Phe Ser Thr Ile Ile Gly
        115                 120                 125

Val Gly Val Gly Ala Gly Ala Tyr Ile Leu Ala Arg Tyr Ala Leu Asn
    130                 135                 140

His Pro Asp Thr Val Glu Gly Leu Val Leu Ile Asn Ile Asp Pro Asn
145                 150                 155                 160

Ala Lys Gly Trp Met Asp Trp Ala Ala His Lys Leu Thr Gly Leu Thr
                165                 170                 175

Ser Ser Ile Pro Glu Met Ile Leu Gly His Leu Phe Ser Gln Glu Glu
            180                 185                 190

Leu Ser Gly Asn Ser Glu Leu Ile Gln Lys Tyr Arg Asn Ile Ile Thr
        195                 200                 205

His Ala Pro Asn Leu Asp Asn Ile Glu Leu Tyr Trp Asn Ser Tyr Asn
    210                 215                 220

Asn Arg Arg Asp Leu Asn Phe Glu Arg Gly Gly Asp Ile Thr Leu Arg
225                 230                 235                 240

Cys Pro Val Met Leu Val Val Gly Asp Gln Ala Pro His Glu Asp Ala
                245                 250                 255

Val Val Glu Cys Asn Ser Lys Leu Asp Pro Thr Gln Thr Ser Phe Leu
            260                 265                 270

Lys Met Ala Asp Ser Gly Gly Gln Pro Gln Leu Thr Gln Pro Gly Lys
        275                 280                 285

Leu Thr Glu Ala Phe Lys Tyr Phe Leu Gln Gly Met Gly Tyr Met Ala
    290                 295                 300

Ser Ser Cys Met Thr Arg Leu Ser Arg Ser Arg Thr Ala Ser Leu Thr
305                 310                 315                 320

Ser Ala Ala Ser Val Asp Gly Asn Arg Ser Arg Ser Arg Thr Leu Ser
                325                 330                 335

Gln Ser Ser Glu Ser Gly Thr Leu Ser Ser Gly Pro Pro Gly His Thr
            340                 345                 350

Met Glu Val Ser Cys
        355

<210> SEQ ID NO 109

```
<211> LENGTH: 152
<212> TYPE: PRT
<213> ORGANISM: Homo sapiens

<400> SEQUENCE: 109

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150

<210> SEQ ID NO 110
<211> LENGTH: 211
<212> TYPE: PRT
<213> ORGANISM: Homo sapiens

<400> SEQUENCE: 110

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Gln Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Gly Thr
                165                 170                 175

Ser His Leu Val Lys Cys Ala Glu Lys Glu Lys Thr Phe Cys Val Asn
            180                 185                 190
```

```
Gly Gly Glu Cys Phe Met Val Lys Asp Leu Ser Asn Pro Ser Arg Tyr
            195                 200                 205

Leu Cys Lys
    210

<210> SEQ ID NO 111
<211> LENGTH: 273
<212> TYPE: PRT
<213> ORGANISM: Homo sapiens

<400> SEQUENCE: 111

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
                20                  25                  30

Pro Trp Trp Cys Leu Ala Ala Thr Leu Gly Val Leu Cys Leu Gly
            35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
        195                 200                 205

Arg Asn Pro Ser Tyr Pro Trp Leu Trp Glu Asp Gly Ser Pro Leu Met
    210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln

<210> SEQ ID NO 112
<211> LENGTH: 349
<212> TYPE: PRT
<213> ORGANISM: Homo sapiens

<400> SEQUENCE: 112

Met Ala His Gln Thr Gly Ile His Ala Thr Glu Glu Leu Lys Glu Phe
1               5                   10                  15

Phe Ala Lys Ala Arg Ala Gly Ser Val Arg Leu Ile Lys Val Val Ile
                20                  25                  30
```

```
Glu Asp Glu Gln Leu Val Leu Gly Ala Ser Gln Glu Pro Val Gly Arg
            35                  40                  45

Trp Asp Gln Asp Tyr Asp Arg Ala Val Leu Pro Leu Leu Asp Ala Gln
 50                  55                  60

Gln Pro Cys Tyr Leu Leu Tyr Arg Leu Asp Ser Gln Asn Ala Gln Gly
 65                  70                  75                  80

Phe Glu Trp Leu Phe Leu Ala Trp Ser Pro Asp Asn Ser Pro Val Arg
                85                  90                  95

Leu Lys Met Leu Tyr Ala Ala Thr Arg Ala Thr Val Lys Lys Glu Phe
            100                 105                 110

Gly Gly Gly His Ile Lys Asp Glu Leu Phe Gly Thr Val Lys Asp Asp
            115                 120                 125

Leu Ser Phe Ala Gly Tyr Gln Lys His Leu Ser Ser Cys Ala Ala Pro
        130                 135                 140

Ala Pro Leu Thr Ser Ala Glu Arg Glu Leu Gln Gln Ile Arg Ile Asn
145                 150                 155                 160

Glu Val Lys Thr Glu Ile Ser Val Glu Ser Lys His Gln Thr Leu Gln
                165                 170                 175

Gly Leu Ala Phe Pro Leu Gln Pro Glu Ala Gln Arg Ala Leu Gln Gln
            180                 185                 190

Leu Lys Gln Lys Met Val Asn Tyr Ile Gln Met Lys Leu Asp Leu Glu
        195                 200                 205

Arg Glu Thr Ile Glu Leu Val His Thr Glu Pro Thr Asp Val Ala Gln
210                 215                 220

Leu Pro Ser Arg Val Pro Arg Asp Ala Ala Arg Tyr His Phe Phe Leu
225                 230                 235                 240

Tyr Lys His Thr His Glu Gly Asp Pro Leu Gly Ser Val Val Phe Ile
                245                 250                 255

Tyr Ser Met Pro Gly Tyr Lys Cys Ser Ile Lys Glu Arg Met Leu Tyr
            260                 265                 270

Ser Ser Cys Lys Ser Arg Leu Leu Asp Ser Val Glu Gln Asp Phe His
        275                 280                 285

Leu Glu Ile Ala Lys Lys Ile Glu Ile Gly Asp Gly Ala Glu Leu Thr
290                 295                 300

Ala Glu Phe Leu Tyr Asp Glu Val His Pro Lys Gln His Ala Phe Lys
305                 310                 315                 320

Gln Ala Phe Ala Lys Pro Lys Gly Pro Gly Lys Arg Gly His Lys
                325                 330                 335

Arg Leu Ile Arg Gly Pro Gly Glu Asn Gly Asp Asp Ser
            340                 345

<210> SEQ ID NO 113
<211> LENGTH: 298
<212> TYPE: PRT
<213> ORGANISM: Homo sapiens

<400> SEQUENCE: 113

Met Ser Leu Tyr Pro Ser Leu Glu Asp Leu Lys Val Asp Lys Val Ile
 1               5                  10                  15

Gln Ala Gln Thr Ala Phe Ser Ala Asn Pro Ala Asn Pro Ala Ile Leu
                20                  25                  30

Ser Glu Ala Ser Ala Pro Ile Pro His Asp Gly Asn Leu Tyr Pro Arg
            35                  40                  45

Leu Tyr Pro Glu Leu Ser Gln Tyr Met Gly Leu Ser Leu Asn Glu Glu
        50                  55                  60
```

Glu Ile Arg Ala Asn Val Ala Val Ser Gly Ala Pro Leu Gln Gly
65                  70                  75                  80

Gln Leu Val Ala Arg Pro Ser Ser Ile Asn Tyr Met Val Ala Pro Val
                85                  90                  95

Thr Gly Asn Asp Val Gly Ile Arg Ala Glu Ile Lys Gln Gly Ile
            100                 105                 110

Arg Glu Val Ile Leu Cys Lys Asp Gln Asp Gly Lys Ile Gly Leu Arg
        115                 120                 125

Leu Lys Ser Ile Asp Asn Gly Ile Phe Val Gln Leu Val Gln Ala Asn
    130                 135                 140

Ser Pro Ala Ser Leu Val Gly Leu Arg Phe Gly Asp Gln Val Leu Gln
145                 150                 155                 160

Ile Asn Gly Glu Asn Cys Ala Gly Trp Ser Ser Asp Lys Ala His Lys
                165                 170                 175

Val Leu Lys Gln Ala Phe Gly Glu Lys Ile Thr Met Thr Ile Arg Asp
            180                 185                 190

Arg Pro Phe Glu Arg Thr Ile Thr Met His Lys Asp Ser Thr Gly His
        195                 200                 205

Val Gly Phe Ile Phe Lys Asn Gly Lys Ile Thr Ser Ile Val Lys Asp
    210                 215                 220

Ser Ser Ala Ala Arg Asn Gly Leu Leu Thr Glu His Asn Ile Cys Glu
225                 230                 235                 240

Ile Asn Gly Gln Asn Val Ile Gly Leu Lys Asp Ser Gln Ile Ala Asp
                245                 250                 255

Ile Leu Ser Thr Ser Gly Thr Val Val Thr Ile Thr Ile Met Pro Ala
            260                 265                 270

Phe Ile Phe Glu His Ile Ile Lys Arg Met Ala Pro Ser Ile Met Lys
        275                 280                 285

Ser Leu Met Asp His Thr Ile Pro Glu Val
    290                 295

<210> SEQ ID NO 114
<211> LENGTH: 79
<212> TYPE: PRT
<213> ORGANISM: Homo sapiens

<400> SEQUENCE: 114

Met Lys Val Thr Gly Ile Phe Leu Leu Ser Ala Leu Ala Leu Leu Ser
1               5                   10                  15

Leu Ser Gly Asn Thr Gly Ala Asp Ser Leu Gly Arg Glu Ala Lys Cys
            20                  25                  30

Tyr Asn Glu Leu Asn Gly Cys Thr Lys Ile Tyr Asp Pro Val Cys Gly
        35                  40                  45

Thr Asp Gly Asn Thr Tyr Pro Asn Glu Cys Val Leu Cys Phe Glu Asn
    50                  55                  60

Arg Lys Arg Gln Thr Ser Ile Leu Ile Gln Lys Ser Gly Pro Cys
65                  70                  75

<210> SEQ ID NO 115
<211> LENGTH: 246
<212> TYPE: PRT
<213> ORGANISM: Homo sapiens

<400> SEQUENCE: 115

Met Gly Asp Arg Glu Gln Leu Leu Gln Arg Ala Arg Leu Ala Glu Gln
1               5                   10                  15

```
Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
 50                  55                  60

Ser Ile Glu Gln Lys Thr Met Ala Asp Gly Asn Glu Lys Lys Leu Glu
 65                  70                  75                  80

Lys Val Lys Ala Tyr Arg Glu Lys Ile Glu Lys Leu Glu Thr Val
                85                  90                  95

Cys Asn Asp Val Leu Ser Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

<210> SEQ ID NO 116
<211> LENGTH: 97
<212> TYPE: PRT
<213> ORGANISM: Homo sapiens

<400> SEQUENCE: 116

Met Pro Ser Gln Met Glu His Ala Met Glu Thr Met Met Phe Thr Phe
 1               5                  10                  15

His Lys Phe Ala Gly Asp Lys Gly Tyr Leu Thr Lys Glu Asp Leu Arg
            20                  25                  30

Val Leu Met Glu Lys Glu Phe Pro Gly Phe Leu Glu Asn Gln Lys Asp
        35                  40                  45

Pro Leu Ala Val Asp Lys Ile Met Lys Asp Leu Asp Gln Cys Arg Asp
 50                  55                  60

Gly Lys Val Gly Phe Gln Ser Phe Phe Ser Leu Ile Ala Gly Leu Thr
 65                  70                  75                  80

Ile Ala Cys Asn Asp Tyr Phe Val Val His Met Lys Gln Lys Gly Lys
                85                  90                  95

Lys

<210> SEQ ID NO 117
<211> LENGTH: 158
<212> TYPE: PRT
<213> ORGANISM: Homo sapiens

<400> SEQUENCE: 117
```

```
Met Ser His Gly Lys Gly Thr Asp Met Leu Pro Glu Ile Ala Ala Ala
1               5                   10                  15

Val Gly Phe Leu Ser Ser Leu Leu Arg Thr Arg Gly Cys Val Ser Glu
            20                  25                  30

Gln Arg Leu Lys Val Phe Ser Gly Ala Leu Gln Glu Ala Leu Thr Glu
        35                  40                  45

His Tyr Lys His His Trp Phe Pro Glu Lys Pro Ser Lys Gly Ser Gly
    50                  55                  60

Tyr Arg Cys Ile Arg Ile Asn His Lys Met Asp Pro Ile Ile Ser Arg
65                  70                  75                  80

Val Ala Ser Gln Ile Gly Leu Ser Gln Pro Gln Leu His Gln Leu Leu
                85                  90                  95

Pro Ser Glu Leu Thr Leu Trp Val Asp Pro Tyr Glu Val Ser Tyr Arg
            100                 105                 110

Ile Gly Glu Asp Gly Ser Ile Cys Val Leu Tyr Glu Glu Ala Pro Leu
        115                 120                 125

Ala Ala Ser Cys Gly Leu Leu Thr Cys Lys Asn Gln Val Leu Leu Gly
    130                 135                 140

Arg Ser Ser Pro Ser Lys Asn Tyr Val Met Ala Val Ser Ser
145                 150                 155
```

<210> SEQ ID NO 118
<211> LENGTH: 624
<212> TYPE: PRT
<213> ORGANISM: Homo sapiens

<400> SEQUENCE: 118

```
Met Glu Ile Pro Gly Ser Leu Cys Lys Lys Val Lys Leu Ser Asn Asn
1               5                   10                  15

Ala Gln Asn Trp Gly Met Gln Arg Ala Thr Asn Val Thr Tyr Gln Ala
            20                  25                  30

His His Val Ser Arg Asn Lys Arg Gly Gln Val Val Gly Thr Arg Gly
        35                  40                  45

Gly Phe Arg Gly Cys Thr Val Trp Leu Thr Gly Leu Ser Gly Ala Gly
    50                  55                  60

Lys Thr Thr Val Ser Met Ala Leu Glu Glu Tyr Leu Val Cys His Gly
65                  70                  75                  80

Ile Pro Cys Tyr Thr Leu Asp Gly Asp Asn Ile Arg Gln Gly Leu Asn
                85                  90                  95

Lys Asn Leu Gly Phe Ser Pro Glu Asp Arg Glu Asn Val Arg Arg
            100                 105                 110

Ile Ala Glu Val Ala Lys Leu Phe Ala Asp Ala Gly Leu Val Cys Ile
        115                 120                 125

Thr Ser Phe Ile Ser Pro Tyr Thr Gln Asp Arg Asn Asn Ala Arg Gln
    130                 135                 140

Ile His Glu Gly Ala Ser Leu Pro Phe Phe Glu Val Phe Val Asp Ala
145                 150                 155                 160

Pro Leu His Val Cys Glu Gln Arg Asp Val Lys Gly Leu Tyr Lys Lys
                165                 170                 175

Ala Arg Ala Gly Glu Ile Lys Gly Phe Thr Gly Ile Asp Ser Glu Tyr
            180                 185                 190

Glu Lys Pro Glu Ala Pro Glu Leu Val Leu Lys Thr Asp Ser Cys Asp
        195                 200                 205

Val Asn Asp Cys Val Gln Gln Val Val Glu Leu Leu Gln Glu Arg Asp
    210                 215                 220
```

```
Ile Val Pro Val Asp Ala Ser Tyr Glu Val Lys Glu Leu Tyr Val Pro
225                 230                 235                 240

Glu Asn Lys Leu His Leu Ala Lys Thr Asp Ala Glu Thr Leu Pro Ala
            245                 250                 255

Leu Lys Ile Asn Lys Val Asp Met Gln Trp Val Gln Val Leu Ala Glu
                260                 265                 270

Gly Trp Ala Thr Pro Leu Asn Gly Phe Met Arg Glu Arg Glu Tyr Leu
            275                 280                 285

Gln Cys Leu His Phe Asp Cys Leu Leu Asp Gly Gly Val Ile Asn Leu
        290                 295                 300

Ser Val Pro Ile Val Leu Thr Ala Thr His Glu Asp Lys Glu Arg Leu
305                 310                 315                 320

Asp Gly Cys Thr Ala Phe Ala Leu Met Tyr Glu Gly Arg Arg Val Ala
                325                 330                 335

Ile Leu Arg Asn Pro Glu Phe Phe Glu His Arg Lys Glu Glu Arg Cys
            340                 345                 350

Ala Arg Gln Trp Gly Thr Thr Cys Lys Asn His Pro Tyr Ile Lys Met
        355                 360                 365

Val Met Glu Gln Gly Asp Trp Leu Ile Gly Gly Asp Leu Gln Val Leu
370                 375                 380

Asp Arg Val Tyr Trp Asn Asp Gly Leu Asp Gln Tyr Arg Leu Thr Pro
385                 390                 395                 400

Thr Glu Leu Lys Gln Lys Phe Lys Asp Met Asn Ala Asp Ala Val Phe
                405                 410                 415

Ala Phe Gln Leu Arg Asn Pro Val His Asn Gly His Ala Leu Leu Met
            420                 425                 430

Gln Asp Thr His Lys Gln Leu Leu Glu Arg Gly Tyr Arg Arg Pro Val
        435                 440                 445

Leu Leu Leu His Pro Leu Gly Gly Trp Thr Lys Asp Asp Asp Val Pro
450                 455                 460

Leu Met Trp Arg Met Lys Gln His Ala Ala Val Leu Glu Glu Gly Val
465                 470                 475                 480

Leu Asn Pro Glu Thr Thr Val Val Ala Ile Phe Pro Ser Pro Met Met
                485                 490                 495

Tyr Ala Gly Pro Thr Glu Val Gln Trp His Cys Arg Ala Arg Met Val
            500                 505                 510

Ala Gly Ala Asn Phe Tyr Ile Val Gly Arg Asp Pro Ala Gly Met Pro
        515                 520                 525

His Pro Glu Thr Gly Lys Asp Leu Tyr Glu Pro Ser His Gly Ala Lys
530                 535                 540

Val Leu Thr Met Ala Pro Gly Leu Ile Thr Leu Glu Ile Val Pro Phe
545                 550                 555                 560

Arg Val Ala Ala Tyr Asn Lys Lys Lys Arg Met Asp Tyr Tyr Asp
                565                 570                 575

Ser Glu His His Glu Asp Phe Glu Phe Ile Ser Gly Thr Arg Met Arg
            580                 585                 590

Lys Leu Ala Arg Glu Gly Gln Lys Pro Pro Glu Gly Phe Met Ala Pro
        595                 600                 605

Lys Ala Trp Thr Val Leu Thr Glu Tyr Tyr Lys Ser Leu Glu Lys Ala
            610                 615                 620

<210> SEQ ID NO 119
<211> LENGTH: 99
<212> TYPE: PRT
```

<213> ORGANISM: Homo sapiens

<400> SEQUENCE: 119

Met Phe Ser Lys Met Ala Thr Tyr Leu Thr Gly Glu Leu Thr Ala Thr
1               5                   10                  15

Ser Glu Asp Tyr Lys Leu Leu Glu Asn Met Asn Lys Leu Thr Ser Leu
                20                  25                  30

Lys Tyr Leu Glu Met Lys Asp Ile Ala Ile Asn Ile Ser Arg Asn Leu
            35                  40                  45

Lys Asp Leu Asn Gln Lys Tyr Ala Gly Leu Gln Pro Tyr Leu Asp Gln
        50                  55                  60

Ile Asn Val Ile Glu Glu Gln Val Ala Ala Leu Glu Gln Ala Ala Tyr
65                  70                  75                  80

Lys Leu Asp Ala Tyr Ser Lys Lys Leu Glu Ala Lys Tyr Lys Lys Leu
                85                  90                  95

Glu Lys Arg

<210> SEQ ID NO 120
<211> LENGTH: 491
<212> TYPE: PRT
<213> ORGANISM: Homo sapiens

<400> SEQUENCE: 120

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
                20                  25                  30

Leu Leu Leu Lys Leu Leu Lys Ser Val Gly Ala Gln Lys Asp Thr Tyr
            35                  40                  45

Thr Met Lys Glu Val Leu Phe Tyr Leu Gly Gln Tyr Ile Met Thr Lys
        50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
            115                 120                 125

Leu Glu Gly Gly Ser Asp Gln Lys Asp Leu Val Gln Glu Leu Gln Glu
        130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

-continued

```
Glu Asp Tyr Ser Leu Ser Glu Glu Gly Gln Glu Leu Ser Asp Glu Asp
                260                 265                 270

Asp Glu Val Tyr Gln Val Thr Val Tyr Gln Ala Gly Glu Ser Asp Thr
            275                 280                 285

Asp Ser Phe Glu Glu Asp Pro Glu Ile Ser Leu Ala Asp Tyr Trp Lys
        290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
        355                 360                 365

Asp Ser Arg Glu Ser Cys Val Glu Glu Asn Asp Asp Lys Ile Thr Gln
    370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
            420                 425                 430

Asn Ala Ile Glu Pro Cys Val Ile Cys Gln Gly Arg Pro Lys Asn Gly
        435                 440                 445

Cys Ile Val His Gly Lys Thr Gly His Leu Met Ala Cys Phe Thr Cys
    450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490
```

BIOMARKERS FOR LIVER FIBROTIC INJURY

CROSS REFERENCE TO RELATED APPLICATIONS

The present invention is related to and claims the benefit of, under U.S.C. §119(e), U.S. provisional patent application Ser. No. 60/761,959, filed on Jan. 24, 2006, which is expressly incorporated fully herein by reference.

FIELD OF THE INVENTION

Herein described are methods of detecting liver fibrosis and/or cirrhosis based on the differential expression of various proteins, and kits for diagnosing fibrosis and/or cirrhosis.

BACKGROUND

Liver fibrosis represents a continuous disease spectrum characterized by an increase in total liver collagen and other matrix proteins that disrupt the architecture of the liver and impair liver function (1, 2). The progression of fibrosis in the liver is a response to necroinflammatory changes. The overall liver fibrosis process is one of dynamic inflammation and repair and has the potential to be resolved (3). Fibrosis is seen as scar formation in the patient's liver. When the liver becomes permanently injured and scarred, the condition is called cirrhosis.

Liver fibrosis and/or cirrhosis are the major risk factors of hepatocellular carcinoma (HCC). A range of factors, such as hepatitis B virus (HBV), hepatitis C virus (HCV), hepatotoxins, metabolic disorders and alcoholism, can induce both liver fibrosis and/or cirrhosis, which share similar phenotypes (3-7), with cirrhosis being the end-stage of fibrosis. However, it is not clear what types of genes are involved or how they act when liver injury and repair occur. Moreover, the cirrhosis caused by these risk factors often progresses insidiously. Patients with end-stage liver cirrhosis can die within one year unless they accept liver transplantation, which has a 75% five-year survival rate (3).

Previous biochemical studies have reported that there are 39 well-known fibrosis or cirrhosis markers (3, 8, 9), but some markers are obtained through invasive sampling.

Studies for additional markers have proceeded based on microarray analysis of transcriptomes as well as quantitative proteomics. Microarray technologies have been widely used for comprehensive gene expression analysis. In particular, large-scale microarray analysis of gene expression enables researchers to analyze simultaneous changes in thousands of genes and identify significant patterns (10, 11). To date, the most widely used technologies in differential proteomics research were two-dimensional gel electrophoresis (2DE) and liquid chromatography-based isotope-coded affinity tagging (ICAT) technologies (12). Recently, a variation of the ICAT technology, iTRAQ (isobaric tags for relative and absolute quantitation), has been introduced. Both ICAT and iTRAQ tagging permit online identification of multiple markers and relative quantification of these proteins.

SUMMARY OF THE INVENTION

The inventors have used differential analysis such as microarray mRNA expression profiling and quantitative protein profiling to find additional unique and identifiable signatures potentially valuable for the diagnosis and treatment of liver fibrosis and/or cirrhosis.

The invention provides a method of detecting liver fibrosis and/or cirrhosis comprising obtaining a biological sample from a patient and assaying the sample for differential expression of at least one gene encoding a protein chosen from SEQ ID NO: 1-SEQ ID NO: 63 and human orthologs thereof, wherein the differential expression of at least one gene suggests the presence of liver fibrosis and/or cirrhosis.

Also provided is a method of detecting liver fibrosis and/or cirrhosis by assaying the biological sample for differential expression of the human orthologs described above, wherein the human orthologs comprise at least one gene encoding a protein chosen from SEQ ID NO: 64-SEQ ID NO: 120.

Also provided is a kit for diagnosing liver fibrosis and/or cirrhosis, which comprises one or more nucleic acid probes that hybridize to nucleic acid molecules of at least one gene encoding a protein chosen from SEQ ID NO: 1-SEQ ID NO: 63 and human orthologs thereof and packaging indicating use for detection of liver fibrosis and/or cirrhosis.

In addition, a kit is provided for diagnosing liver fibrosis comprising one or more nucleic acid probes as described above, wherein the human orthologs comprise at least one gene encoding a protein chosen from SEQ ID NO: 64-SEQ ID NO: 120.

The invention further provides a kit for diagnosing liver fibrosis and/or cirrhosis that comprises one or more antibodies that specifically bind to at least one protein encoded by a sequence chosen from SEQ ID NO: 1-SEQ ID NO: 63 and human orthologs thereof, and packaging indicating use for detection of liver fibrosis and/or cirrhosis.

Also provided is a kit for diagnosis of liver fibrosis and/or cirrhosis comprising one or more antibodies as described above, wherein the human orthologs comprise at least one gene encoding a protein chosen from SEQ ID NO: 64-SEQ ID NO: 120.

The invention also provides a method of identifying a compound that decreases the differential expression of at least one gene-encoding a protein chosen from SEQ ID NO: 7-SEQ ID NO: 23 and SEQ ID NO: 42-SEQ ID NO: 63 and human orthologs thereof, comprising providing a cell expressing at least one of the aforementioned genes, contacting the cell with a test compound, and determining whether the differential expression of the at least one gene is decreased in the presence of the test compound, wherein the decreased differential expression is an indication of halting or reversing liver fibrosis and/or cirrhosis.

The invention further provides a method of identifying a compound that increases the differential expression of at least one gene encoding a protein chosen from SEQ ID NO: 1-SEQ ID NO: 6 and SEQ ID NO: 24-SEQ ID NO: 41 and human orthologs thereof, comprising providing a cell expressing at least one of the aforementioned genes, contacting the cell with a test compound, and determining whether the differential expression of the at least one gene is increased in the presence of the test compound, wherein the increased differential expression is an indication of halting or reversing liver fibrosis and/or cirrhosis.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and do not limit the invention as claimed.

The accompanying drawings, which are incorporated in and constitute a part of this specification, illustrate several embodiments of the invention and together with the description, serve to explain the principles of the invention.

SUMMARY OF THE TABLES

Table 1 is the result of a biochemical analysis of the serum of rats treated with dimethylnitrosamine (DMN) as compared with that of the control rats over a six-week time period.

Table 2 is a list of genes showing significant changes in gene expression and their human orthologs. The genes were selected from the combined results of microarray analysis and quantitative proteomic analysis and those whose relationship to fibrosis are not yet disclosed in public literature.

Table 3 is the result of interacting network analysis for the proteins showing significant changes in expression in oligonucleotide microarray (Table 3A) and iTRAQ proteomic (Table 3B) studies. Proteins in the network identified in the present study which have not previously been reported to associate with liver injury are shown in bold.

BRIEF DESCRIPTION OF THE DRAWINGS

FIG. 2B is a summary of the histopathological scores for the rat model. The results are ranked by time course. The necroinflammatory change is divided into three grades: A0=none, A(1-3)=mild and A(4-6)=moderate necroinflammatory. The fibrosis change is divided into two grades: F(0-1)=normal to fibrous expansion of portal tracts, F(2-3)= bridge fibrosis to frequent bridging fibrosis with nodule formation. The fatty change is shown as presence or absence (+/−). The number of rats is counted and used to calculate the percentage of rats in each histopathological level at each time point.

DESCRIPTION OF THE EMBODIMENTS

Definitions

Figure 1A:
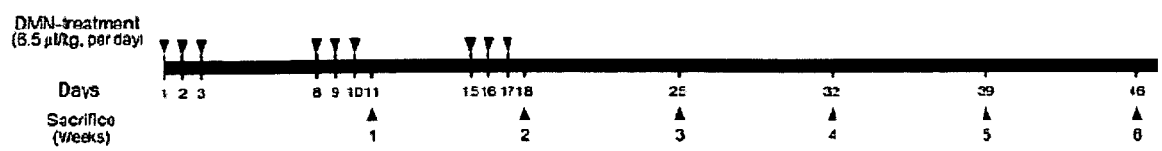
FIG. 1A is a schematic illustration of DMN treatment for inducing fibrosis in rats. Each rat was either injected with DMN three times per week for three consecutive weeks (shown as inverted triangles) or with normal saline as control. Rats were weighed and sacrificed each week (shown as triangles, starting on day 11, which is referred to as first week, until week six). Blood samples were collected for biochemical assays (summary in Table 1) and livers were excised and weighed. Livers were then either fixed in formaldehyde for histopathology or used to isolate RNA and protein for microarray and iTRAQ proteomic studies, respectively.

As used herein, the term "biological sample" refers to any biological material collected from cells, tissues, or organs of the subject. The source of the biological sample may vary depending on the particular symptoms present in the subject to be diagnosed. The biological sample may be analyzed immediately after it is taken, or stored. If stored, the sample may be equilibrated with an appropriate storage buffer, and kept at 4° C., at −20° C., at −70° C., or even in cryogenic liquids, such as liquid nitrogen or liquid helium. In one embodiment, the biological sample may consist of blood, serum, or plasma. In another embodiment, the biological sample may consist of a biopsy or tissue sample. In additional embodiments of the invention, the biological sample may consist of aminotic fluid, milk, saliva, cerebrospinal fluid, lymph, sweat, mucus, synovial fluid, lacrimal fluid, or other clinical specimens or samples.

As used herein, the term "patient" refers to a mammalian animal, including but not limited to human, primates, domestic mammals, laboratory mammals, etc.

As used herein, the term "differential expression" refers to gene expression on the RNA/mRNA level, protein level, or both RNA/mRNA and protein levels as compared to normal gene expression, e.g., an increased or decreased gene expression on the RNA/mRNA level, protein level, or both RNA/mRNA and protein levels.

As used herein, the terms "gene" and "gene encoding a protein" refer to any nucleic acid sequence or portion thereof with a functional role in encoding or transcribing a protein. The gene may encompass all the nucleic acids responsible for encoding a functional protein of certain SEQ ID NO or only a portion of the nucleic acids responsible for encoding or expressing a protein of certain SEQ ID NO. The nucleic acid sequence may contain normal sequences as well as genetic abnormalities within exons, introns, initiation or termination regions, promoter sequences, other regulatory sequences or unique adjacent regions to the gene.

As used herein, the term "human ortholog" refers to a corresponding human gene wherein the non-human gene and the human gene are derived from a single ancestral gene in the last common ancestor of human and non-human, and the human genes have the same function.

As used herein, the term "probes" refers to hybridization probes that are oligonucleotides that bind in a base-specific manner to a complementary strand of nucleic acid. Such probes also include peptide nucleic acids, as described in Nielsen et al., 1991, (13), and other nucleic acid analogs and nucleic acid mimetics. See, e.g., U.S. Pat. No. 6,156,501, which is incorporated herein by reference.

As used herein, the term "nucleic acid" refers to any DNA or RNA/mRNA, for example, chromosomal, mitochondrial, viral and/or bacterial nucleic acid present in tissue sample as well as synthetic nucleic acids. The term "nucleic acid" encompasses either or both strands of a double stranded nucleic acid molecule and includes any fragment or portion of an intact nucleic acid molecule.

As used herein, the term "packaging" refers generally to packaging material comprising external labeling and internal material in the container, including but not limited to instructions for using the kit.

As used herein, the term "antibody," refers to an immunoglobulin or a fragment or a derivative thereof, and encompasses any polypeptide comprising an antigen-binding site, whether produced in vitro or in vivo. The term includes, but is not limited to, polyclonal, monoclonal, monospecific, polyspecific, humanized, single-chain, chimeric, synthetic, recombinant, hybrid, mutated, and grafted antibodies. The term "antibody" also includes antibody fragments such as Fab, F(ab')$_2$, Fv, scFv, Fd, dAb, and other antibody fragments that retain antigen-binding function, i.e., the ability to bind a specific antigen. Typically, such fragments would comprise an antigen-binding domain, i.e., a part of an antibody molecule that comprises amino acids responsible for the specific binding between the antibody and the antigen. An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

As used herein, the term "specifically binds," or the like, means that two molecules form a complex that is relatively stable under physiologic conditions (e.g., a stable antigen/antibody complex). The term is also applicable where, for example, an antigen-binding domain is specific for a particular epitope, which is found on a number of molecules. Thus, an antibody may specifically bind multiple proteins when it binds to an epitope present in each. Specific binding is characterized by a selective interaction, often including high affinity binding with a low to moderate capacity. Nonspecific binding is usually a less selective interaction, and may have a low affinity with a moderate to high capacity. Typically, binding is considered specific when the affinity is at least $10^5$ M$^{-1}$, $10^6$ M$^{-1}$, $10^7$ M$^{-1}$ or $10^8$ M$^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentrations of antibodies, ionic strength of the solution, temperature, time allowed for binding, concentration of non-related molecules (e.g., blocking agents such as serum albumin or milk casein), and so forth. See, e.g., Morgan et al., "The Matrix Effects on Kinetic Rate Constants of Antibody-Antigen Interactions Reflect Solvent Viscosity," *J. Immunol. Meth.* 217:51:60 (1998); and Zhuang et al., "Measurement of Association Rate Constant of Antibody-Antigen Interactions in Solution Based on Enzyme-Linked Immunosorbent Assay," *J. Biosci. Bioeng.* 92(4):330-336 (2001).

As used herein, the term "protein" refers to a polymeric form of any length of amino acids, which can include naturally-occurring or synthetic amino acids and coded and non-coded amino acids, peptides, depsipeptides, polypeptides with cyclic, bicyclic, depsicyclic, or depsibicyclic peptide backbones, single chain protein as well as multimers, as well as any fragment or portion of the intact protein molecule.

As used herein, the term "compound" refers to a substance comprising one or more chemical elements in any proportion and of any structure, including but not limited to cyclic, bicyclic, branched or straight chain. The compound may be organic or inorganic. The compound also refers to a composition comprising one or more chemical elements, one or more herbal/plant elements or herbal/plant extractions, or both chemical elements and herbal/plant elements or extractions.

EMBODIMENTS

Chronic liver disease is a common and potentially lethal problem in Asia. The development of hepatocellular carcinoma (HCC) is generally preceded by hepatic cirrhosis, which occurs at the end stage of fibrosis. The same proteins are expressed in both cirrhosis and fibrosis. Changes in gene expression of these proteins during liver fibrosis are examined to identify markers of liver fibrosis to assist in the diagnosis of fibrosis and/or cirrhosis. The study begins with the establishment of a liver fibrosis model. Dimethylnitrosamine (DMN), a non-genotoxic hepatotoxin, is used to induce rat necroinflammatory and hepatic fibrosis, as described in Jezequel A. M. et al. (14), which is a known model for studying human liver damage (15). During a six-week time course, histopathological, biochemical and quantitative RT-PCR analyses confirmed the incidence of hepatic fibrosis in the rat model system.

The microarray and the iTRAQ quantitative proteomics technology were used. The iTRAQ technology permits the identification of multiple proteins at the same time as well as the relative quantification of these proteins. Applied Biosystems iTRAQ Reagents are a multiplexed set of four isobaric reagents. The four reagents are amine-specific and yield labeled peptides. The labeled peptides are identical in mass and hence also identical in single MS mode. They produce strong, diagnostic, low-mass MS/MS signature ions allowing for quantification of up to four different samples simultaneously. Quantification is performed via the differences in abundance of four product ions, i.e., product ions weighing 114, 115, 116, and 117 daltons that are each cleaved from one of the four possible tags. Since all peptides are tagged, proteome coverage is expanded and analysis of multiple peptides per protein improves the confidence in those identified (16). The multi-sample capability of the iTRAQ technology provides a way to compare the protein expression profile of different liver states simultaneously.

The model employed in the present study is very similar to the human liver study model, and thus findings from this study can have human clinical applications. This study employed DMN, a potent non-genotoxic hepatotoxin, to simulate liver fibrosis (17, 18). DMN has been demonstrated to induce liver damage rapidly and also has been empirically proven to be useful for the study of human fibrosis formation (14-15, 19) as mentioned above. Also, the serum markers that showed significant differences in expression in the rat liver fibrosis model established in this study as compared to the controls, see Table 1, are the same serum markers for human liver fibrosis, e.g., the thirteen serum markers of albumin, glutamic oxaloacetic transaminase (GOT), glutamic pyruvic transaminase (GPT), total bilirubin, alkaline phosphatase (AKP), acid phosphatases (ACP), α-fetoprotein (AFP), blood urea nitrogen (BUN), cholesterol (CHOL), lactate dehydrogenase (LDH), globulin, prothrombin time (PT) and blood platelets (PLT). Thus, the markers identified from this study can be used to diagnose liver fibrosis and/or cirrhosis in humans.

Detection Methods

The present study identified nearly 97 genes as biomarkers for liver fibrotic injury. Results of a PubMed literature search indicate that approximately 30% of the differentially expressed genes identified in this study by microarray and proteomics approach had been proven to be related to fibrosis or cirrhosis. The remaining 70% are not yet reported in any literature. Combining all the information obtained by both microarray and quantitative proteomics technology, sixty-three (63) genes were selected, all of which showed significant changes in expression between DMN-treated and DMN-untreated groups, but have not been previously reported in any literature in relation to liver fibrosis or cirrhosis (Table 2). The 63 genes in DMN-treated rats have a difference in gene expression on the RNA/mRNA level and/or the protein level when compared to normal gene expression. Some genes are up-regulated while others are down-regulated. Those 63 rat genes were converted into their human ortholog genes according to the ortholog assertions from the EnsEMBL and HomoloGene database (Table 2—SEQ ID NO: 1-SEQ ID NO: 120).

Thus the invention provides a method for detecting liver fibrotic injury based on the liver injury-related differential gene expression study described herein. In the detection method, differential expression of a gene encoding a protein includes differential expression of the full length gene encoding a full length protein or a portion of the gene encoding a portion of the protein.

Accordingly, the invention provides a method of detecting liver fibrosis and/or cirrhosis comprising obtaining a biological sample from a patient, and assaying the sample for differential expression of at least one gene encoding a protein chosen from SEQ ID NO: 1 to SEQ ID NO: 63 and human orthologs thereof, wherein the differential expression of at least one gene suggests the presence of liver fibrosis and/or cirrhosis. In another embodiment, the invention provides a method of detecting liver fibrosis and/or cirrhosis by assaying the sample for differential expression of at least one gene encoding a protein chosen from the human orthologs comprising SEQ ID NO: 64 to SEQ ID NO: 120.

Human orthologs of proteins identified in this study can be derived from the search using gene/protein on the Ensembl database together with the HomoloGene NCBI database.

In the practice of this invention, differential gene expression may be assayed by transcription analysis or quantitative proteomic analysis such as microarray, Q-RT-PCR, ICAT and iTRAQ, or any other appropriate methods known to one skilled in the art.

In another embodiment, the invention relates to assaying the up-regulation or increased expression of one or more genes encoding a protein chosen from SEQ ID NO: 7-SEQ ID NO: 23 and SEQ ID NO: 42-SEQ ID NO: 63 and human orthologs thereof, wherein the increased expression suggests the presence of liver fibrosis and/or cirrhosis. In yet another embodiment, the invention relates to assaying for the increased expression of at least one gene encoding a protein chosen from the human orthologs comprising SEQ ID NO: 68-SEQ ID NO: 82 and SEQ ID NO: 100-SEQ ID NO: 120.

The invention also provides, in another embodiment, assaying for the down-regulation or decreased expression of one or more genes encoding a protein chosen from SEQ ID NO: 1-SEQ ID NO: 6 and SEQ ID NO: 24-SEQ ID NO: 41 and human orthologs thereof, wherein the decreased expression suggests the presence of liver fibrosis and/or cirrhosis. In yet another embodiment, the invention relates to assaying for the decreased expression of at least one gene encoding a protein chosen from the human orthologs comprising SEQ ID NO: 64-SEQ ID NO: 67 and SEQ ID NO: 83-SEQ ID NO: 99.

The invention also provides a clustering of the genes by functional groups. Thus, the invention provides a method of detecting liver fibrosis and/or cirrhosis comprising assaying a biological sample for differential expression of at least one gene encoding a protein that functions in cancer, cell cycle, and cell morphology chosen from sequences comprising SEQ ID NO: 9, SEQ ID NO: 69, SEQ ID NO: 12, SEQ ID NO: 72, SEQ ID NO: 4, SEQ ID NO: 65, SEQ ID NO: 17, SEQ ID NO: 76, SEQ ID NO: 7, SEQ ID NO: 68, SEQ ID NO: 19, SEQ ID NO: 78, SEQ ID NO: 5, SEQ ID NO: 66, SEQ ID NO: 20, SEQ ID NO: 79, SEQ ID NO: 22, SEQ ID NO: 81, SEQ ID NO: 21, and SEQ ID NO: 80; a protein that functions in lipid metabolism, small molecule biochemistry, organismal injury and abnormalities chosen from sequences comprising SEQ ID NO: 10, SEQ ID NO: 70, SEQ ID NO: 3, SEQ ID NO: 64, SEQ ID NO: 14, SEQ ID NO: 73, SEQ ID NO: 15 and SEQ ID NO: 74; a protein that functions in hematological disease, endocrine system development and function, nervous system development and function comprising SEQ ID NO: 13; a protein that functions in cancer, cell morphology, dermatological diseases and conditions chosen from sequences comprising SEQ ID NO: 8, SEQ ID NO: 44, SEQ ID NO: 102, SEQ ID NO: 45, SEQ ID NO: 103, SEQ ID NO: 48, SEQ ID NO: 106, SEQ ID NO: 31, SEQ ID NO: 90, SEQ ID NO: 35, SEQ ID NO: 93, SEQ ID NO: 50, SEQ ID NO: 108, SEQ ID NO: 51, SEQ ID NO: 109, SEQ ID NO: 40, and SEQ ID NO: 98; a protein that functions in lipid metabolism, small molecule biochemistry, and molecular transport chosen from sequences comprising SEQ ID NO: 25, SEQ ID NO: 84, SEQ ID NO: 42, SEQ ID NO: 100, SEQ ID NO: 27, SEQ ID NO: 86, SEQ ID NO: 47, SEQ ID NO: 105, SEQ ID NO: 36, SEQ ID NO: 94, SEQ ID NO: 16, SEQ ID NO: 75, SEQ ID NO: 53, SEQ ID NO: 11, SEQ ID NO: 37, SEQ ID NO: 95, SEQ ID NO: 38, SEQ ID NO: 96, and SEQ ID NO: 107; and a protein that functions in cancer, cellular movement, cellular growth and proliferation chosen from sequences comprising SEQ ID NO: 59, SEQ ID NO: 117, SEQ ID NO: 46, SEQ ID NO: 104, SEQ ID NO: 30, SEQ ID NO: 89, SEQ ID NO: 52, SEQ ID NO: 110, SEQ ID NO: 58, SEQ ID NO: 116, SEQ ID NO: 55, SEQ ID NO: 113, SEQ ID NO: 39, SEQ ID NO: 97, SEQ ID NO: 56, SEQ ID NO: 114, SEQ ID NO: 57, and SEQ ID NO: 115.

Diagnostic Kits

The invention also provides diagnostic kits based on the genes and/or proteins described above. In one embodiment, there is a kit for diagnosing liver fibrosis and/or cirrhosis that comprises one or more nucleic acid probes that hybridize to nucleic acid molecules of at least one gene encoding a protein marker chosen from SEQ ID NO: 1-SEQ ID NO: 63 and human orthologs thereof and packaging indicating the use for detecting liver fibrosis. The kit can detect the differential expression, e.g., the up-regulation or down-regulation, of these genes, wherein the differential expression would suggest liver fibrosis and/or cirrhosis. In another embodiment, the invention also provides a kit for diagnosing fibrosis and/or cirrhosis comprising nucleic acid probes that hybridize to nucleic acid molecules of at least one gene encoding a protein marker chosen from SEQ ID NO: 1-SEQ ID NO: 63 and human orthologs thereof. The differential expression of the genes would suggest fibrosis and/or cirrhosis. In another embodiment, the diagnostic kit comprises one or more nucleic acid probes that hybridize to nucleic acid molecules of at least one gene encoding the human orthologs comprising proteins chosen from SEQ ID NO: 64-SEQ ID NO: 120 for diagnosing liver fibrosis and/or cirrhosis.

The kit may be prepared by techniques known to one skilled in the art. By way of example, the probes may be labeled, using labeling techniques that are known to one skilled in the art, to facilitate detection, including but not limited to radioisotope labels or fluorescent labels. The probes can hybridize to nucleic acid molecules that are either or both strands of a double stranded nucleic acid molecule and include any fragment or portion of an intact nucleic acid molecule.

Nucleic acid hybridization is affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringency conditions depend on the length and base composition of the nucleic acid, which can be determined by techniques well known in the art. Generally, stringency can be altered or controlled by, for example, manipulating temperature and salt concentration during hybridization and washing. For example, a combination of high temperature and low salt concentration increases stringency. Such conditions are known to those skilled in the art and can be found in, for example, Strauss, W. M. "Hybridization With Radioactive Probes," in Current Protocols in Molecular Biology 6.3.1-6.3.6, (John Wiley & Sons, N.Y. 2000). Both aqueous and nonaqueous conditions as described in the art can be used.

An example of stringent hybridization conditions is hybridization in 0.1×SSC (15 mM sodium chloride/1.5 mM sodium citrate) at 50° C. or higher. Another example of stringent hybridization conditions is hybridization overnight at 42° C. in 50% formamide, 1×SSC (150 mM NaCl, 15 mM sodium citrate), 50 mM sodium phosphate (pH 7.6), 5×Denhardt's solution, 10% (w/v) dextran sulfate, and 20 µg/ml denatured, sheared salmon sperm DNA, followed by washing in 0.1×SSC at about 65° C. Highly stringent conditions can include, for example, aqueous hybridization (e.g., free of form amide) in 6×SSC (where 20×SSC contains 3.0 M NaCl and 0.3 M sodium citrate), 1% (w/v) sodium dodecyl sulfate (SDS) at 65° C. for about 8 hours (or more), followed by one or more washes in 0.2×SSC, 0.1% SDS at 65° C.

Moderately stringent hybridization conditions permit a nucleic acid to bind a complementary nucleic acid that has at least about 60%, at least about 75%, at least about 85%, or greater than about 90% identity to the complementary nucleic acid. Stringency of hybridization is generally reduced by decreasing hybridization and washing temperatures, adding formamide to the hybridization buffer, or increasing salt concentration of the washing buffer, either individually or in combination. Moderately stringent conditions can include, for example, aqueous hybridization (e.g., free of formamide) in 6×SSC, 1% (w/v) SDS at 65° C. for about 8 hours (or more), followed by one or more washes in 2×SSC, 0.1% SDS at room temperature. Another exemplary hybridization under moderate stringency comprises hybridization in 6×SSC, 5×Denhardt's reagent, 0.5% (w/v) SDS, and optionally 100 µg/ml sonicated salmon or herring sperm DNA, at about 42° C., followed by washing in 2×SSC, 0.1% (w/v) SDS at 65° C. Other permutations and possibilities will be readily apparent to those of ordinary skill in the art, and are considered as equivalents within the scope of the instant invention.

In yet another embodiment, the invention provides a kit for diagnosing liver fibrosis and/or cirrhosis comprising one or more antibodies that specifically bind to at least one protein encoded by a sequence chosen from SEQ ID NO: 1-SEQ ID NO: 63 and human orthologs thereof, and further comprises packaging that indicates use for detection of liver fibrosis and/or cirrhosis. In an alternative embodiment, the kit comprises one or more antibodies that specifically bind to at least one human ortholog protein encoded by a sequence chosen from SEQ ID NO: 64-SEQ ID NO: 120, and further comprises packaging that indicates use for detection of liver fibrosis and/or cirrhosis. Differential expression of these genes suggests the presence of fibrosis and/or cirrhosis.

The antibodies specific to the proteins may be obtained by monoclonal or polyclonal techniques known to one skilled in the art. The antibody can be labeled with radioisotopes such as $^{35}S$, $^{14}C$, $^{125}I$, $^{3}H$, and $^{131}I$, using the techniques described in Current Protocols in Immunology (20), as an example. The radioactivity can be measured using scintillation counting. The antibody may also be fluorescently labeled by, for example, rare earth chelates (europium chelates), Texas Red, rhodamine, fluorescein, dansyl, Lissamine, umbelliferone, phycoerytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in Current Protocols in Immunology, supra., for example. Fluorescence can be quantified using a fluorimeter.

Differential protein expression may be assayed using antibodies with commonly used methods known in the art, such as Western blotting or enzyme-linked immunosorbent assay (ELISA). Western blotting begins with an electrophoresis step, where proteins from a biological sample of interest are separated on the basis of size and electromagnetic charge by sodium dodecyl sulfate-polyacrylamide gel electrophoresis (SDS-PAGE), according to standard methods known in the art. See, e.g., SAMBROOK ET AL., 3 MOLECULAR CLONING: A LABORATORY MANUAL A8.40-A8.45 (2001) (describing various reagents and methods for electrophoresis of proteins by SDS-PAGE). The contents of the gel are then transferred to nitrocellulose, nylon, PVDF, or other membrane or filter suitable for fixation and Western blotting by standard methods also known in the art. The transfer may be by immersion, semi-dry blotting, or by other comparable methods known in the art. Next, the filters or membranes are fixed to prevent loss of the target proteins during the several hybridization, washing, and staining steps comprising Western blotting. Fixation may be accomplished by heat, cross-linking with ultraviolet light, or by other comparable methods known in the art. See, e.g., SAMBROOK ET AL., 3 MOLECULAR CLONING: A LABORATORY MANUAL A8.52-A8.55 (describing various reagents and methods for immunoblotting and detection of antigen/antibody complexes).

Non-specific antibody binding sites on the fixed filter or membrane are blocked with buffered solutions (e.g., phosphate-buffered saline ("PBS") or the like) containing a blocking agent such as, for example, 0.5% (w/v) low-fat dry milk or 5% (w/v) bovine serum albumin (BSA). After blocking, the filter or membrane then undergoes the primary antibody incubation. After primary antibody incubation, the filter or membrane is washed, and the presence of antibody-antigen complexes detected using a secondary antibody labeled with chromogenic, fluorogenic, or chemiluminescent means. Antibody-antigen complexes are then detected colorimetrically (e.g., with horseradish peroxidase and TMB), or by autoradiography (e.g., alkaline phosphatase). If detected colorimetrically, or by chemiluminescence, the amount of color of fluorescence may be measured using a luminometer, a spectrophotometer, or other similar instruments. If detected autoradiographically, the amount of bound antibody may be measured from the exposed x-ray film using a densitometer, or similar instrument. See, e.g., SAMBROOK ET AL., 3 MOLECULAR CLONING: A LABORATORY MANUAL A8.52-A8.55.

Secondary antibodies used in Western blotting, whether polyclonal or monoclonal, may be labeled with a ligand (such as biotin) or a detectable marker (such as a fluorescent group or an enzyme) using conventional techniques. Suitable labels include fluorophores, chromophores, electron-dense reagents (e.g., silver or gold), enzymes, and ligands having specific binding partners. Enzymes such as horseradish peroxidase or alkaline phosphatase are typically detected by their activity. For example, horseradish peroxidase can be detected by its ability to convert tetramethylbenzidine (TMB) to a blue pigment, quantifiable with a spectrophotometer. Other suitable ligands and/or detectable markers include bioting and avidin or streptavidin, IgG and protein A, and the numerous additional receptor-ligand couples known in the art. Other permutations and possibilities will be readily apparent to those of ordinary skill in the art, and are considered as equivalents within the scope of the instant invention.

An ELISA begins with an antigen adsorption step, where the target antigen or antigens are adsorbed to the wells of a microtiter plate. See, e.g., KIERKEGAARD & PERRY LABORATORIES, INC., TECHNICAL GUIDE FOR ELISA 9-13 (2003). The most commonly used adsorption buffers for antibodies are 50 mM Carbonate, pH=9.6; 10 mM Tris-HCl, pH=8.5; and 10 mM PBS, pH=7.2. These buffers work well for many proteins. If the target antigens are not readily adsorbed to the surface of the microtiter plate, plates with surfaces modified or derivatized to permit covalent linkage of proteins to their surface by a variety of chemical means are widely available from commercial suppliers. Time and temperature are the most important factors affecting the amount of protein adsorbed.

Once the wells of a microtiter plate are coated with the desired antigen or antigens, they are washed with a blocking buffer to block non-specific antibody binding and to minimize false positive results. See, e.g., id. at 13-14 (discussing methods and reagents for blocking microtiter plates). Commonly used blocking agents are either protein solutions, such as BSA (typically used at concentrations between 1% and 5% (w/v) in PBS, pH=7.0), non-fat dry milk, casein (the main protein component of non-fat dry milk), or caseinate (a more soluble version of casein, produced by partial digestion with sodium hydroxide), normal serum (typically used at concentrations between 1% and 5% (v/v)), and gelatin (normally used at concentrations between 1% and 5% (w/v)), or non-ionic detergents, such as TWEEN-20™ and TRITON X-100™.

Washing reagents are selected for their ability to disrupt low-affinity interactions between various reaction components that can affect the ability to detect specific antigen-antibody interactions. See, e.g., id. at 14-15 (discussing methods and reagents for washing microtiter plates). Wash solutions commonly contain a physiological buffer to prevent denaturation of antigens and their cognate antibodies, and to preserve enzyme activity. Buffers such as PBS, Tris-saline, or imidizole-buffered saline at neutral pH are widely used. Specific buffers are typically selected based on the method of detection to be employed in a particular assay. Wash buffers should also include non-ionic detergents such as TWEEN 20™, TRITON X-100™, or the like, at concentrations of between 0.01% to 0.05% (v/v), in order to disrupt low-affinity, non-specific interactions between reaction components.

After the blocking step, the wells of the microtiter plate are washed. The adsorbed antigen then undergoes the primary antibody incubation, after which it is washed again. Antibody/antigen complexes are then detected using a secondary antibody labeled with chromogenic (e.g., horseradish peroxidase and TMB), fluorescent or chemiluminescent (e.g., alkaline phosphatase) means. See, e.g., id. at 15-21 (discussing antibody preparation and use, as well as commonly used detection molecules). The amount of color or fluorescence may be measured using a luminometer, a spectrophotometer, or other similar instruments. There are many common variations on the standard ELISA protocol, including competitive ELISA, sandwich ELISA, and numerous others. One of ordinary skill in the art will select the appropriate protocol to use, depending on the antigen to be detected, the source of antigen and/or primary antibody used in the assay, and any other relevant experimental parameters. These and many other permutations will be readily apparent to those of ordinary skill in the art, are considered as equivalents within the scope of the invention.

Screening Methods

Also described is a method that identifies a compound that would decrease the differential expression of at least one gene encoding a protein chosen from SEQ ID NO: 7-SEQ ID NO: 23 and SEQ ID NO: 42-SEQ ID NO: 63 and human orthologs thereof. The method provides a cell expressing at least one of these genes, contacting the cell with a test compound to determine whether the differential expression is decreased in the presence of the test compound, wherein the differential expression is an indication of halting or reversing liver fibrosis and/or cirrhosis. The same method can also identify a compound that would increase the differential expression of at least one gene encoding a protein chosen from SEQ ID NO: 1-SEQ ID NO: 6 and SEQ ID NO: 24-SEQ ID NO: 41 and human orthologs thereof.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

With respect to ranges of values, the invention encompasses the upper and lower limits and each intervening value between the upper and lower limits of the range to at least a tenth of the upper and lower limit's unit, unless the context clearly indicates otherwise. Further, the invention encompasses any other stated intervening values.

Further, all numbers expressing quantities of ingredients, reaction conditions, percent purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

It must be noted that, as used herein and in the appended claims, the singular forms "a," "or," and "the" include plural referents and plural referents include singular forms unless the context clearly dictates otherwise. Thus, for example, reference to "a subject polypeptide" includes a plurality of such polypeptides, reference to "the agent" includes reference to one or more agents and equivalents thereof known to those skilled in the art, reference to "nucleic acid molecules" includes reference to one or more nucleic acid molecules, and reference to "antibodies" includes reference to one or more antibodies and so forth.

The following examples further illustrate the invention. They are merely illustrative of the invention and disclose various beneficial properties of certain embodiments of the invention. The following examples should not be construed as limiting the invention.

EXAMPLES

The practice of the present invention will employ, unless otherwise indicated, conventional techniques for the study of differential gene expression, differential proteomic expression, and histopathology, which are within the level of ordinary skill in the art. Such techniques are explained fully in the applicable literature.

The following examples illustrate the study of the expression of different proteins in liver fibrosis through the use of animal models.

Example 1

Establishment of the Rat Hepatic Fibrosis Model

A rat hepatic fibrosis model was set up through the use of DMN. DMN is a potent hepatoxin that specifically targets the liver and can cause liver fibrosis. The histopathological changes resulting from DMN treatment involve the rapid deposition of collagen, the major protein of fibrosis and important to the process of cirrhosis. DMN-induced liver injury in rats displays many features, such as portal hypertension ascites as well as a number of other histopathological and biochemical abnormalities. Previous study has suggested that DMN-induced liver injury in rats could reflect changes that occur in human hepatic fibrosis and/or cirrhosis and that it is an appropriate animal model for studying human hepatic fibrosis and/or cirrhosis (15). The DMN-induced liver fibrosis model was performed as described in Jezequel A. M. et al. (14). Male Sprague-Dawley rats (Slc:SD; Japan SLC, Shizuoka, Japan), weighing from 300 to 350 grams, were used in the experiments. To induce hepatic fibrosis over a six-week time course experiment, the rats were given DMN (Sigma, Saint Louis, Mo.), dissolved in normal saline, three consecutive days a week for the first three consecutive weeks at the dosage of 6.7 mg/kg per body weight by intraperitoneal injection. Injection time points are shown as inverted triangles in FIG. 1. Injections were at a much lower dosage than those used in other experiments where the dosage was 100 mg/kg/day. The higher dosage can cause toxicity in rat liver (21, 22).)

Two to seven rats at each time point were treated with either DMN or with an equal volume of normal saline without DMN as the control (26 DMN-treated rats and 24 control rats). Rats were weighed and sacrificed on days 11, 18, 25, 32, 39, and 46 (sacrifice time points are shown as triangles in FIG. 1A) respectively. These triangular time points were designated as weeks 1 through 6 (FIG. 1A).

To confirm the establishment of a rat liver fibrosis model, Q-RT-PCR, serum analysis, and histopathological analysis were employed.

Histopathological Examination of DMN-Induced Liver Damage

Liver tissues were immediately removed after sacrifice and subject to histopathological examination. The fixed liver samples were then processed for paraffin embedding. Five micrometer (5 µm) sections were prepared for hematoxylin and eosin staining (to score necroinflammatory and fatty changes) and for Sirius red/fast green collagen staining (to score for fibrosis) (23). The fatty changes were classified as presence (+) or absence (−).

Figure 2A:
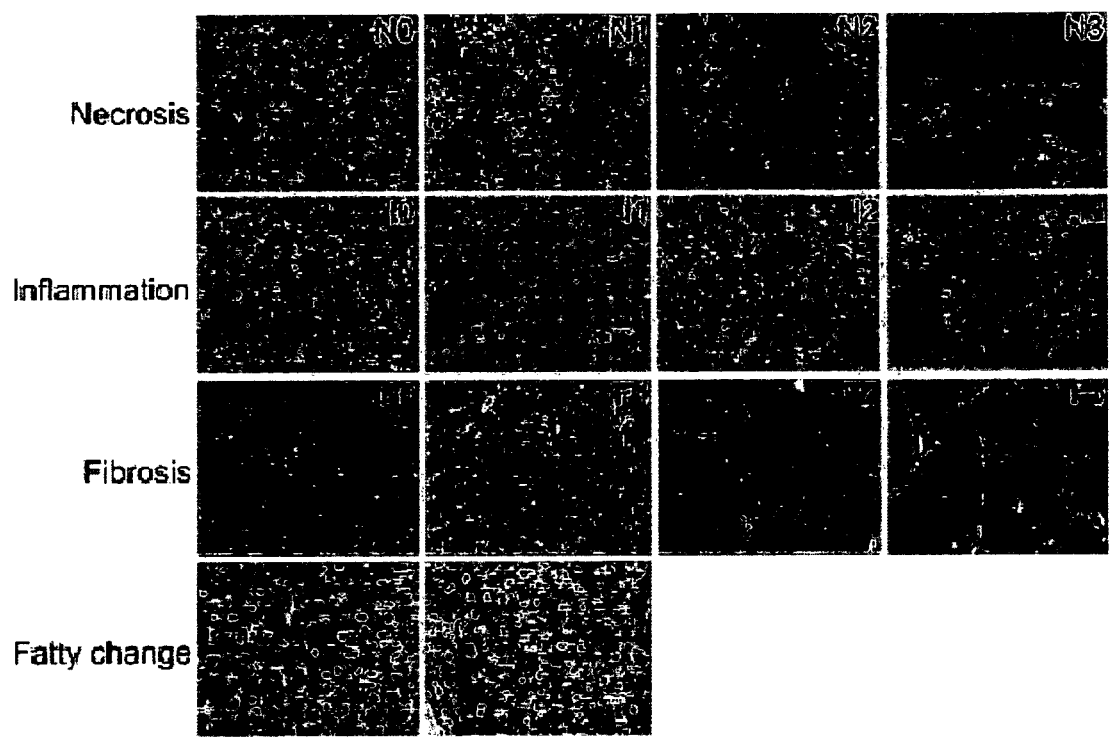
FIG. 2A shows the histopathological examination results of liver tissues from DMN-treated rats. The representative phenotype of the rat liver tissue was characterized by scoring the four histopathological features as follows: the necrosis scores are from N0 to N3 (the first row), the inflammation scores are from I0 to I3 (the second row), the fibrosis scores are from F0 to F3 (the third row), and the fatty change scores are presence or absence (+ and −) in the last row.

Phenotypic changes resulting from DMN-induced liver damage are shown in FIG. 2A. In FIG. 2A, the representative phenotypes of the DMN-induced rat liver fibrosis were characterized by scoring the four histopathological features (necrosis, inflammation, fibrosis, and fatty change) as follows: the necrosis scores were from N0 to N3 (the first panel), and the inflammation scores were from I0 to I3. The scoring system for examining the intensity of liver fibrosis was modified from the scoring system of the Hepatitis Activity Index (HAI) (29, 30). Fibrosis was divided into four scores: normal (F0), fibrous expansion of portal tracts (F1), bridging fibrosis (F2) and frequent bridging fibrosis with focal nodule formation (F3). The fatty change was scored as present (+) or absent (−), respectively (the last panel). The images of the fatty change are shown at 200× magnification, whereas the others are shown at 100× magnification (FIG. 2A).

FIG. 2B shows a summary of histopathological scores for the rat model. The results were ranked by time course. The necroinflammatory scores were the sum of the necrosis and inflammation scores and range from A0 to A6. The necroinflammatory change was divided into three grades: A0=none, A(1-3)=mild and A(4-6)=moderate necroinflammation. The fibrosis change was divided into two grades: F(0-1)=normal to fibrous expansion of portal tracts, F(2-3)=bridge fibrosis to frequent bridging fibrosis with nodule formation. The fatty change was shown as presence (+) or absence (−). The number of rats was counted and used to calculate the percentage of each histopathological level at each time point.

As shown in FIG. 2B, seventy-five percent of the DMN-treated rats had none (F0) or low levels of fibrosis (F1) in the first two weeks. By the third to fourth week, nearly 90% of the DMN-treated rats had high levels of fibrosis, from bridging fibrosis (F2) to frequent bridging fibrosis with focal nodule formation (F3). In the last two weeks, F2 and F3 were still present in 78% of DMN-treated rats. The fatty changes were only present in a few treated rats (3.7%). In contrast, there were no abnormal pathological patterns present in the control group at all. In addition, no clear abnormality was found in the kidney or spleen of the DMN-treated and normal rats (data not shown). Together, the detailed necroinflammatory and fibrosis scoring systems of the process of the DMN-induced liver damage suggest that dramatic necrosis and inflammation took place during early liver damage progression (week 1-4), followed by fibrosis formation at 3-6 weeks. Collagen fiber deposition in rat liver could be observed, along with bile duct proliferation, centrilobular necrosis, bridge fibrosis and fibrosis surrounding the central veins, after three weeks of DMN treatment.

Quantitative Real-Time Polymerase Chain Reaction (Q-RT-PCR)

Figure 1B:
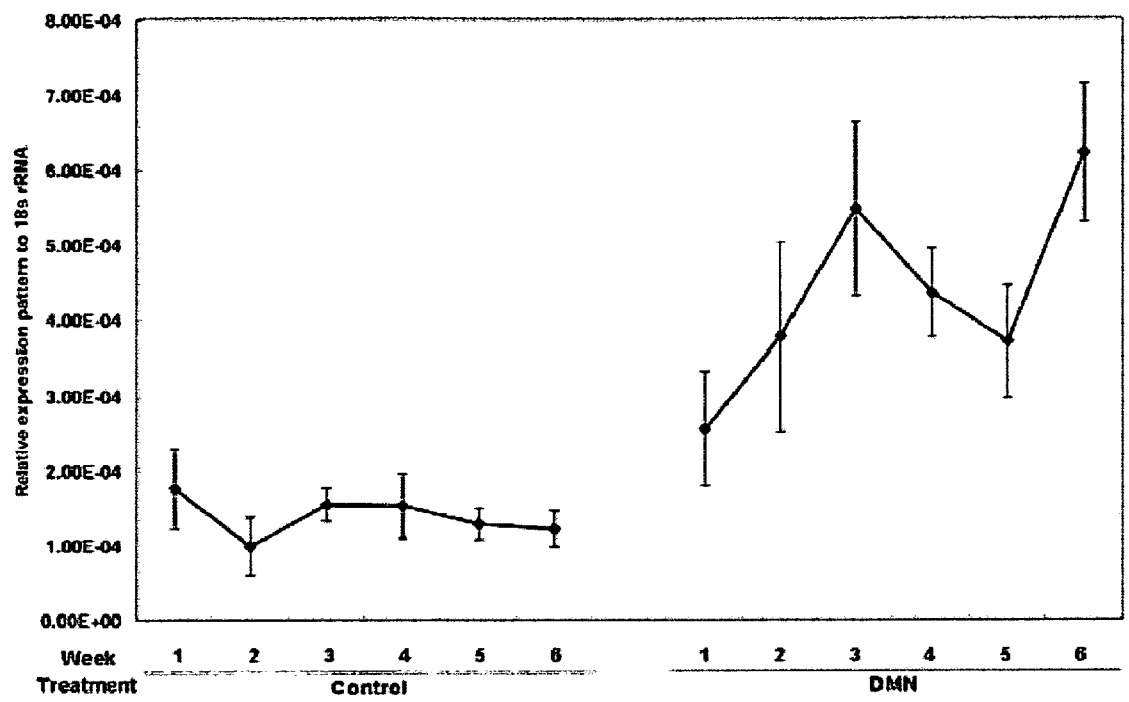
FIG. 1B is the quantitative real-time PCR (Q-RT-PCR) result of Tgfβ1 (transforming growth factor-β1) in DMN-treated rats, showing a higher level of Tgfβ1 expression, the strongest known inducer of fibrogenesis.

To gain additional information about the established animal model, Q-RT-PCR was used to evaluate the gene expression profile of transforming growth factor-1 (Tgfβ1), which is the strongest known inducer of fibrogenesis in the effector cells of hepatic fibrosis that can stimulate the adipocyte transformation (24-27). The same total RNA samples were used for both microarray and Q-RT-PCR analyses. RNA preparation and analysis were performed according to Affymetrix's (Santa Clara, Calif., U.S.A.) instructions. The TAQMAN® assays were conducted in triplicate for each sample, and a mean value was used for calculation of expression levels. To standardize the quantification of the target genes, 18S ribosomal RNA (18S rRNA) from each sample was quantified on the same plate with the target genes. The Q-RT-PCR result showed that a higher level of mRNA expression of Tgfβ1 was observed in DMN-treated rat livers than in the controls (FIG. 1B). The changes were in agreement with observations described in Jezequel A. M. et al. (14). In sum, these examinations support the DMN-induced rat hepatic fibrosis model.

Analysis of Serum Biochemical Data from the DMN-Induced Hepatic Fibrosis Rat Model Experiment The serum of each rat, 50 rats in total, was subjected to various biochemical examinations related to liver damages. Blood samples, collected from the animals at necropsy, were used to measure serum concentrations or activity of albumin, glutamic oxaloacetic transaminase (GOT), glutamic pyruvic transaminase (GPT), total bilirubin, alkaline phosphatase (AKP), acid phosphatases (ACP), α-fetoprotein (AFP), blood urea nitrogen (BUN), cholesterol (CHOL), lactate dehydrogenase (LDH), globulin, prothrombin time (PT) and blood platelets (PLT) using an Hitachi 747 and ACL 3000 clinical chemistry analyzer system (MYCO, Renton, Wash.). When the DMN-treated samples and controls were compared, thirteen serum markers showed significant differences and confirmed the DMN-treated group had suffered liver damage. The biochemical data for the DMN-treated group suggest that there were changes in many serum markers and that the protein expression levels or physical responses are similar to human liver damage phenotypes (1, 2). The thirteen serum markers identified in these experiments are the same serum markers for human liver fibrosis.

Example 2

Establishment of Gene Expression Profile During DMN-Induced Liver Fibrosis

Microarray Analysis

The quality of the total RNA for microarray analysis was determined using Spectra Max Plus (Molecular Devices, Sunnyvale, Calif., U.S.A.) and had an $A_{260}/A_{280}$ ratio ranging from 1.9 to 2.1. Protocols and reagents for hybridization, washing and staining followed Affymetrix's instructions, which may be retrieved from Affymetrix's company website. Labeled cRNA was hybridized to the Affymetrix GeneChip Test 3 Array to verify the quality prior to hybridization to the Affymetrix Rat Genome U34A Array.

Data Analysis and Clustering Algorithm

The microarray images were transformed into text files containing intensity information using GENECHIP® Operating Software (GCOS) developed by ® Affymetrix. The microarray datasets were then analyzed using GENESPRING® 7.2 software (Silicon Genetics, Redwood City, Calif., U.S.A.)

Gene Expression Profiling

Over the six week time course of the experiment, the liver tissues of 12 control animals and 12 DMN-treated rats (2 rats for each time point) were selected to perform microarray experiments. Before any statistical analyses were applied to the microarray data, reproducibility was assessed. Genes were selected as present when they were assigned a present call according to the perfect match (PM)/mismatch (MM) algorithm of Affymetrix in all gene chips (28). Of the 8799 probe sets analyzed, overall expression patterns for 2385 transcripts on the chips were reported to be present (P<0.05). To verify that intra-sample variability did not obscure differences between the controls and DMN-treated groups, as well as to determine the fold-change that should be considered as significant, expression profiles among the 24 control datasets were compared. Scattered graphs of expression levels of the 2385 transcripts represented on the microarray were compared with each other. The relationship between the experimental chips in the microarray analysis was analyzed by linear regression. Overall, there was no statistical difference, with 3.2% of transcripts deviating more than 2-fold. To investigate the time course variability, the reliable signals of these 2385 probe sets between the first and sixth week of controls, were calculated. Again, there was no statistical difference, with 4.6% of transcripts deviating more than 2-fold. In contrast, a significant scatter was found between controls and DMN-treated groups, with 28.7% of transcripts deviating more than 2-fold.

As a first step to minimize the likelihood of false positives, all transcripts were filtered by forming two independent clusters from the microarray data and identifying those that were differentially expressed. For detailed analysis, the first cluster generated 2385 transcripts as previously described. Of these, 268 were differentially expressed transcripts either higher or lower by 1.5 fold or more when comparing the controls and DMN-treated groups. The second method, which used the "detection flag" selection (24), reported 23 transcripts as "present" in the DMN-treated groups but not in the controls. In contrast, there was only one transcript reported "absent" in all DMN-treated groups but "present" in the controls.

Figure 3A:
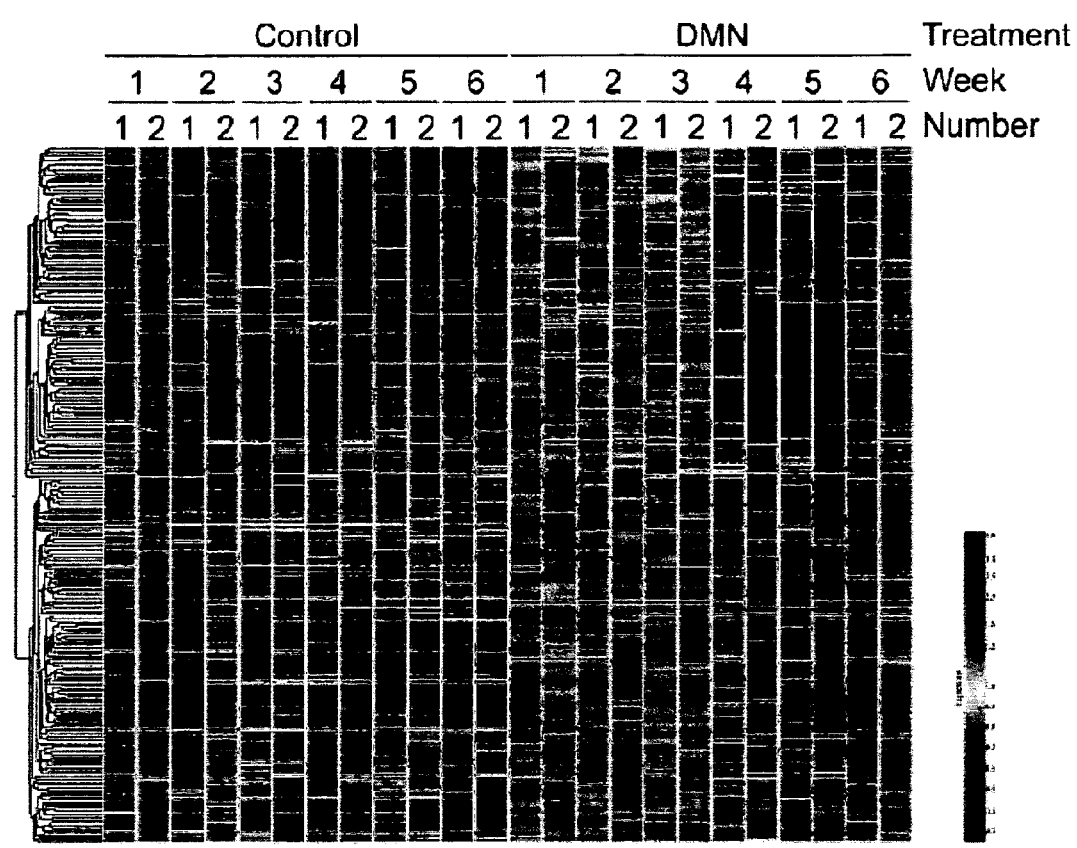
FIG. 3A shows the dendrogram of two hundred and fifty-six (256) gene expression patterns from the DMN-induced fibrosis model in rats.

Altogether, 292 transcripts representing 256 genes, including 137 up-regulated and 119 down-regulated genes, exhibited differentially expressed gene expression patterns when the DMN-treated groups and controls were compared. Hierarchical clustering generated a dendrogram for the gene expression patterns of these 292 transcripts across the 24 samples as shown in FIG. 3A. The rows represent individual transcripts and columns represent time course samples. The color in each cell reflects the expression level of the corresponding tissue, relative to its mean expression level. The scale extends from fluorescence radios of 0.25 to 4 relative to the mean level for all samples.

Quantitative-Real-Time-Reverse-Transcriptase Polymerase Chain Reaction (O-RT-PCR)

To validate the microarray data, Q-RT-PCR analysis was performed for tissue inhibitor of metalloproteinase 1 (Timp1), tissue inhibitor of metalloproteinase 2 (Timp2), matrix metalloproteinase 3 (Mmp3) and gamma-glutamyl transpeptidase (Ggtp). These genes were chosen for validation because these genes occurred both in this GeneChip study and in previous studies.

As determined by Q-RT-PCR, Timp1 (FIG. 3B), Timp2, Mmp3, Ggtp (data not shown) and Tgfβ1 (shown previously in FIG. 1B) were elevated in DMN-treated samples. The results of Q-RT-PCR analysis of these five genes were consistent with previous reports examining these individual markers (8, 9).

Figure 3B:
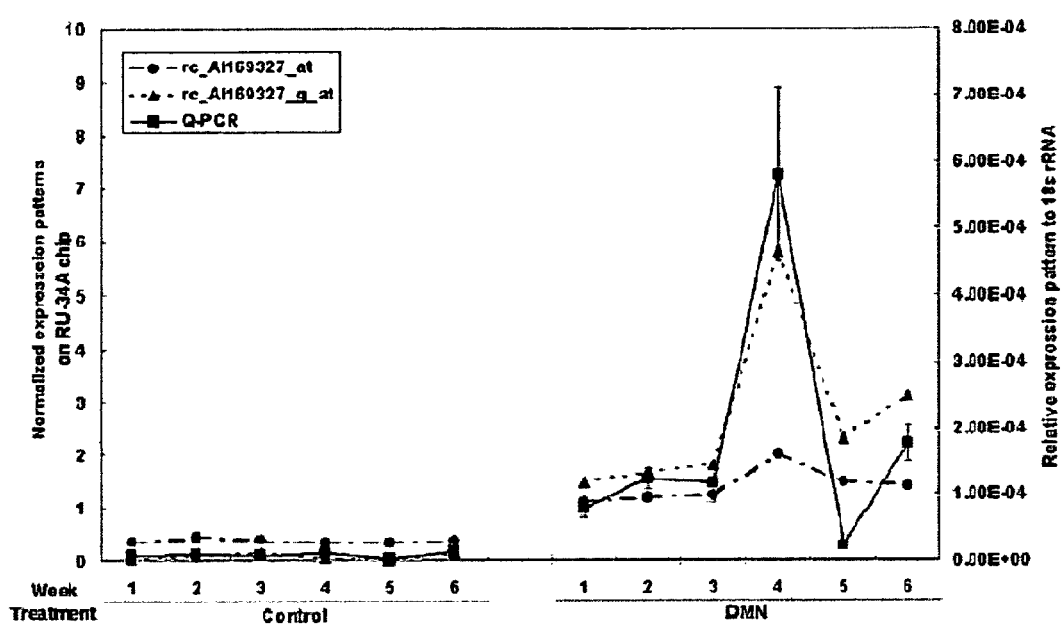
FIG. 3B shows the comparison of Timp1 (tissue inhibitor of metalloproteinase 1) expression between the Q-RT-PCR result and the microarray data, and a good concordance between the two results is shown. For the Q-RT-PCR assay of Timp 1, expression levels (marked by the square) are relative to the mean of all gene expression, and are measured by the log scale on the right side of the plot. The expression levels of two Timp1 transcripts, rc_AI169327_at and rc_AI169327_g_at (marked by circle and triangle), are relative to the mean of all gene expression levels, and are measured by the scale indicated on the left side of the plot.

Moreover, a good concordance based on the fold changes between microarray data and Q-RT-PCR results was observed. As shown in FIG. 3B, Timp1 expression was elevated over 20-fold in DMN-treated rats in both microarray and Q-RT-PCR experiments. TAQMAN® assays were conducted in triplicate for each sample, and a mean value was used for calculation of expression levels (marked by the square). To standardize the quantification of the Timp1 transcript, 18S rRNA from each sample was quantified on the same plate as the target gene, as indicated by the log scale on the right side of plot. The expression levels of the two Timp1 transcripts, rc_AI169327_at and rc_AI169327_g_at (marked by a circle and a triangle, respectively), were set forth relative to the mean of all gene expression levels as indicated by the scale on the left side of plot. The expression pattern of Timp1 was highly correlated between the Q-RT-PCR results and the GeneChip analysis (the Pearson's correlation coefficients were 0.79 and 0.92, respectively) (FIG. 3B), suggesting that the gene expression results were reliable when subject to more detailed analysis.

Fibrosis Candidate Genes

Necroinflammatory and fibrosis have been suggested to play important roles in the progression of liver cirrhosis in the rat model (8, 23, 24, 29, 30). To clarify the factors responsible for the histopathological phenotype, all rat samples were classified by histopathological evaluation with histopathological scores for necroinflammation (A0-A6) and fibrosis (F0-F3) as described earlier in FIG. 2B. The student t-test statistic analysis was used for fibrosis-related genes analysis as it was based on the two-subgroup (F(0-1) and F(2-3)) variation in fibrosis score. A P-value of less than 0.05 was considered to be statistically significant.

Using the student's t-test, the inventors analyzed those 256 genes with expression either higher or lower by 1.5 fold or more in DMN-induced rats than in control rats. A total of 62 differentially expressed genes (32 up regulated and 30 down regulated) between the F(0-1) and F(2-3) level of fibrosis were identified, estimated using only two subgroup variations for the fibrosis score, at the 5% significance level. In agreement with previous studies, three genes, including Timp1, CD63 and annexin A1 (Anxa1), exhibited similar gene expression patterns during liver fibrosis (31-34).

Timp1 is a well-known fibrosis marker and has been proven to play a significant role in the progression of liver fibrosis. In the later stages of liver injury, hepatic stellate cells (HSCs) express a combination of matrix metalloproteinases (MMPs) that have the ability to degrade normal liver matrix, while inhibiting degradation of the fibrillar collagens that accumulate in liver fibrosis. An increase in expression of Timp1 leads to a more global inhibition of degradation of fibrillar liver collagens by interstitial collagenases (MMP-1/MMP-13) (35). As shown in FIG. 3B, expression of Timp1 was elevated more than twenty fold in DMN treated rats in microarray.

CD63, a transmembrane protein, one of the fibrosis gene signatures observed, is also up-regulated after DMN treatment. Following chronic injury, HSCs activate or differentiate into myofibroblast-like cells, acquiring contractile, proinflammatory, and fibrogenic properties. Activated HSCs migrate and accumulate at the sites of tissue repair, secreting large amounts of extracellular matrix proteins during the progression of fibrosis. Activated HSCs have been identified as major collagen-producing cells (collagen is an extracellular matrix protein) and an initiator of liver fibrosis when the liver is injured (7). It has been demonstrated that inhibition of CD63 might be a novel diagnostic marker for the injured liver.

Annexin A1 (Anxa1) is highly expressed after liver injury in an alcoholic liver disease (ALD) study (34). Alcohol initiated liver injury occurs via inflammation. ALD progression involves continuing liver injury, fibrosis, and impaired liver regeneration. It has been suggested that Anxa1 might play a role in the progression of fibrosis.

The fact that the present study agrees with previous studies for the three genes as described above indicated that oligonucleotide microarray analysis is a powerful approach for monitoring molecular events during liver injury and repair where the pathogenesis is unknown. Also, the signature genes identified in this study could discriminate successfully between the low-score and the high-score histopathology groups. Together, the genes would seem to be responsible for fibrosis formation and are possible markers for the detection of fibrosis.

Example 3

Protein Expression Profiling During DMN-Induced Liver Fibrosis

Experiments using iTRAQ tagging were performed to identify differentially expressed proteins in liver fibrosis.

Isobaric Tagging Method: Sample Preparation and Reagent Labeling

The liver tissues of 6 control and 6 DMN-treated rats were used to perform duplicate iTRAQ labeling experiments. Liver tissue was frozen in liquid nitrogen and then pulverized to powder using a mortar and pestle pre-cooled with liquid nitrogen. Then, the liquid nitrogen was allowed to evaporate, and the powdered tissue was separated into tubes and stored at −80° C. Twenty volumes (w/v) of lysis buffer (containing 2% (w/v) SDS in 20 mM phosphate buffer at pH 7.6) was added to the powdered tissue and incubated at room temperature for 1 hour. Samples were centrifuged at 12000 rpm for 10 minutes and the supernatant was taken for acetone precipitation by adding six volumes of cold acetone to the sample tubes. Tubes were incubated at −20° C. until precipitate formed. After decanting the acetone, pellets were resuspended with 0.1% SDS and 6M urea in dissolution buffer (provided by iTRAQ Reagents Kit, Applied Biosystems, Foster City, Calif., U.S.A.).

The total protein contents were determined using the Coomassie Plus Protein Assay Reagent (PIERCE, Rockford, Ill., U.S.A.). Two hundred (200) μg of proteins were taken and diluted by an equal volume (w/v) of dissolution buffer containing 0.1% (w/v) SDS. Proteins were reduced and cysteines blocked as described in the iTRAQ protocol (Applied Biosystems, Foster City, Calif., U.S.A.). Four volumes of dissolution buffer were added to each tube and incubated with 20 μg Trypsin at 37° C. for 16 hours. Tryptic peptides extracted from liver tissue of controls and DMN-treated rats were labeled with iTRAQ 114 and 115, respectively, at each time point of the experiment.

Peptide Separation and Analysis

Peptides with different isobaric tags were pooled and acidified by mixing with 10 mM phosphoric acid (in 25% (v/v) acetonitrile and 75% H.sub.2O) to a total volume of 4.0 mL for strong cation exchange (SCX) chromatography. The resulting sample was injected into a liquid chromatography system (Ettan, GE Healthcare Bio-Science, Umea, Sweden) using a 2.1 mm.×200 mm Polysulfoethyl A column packed with 5 micron 300 Å beads (PolyLC, Columbia, Md., U.S.A.) at a flow rate of 0.08 ml/min. A guard column of the same material was plumbed upstream from the analytical column. The buffers used were 10 mM $KH_2PO_4$, 25% (v/v) acetonitrile at pH 3.0 for buffer A and 10 mM $KH_2PO_4$, 1M KCl, 25% (v/v) acetonitrile at pH 3.0 for buffer B. The elution gradient was changed linearly from 0 to 40% buffer B within 16 mL and then up to 100% buffer B in another 4 mL. A total of 30 fractions were collected and dried by speed vacuuming centrifugation. All the fractions were desalted on PEPCLEAN™ C-18 spin columns (PIERCE, Rockford, Ill., U.S.A.). The desalted peptide from each SCX fraction was dried by speed vacuuming centrifugation and then analyzed by nanoLC hybrid mass spectrometry. The nanoLC system was from LC Packings (Amsterdam, The Netherlands), coupled to an API QSTAR Pulsar Hybrid QqTOF mass spectrometer (Applied Biosystems/MDS Sciex, Foster City, Calif., U.S.A.). Peptide separation was performed using a reversed-phase $C_{18}$ column (75 μm in diameter×15 cm in length, 3 μm particles) with a two-step linear gradient of 5-50% Buffer A over 45 minutes and 50-95% Buffer B over 10 minutes at a flow rate of 0.2.mu.l/minute (Buffer A: 2% (v/v) acetonitrile, 0.1% (w/v) formic acid; Buffer B: 80% (v/v) acetonitrile, 0.1% (w/v) formic acid). The m/z scanning range for MS and tandem MS (MS/MS) were 400-1200 and 75-1500 Da, respectively. MS/MS mass spectra were analyzed in continuous flow mode with a 10 mm I.D. fused silica tip. MS/MS spectra were analyzed against rat.fasta databases from NCBI by Pro-QUANT 2.0 (Applied Biosystems/MDS Sciex, Foster City, Calif., U.S.A.). The accuracy tolerance for peptide identification was 0.5 Da for MS and 0.5 Da for MS/MS, respectively. The cut off for the confidence settings was at 95 and for the score was at 20. Relative quantification of peptide was performed on the MS/MS scans, using ratio of the areas under the peaks. Relative quantification of protein was obtained by averaging the constituted peptides identified.

Figure 4:
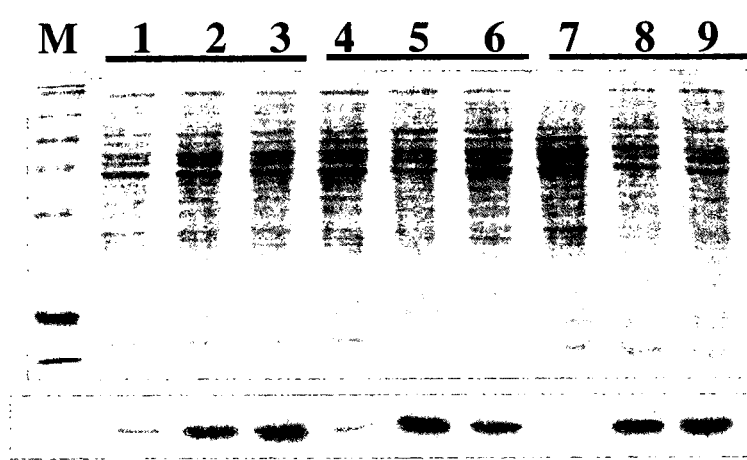
FIG. 4A shows the vimentin expression ratios in DMN-treated and control rats at 2, 4, and 6 weeks as determined by iTRAQ proteomics. Vimentin expression increased 2.4- to 3.4-fold in the liver when rats were treated with DMN.
FIG. 4B shows the result of Western blot analysis of DMN-induced vimentin expression. The observed result matched with the trend measured by mass spectrometry in iTRAQ proteomic experiments.
Figure 5:
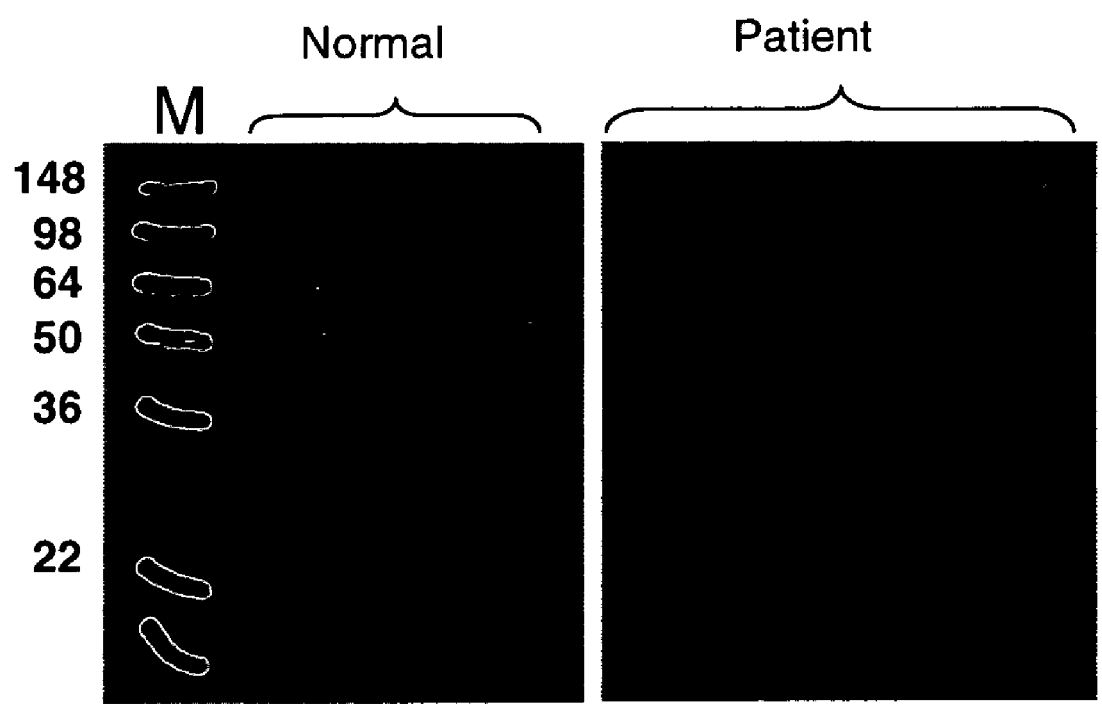
FIG. 5 shows the result of Western blot analysis comparing the expression of carbonic anhydrase I in human sera from normal volunteers and from patients with hepatitis B-related cirrhosis.

To validate the method and results obtained from iTRAQ proteomic studies, the expression changes of vimentin quantified by mass spectrometry in iTRAQ experiments were compared with those obtained through Western blot with anti-vimentin antibody. Proteins were extracted with 2% (w/v) SDS in 20 mM phosphate buffer at pH 7.6 from control and DMN-induced rat livers. After resolving by 12% SDS-PAGE, proteins were transferred to polyvinylidene difluoride membranes and subsequently immunostained with mouse anti-vimentin monoclonal antibody (Chemicon, Temecula, Calif., U.S.A.) for 1 hour, then with horseradish peroxidase-labeled goat anti-rat IgG for another hour. The immunoreactive bands were detected using an enhanced chemiluminescence system (ECL, Perkin-Elmer Life Sciences, Wellesley, Mass., U.S.A.). As demonstrated in FIG. 4, the results observed in Western blots matched the trend as measured by mass spectrometry.

Results

The numbers of distinct peptides identified range from 624-1591 when the confidence threshold was set at 95%. A significant number of these peptides were identified more than once. More than 351 unique proteins were identified in each experiment. Thirty-nine proteins show significant and consistent differences (1.5 fold or more) in protein expression in DMN-treated liver tissue with F2 and F3 fibrosis score compared to control rats. Among these 39 proteins, several have previously been reported to associate with fibrosis formation, including, fibrinogen, and fibronectin.

Fibrinogen was found to be up-regulated in DMN-induced rats in the present study. This is consistent with the results of fibrinogen gene expression in a model $CCl_4$-induced rat liver damage. The $CCl_4$-induced rat liver damage also showed increased fibrinogen mRNA levels and fibrinogen/fibrin deposition during short-term liver injury and liver fibrogenesis. This may suggest that fibrinogen involves a "clotting-like process" in short term liver damage and liver fibrosis (36). Fibronectin consists of two polypeptide chains. It mediates adhesion of collagen, fibrin and heparin to cells and is thus involved in the organization of thrombi and in wound healing by inducing attachment of these structures to cells. Fibronectin and collagen types I and III have been used as a characteristic feature of a liver cirrhotic state in the $CCl_4$-induced liver cirrhosis rat model (37).

In addition, glycine N-methyltransferase (Gnmt), aldolase A(Aldoa), Myosin light polypeptide 6 (Myl6) and, cytoplasmic γ actin, (Actγ)) were identified in both RNA expression microarray and proteomic studies as exhibiting differential expression.

Example 4

Network Analysis

To further refine the genes with differential expression in the fibrotic liver, we carried out network analysis using the Ingenuity Pathway Analysis (IPA) software (Ingenuity Systems, Mountain View, Calif., U.S.A.). The genes, which were identified by microarray and iTRAQ proteomic analyses, were subjected to interacting network analyses. Gene accession numbers were imported into IPA software. These networks described functional relationships between gene products based on known interactions in the literature. The IPA tool then associated these networks with known biologic pathways. Of sixty-two genes identified from the microarray study, forty-two genes fall into 3 groups, i.e., gene networks associated with 1) cancer, cell morphology, and dermatological diseases and conditions; 2) lipid metabolism, small molecule biochemistry, molecular transport; and 3) cancer, cellular movement, cellular growth and profileration. See Table 3A. Twenty-two out of thirty-nine proteins identified in the proteomic study fall into another 3 networks associated with 1) cancer, cell cycle and cell morphology; 2) lipid metabolism, small molecule biochemistry, organismal injury and abnormalities; and 3) hematological disease, endocrine system development and function, nervous system development and function. See Table 3B. Table 3A and 3B list the networks' protein functions and members. Genes identified in the present study are underlined. The underlined genes that have not been reported to associate with liver injury are shown in bold.

Example 5

Clinical Validation of Biomarkers Identified in the DMN-Induced Liver Fibrosis Rat Model with Human Samples To confirm that the biomarkers identified in the DMN-induced liver fibrosis rat model could be used to diagnose liver fibrosis or cirrhosis in humans, we examined expression of the enzyme carbonic anhydrase I (see Table 2, SEQ ID NOS: 11 and 71) in human sera by Western blot analysis. Serum samples (8 ÿl from each patient) from normal volunteers and from patients suffering from hepatitis B-related cirrhosis were first treated to remove the twenty high abundance serum proteins using the PROTEOPREP® 20 Plasma Immunodepletion Kit (Sigma-Aldrich, St. Louis, Mo., U.S.A.). After depletion, the low abundance serum proteins were precipitated with 5 volumes of cold acetone at −20° C. for 2 hours. The protein/acetone mixture was then centrifuged at 12,000 rpm for 10 minutes. The protein pellet was resuspended, separated by electrophoresis on a 12% SDS-PAGE gel, and transferred to polyvinylidene difluoride (PVDF) membranes (Millipore, Billerica, Mass., U.S.A.). After blocking in 5% (w/v) nonfat milk, the membranes were washed with TBST buffer (20 mM Tris-HCl, pH 7.6, 137 mM NaCl, 0.1% (v/v) TWEEN-20) and incubated with goat polyclonal antibody specific for carbonic anhydrase I (Abcam, Cambridge, UK) for 1 hour. The membranes were washed again with TBST buffer and immunostained with horseradish peroxidase-conjugated donkey anti-goat IgG (Jackson ImmunoResearch Laboratories, Pa., U.S.A.). The immunoreactive bands were visualized using an enhanced chemiluminescence system (ECL, Perkin-Elmer Life Sciences, Wellesley, Mass., U.S.A.). The Western blots clearly show that some serum samples from the cirrhosis patients have higher concentrations of carbonic anhydrase I than samples from normal individuals not suffering from cirrhosis. This result confirms that the markers identified in the rat model for liver fibrosis and/or cirrhosis are also associated with liver fibrosis and/or cirrhosis in humans.

REFERENCES

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

1. Friedman, S. L. Molecular regulation of hepatic fibrosis, an integrated cellular response to tissue injury, *J. Biol. Chem.* 275:2247-2250 (2000).
2. Friedman, S. L. Seminars in medicine of the Beth Israel Hospital, Boston. The cellular basis of hepatic fibrosis. Mechanisms and treatment strategies, *N. Engl. J. Med.* 328:1828-1835 (1993).
3. Iredale, J. P. Cirrhosis: new research provides a basis for rational and targeted treatments, *BMJ* 327:143-147 (2003).
4. Okita, K., Sakaida, I., and Hino, K. Current strategies for chemoprevention of hepatocellular carcinoma, *Oncology* 62 Suppl. 1:24-28 (2002).
5. Iizuka, N., Oka, M., Yamada-Okabe, H., Mori, N., Tamesa, T., Okada, T., and Takemoto, N. Differential gene expression in distinct virologic types of hepatocellular carcinoma: association with liver cirrhosis, *Oncogene* 22:3007-3014 (2003).
6. Day, C. P. Non-alcoholic steatohepatitis (NASH): where are we now and where are we going?, *Gut* 50:585-588 (2002).
7. Bataller, R., and Brenner, D. A. Liver fibrosis, *J. Clin. Invest.* 115:209-218 (2005).
8. Friedman, S. L. Liver fibrosis—from bench to bedside, *J. Hepatol.* 38 Suppl. 1:S38-53 (2003).
9. Hayasaka, A., and Saisho, H. Serum markers as tools to monitor liver fibrosis, *Digestion* 59:381-384 (1998).
10. Hippo, Y., Taniguchi, H., Tsutsumi, S., Machida, N., Chong, J.-M., and Fukayama, M. Global gene expression analysis of gastric cancer by oligonucleotide microarrays, *Cancer Res.* 62:233-240 (2002).
11. Ji, J., Chen, X., Leung, S. Y., Chi, J.-T. A., Chu, K. M., and Yuen, S. T. Comprehensive analysis of the gene expression profiles in human gastric cancer cell lines, *Oncogene* 21:6549-6556 (2002).
12. Wright, M. E., Han, D. K., and Aebersold, R. Mass spectrometry-based expression profiling of clinical prostate cancer, *Mol. Cell. Proteomics* 4(4):545-54 (2005).
13. Nielsen, P. E., Egholm, M., Berg, R. H., and Buchardt, O. Sequence-selective recognition of DNA by strand displacement with a thymine-substituted polyamide, *Science.* 254(5037): 1497-500 (1991).
14. Jezequel, A. M., Mancini, R., Rinaldesi, M. L., Macarri, G., Venturini, C., and Orlandi, F. A morphological study of the early stages of hepatic fibrosis induced by low doses of dimethylnitrosamine in the rat, *J. Hepatol.* 5:174-181 (1987).
15. George, J., Rao, K. R., Stern, R., and Chandrakasan, G. Dimethylnitrosamine-induced liver injury in rats: the early deposition of collagen, *Toxicol.* 156:129-138 (2001).
16. DeSouza, L., Diehl, G., Rodrigues, M. J., Guo, J., Romaschin, A. D., Colgan, T. J., and Siu, K. W. Search for cancer markers from endometrial tissues using differentially labeled tags iTRAQ and cICAT with multidimensional liquid chromatography and tandem mass spectrometry, *J. Proteome Res.* 4(2):377-86 (2005).
17. Mirsalis, J. C., and Butterworth, B. E. Detection of unscheduled DNA synthesis in hepatocytes isolated from rats treated with genotoxic agents: an in vivo-in vitro assay for potential carcinogens and mutagens, *Carcinogenesis* 1:621-625 (1980).
18. Haggerty, H. G., and Holsapple, M. P. Role of metabolism in dimethylnitrosamine-induced immunosuppression: a review, *Toxicol.* 63:1-23 (1990).
19. Ala-Kokko, L., Pihlajaniemi, T., Myers, J. C., Kivirikko, K. I., and Savolainen, E. R. Gene expression of type I, III and IV collagens in hepatic fibrosis induced by dimethylnitrosamine in the rat, *Biochem. J.* 244:75-79 (1987).
20. Coligen, J. E. *Current Protocols in Immunology*, Volumes 1 and 2, (Wiley-Interscience, New York, N.Y., 1991).
21. Waring, J. F., Jolly, R. A., Ciurlionis, R., Lum, P. Y., Praestgaard, J. T., Morfitt, D. C., and Buratto, B. Clustering of hepatotoxins based on mechanism of toxicity using gene expression profiles, *Toxicol. Appl. Pharmacol.* 175:28-42 (2001).
22. Waring, J. F., Ciurlionis, R., Jolly, R. A., Heindel, M., and Ulrich, R. G. Microarray analysis of hepatotoxins in vitro reveals a correlation between gene expression profiles and mechanisms of toxicity *Toxicol. Lett.* 120:359-368 (2001).
23. Lopez-De Leon, A., and Rojkind, M. A simple micromethod for collagen and total protein determination in formalin-fixed paraffin-embedded sections, *J. Histochem. Cytochem.* 33:737-743 (1985).
24. Schuppan, D., Krebs, A, Bauer, M., and Hahn, E. G. Hepatitis C and liver fibrosis, *Cell Death Differ.* 10 Suppl. 1:S59-67 (2003).
25. Gressner, A. M., Weiskirchen, R., Breitkopf, K., and Dooley, S. Roles of TGF-β in hepatic fibrosis, *Front. Biosci.* 7:d793-807 (2002).
26. Bauer, M., and Schuppan, D. TGFβ1 in liver fibrosis: time to change paradigms?, *FEBS Lett.* 502:1-3 (2001).
27. Dooley, S., Delvoux, B., Streckert, M., Bonzel, L., Stopa, M., ten Dijke, P., and Gressner, A. M. Transforming growth factor beta signal transduction in hepatic stellate cells via Smad2/3 phosphorylation, a pathway that is abrogated during in vitro progression to myofibroblasts. TGFβ signal transduction during transdifferentiation of hepatic stellate cells, *FEBS Lett.* 502:4-10 (2001).
28. Marvanova, M., Menager, J., Bezard, E., Bontrop, R. E., Pradier, L., and Wong, G. Microarray analysis of nonhuman primates: validation of experimental models in neurological disorders, *FASEB J.* 17:929-931 (2003).
29. Knodell, R. G., Ishak, K. G., Black, W. C., Chen, T. S., Craig, R., Kaplowitz, N., and Kiernan, T. W. Formulation and application of a numerical scoring system for assessing histological activity in asymptomatic chronic active hepatitis, *Hepatol.* 1:431-435 (1981).
30. Ishak, K., Baptista, A., Bianchi, L., Callea, F., De Groote, J., Gudat, F., and Denk, H., et al. Histological grading and staging of chronic hepatitis, *J. Hepatol.* 22:696-699 (1985).
31. Iredale, J. P. Tissue inhibitors of metalloproteinases in liver fibrosis, *Int. J. Biochem. Cell Biol.* 29:43-54 (1997).

32. Arthur, M. J., Mann, D. A., and Iredale, J. P. Tissue inhibitors of metalloproteinases, hepatic stellate cells and liver fibrosis, *J. Gastroenterol. Hepatol.* 13 Suppl.:S33-38 (1998).
33. Mazzocca, A., Carloni, V., Sciammetta, S., Cordella, C., Pantaleo, P., Caldini, A., and Gentilini, P. Expression of transmembrane 4 superfamily (TM4SF) proteins and their role in hepatic stellate cell motility and wound healing migration, *J. Hepatol.* 37:322-330 (2002).
34. Seth, D., Leo, M. A., McGuinness, P. H., Lieber, C. S., Brennan, Y., Williams, R., and Wang, X. M., Gene expression profiling of alcoholic liver disease in the baboon (*Papio hamadryas*) and human liver, *Am. J. Pathol.* 163:2303-2317 (2003).
35. Benyon, R. C. and Arthur, M. J. Extracellular matrix degradation and the role of hepatic stellate cells, *Semin. Liver Dis.* 21(3):373-84 (2001).
36. Neubauer, K., Knittel, T., Armbrust, T., and Ramadori, G. Accumulation and cellular localization of fibrinogen/fibrin during short-term and long-term rat liver injury, *Gastroenterol.* 108(4):1124-35 (1995).
37. Hernandez-Munoz, R., Diaz-Munoz, M., Suarez-Cuenca, J. A., Trejo-Solis, C., Lopez, V., Sanchez-Sevilla, L., Yanez, L., De Sanchez, V. C. Adenosine reverses a preestablished $CCl_4$-induced micronodular cirrhosis through enhancing collagenolytic activity and stimulating hepatocyte cell proliferation in rats, *Hepatol.* 34(4 Pt 1):677-87 (2001).
38. Morgan et al., "The Matrix Effects on Kinetic Rate Constants of Antibody-Antigen Interactions Reflect Solvent Viscosity," *J. Immunol. Meth.* 217:51-60 (1998).
39. Zhuang et al., "Measurement of Association Rate Constant of Antibody-Antigen Interactions in Solution Based on Enzyme-Linked Immunosorbent Assay," *J. Biosci. Bioeng.* 92(4):330-336 (2001).
40. Strauss, W. M. "Hybridization With Radioactive Probes," in Current Protocols in Molecular Biology 6.3.1-6.3.6, (John Wiley & Sons, N.Y. 2000).
41. SAMBROOK ET AL., 3 MOLECULAR CLONING: A LABORATORY MANUAL A8.40-A8.45, and A8.52-A8.55 (2001).

TABLE 1

Clinical, chemical and fibrosis parameters in treated and untreated groups of rats

| Numeric variable | control | | | DMN-treatment | | |
|---|---|---|---|---|---|---|
| | 1-2 wk (n)[a] | 3-4 wk (n)[a] | 5-6 wk (n)[a] | 1-2 wk (n)[a] | 3-4 wk (n)[a] | 5-6 wk (n)[a] |
| Albumin (g/dl) | 4.4 ± 0.4 (7) | 4.6 ± 0.2 (8) | 4.7 ± 0.2 (8) | 3.9 ± 0.7 (7) | 3.5 ± 0.6 (11) | 3.2 ± 0.1 (7) |
| GPT (U/l) | 61.1 ± 26.7 (8) | 65.9 ± 19.7 (7) | 50.3 ± 4.9 (8) | 459.5 ± 78.5 (8) | 566.6 ± 313.5 (11) | 763.6 ± 405.2 (7) |
| GOT (U/l) | 110.3 ± 37.6 (8) | 84.0 ± 23.5 (7) | 109.1 ± 23.5 (8) | 661.5 ± 134.4 (8) | 1006.1 ± 749.6 (11) | 1572.9 ± 965.3 (7) |
| Bilirubin (mg/dl) | 0.13 ± 0.05 (8) | 0.10 ± 0.01 (8) | 0.13 ± 0.05 (8) | 0.72 ± 0.53 (8) | 1.01 ± 0.74 (11) | 1.13 ± 1.00 (7) |
| AKP (KA) | 46.0 ± 3.7 (4) | 44.8 ± 2.2 (4) | 47.0 ± 13.6 (4) | 600.8 ± 93.0 (4) | 668.3 ± 222.0 (3) | 468 ± 12.7 (2) |
| LDH (IU/l) | 262.3 ± 75.1 (4) | 289.3 ± 31.7 (3) | 292.3 ± 31.3 (4) | 414.8 ± 102.7 (4) | 562.0 ± 120.8 (3) | 853.5 ± 91.2 (2) |
| Globulin (g/dl) | 6.9 ± 0.3 (3) | 6.9 ± 0.5 (4) | 7.3 ± 0.2 (4) | 6.7 ± 0.1 (2) | 5.0 ± 0.8 (4) | 3.6 ± 0.3 (2) |
| AFP (ng/dl) | 0.32 ± 0.04 (4) | 0.2 ± 0.01 (2) | 0.24 ± 0.03 (4) | 0.40 ± 0.19 (4) | 0.38 ± 0.05 (4) | 0.35 ± 0.07 (2) |
| CHOL (mg/dl) | 88 ± 5 (4) | 71 ± 20 (4) | 91 ± 5 (4) | 77 ± 8 (4) | 70 ± 13 (6) | 67 ± 18 (5) |
| BUN (mg/dl) | 31 ± 2 (4) | 25 ± 6 (4) | 26 ± 9 (4) | 33 ± 4 (4) | 36 ± 2 (4) | 31 ± 5 (2) |
| ACP (mg/dl) | 2.3 ± 0.8 (4) | 2.6 ± 0.5 (4) | 2.3 ± 0.8 (4) | 1.9 ± 0.6 (4) | 6.2 ± 1.1 (4) | 8.2 ± 0.6 (2) |
| PT (sec) | 14 ± 1 (7) | 13 ± 1 (8) | 13 ± 1 (7) | 18 ± 4 (8) | 20 ± 4 (9) | 22 ± 5 (6) |
| PLT ($10^3$/−1) | 741 ± 245 (8) | 981 ± 124 (8) | 893 ± 109 (8) | 407 ± 72 (7) | 300 ± 165 (11) | 229 ± 302 (7) |

GPT, glutamic pyruvic transaminase;
GOT, glutamic oxaloacetic transaminase;
Bilirubin, total bilirubin;
AKP, alkaline phosphatase;
LDH, lactate dehydrogenase;
AFP, a-fetoprotein;
CHOL, cholesterol;
BUN, blood urea nitrogen;
ACP, acid phosphatase;
PT, prothrombin time;
PLT, blood platelets.
[a]Mean ± SD of value from 1-2, 3-4 or 5-6 week in treated and untreated groups.

TABLE 2

The 63 selected genes and their human orthologs

| ID | Method | Expression | Protein name-Rat | Official Symbol | Gene ID | ID | Human orthologs-name | Official Symbol | Human Homolog GeneID |
|---|---|---|---|---|---|---|---|---|---|
| SEQ ID NO: 1 | Proteomics | down | cytochrome P450, family 2, subfamily c, polypeptide 23 | Cyp2c23 | 83790 | | | | — |
| SEQ ID NO: 2 | Proteomics | down | cytochrome P450, family 2, subfamily d, polypeptide 13 | Cyp2d13 | 24303 | | | | — |
| SEQ ID NO: 3 | Proteomics | down | fatty acid synthase | Fasn | 50671 | SEQ ID NO: 64 | fatty acid synthase | FASN | 2194 |

TABLE 2-continued

The 63 selected genes and their human orthologs

| ID | Method | Expression | Protein name-Rat | Official Symbol | Gene ID | ID | Human orthologs-name | Official Symbol | Human Homolog GeneID |
|---|---|---|---|---|---|---|---|---|---|
| SEQ ID NO: 4 | Proteomics | down | hydroxysteroid (17-beta) dehydrogenase 2 | Hsd17b2 | 79243 | SEQ ID NO: 65 | hydroxysteroid (17-beta) dehydrogenase 2 | HSD17B2 | 3294 |
| SEQ ID NO: 5 | Proteomics | down | Estrogen sulfotransferase, isoform 2 | Ste2 | — | SEQ ID NO: 66 | sulfotransferase, estrogen-preferring | SULT1E1 | 6783 |
| SEQ ID NO: 6 | Proteomics | down | similar to cDNA sequence BC022133 | | 362399 | SEQ ID NO: 67 | ZXD family zinc finger C | ZXDC | 79364 |
| SEQ ID NO: 7 | Proteomics | up | S100 calcium binding protein A9 (calgranulin B) | S100a9 | 94195 | SEQ ID NO: 68 | S100 calcium-binding protein A9 | S100A9 | 6280 |
| SEQ ID NO: 8 | Proteomics | up | actin, gamma, cytoplasmic | Actg(Actg1) | 287876 | — | — | | — |
| SEQ ID NO: 9 | Proteomics | up | aldehyde dehydrogenase family 1, member A1 | Aldh1a1 | 24188 | SEQ ID NO: 69 | aldehyde dehydrogenase 1A1 | ALDH1A1 | 216 |
| SEQ ID NO: 10 | Proteomics | up | Rho GDP dissociation inhibitor (GDI) alpha | Arhgdia | 360678 | SEQ ID NO: 70 | Rho GDP dissociation inhibitor (GDI) alpha | ARHGDIA | 396 |
| SEQ ID NO: 11 | Proteomics | up | carbonic anhydrase I (predicted) | Ca1_predicted | 310218 | SEQ ID NO: 71 | carbonic anhydrase I | CA1 | 759 |
| SEQ ID NO: 12 | Proteomics | up | carbonic anhydrase 2 | Ca2 | 54231 | SEQ ID NO: 72 | carbonic anhydrase II | CA2 | 760 |
| SEQ ID NO: 13 | Proteomics | up | cytochrome P450 2c13 | Cyp2c13 | 171521 | — | — | | — |
| SEQ ID NO: 14 | Proteomics | up | thyroid autoantigen | G22p1 | 25019 | SEQ ID NO: 73 | ATP-dependent DNA helicase II, 70 kDa subunit | XRCC6 | 2547 |
| SEQ ID NO: 15 | Proteomics | up | myosin, heavy polypeptide 9 | Myh9 | 25745 | SEQ ID NO: 74 | myosin, heavy polypeptide 9, non-muscle | MYH9 | 4627 |
| SEQ ID NO: 16 | Proteomics | up | Myosin light polypeptide 6 | Myl6 | — | SEQ ID NO: 75 | similar to Myosin light polypeptide 6 (Myosin light chain alkali 3) (Myosin light chain 3) (MLC-3) (LC17) | | 124685 |
| SEQ ID NO: 17 | Proteomics | up | prosaposin | Psap | 25524 | SEQ ID NO: 76 | prosaposin | PSAP | 5660 |
| SEQ ID NO: 18 | Proteomics | up | similar to Myosin regulatory light chain 2-A, smooth muscle isoform (Myosin RLC-A) (predicted) | RGD1309537_predicted | 501203 | SEQ ID NO: 77 | myosin regulatory light chain MRCL3 | | 10627 |
| SEQ ID NO: 19 | Proteomics | up | solute carrier family 4, member 1 | Slc4a1 | 24779 | SEQ ID NO: 78 | solute carrier family 4, anion exchanger, member 1 (erythrocyte membrane protein band 3, Diego blood group) | SLC4A1 | 6521 |
| SEQ ID NO: 20 | Proteomics | up | transgelin 2 (predicted) | Tagln2 | 304983 | SEQ ID NO: 79 | transgelin 2 | TAGLN2 | 8407 |

TABLE 2-continued

The 63 selected genes and their human orthologs

| ID | Method | Expression | Protein name-Rat | Official Symbol | Gene ID | ID | Human orthologs-name | Official Symbol | Human Homolog GeneID |
|---|---|---|---|---|---|---|---|---|---|
| SEQ ID NO: 21 | Proteomics | up | tropomyosin 3, gamma | Tpm3 | 117557 | SEQ ID NO: 80 | tropomyosin 3 | TPM3 | 7170 |
| SEQ ID NO: 22 | Proteomics | up | talin | Tln | 313494 | SEQ ID NO: 81 | talin 1 | TLN1 | 7094 |
| SEQ ID NO: 23 | Proteomics | up | similar to hypothetical protein D4Ertd765e (predicted) | RGD1308525_predicted | 298381 | SEQ ID NO: 82 | enoyl Coenzyme A hydratase domain containing 2 | ECHDC2 | 55268 |
| SEQ ID NO: 24 | Microarray | down | aminoadipate aminotransferase | Aadat | 29416 | SEQ ID NO: 83 | alpha-aminoadipate aminotransferase | AADAT | 51166 |
| SEQ ID NO: 25 | Microarray | down | acyl-CoA synthetase long-chain family member 1 | Acsl1 | 25288 | SEQ ID NO: 84 | acyl-CoA synthetase long-chain family member 1 | ACSL1 | 2180 |
| SEQ ID NO: 26 | Microarray | down | aldehyde dehydrogenase 1 family, member L1 | Fthfd | 64392 | SEQ ID NO: 85 | aldehyde dehydrogenase 1 family, member L1 | ALDH1L1 | 10840 |
| SEQ ID NO: 27 | Microarray | down | arginosuccinate synthetase | Ass | 25698 | SEQ ID NO: 86 | argininosuccinate synthetase | ASS | 445 |
| SEQ ID NO: 28 | Microarray | down | dimethylglycine dehydrogenase | Dmgdh | 245961 | SEQ ID NO: 87 | dimethylglycine dehydrogenase | DMGDH | 29958 |
| SEQ ID NO: 29 | Microarray | down | dihydropyrimidinase | Dpys | 65135 | SEQ ID NO: 88 | dihydropyrimidinase | DPYS | 1807 |
| SEQ ID NO: 30 | Microarray | down | phosphodiesterase I/nucleotide pyrophosphatase 2 | Enpp2 | 84050 | SEQ ID NO: 89 | ectonucleotide pyrophosphatase/ phosphodiesterase 2 (autotaxin) | ENPP2 | 5168 |
| SEQ ID NO: 31 | Microarray | down | fatty acid amide hydrolase | Faah | 29347 | SEQ ID NO: 90 | fatty acid amide hydrolase | FAAH | 2166 |
| SEQ ID NO: 32 | Microarray | down | guanidinoacetate methyltransferase | Gamt | 25257 | SEQ ID NO: 91 | guanidinoacetate N-methyltransferase | GAMT | 2593 |
| SEQ ID NO: 33 | Microarray | down | L-gulono-gamma-lactone oxidase | Gulo | 60671 | — | — | | |
| SEQ ID NO: 34 | Microarray | down | 3-hydroxyisobutyrate dehydrogenase | Hibadh | 63938 | SEQ ID NO: 92 | 3-hydroxyisobutyrate dehydrogenase | HIBADH | 11112 |
| SEQ ID NO: 35 | Microarray | down | ketohexokinase | Khk | 25659 | SEQ ID NO: 93 | ketohexokinase | KHK | 3795 |
| SEQ ID NO: 36 | Microarray | down | kynureninase (L-kynurenine hydrolase) | Kynu | 116682 | SEQ ID NO: 94 | kynureninase (L-kynurenine hydrolase) | KYNU | 8942 |
| SEQ ID NO: 37 | Microarray | down | Pyruvate carboxylase | Pc | 25104 | SEQ ID NO: 95 | pyruvate carboxylase | PC | 5091 |
| SEQ ID NO: 38 | Microarray | down | pyruvate dehydrogenase kinase 2 subunit p45 (PDK2) | Pdk2 | 81530 | SEQ ID NO: 96 | pyruvate dehydrogenase kinase, isoenzyme 2 | PDK2 | 5164 |

TABLE 2-continued

The 63 selected genes and their human orthologs

| ID | Method | Expression | Protein name-Rat | Official Symbol | Gene ID | ID | Human orthologs-name | Official Symbol | Human Homolog GeneID |
|---|---|---|---|---|---|---|---|---|---|
| SEQ ID NO: 39 | Microarray | down | solute carrier family 10, member 1 | Slc10a1 | 24777 | SEQ ID NO: 97 | solute carrier family 10 (sodium/bile acid cotransporter family), member 1 | SLC10A1 | 6554 |
| SEQ ID NO: 40 | Microarray | down | solute carrier family 37 (glycerol-6-phosphate transporter), member 4 | Slc37a4 | 29573 | SEQ ID NO: 98 | solute carrier family 37 (glycerol-6-phosphate transporter), member 4 | SLC37A4 | 2542 |
| SEQ ID NO: 41 | Microarray | down | similar to Sulfotransferase K2 (rSULT1C2A) | — | 501086 | SEQ ID NO: 99 | sulfotransferase family, cytosolic, 1C, member 1 | SULT1C1 | 6819 |
| SEQ ID NO: 42 | Microarray | up | arachidonate 5-lipoxygenase activating protein | Alox5ap | 29624 | SEQ ID NO: 100 | arachidonate 5-lipoxygenase-activating protein | ALOX5AP | 241 |
| SEQ ID NO: 43 | Microarray | up | adenine phosphoribosyl transferase (predicted) | Aprt_predicted | 292072 | SEQ ID NO: 101 | adenine phosphoribosyl-transferase | APRT | 353 |
| SEQ ID NO: 44 | Microarray | up | brain abundant, membrane attached signal protein 1 | Basp1 | 64160 | SEQ ID NO: 102 | brain abundant, membrane attached signal protein 1 | BASP1 | 10409 |
| SEQ ID NO: 45 | Microarray | up | benzodiazepin receptor | Bzrp | 24230 | SEQ ID NO: 103 | peripheral benzodiazapine receptor | BZRP | 706 |
| SEQ ID NO: 46 | Microarray | up | carbonyl reductase | Cbr1 | 29224 | SEQ ID NO: 104 | carbonyl reductase 1 | CBR1 | 873 |
| SEQ ID NO: 47 | Microarray | up | CD47 antigen (Rh-related antigen, integrin-associated signal transducer) | Cd47 | 29364 | SEQ ID NO: 105 | CD47 antigen | CD47 | 961 |
| SEQ ID NO: 48 | Microarray | up | embigin | Emb | 114511 | SEQ ID NO: 106 | embigin homolog | EMB | 133418 |
| SEQ ID NO: 49 | Microarray | up | myeloid differentiation primary response gene 116 | Myd116 | 171071 | SEQ ID NO: 107 | protein phosphatase 1, regulatory subunit 15A | PPP1R15A | 23645 |
| SEQ ID NO: 50 | Microarray | up | N-myc downstream regulated gene 2 | Ndrg2 | 171114 | SEQ ID NO: 108 | N-myc downstream-regulated gene 2 | NDRG2 | 57447 |
| SEQ ID NO: 51 | Microarray | up | expressed in non-metastatic cells 1, protein (NM23A) (nucleoside diphosphate kinase) | Nme1 | 191575 | SEQ ID NO: 109 | non-metastatic cells 1, protein (NM23A) expressed in | NME1 | 4830 |
| SEQ ID NO: 52 | Microarray | up | neuregulin 1 | Nrg1 | 112400 | SEQ ID NO: 110 | neuregulin 1 | NRG1 | 3084 |
| SEQ ID NO: 53 | Microarray | up | oxidized low density lipoprotein (lectin-like) receptor 1 | Oldlr1 | 140914 | SEQ ID NO: 111 | oxidised low density lipoprotein (lectin-like) receptor 1 | OLR1 | 4973 |
| SEQ ID NO: 54 | Microarray | up | protein tyrosine kinase 9 | Ptk9 | 315265 | SEQ ID NO: 112 | twinfilin-like protein | PTK9L | 11344 |
| SEQ ID NO: 55 | Microarray | up | syndecan binding protein | Sdcbp | 83841 | SEQ ID NO: 113 | syntenin | SDCBP | 6386 |
| SEQ ID NO: 56 | Microarray | up | serine protease inhibitor, Kazal type 1 | Spink1 | 24833 | SEQ ID NO: 114 | serine protease inhibitor, Kazal type 1 | SPINK1 | 6690 |

TABLE 2-continued

The 63 selected genes and their human orthologs

| ID | Method | Expression | Protein name-Rat | Official Symbol | Gene ID | ID | Human orthologs-name | Official Symbol | Human Homolog GeneID |
|---|---|---|---|---|---|---|---|---|---|
| SEQ ID NO: 57 | Microarray | up | tyrosine 3/tryptophan 5-monooxygenase activation protein, eta polypeptide | Ywhah | 25576 | SEQ ID NO: 115 | tyrosine 3/tryptophan 5-monooxygenase activation protein, eta polypeptide | YWHAH | 7533 |
| SEQ ID NO: 58 | Microarray | up | S100 calcium binding protein A10 | S100a10 | 81778 | SEQ ID NO: 116 | S100 calcium-binding protein A10 | S100A10 | 6281 |
| SEQ ID NO: 59 | Microarray | up | B-cell translocation gene 2 | Btg2 | 29619 | SEQ ID NO: 117 | B-cell translocation gene 2 | BTG2 | 7832 |
| SEQ ID NO: 60 | Microarray | up | 3'-phosphoadenosine 5'-phosphosulfate synthase 2 (predicted) | Papss2_predicted | 294103 | SEQ ID NO: 118 | 3'-phosphoadenosine 5'-phosphosulfate synthase 1 | PAPSS1 | 9061 |
| SEQ ID NO: 61 | Microarray | up | biogenesis of lysosome-related organelles complex-1, subunit 2 | Bloc1s2 | 293938 | SEQ ID NO: 119 | biogenesis of lysosome-related organelles complex-1, subunit 2 | BLOC1S2 | 282991 |
| SEQ ID NO: 62 | Microarray | up | Similar to RIKEN cDNA 6720467C03 (predicted) | RGD1310681_predicted | 297903 | | — | | — |
| SEQ ID NO: 63 | Microarray | up | transformed mouse 3T3 cell double minute 2 (predicted) | Mdm2_predicted | 314856 | SEQ ID NO: 120 | mouse double minute 2 homolog | MDM2 | 4193 |

TABLE 3A

Interacting network analysis of proteins selected from microarray study

| | Genes* | Top functions |
|---|---|---|
| 1 | ACTG1, ADARB1, AHCY, AKT1, ALDOA, BASP1, BZRP, CD63, Crisp1 (MGI: 102553), EMB, FAAH, GLI1, GNMT, HRAS, IFNG, KHK, KRT18, MYC, MYCN, NDRG2, NME1, OTC, PPARA, RHOB, RPL23, RPL27, RPL35, RPL38, RPL41, Rpm12, RPS16, RPS27, RT1-A, SARDH, SLC37A4 | Cancer, Cell Morphology, Dermatological Diseases and Conditions |
| 2 | ACSL1, ALOX5AP, ANXA1, ASS, ATF3, CD47, CIDEC, CP, DF, FABP1, GPD1, HOXA11, KYNU, MMP16, MTP, MYL6, OLR1, PC, PDK2, PF4, PLIN, PLP1, PPARG, PPP1R15A, PROC, PTGES, RGS7, SLC27A1, SPHK1, TIMP1, TNF, UBQLN2, UCP2, UCP3, Wap | Lipid Metabolism, Small Molecule Biochemistry, Molecular Transport |
| 3 | ACO2, AKR1B10, BTG2, CBR1, DAD1, DUSP5, ELF3, ENPP2, FGF2, GBP1, GLG1, GPI, GRIN2C, HSPA1A, IGFALS, IL1B, JUN, KCNH2, MAOB, MT1L, MT2A, NR3C1, NRG1, P53AIP1, PHKG1, S100A10, SDCBP, SHBG, SLC10A1, SLC10A2, SPINK1, SPRY1, TP53, YWHAH, ZFP36L2 | Cancer, Cellular Movement, Cellular Growth and Proliferation |

*Genes identified in the present study are underlined. The underlined genes that have not been reported to associate with liver injury are in bold.

TABLE 3B

Interacting network analysis of proteins selected from iTRAQ proteomic study

| | Genes* | Top functions |
|---|---|---|
| 1 | ADD1, ALB, ALDH1A1, CA2, CASP3, CNN2, CTNNB1, DIA1, ENPP1, GBA, GM2A, HGF, HSD17B2, IL1B, ITPA, JTV1, KRT17, LMNA, LMNB2, MAP4, MYC, OAT, PLS3, PSAP, S100A9, SERPINH1, SLC4A, SRM, SULT1E1, TAGLN2, TGFB1, TLN1, TPM3, UGDH, VIM | Cancer, Cell Cycle, Cell Morphology |
| 2 | ACADM, ACTC, ADCY7, ALDH2, ALDOA, ALDOB, ARG2, ARHGDIA, CD276, CNR2, CPS1, CROT, Cyp4a10, Cyp4a14, EHHADH, EPHX1, FAAH, FASN, FN1, G22P1, GNMT, GOT2, HOXD4, HPX, HRSP12, Ifi1, IFNG, IL4, LEP, Mug1, MYH9, MYOD1, PPARA, SORD, TGM2 | Lipid Metabolism, Small Molecule Biochemistry, Organismal Injury and Abnormalities |

TABLE 3B-continued

Interacting network analysis of proteins selected from iTRAQ proteomic study

| Genes* | Top functions |
|---|---|
| 3 <u>ALB</u>, ANXA1, CLU, <u>CYP2C13</u>, CYP3A2, FGA, FGB, <u>FGG</u>, FLI1, GAL, GFAP, GH1, GHRH, GHRL, <u>HBA1</u>, <u>HBA2</u>, <u>HBB</u>, Hbb-ar, Hbb-b1, Hbb-b2, Hbb-bh1, Hbb-y, HBD, HBE1, HBG1, HBG2, HBQ1, HBZ, IL6, NTS, SOCS2, Stat5, TF, TG, <u>TTR</u> | Hematological Disease, Endocrine System Development and Function, Nervous System Development and Function |

*Genes identified in the present study are underlined. The underlined genes that have not been reported to associate with liver injury are in bold.

What is claimed is:

1. A method of detecting liver fibrosis and/or cirrhosis comprising:
   obtaining a first biological sample from a first subject without liver fibrosis and/or cirrhosis, wherein the first subject is a normal subject;
   obtaining a second biological sample from a second subject known or suspected of having liver fibrosis and/or cirrhosis; and
   determining an amount of at least one protein chosen from SEQ ID NO: 7 and SEQ ID NO: 68 in said first and second biological samples;
   wherein a difference of 1.5 fold or more between the amount of said protein present in the first biological sample from said first subject and the amount of said protein present in the second biological sample from said second subject assists in the diagnosis of whether the second subject has liver fibrosis and/or cirrhosis.

2. The method of claim 1, wherein the amount of at least one protein is determined by Western blot or ELISA.

3. A method of evaluating the expression level of a biomarker for liver fibrosis and/or cirrhosis comprising:
   obtaining a first biological sample from a first subject without liver fibrosis and/or cirrhosis, wherein the first subject is a normal subject;
   obtaining a second biological sample from a second subject known or suspected of having liver fibrosis and/or cirrhosis; and
   determining an amount of at least one protein chosen from SEQ ID NO: 7 and SEQ ID NO: 68 in said first and second biological samples;
   wherein a difference of 1.5 fold or more between the amount of said protein present in the first biological sample from said first subject and the amount of said protein present in the second biological sample from said second subject assists in the diagnosis of whether the second subject has liver fibrosis and/or cirrhosis.

* * * * *